United States Patent
O'Malley et al.

(10) Patent No.: US 12,171,756 B2
(45) Date of Patent: Dec. 24, 2024

(54) NLRP3 MODULATORS

(71) Applicant: Innate Tumor Immunity, Inc., Princeton, NJ (US)

(72) Inventors: Daniel O'Malley, New Hope, PA (US); Ashvinikumar V. Gavai, Princeton Junction, NJ (US); Patrice Gill, Levittown, PA (US); Christine M. Tarby, Lawrenceville, NJ (US); Scott Hunter Watterson, Pennington, NJ (US); Hua Gong, King of Prussia, PA (US); David K. Williams, Delran, NJ (US); Shomir Ghosh, Brookline, MA (US); William R. Roush, Tequesta, FL (US)

(73) Assignee: INNATE TUMOR IMMUNITY, INC., Princeton, NJ (US)

( * ) Notice: Subject to any disclaimer, the term of this patent is extended or adjusted under 35 U.S.C. 154(b) by 238 days.

(21) Appl. No.: 17/731,279

(22) Filed: Apr. 28, 2022

(65) Prior Publication Data
US 2022/0257587 A1    Aug. 18, 2022

Related U.S. Application Data

(62) Division of application No. 16/629,980, filed as application No. PCT/US2018/041723 on Jul. 12, 2018, now Pat. No. 11,344,543.

(60) Provisional application No. 62/532,932, filed on Jul. 14, 2017, provisional application No. 62/662,405, filed on Apr. 25, 2018, provisional application No. 62/689,412, filed on Jun. 25, 2018.

(51) Int. Cl.

| | | |
|---|---|---|
| *C07D 401/10* | (2006.01) | |
| *A61K 31/4709* | (2006.01) | |
| *A61K 31/496* | (2006.01) | |
| *A61K 31/501* | (2006.01) | |
| *A61K 31/5377* | (2006.01) | |
| *A61K 31/551* | (2006.01) | |
| *A61K 31/553* | (2006.01) | |
| *A61K 45/06* | (2006.01) | |
| *C07D 401/14* | (2006.01) | |
| *C07D 405/14* | (2006.01) | |
| *C07D 409/14* | (2006.01) | |
| *C07D 413/14* | (2006.01) | |
| *C07D 417/14* | (2006.01) | |
| *C07D 471/04* | (2006.01) | |

(52) U.S. Cl.
CPC ........ *A61K 31/4709* (2013.01); *A61K 31/496* (2013.01); *A61K 31/501* (2013.01); *A61K 31/5377* (2013.01); *A61K 31/551* (2013.01); *A61K 31/553* (2013.01); *A61K 45/06* (2013.01); *C07D 401/10* (2013.01); *C07D 401/14* (2013.01); *C07D 405/14* (2013.01); *C07D 409/14* (2013.01); *C07D 413/14* (2013.01); *C07D 417/14* (2013.01); *C07D 471/04* (2013.01)

(58) Field of Classification Search
CPC .. C07D 401/10; C07D 401/14; C07D 405/14; C07D 409/14; C07D 413/14; C07D 417/14; C07D 471/04
See application file for complete search history.

(56) References Cited

U.S. PATENT DOCUMENTS

| | | |
|---|---|---|
| 4,247,699 A | 1/1981 | Kadin |
| 5,112,837 A | 5/1992 | Burrows et al. |
| 6,352,989 B1 | 3/2002 | Miyazaki |
| 10,533,005 B2 | 1/2020 | Glick et al. |
| 10,533,007 B2 | 1/2020 | Glick et al. |
| 10,556,903 B2 | 2/2020 | Glick et al. |
| 2002/0198194 A1 | 12/2002 | Mueller et al. |
| 2003/0229119 A1 | 12/2003 | Kym et al. |
| 2007/0173508 A1 | 7/2007 | Hutchinson |
| 2008/0188521 A1 | 8/2008 | Grimm et al. |
| 2010/0041698 A1 | 2/2010 | Amberg et al. |
| 2016/0332971 A1 | 11/2016 | Watt et al. |
| 2022/0056043 A1* | 2/2022 | Li .................. C07D 401/14 |

FOREIGN PATENT DOCUMENTS

| | | |
|---|---|---|
| GB | 1567875 A1 | 5/1980 |
| WO | WO2004002960 A1 | 1/2004 |
| WO | WO2005030140 A2 | 4/2005 |
| WO | WO2007092854 A2 | 8/2007 |

(Continued)

OTHER PUBLICATIONS

U.S. Appl. No. 16/703,974, filed Nov. 25, 2019, Glick et al.

(Continued)

*Primary Examiner* — Erich A Leeser

(74) *Attorney, Agent, or Firm* — Jing G. Sun

(57) ABSTRACT

The present invention provides compounds of Formula (I):

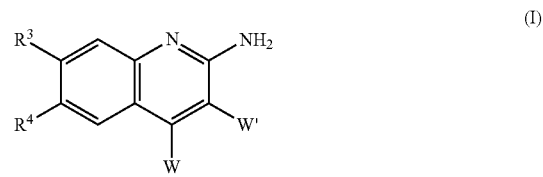

wherein all of the variables are as defined herein. These compounds are modulators of NLRP3, which may be used as medicaments for the treatment of proliferative disorders, such as cancer in a subject (e.g., a human).

10 Claims, No Drawings

(56) References Cited

FOREIGN PATENT DOCUMENTS

| | | | |
|---|---|---|---|
| WO | WO2009097278 A1 | 8/2009 | |
| WO | WO2009097401 A1 | 8/2009 | |
| WO | WO2011063233 A1 | 5/2011 | |
| WO | WO2011063272 A1 | 5/2011 | |
| WO | WO2011090911 A1 | 7/2011 | |
| WO | WO2012037108 A1 | 3/2012 | |
| WO | WO2015077550 A1 | 5/2015 | |
| WO | WO2017034986 A1 | 3/2017 | |
| WO | WO2017040670 A1 | 3/2017 | |
| WO | WO2017184735 A1 | 10/2017 | |
| WO | WO2017184746 A1 | 10/2017 | |
| WO | WO2018118842 A1 | 6/2018 | |

OTHER PUBLICATIONS

U.S. Appl. No. 16/703,974, filed Dec. 5, 2019, Glick, et al.

Ahyong, et al, Identification of Plasmodium falciparum specific translation inhibitors from the MMV Malaria Box using a high throughput in vitro translation screen, Malaria Journal, 2016, 1-8, vol. 15.

Althuis, et al., Structure-Activity Relationships in a Series of Novel 3,4-Dihydro-4-oxopyrimido[4,5-b]quinoline-2-carboxylic Acid Antiallergy Agents1, J. Med. Chemistry, 1980, 262-269, vol. 23.

Baldwin, Alex G. et al., "Inhibiting the Inflammasome: A Chemical Perspective", Journal of Medicinal Chemistry, vol. 59, pp. 1691-1710 (2016).

Ballell et al, Fueling Open-Source Drug Discovery: 177 Small-Molecule Leads against Tuberculosis, Chemistry and Drug Discovery, 2013, 313-321, vol. 8.

Bauernfeind, F. et al., "Of inflammasomes and pathogens—sensing of microbes by the inflammasome", EMBO Molecular Medicine, vol. 5, pp. 814-826 (2013).

Beesu, et al., Structure-Based Design of,Human TLR8-Specific Agonists with Augmented Potency and Adjuvanticity, Journal of Medicinal Chemistry, 2015, 7833-7849, vol. 58.

Boezio, et al, 1,2,4-Triazolsulfone: A novel isosteric replacement of acylsulfonamides in the context of Nav1.7 inhibition, Bioorganic & Medicinal Chemistry Letters, 2018, 2103-2108, vol. 28.

Burikhanov, et al, Arylquins target vimentin to trigger Par-4 secretion for tumor cell apoptosis, Nature Chemical Biology, 2014, 924-928, vol. 10.

Chaput, Catherine et al., "NOD-like receptors in lung diseases" Frontiers in Immunology, vol. 4, Article 393 pp. 1-12 (2013).

Chen, Lih-Chyang et al., "Tumour inflammasome-derived IL-1β recruits neutrophils and improves local recurrence-free survival in EBV-induced nasopharyngeal carcinoma", EMBO Molecular Medicine, vol. 4, pp. 1276-1293 (2012).

Cheng, et al., From Fragment Screening to In Vivo Efficacy: Optimization of a Series of 2-Aminoquinolines as Potent Inhibitors of Beta-Site Amyloid Precursor Protein Cleaving Enzyme 1 (BACE1) +, Journal of Medicinal Chemistry, 2011, 5836-5837, vol. 54.

Cinelli, et al, Nitrile in the Hole: Discovery of a Small Auxiliary Pocket in Neuronal Nitric Oxide Synthase Leading to the Development of Potent and Selective 2-Aminoquinoline Inhibitors, Journal of Medicinal Chemistry, 2017, 3958-3978, vol. 60.

Fuertes, Mercedes B. et al., "Type I interferon response and innate immune sensing of cancer", Trends in Immunology, vol. 34(2), pp. 67-73 (2013).

Hale, et al, From fragments to leads: novel bacterial NAD+ −dependent DNA ligase inhibitors, Tetrahedron Letters, 2014, 3108-3112, vol. 56.

Hirota, Jeremy A. et al., "The airway epithelium nucleotide-binding domain and leucine-rich repeat protein 3 inflammasome is activated by urban particulate matter", J. Allergy Clinical Immunology, vol. 129, pp. 1116-1125 (2012).

Jain, et al, Recent advances in selective alpha-1adrenoreceptor antagonists as antihypertensive agents, Bioorganic & Medicinal Chemistry, 2008, 4759-4800, vol. 16.

Lin, Chu et al., "Inflammasomes in Inflammation-Induced Cancer", Frontiers in Immunology, vol. 8, Article 271, pp. 1-22 (2017).

Ma, Zhifeng et al., "Augmentation of Immune Checkpoint Cancer Immunotherapy with IL18" Clinical Cancer Research, vol. 22(12), pp. 2969-2980 (2016).

Ostrynska et al., Chemical optimization of 3-arboxyquinoline amides as inhibitors of protein kinase CK2, XP-002785985, 2016, 38-45, vol. 14 (1).

Sviripa, Par-4 secretion: stoichiometry of 3-arylquinoline binding to vimentin, Organic & Biomolecular Chemistry, 2016, 74-84, vol. 14.

Ting, Jenny P.Y. et al., "The NLR Gene Family: A Standard Nomenclature", Immunity, vol. 28, pp. 285-287 (2008).

* cited by examiner

NLRP3 MODULATORS

CROSS-REFERENCE TO RELATED APPLICATIONS

This application is a divisional application of patent application Ser. No. 16/629,980, filed Jan. 10, 2020, (issued as U.S. Pat. No. 11,344,543 B2), which is a 371 of International Application No. PCT/US2018/041723 filed on Jul. 12, 2018, which claims the priority benefit of U.S. Provisional Application No. 62/532,932, filed Jul. 14, 2017, U.S. Provisional Application No. 62/662,405, filed Apr. 25, 2018, and U.S. Provisional Application No. 62/689,412, filed Jun. 25, 2018; the contents of which are herein incorporated by reference in their entirety.

TECHNICAL FIELD

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity that contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

BACKGROUND

Nucleotide-binding oligomerization domain-like receptors ("NLRs") include a family of intracellular receptors that detect pathogen-associated molecular patterns ("PAMPs") and endogenous molecules (see, e.g., Ting, J. P. Y. et al., "The NLR gene family: a standard nomenclature," *Immunity*, 28(3):285-287, (2008)).

NLRPs represent a subfamily of NLRs that include a Pyrin domain and are constituted by proteins such as NLRP1, NLRP3, NLRP4, NLRP6, NLRP7, and NLRP12. NLRPs are believed to be involved with the formation of multiprotein complexes termed inflammasomes (see, e.g., Chaput, C. et al., "NOD-like receptors in lung diseases," *Frontiers in Immunology*, 4: article 393, (2013)). These complexes typically include one or two NLR proteins, the adapter molecule apoptosis associated speck-like containing a CARD domain (ASC) and pro-caspase-1 F (see, e.g., Bauernfeind, F and Hornung, V. "Of inflammasomes and pathogens—sensing of microbes by the inflammasome," *EMBO Molecular Medicine*, 5(6):814-826, (2013)).

One such inflammasome is formed by the NLRP3 scaffold, the ASC adaptor and pro-caspase-1 (see, e.g., Hirota, J. A., et al., "The airway epithelium nucleotide-binding domain and leucine-rich repeat protein 3 inflammasome is activated by urban particulate matter," *Journal of Allergy and Clinical Immunology*, 129(4):1116.e6-1125.e6, (2012)), and its expression is believed to be induced by inflammatory cytokines and TLR agonists in myeloid cells and human bronchial epithelial cells (Id.). The NLRP3 inflammasome is believed to mediate the caspase-1-dependent conversion of pro-IL-1β and pro-IL-18 to IL-1β and IL-18. Further, IL-1β and IL-18 have potential in the treatment of various types of cancer (see, e.g., Chen, L-C. et al., *EMBO Mol Med.*, 4(12):1276-1293 (2012) and Tse, B. W-C. et al., *PLoS One*, 6(9):e24241 (2011)). IL-18 has been shown to override resistance to checkpoint inhibitors in colon cancer animal tumor models (see e.g., Ma, Z. et al., *Clin. Cancer Res.* January 11. (2016) DOI: 10.1158/1078-0432.CCR-15-1655).

SUMMARY

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity contributes to the pathology and/or symptoms and/or progression and/or treatment refractory state of the condition, disease or disorder (e.g., cancers with low T-cell infiltration) in a subject (e.g., a human). This disclosure also features compositions as well as other methods of using and making the same.

An "agonist" of NLRP3 includes compounds that, at the protein level, directly bind or modify NLRP3 such that an activity of NLRP3 is increased, e.g., by activation, stabilization, altered distribution, or otherwise.

Certain compounds described herein that agonize NLRP3 to a lesser extent than a NLRP3 full agonist can function in assays as antagonists as well as agonists. These compounds antagonize activation of NLRP3 by a NLRP3 full agonist because they prevent the full effect of NLRP3 interaction. However, the compounds also, on their own, activate some NLRP3 activity, typically less than a corresponding amount of the NLRP3 full agonist. Such compounds may be referred to as "partial agonists of NLRP3".

In some embodiments, the compounds described herein are agonists (e.g. full agonists) of NLRP3. In other embodiments, the compounds described herein are partial agonists of NLRP3.

Generally, a receptor exists in an active (Ra) and an inactive (Ri) conformation. Certain compounds that affect the receptor can alter the ratio of Ra to Ri (Ra/Ri). For example, a full agonist increases the ratio of Ra/Ri and can cause a "maximal", saturating effect. A partial agonist, when bound to the receptor, gives a response that is lower than that elicited by a full agonist (e.g., an endogenous agonist). Thus, the Ra/Ri for a partial agonist is less than for a full agonist. However, the potency of a partial agonist may be greater or less than that of the full agonist.

In one aspect, compounds of Formula (I), or a pharmaceutically acceptable salt thereof, are featured:

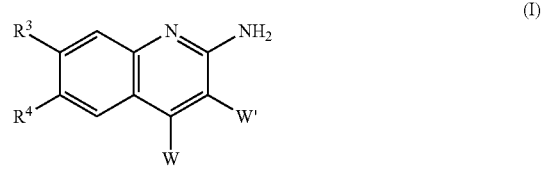

(I)

in which W, W', $R^3$, and $R^4$ can be as defined anywhere herein.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). In preferred embodiments, methods for modulating NLRP3 activity are agonizing and partially agonizing. In certain embodiments, methods for modulating NLRP3 activity are agonizing. In certain embodiments, methods for modulating NLRP3 activity are partially agonizing. Methods include in vitro methods, e.g., contacting a sample that includes one or more cells comprising NLRP3 (e.g., THP-1 cells) with the chemical entity. Methods can also include in vivo methods; e.g., administering the chemical entity to a subject (e.g., a human) having a disease in which an increase in NLRP3 signaling may correct a deficiency in innate immune activity that contributes to the pathology and/or symptoms and/or progression of the disease (e.g., cancer; e.g., a refractory cancer).

In some embodiments, compounds of the invention are useful for treating a condition, disease or disorder in which a decrease in NLRP3 activity (e.g., a condition, disease or disorder associated with repressed or impaired NLRP3 signaling) contributes to the pathology and/or symptoms and/or progression of the condition, disease or disorder (e.g., cancer) in a subject (e.g., a human).

A cancer is said to be refractory when it does not respond to (or is resistant to) cancer treatment. Refractory cancer is also known as resistant cancer.

In another aspect, methods of treating cancer are featured that include administering to a subject in need of such treatment an effective amount of a chemical entity described herein (e.g., a compound described generically or specifically herein or a pharmaceutically acceptable salt thereof or compositions containing the same). In some embodiments, the cancer may be a refractory cancer.

In a further aspect, methods of treatment of a disease in which an increase in NLRP3 signaling may correct a deficiency in innate immune activity that contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In another aspect, methods of treatment are featured that include administering to a subject having a disease in which an increase in NLRP3 signaling may correct a deficiency in innate immune activity that contributes to the pathology and/or symptoms and/or progression of the disease an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which an increase in NLRP3 signaling may correct a deficiency in innate immune activity that contributes to the pathology and/or symptoms and/or progression of the disease, thereby treating the disease.

Embodiments can include one or more of the following features.

The chemical entity can be administered in combination with one or more additional cancer therapies (e.g., surgery, radiotherapy, chemotherapy, toxin therapy, immunotherapy, cryotherapy or gene therapy, or a combination thereof; e.g., cancer therapies that include administering one or more (e.g., two, three, four, five, six, or more) additional anti-cancer agents. Non-limiting examples of additional anti-cancer agents (chemotherapeutic agents) are selected from an alkylating agent (e.g., cisplatin, carboplatin, mechlorethamine, cyclophosphamide, chlorambucil, ifosfamide and/or oxaliplatin); an anti-metabolite (e.g., azathioprine and/or mercaptopurine); a terpenoid (e.g., a vinca alkaloid and/or a taxane; e.g., Vincristine, Vinblastine, Vinorelbine and/or Vindesine, Taxol, Paclitaxel and/or Docetaxel); a topoisomerase (e.g., a type I topoisomerase and/or a type 2 topoisomerase; e.g., camptothecins, such as irinotecan and/or topotecan; amsacrine, etoposide, etoposide phosphate and/or teniposide); a cytotoxic antibiotic (e.g., actinomycin, anthracyclines, doxorubicin, daunorubicin, valrubicin, idarubicin, epirubicin, bleomycin, plicamycin and/or mitomycin); a hormone (e.g., a lutenizing hormone releasing hormone agonist; e.g., leuprolidine, goserelin, triptorelin, histrelin, bicalutamide, flutamide and/or nilutamide); an antibody (e.g., Abciximab, Adalimumab, Alemtuzumab, Atlizumab, Basiliximab, Belimumab, Bevacizumab, Bretuximab vedotin, Canakinumab, Cetuximab, Ceertolizumab pegol, Daclizumab, Denosumab, Eculizumab, Efalizumab, Gemtuzumab, Golimumab, Ibritumomab tiuxetan, Infliximab, Ipilimumab, Muromonab-CD3, Natalizumab, Ofatumumab, Omalizumab, Palivizumab, Panitumuab, Ranibizumab, Rituximab, Tocilizumab, Tositumomab and/or Trastuzumab); an anti-angiogenic agent; a cytokine; a thrombotic agent; a growth inhibitory agent; an anti-helminthic agent; and an immune checkpoint inhibitor that targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-β (TGFβ), CD39, CD73 Adenosine-CD39-CD73, and CXCR4-CXCL12.

The subject can have cancer; e.g., the subject has undergone and/or is undergoing and/or will undergo one or more cancer therapies.

Non-limiting examples of cancer include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In other embodiments, the mammal has been identified as having a cancer or an infectious disease. Representative infectious diseases include, without limitation, Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, *chlamydia*, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium* myonecrosis, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, Kingella kingae infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

The chemical entity can be administered intratumorally.

The chemical entity can be administered systemically (including but not limited to orally, subcutaneously, intramuscular, intravenously).

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a mitochondrial uncoupling agent or a pharmaceutically acceptable salt and/or hydrate and/or cocrystal thereof; e.g., a compound, such as niclosamide or a pharmaceutically acceptable salt and/or hydrate and/or cocrystal thereof; e.g., a compound, such as a niclosamide analog, or a pharmaceutically acceptable salt and/or hydrate and/or cocrystal thereof) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See. e.g., *Remington: The Science and Practice of Pharmacy.* 22nd Edition, Pharmaceutical Press, London, UK (2012); *Handbook of Pharmaceutical Excipients. 6th ed.*; Rowe et al., Eds.; The Pharmaceutical Press and the American Pharmaceutical Association: (2009); *Handbook of Pharmaceutical Additives, 3rd ed.*; Ash and Ash Eds.; Gower Publishing Company: (2007); *Pharmaceutical Preformulation and Formulation, 2nd ed.*; Gibson Ed.; CRC Press LLC: Boca Raton, FL, (2009).

The term "pharmaceutically acceptable salt" refers to a formulation of a compound that does not cause significant irritation to an organism to which it is administered and does not abrogate the biological activity and properties of the compound. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. In some instances, pharmaceutically acceptable salts are obtained by reacting a compound having acidic group described herein with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt is not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and omithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii)

reducing tumor size, (iii) slowing the growth of a tumor, (iv) reducing, slowing or preventing invasion and/or (8) relief, to some extent, of the severity or number of one or more symptoms associated with the disorder.

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a branched or unbranched divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aromatic" refers generally to a ring that includes a cyclic array of resonance-stabilized 4n+2 pi electrons, wherein n is an integer (e.g., 1 or 2). Aromatic moieties include aryl and heteroaryl groups. The term "nonaromatic" describes any moiety that does not fall within the definition of "aromatic".

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic e.g. tetrahydronaphthyl. Examples of aryl groups also include phenyl, naphthyl and the like.

The term "cycloalkyl" as used herein includes saturated cyclic hydrocarbon groups having 3 to 10 carbons, preferably 3 to 8 carbons, and more preferably 3 to 6 carbons, wherein the cycloalkyl group may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl. The term "cycloalkylene" as used herein refers to divalent cycloalkyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent, and wherein the ring comprising a monocyclic radical is aromatic and wherein at least one of the fused rings comprising a bicyclic or tricyclic radical is aromatic (but does not have to be a ring which contains a heteroatom, e.g. tetrahydroisoquinolinyl. Examples of heteroaryl groups also include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like. The term "heterocycloalkylene" refers to divalent heterocyclyl.

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

The details of one or more embodiments of the invention are set forth in the accompanying drawings and the description below. Other features and advantages of the invention will be apparent from the description and drawings, and from the claims.

DETAILED DESCRIPTION

This disclosure features chemical entities (e.g., a compound or a pharmaceutically acceptable salt, and/or hydrate, and/or cocrystal, and/or drug combination of the compound) that modulate (e.g., agonizes or partially agonizes) NLRP3 that are useful, e.g., for treating a condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) in a subject (e.g., a human). This disclosure also features compositions as well as other methods of using and making the same.

Compounds of Invention

In one aspect, compounds of Formula I, or a pharmaceutically acceptable salt thereof are featured:

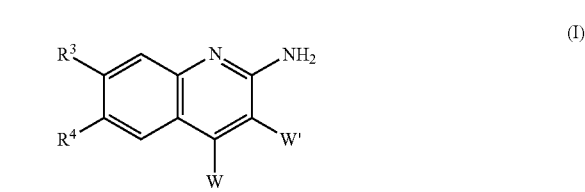

(I)

W' is $R^2$ or Q'-$R^2$;
Q' is NH, O, or S;
W is H, $R^2$, or Q-$R^2$
Q is $NR^1$, $CHR^1$, O, or S;
$R^1$ is independently H or X—$R^5$; wherein:
  X is selected from: $C_{1-10}$ alkylene, $C_{2-10}$ alkenylene, and $C_{2-10}$ alkynylene, wherein each of which is optionally interrupted by one O or S and/or each of which is optionally substituted with from 1-4 $R^e$;

$R^5$ is selected from:
(i) hydrogen;
(ii) —OH;
(iii) $C_{1-4}$ alkoxy;
(iv) $C_{1-4}$ haloalkoxy;
(v) —$CO_2R^a$;
(vi) —CONR'R";
(vi) cyano;
(vii) —$NR^bR^c$;
(viii) $Q^1$-aryl that is optionally substituted with from 1-3 $R^d$;
(ix) $Q^1$-heteroaryl including from 5-6 ring atoms, wherein from 1-4 ring atoms are each independently selected from N, N($R^f$), O, and S, wherein the heteroaryl is optionally substituted with from 1-3 $R^d$;
(x) $Q^1$-$C_{3-10}$ cycloalkyl that is optionally substituted with from 1-4 $R^g$,
(xi) $Q^1$-heterocyclyl including from 3-10 ring atoms, wherein from 1-3 ring atoms are each independently selected from N, N($R^f$) and O, wherein the heterocyclyl is optionally substituted with from 1-4 $R^g$,
(xii) $C_{1-4}$ thioalkoxy;
(xiii) —SH
(xiv) —$N_3$;
(xv) —$CO_2H$;
(xvi) —$C(O)R^a$; and
(xvii) —$SO_{1-2}(R^h)$;
$Q^1$ is selected from: a bond, O, —O($C_{1-3}$ alkylene)-, S, and —S($C_{1-3}$ alkylene)-;
$R^2$ is selected from: H, $R^6$, and -$Q^2$-Y—$R^6$;
$Q^2$ is selected from: a bond, C(O), N($R^f$), O, and S;
Y is selected from: $C_{1-10}$ alkylene, $C_{2-10}$ alkenylene, and $C_{2-10}$ alkynylene, each of which is optionally substituted with from 1-4 $R^e$ and/or each of which is optionally interrupted by one or more of the following:
(i) O;
(ii) S;
(iii) N($R^f$);
(iv) $C_{3-6}$ cycloalkylene optionally substituted with from 1-4 $R^g$,
(v) $C_{6-10}$ arylene, optionally further substituted with from 1-4 $R^d$,
(vi) heteroarylene including from 5-10 ring atoms, wherein from 1-4 ring atoms are each independently selected from N, N($R^f$), O, and S, and which is optionally substituted with from 1-4 $R^g$, or
(vii) heterocycloalkylene including from 3-10 ring atoms, wherein from 1-3 ring atoms are each independently selected from N, N($R^f$) and O, and which is optionally further substituted with from 1-4 $R^g$, and
$R^6$ is selected from:
(i) hydrogen;
(ii) —OH;
(iii) $C_{1-4}$ alkoxy;
(iv) $C_{1-4}$ haloalkoxy;
(v) —$CO_2R^a$;
(vi) —CONR'R";
(vi) cyano;
(vii) —$NR^bR^c$;
(viii) $Q^1$-aryl that is optionally substituted with from 1-3 $R^d$;
(ix) $Q^1$-heteroaryl including from 5-10 ring atoms, wherein from 1-4 ring atoms are each independently selected from N, N($R^f$), O, and S, wherein the heteroaryl is optionally substituted with from 1-3 $R^d$;
(x) $Q^1$-$C_{3-10}$ cycloalkyl that is optionally substituted with from 1-4 $R^g$,
(xi) $Q^1$-heterocyclyl including from 3-10 ring atoms, wherein from 1-3 ring atoms are each independently selected from N, N($R^f$) and O, wherein the heterocyclyl is optionally substituted with from 1-4 $R^g$,
(xii) $C_{1-4}$ thioalkoxy;
(xiii) —SH
(xiv) —$N_3$;
(xv) —$CO_2H$;
(xvi) —$C(O)R^a$; and
(xvii) —$SO_{1-2}(R^h)$;
$R^3$ and $R^4$ are each independently selected from:
(i) hydrogen;
(ii) halo;
(iii) cyano;
(iv) —$CO_2R^a$;
(v) —CONR'R";
(vi) $C_{1-4}$ alkyl, optionally substituted with from 1-2 independently selected $R^e$;
(vii) $C_{1-4}$ haloalkyl;
(viii) $C_{1-4}$ alkoxy;
(ix) $C_{1-4}$ haloalkoxy;
(x) $Y^4$—($C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, N($R^f$), O, or S;
(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;
(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;
(xiv) —$N_3$;
(xv) —$CO_2H$;
(xvi) —OH;
(xvii) —$SO_{1-2}(R^h)$;
(xviii) —$NR^bR^c$;
(xvix) —$SO_{1-2}(NR'R")$; and
(xx) thioalkoxy;
$R^a$ is:
(i) $C_{1-8}$ alkyl optionally substituted with from 1-2 independently selected $R^e$;
(ii) —($C_{0-6}$ alkylene)-$C_{3-10}$ cycloalkyl, wherein the cycloalkyl is optionally substituted with from 1-4 independently selected $R^g$;
(iii) —($C_{0-6}$ alkylene)-heterocyclyl including from 3-10 ring atoms, wherein from 1-3 ring atoms are each independently selected from N($R^f$), O, and S, wherein the heterocyclyl is optionally substituted with from 1-4 independently selected $R^g$;
(iv) —($C_{0-6}$ alkylene)-($C_{6-10}$ aryl), wherein the aryl is optionally substituted with from 1-5 independently selected $R^d$; or
(v) —($C_{0-6}$ alkylene)-heteroaryl including from 5-10 ring atoms, wherein from 1-4 ring atoms are each independently selected from N, N(R$^f$), O, and S, wherein the heteroaryl is optionally substituted with from 1-3 independently selected R$^d$;

each occurrence of R$^b$ and R$^c$ is independently selected from: H; R$^a$; —C(O)(R$^a$), —C(O)O(R$^a$), —S(O)$_{1-2}$ (R$^h$), —C(O)NR'R", —S(O)$_{1-2}$(NR'R"), —OH, and C$_{1-4}$ alkoxy;

each occurrence of R$^d$ is independently selected from:
(i) halo;
(ii) cyano;
(iii) C$_{1-6}$ alkyl optionally substituted with from 1-2 independently selected R$^e$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl including from 3-10 ring atoms, wherein from 1-3 ring atoms are each independently selected from N(R$^f$), O, and S, wherein the heterocyclyl is optionally substituted with from 1-4 independently selected C$_{1-4}$ alkyl;
(xi) —(C$_{0-3}$ alkylene)-phenyl optionally substituted with from 1-3 R$^m$;
(xii) —(C$_{0-3}$ alkylene)-heteroaryl including from 5-10 ring atoms, wherein from 1-4 ring atoms are each independently selected from N, N(R$^f$), O, and S, wherein the heteroaryl is optionally substituted with from 1-3 R$^m$;
(xiii) —S(O)$_{1-2}$(R$^h$); and
(xiv) —NR$^j$R$^k$;
(xv) —OH;
(xvi) —S(O)$_{1-2}$(NR'R");
(xvii) —C$_{1-4}$ thioalkoxy;
(xviii) —NO$_2$;
(xix) —N(R$''$)(C(═O)C$_{1-3}$ alkyl);
(xx) —C(═O)(C$_{1-4}$ alkyl);
(xxi) —C(═O)O(C$_{1-4}$ alkyl);
(xxii) —C(═O)OH, and
(xxiii) —C(═O)N(R')(R");

each occurrence of R$^e$ is independently selected from: —OH; F; —NR$^j$R$^k$; —N(R$''$)(C(═O)C$_{1-4}$ alkyl); —N(R$''$)(C(═O)OC$_{1-4}$ alkyl); C$_{1-4}$ alkoxy; C$_{1-4}$ haloalkoxy; —C(═O)O(C$_{1-4}$ alkyl); —C(═O)(C$_{1-4}$ alkyl); —C(═O)OH; —CON(R')(R"); —S(O)$_{1-2}$(NR'R"); —S(O)$_{1-2}$(C$_{1-4}$ alkyl); and cyano;

each occurrence of R$^f$ is independently selected from: H; C$_{1-4}$ alkyl; C$_{3-6}$ cycloalkyl; phenyl; —C(O)(C$_{1-4}$ alkyl); —C(O)O(C$_{1-4}$ alkyl); —CON(R')(R"); —S(O)$_{1-2}$(NR'R"); —S(O)$_{1-2}$R$^h$; —OH; and C$_{1-4}$ alkoxy; wherein each C$_{1-4}$ alkyl is optionally substituted with from 1-2 independently selected R$^e$; each C$_{3-6}$ cycloalkyl is optionally substituted with from 1-2 independently selected R$^g$; and each phenyl is optionally substituted with from 1-2 independently selected R$^d$;

each occurrence of R$^g$ is independently selected from: C$_{1-6}$ alkyl optionally substituted with from 1-2 independently selected R; C$_{1-4}$ haloalkyl; —OH; oxo; F; Cl; Br; —NR$^j$R$^k$; —N(R$''$)(C(═O)C$_{1-4}$ alkyl); C$_{1-4}$ alkoxy; C$_{1-4}$ haloalkoxy; —C(═O)(C$_{1-4}$ alkyl); —C(═O)O(C$_{1-4}$ alkyl); —C(═O)OH; —C(═O)N(R')(R"); —S(O)$_{1-2}$(NR'R"); —S(O)$_{1-2}$(C$_{1-4}$ alkyl); cyano; C$_{3-6}$ cycloalkyl optionally substituted with from 1-4 independently selected C$_{1-4}$ alkyl; heteroaryl including from 5-10 ring atoms, wherein from 1-4 ring atoms are each independently selected from N, N(R$^f$), O, and S, wherein the heteroaryl is optionally substituted with from 1-3 R$^m$; and phenyl optionally substituted with from 1-4 R$^m$;

each occurrence of R$^h$ is independently selected from: C$_{1-4}$ alkyl, C$_{1-4}$ haloalkyl, C$_{1-4}$ alkoxy, C$_{1-4}$ haloalkoxy, phenyl optionally substituted with from 1-3 R$^m$, and heteroaryl including from 5-6 ring atoms, wherein from 1-4 ring atoms are each independently selected from N, N(R$^f$), O, and S, wherein the heteroaryl is optionally substituted with from 1-3 R$^m$;

each occurrence of R$^j$ and R$^k$ is independently selected from: H and C$_{1-4}$ alkyl, which is optionally substituted with from 1-2 independently selected R$^u$, wherein each occurrence of R$^u$ is independently selected from: —OH, —N(R$^p$)R$^q$), —N(R$''$)(C(═O)C$_{1-4}$ alkyl), —N(R$''$)(C(═O)OC$_{1-4}$ alkyl), C$_{1-4}$ alkoxy, C$_{1-4}$ haloalkoxy, —C(═O)(C$_{1-4}$ alkyl); —C(═O)O(C$_{1-4}$ alkyl); —C(═O)OH; —C(═O)N(R$^p$)(R$^q$), —S(O)$_{1-2}$(C$_{1-4}$ alkyl); —S(O)$_{1-2}$(N(R$^p$)(R$^q$)), and cyano;

each occurrence of R$^m$ is independently selected from: C$_{1-4}$ alkyl; C$_{1-4}$ haloalkyl; —OH, F, Cl, Br, —N(R$^j$)(R$^k$), —N(R$''$)(C(═O)C$_{1-4}$ alkyl), —N(R$''$)(C(═O)OC$_{1-4}$ alkyl), C$_{1-4}$ alkoxy, C$_{1-4}$ haloalkoxy, —C(═O)(C$_{1-4}$ alkyl); —C(═O)O(C$_{1-4}$ alkyl); —C(═O)OH, —C(═O)N(R$^p$)(R$^q$), —S(O)$_{1-2}$(C$_{1-4}$ alkyl); —S(O)$_{1-2}$(N(R$^p$)(R$^q$)), and cyano;

each occurrence of R$^n$, R$^p$, and R$^q$ is independently selected from: H and C$_{1-4}$ alkyl;

each occurrence of R' and R" is independently selected from: H and C$_{1-4}$ alkyl, which is optionally substituted with from 1-2 independently selected R$^u$; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and R$^s$; and (b) from 0-3 ring heteroatoms (in addition to the nitrogen atom attached to R' and R"), which are each independently selected from N(R$^t$), O, and S;

each occurrence of R$^s$ is independently selected from: C$_{1-6}$ alkyl optionally substituted with from 1-2 independently selected R$^u$; C$_{1-4}$ haloalkyl; —OH; oxo; F; Cl; Br; —NR$^j$R$^k$; —N(R$''$)(C(═O)C$_{1-4}$ alkyl); C$_{1-4}$ alkoxy; C$_{1-4}$ haloalkoxy; —C(═O)(C$_{1-4}$ alkyl); —C(═O)O(C$_{1-4}$ alkyl); —C(═O)OH; —C(═O)N(R$^p$)(R$^q$); —S(O)$_{1-2}$(N(R$^p$)(R$^q$)); —S(O)$_{1-2}$(C$_{1-4}$ alkyl); cyano; heteroaryl including from 5-10 ring atoms, wherein from 1-4 ring atoms are each independently selected from N, N(R$^f$), O, and S, wherein the heteroaryl is optionally substituted with from 1-3 R$^m$; phenyl optionally substituted with from 1-4 R$^m$; and C$_{3-6}$ cycloalkyl optionally substituted with from 1-4 independently selected R$^u$; and each occurrence of R$^t$ is independently selected from: H; C$_{1-4}$ alkyl; C$_{3-6}$ cycloalkyl; phenyl; —C(O)(C$_{1-4}$ alkyl); —C(O)O(C$_{1-4}$ alkyl); —CON(R$^p$)(R$^q$); —S(O)$_{1-2}$(N(R$^p$)(R$^q$)), —S(O)$_{1-2}$R$^h$; —OH; and C$_{1-4}$ alkoxy; wherein each C$_{1-4}$ alkyl is optionally substituted with from 1-2 independently selected R$^u$; each C$_{3-6}$ cycloalkyl is optionally substituted with from 1-4 independently selected R$^s$; and each phenyl is optionally substituted with from 1-2 independently selected R$^m$.

In some embodiments, it is provided that at least one of R$^3$ and R$^4$ is a substituent other than H.

In one aspect, compounds of Formula I, or a pharmaceutically acceptable salt thereof are featured:

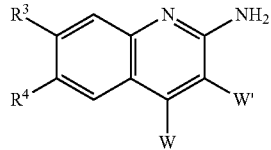

(I)

W' is $R^2$ or $Q'$-$R^2$;
Q' is NH, O, or S;
W is H, $R^2$, or Q-$R^2$
Q is $NR^1$, $CHR^1$, O, or S;
$R^1$ is:
(i) H
(ii) X—$R^5$, wherein X is an unbranched $C_{1-6}$ alkylene, and $R^5$ is hydrogen, —OH, $C_{1-4}$ alkoxy, —$C_{1-4}$ haloalkoxy, $CO_2R^a$, —CONR'R", cyano, or —$NR^bR^c$;
(iii) ($C_{1-3}$ alkylene)-aryl, wherein the aryl is optionally substituted with from 1-3 $R^d$; or
(iv) ($C_{1-3}$ alkylene)-heteroaryl including from 5-6 ring atoms, wherein from 1-4 ring atoms are each independently selected from N, $N(R^f)$, O, and S, wherein the heteroaryl is optionally substituted with from 1-3 $R^d$;
$R^2$ is:
(i) —Y—$R^6$, wherein
  Y is $C_{1-8}$ alkylene, which is optionally substituted with from 1-4 $R^e$; and
  $R^6$ is —OH, —O($C_{1-4}$ alkyl), —C(O)$R^a$, —$CO_2R^a$, —CONR'R", —$NR^bR^c$, cyano, aryl that is optionally substituted with from 1-3 independently selected $R^d$; or heteroaryl including from 5-6 ring atoms, wherein from 1-4 ring atoms are each independently selected from N, $N(R^f)$, O, and S, wherein the heteroaryl is optionally substituted with from 1-3 $R^d$;
OR
(ii) —C(O)—Y—$R^6$;
OR
(iii) —$R^6$;
OR
(iv) —$(Y^1)_n$—$Y^2$—$(Y^3)_p$—$R^{6'}$, wherein:
  each of n and p is independently 0 or 1;
  each of $Y^1$ and $Y^3$ is, independently, $C_{1-3}$ alkylene, which is optionally substituted with from 1-2 $R^e$,
  $Y^2$ is:
    (a) $C_{3-6}$ cycloalkylene optionally substituted with from 1-4 $R^g$,
    (b) $C_{6-10}$ arylene, optionally further substituted with from 1-4 $R^d$,
    (c) heteroarylene including from 5-10 ring atoms, wherein from 1-4 ring atoms are each independently selected from N, $N(R^f)$, O, and S, and which is optionally further substituted with from 1-4 $R^g$, or
    (d) heterocycloalkylene including from 3-10 ring atoms, wherein from 1-3 ring atoms are each independently selected from N, $N(R^f)$ and O, and wherein $Y^2$ is optionally further substituted with from 1-4 $R^g$, and
  $R^{6'}$ is H, —OH, —C(O)$R^a$, —$CO_2R^a$; —CONR'R", —$NR^bR^c$, cyano, or heteroaryl including from 5-6 ring atoms, wherein from 1-4 ring atoms are each independently selected from N, $N(R^f)$, O, and S, in some embodiments $R^{6'}$ cannot be H when $Y^2$ is $C_{3-6}$ cycloalkylene optionally substituted with from 1-4 $R^g$ and/or when $Y^2$ is $C_{6-10}$ arylene, optionally substituted with from 1-4 $R^d$,
OR
(v) —$Z^1$—$Z^2$—$Z^3$—$R^7$, wherein:
  $Z^1$ is $C_{1-3}$ alkylene, which is optionally substituted with from 1-6 F,
  $Z^2$ is —$N(R^f)$—, —O—, or —S—;
  $Z^3$ is $C_{2-5}$ alkylene, which is optionally substituted with from 1-6 F, and
  $R^7$ is —OH, —C(O)$R^a$, $CO_2R^a$; —CONR'R", —$NR^bR^c$, or heteroaryl including from 5-10 ring atoms, wherein from 1-4 ring atoms are each independently selected from N, $N(R^f)$, O, and S, wherein the heteroaryl is optionally substituted with from 1-3 $R^d$;
$R^3$ and $R^4$ are each independently selected from:
(i) hydrogen;
(ii) halo;
(iii) cyano;
(iv) —$CO_2R^a$;
(v) —CONR'R";
(vi) $C_{1-4}$ alkyl, optionally substituted with from 1-2 independently selected $R^e$;
(vii) $C_{1-4}$ haloalkyl;
(viii) $C_{1-4}$ alkoxy;
(ix) $C_{1-4}$ haloalkoxy;
(x) $Y^4$—($C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, $N(R^f)$, O, or S;
(xi) $Y^4$—($C_{1-3}$ alkylene)$_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, $N(R^f)$, O, or S;
(xiii) $Y^4$—($C_{1-3}$ alkylene)$_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S;
(xiv) —$N_3$;
(xv) —$CO_2H$;
(xvi) —OH;
(xvii) —$SO_{1-2}(R^h)$;
(xviii) —$NR^bR^c$;
(xvix) —$SO_{1-2}$(NR'R"); and
(xx) thioalkoxy;
$R^a$ is:
(i) $C_{1-8}$ alkyl optionally substituted with from 1-2 independently selected $R^e$;
(ii) —($C_{0-6}$ alkylene)-$C_{3-10}$ cycloalkyl, wherein the cycloalkyl is optionally substituted with from 1-4 independently selected $R^g$;
(iii) —($C_{0-6}$ alkylene)-heterocyclyl including from 3-10 ring atoms, wherein from 1-3 ring atoms are each independently selected from $N(R^f)$, O, and S, wherein the heterocyclyl is optionally substituted with from 1-4 independently selected $R^g$;
(iv) —($C_{0-6}$ alkylene)-($C_{6-10}$ aryl), wherein the aryl is optionally substituted with from 1-5 independently selected $R^d$; or (v) —($C_{0-6}$ alkylene)-heteroaryl including from 5-10 ring atoms, wherein from 1-4 ring atoms are each independently selected from N, N($R^f$), O, and S, wherein the heteroaryl is optionally substituted with from 1-3 independently selected $R^d$;

each occurrence of $R^b$ and $R^c$ is independently selected from: H; $R^a$; —C(O)($R^a$), —C(O)O($R^a$), —S(O)$_{1-2}$($R^h$), —C(O)NR'R", —S(O)$_{1-2}$(NR'R"), —OH, and $C_{1-4}$ alkoxy;

each occurrence of $R^d$ is independently selected from:
(i) halo;
(ii) cyano;
(iii) $C_{1-6}$ alkyl optionally substituted with from 1-2 independently selected $R^e$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl including from 3-10 ring atoms, wherein from 1-3 ring atoms are each independently selected from N($R^f$), O, and S, wherein the heterocyclyl is optionally substituted with from 1-4 independently selected $C_{1-4}$ alkyl;
(xi) —($C_{0-3}$ alkylene)-phenyl optionally substituted with from 1-3 $R^m$;
(xii) —($C_{0-3}$ alkylene)-heteroaryl including from 5-10 ring atoms, wherein from 1-4 ring atoms are each independently selected from N, N($R^f$), O, and S, wherein the heteroaryl is optionally substituted with from 1-3 $R^m$;
(xiii) —S(O)$_{1-2}$($R^h$); and
(xiv) —NR$^j$R$^k$;
(xv) —OH;
(xvi) —S(O)$_{1-2}$(NR'R");
(xvii) —$C_{1-4}$ thioalkoxy;
(xviii) —NO$_2$;
(xix) —N($R^n$)(C(=O)$C_{1-3}$ alkyl);
(xx) —C(=O)($C_{1-4}$ alkyl);
(xxi) —C(=O)O($C_{1-4}$ alkyl);
(xxii) —C(=O)OH, and
(xxiii) —C(=O)N(R')(R");

each occurrence of $R^e$ is independently selected from: —OH; F; —NR$^j$R$^k$; —N($R^n$)(C(=O)$C_{1-4}$ alkyl); —N($R^n$)(C(=O)O$C_{1-4}$ alkyl); $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R"); —S(O)$_{1-2}$(NR'R"); —S(O)$_{1-2}$($C_{1-4}$ alkyl); and cyano;

each occurrence of $R^f$ is independently selected from: H; $C_{1-4}$ alkyl; $C_{3-6}$ cycloalkyl; phenyl; —C(O)($C_{1-4}$ alkyl); —C(O)O($C_{1-4}$ alkyl); —CON(R')(R"); —S(O)$_{1-2}$(NR'R"); —S(O)$_{1-2}$$R^h$; —OH; and $C_{1-4}$ alkoxy; wherein each $C_{1-4}$ alkyl is optionally substituted with from 1-2 independently selected $R^e$; each $C_{3-6}$ cycloalkyl is optionally substituted with from 1-2 independently selected $R^g$; and each phenyl is optionally substituted with from 1-2 independently selected $R^d$;

each occurrence of $R^g$ is independently selected from: $C_{1-6}$ alkyl optionally substituted with from 1-2 independently selected $R^e$; $C_{1-4}$ haloalkyl; —OH; oxo; F; Cl; Br; —NR$^j$R$^k$; —N($R^n$)(C(=O)$C_{1-4}$ alkyl); $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R"); —S(O)$_{1-2}$(NR'R"); —S(O)$_{1-2}$($C_{1-4}$ alkyl); cyano; $C_{3-6}$ cycloalkyl optionally substituted with from 1-4 independently selected $C_{1-4}$ alkyl; heteroaryl including from 5-10 ring atoms, wherein from 1-4 ring atoms are each independently selected from N, N($R^f$), O, and S, wherein the heteroaryl is optionally substituted with from 1-3 $R^m$; and phenyl optionally substituted with from 1-4 $R^m$;

each occurrence of $R^h$ is independently selected from: $C_{1-6}$ alkyl, $C_{1-4}$ haloalkyl, $C_{1-4}$ alkoxy, $C_{1-4}$ haloalkoxy, phenyl optionally substituted with from 1-3 $R^m$, and heteroaryl including from 5-6 ring atoms, wherein from 1-4 ring atoms are each independently selected from N, N($R^f$), O, and S, wherein the heteroaryl is optionally substituted with from 1-3 $R^m$;

each occurrence of $R^j$ and $R^k$ is independently selected from: H and $C_{1-4}$ alkyl, which is optionally substituted with from 1-2 independently selected $R^u$, wherein each occurrence of $R^u$ is independently selected from: —OH, —N($R^p$)($R^q$), —N($R^n$)(C(=O)$C_{1-4}$ alkyl), —N($R^n$)(C(=O)O$C_{1-4}$ alkyl), $C_{1-4}$ alkoxy, $C_{1-4}$ haloalkoxy, —C(=O)($C_{1-4}$ alkyl); —C(=O)O($C_{1-4}$ alkyl); —C(=O)OH; —C(=O)N($R^p$)($R^q$), —S(O)$_{1-2}$($C_{1-4}$ alkyl); —S(O)$_{1-2}$(N($R^p$)($R^q$)), and cyano;

each occurrence of $R^m$ is independently selected from: $C_{1-4}$ alkyl; $C_{1-4}$ haloalkyl; —OH, F, Cl, Br, —N($R^j$)($R^k$), —N($R^n$)(C(=O)$C_{1-4}$ alkyl), —N($R^n$)(C(=O)O$C_{1-4}$ alkyl), $C_{1-4}$ alkoxy, $C_{1-4}$ haloalkoxy, —C(=O)($C_{1-4}$ alkyl); —C(=O)O($C_{1-4}$ alkyl); —C(=O)OH, —C(=O)N($R^p$)($R^q$), —S(O)$_{1-2}$($C_{1-4}$ alkyl); —S(O)$_{1-2}$(N($R^p$)($R^q$)), and cyano;

each occurrence of $R^n$, $R^p$, and $R^q$ is independently selected from: H and $C_{1-4}$ alkyl;

each occurrence of R' and R" is independently selected from: H and $C_{1-4}$ alkyl, which is optionally substituted with from 1-2 independently selected $R^u$; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $R^s$; and (b) from 0-3 ring heteroatoms (in addition to the nitrogen atom attached to R' and R"), which are each independently selected from N($R^t$), O, and S;

each occurrence of $R^s$ is independently selected from: $C_{1-6}$ alkyl optionally substituted with from 1-2 independently selected $R^u$; $C_{1-4}$ haloalkyl; —OH; oxo; F; Cl; Br; —NR$^j$R$^k$; —N($R^n$)(C(=O)$C_{1-4}$ alkyl); $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N($R^p$)($R^q$); —S(O)$_{1-2}$(N($R^p$)($R^q$)); —S(O)$_{1-2}$($C_{1-4}$ alkyl); cyano; heteroaryl including from 5-10 ring atoms, wherein from 1-4 ring atoms are each independently selected from N, N($R^f$), O, and S, wherein the heteroaryl is optionally substituted with from 1-3 $R^m$; phenyl optionally substituted with from 1-4 $R^m$; and $C_{3-6}$ cycloalkyl optionally substituted with from 1-4 independently selected $R^u$; and each occurrence of $R^t$ is independently selected from: H; $C_{1-4}$ alkyl; $C_{3-6}$ cycloalkyl; phenyl; —C(O)($C_{1-4}$ alkyl); —C(O)O($C_{1-4}$ alkyl); —CON($R^p$)($R^q$); —S(O)$_{1-2}$(N($R^p$)($R^q$)), —S(O)$_{1-2}$$R^h$; —OH; and $C_{1-4}$ alkoxy; wherein each $C_{1-4}$ alkyl is optionally substituted with from 1-2 independently selected $R^u$; each $C_{3-6}$ cycloalkyl is optionally substituted with from 1-4 independently selected $R^s$; and each phenyl is optionally substituted with from 1-2 independently selected $R^m$.

In one aspect, compounds of Formula I, or a pharmaceutically acceptable salt thereof are featured:

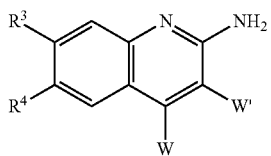

(I)

W' is $R^2$ or $Q'$-$R^2$
$Q'$ is NH, O, or S;
W is H, $R^2$, or Q-$R^2$
Q is $NR^1$, $CHR^1$, O, or S;
$R^1$ is independently H or X—$R^5$; wherein:
  X is selected from: $C_{1-10}$ alkylene, $C_{2-10}$ alkenylene, and $C_{2-10}$ alkynylene, wherein each of which is optionally interrupted by one O or S and/or each of which is optionally substituted with from 1-4 $R^e$;
$R^5$ is selected from:
  (i) hydrogen;
  (ii) —OH;
  (iii) $C_{1-4}$ alkoxy;
  (iv) $C_{1-4}$ haloalkoxy;
  (v) —$CO_2R^a$;
  (vi) —CONR'R";
  (vi) cyano;
  (vii) —$NR^bR^c$;
  (viii) $Q^1$-aryl that is optionally substituted with from 1-3 $R^d$;
  (ix) $Q^1$-heteroaryl including from 5-6 ring atoms, wherein from 1-4 ring atoms are each independently selected from N, $N(R^f)$, O, and S, wherein the heteroaryl is optionally substituted with from 1-3 $R^d$;
  (x) $Q^1$-$C_{3-10}$ cycloalkyl that is optionally substituted with from 1-4 $R^g$,
  (xi) $Q^1$-heterocyclyl including from 3-10 ring atoms, wherein from 1-3 ring atoms are each independently selected from N, $N(R^f)$ and O, wherein the heterocyclyl is optionally substituted with from 1-4 $R^g$,
  (xii) $C_{1-4}$ thioalkoxy;
  (xiii) —SH
  (xiv) —$N_3$;
  (xv) —$CO_2H$;
  (xvi) —$C(O)R^a$; and
  (xvii) —$SO_{1-2}(R^h)$
$Q^1$ is independently selected from: a bond, O, —$O(C_{1-3}$ alkylene)-, S, and —$S(C_{1-3}$ alkylene)-;
$R^2$ is independently selected from: H, $R^6$, and -$Q^2$-Y—$R^6$;
$Q^2$ is selected from: a bond, C(O), $N(R^f)$, O, and S;
Y is selected from: $C_{1-10}$ alkylene, $C_{2-10}$ alkenylene, and $C_{2-10}$ alkynylene, each of which is optionally substituted with from 1-4 $R^e$ and/or each of which is optionally interrupted by one or more of the following:
  (i) O;
  (ii) S;
  (iii) $N(R^f)$;
  (iv) $C_{3-6}$ cycloalkylene optionally substituted with from 1-4 $R^g$,
  (v) $C_{6-10}$ arylene, optionally further substituted with from 1-4 $R^d$,
  (vi) heteroarylene including from 5-10 ring atoms, wherein from 1-4 ring atoms are each independently selected from N, $N(R^f)$, O, and S, and which is optionally substituted with from 1-4 $R^g$, or
  (vii) heterocycloalkylene including from 3-10 ring atoms, wherein from 1-3 ring atoms are each independently selected from N, $N(R^f)$, O and $S(O)_{1-2}$, and which is optionally further substituted with from 1-4 $R^g$, and
$R^6$ is independently selected from:
  (i) hydrogen;
  (ii) —OH;
  (iii) $C_{1-4}$ alkoxy;
  (iv) $C_{1-4}$ haloalkoxy;
  (v) —$CO_2R^a$;
  (vi) —CONR'R";
  (vi) cyano;
  (vii) —$NR^bR^c$;
  (viii) $Q^1$-aryl that is optionally substituted with from 1-3 $R^d$;
  (ix) $Q^1$-heteroaryl including from 5-10 ring atoms, wherein from 1-4 ring atoms are each independently selected from N, $N(R^f)$, O, and S, wherein the heteroaryl is optionally substituted with from 1-3 $R^d$;
  (x) $Q^1$-$C_{3-10}$ cycloalkyl that is optionally substituted with from 1-4 $R^g$,
  (xi) $Q^1$-heterocyclyl including from 3-10 ring atoms, wherein from 1-3 ring atoms are each independently selected from N, $N(R^f)$ and O, wherein the heterocyclyl is optionally substituted with from 1-4 $R^g$,
  (xii) $C_{1-4}$ thioalkoxy;
  (xiii) —SH
  (xiv) —$N_3$;
  (xv) —$CO_2H$;
  (xvi) —$C(O)R^a$; and
  (xvii) —$SO_{1-2}(R^h)$;
$R^3$ and $R^4$ are each independently selected from:
  (i) hydrogen;
  (ii) halo;
  (iii) cyano;
  (iv) —$CO_2R^a$;
  (v) —CONR'R";
  (vi) $C_{1-4}$ alkyl, optionally substituted with from 1-2 independently selected $R^e$;
  (vii) $C_{1-4}$ haloalkyl;
  (viii) $C_{1-4}$ alkoxy;
  (ix) $C_{1-4}$ haloalkoxy;
  (x) $Y^4$—$(C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, $N(R^f)$, O, or S;
  (xi) $Y^4$—$(C_{1-3}$ alkylene)$_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
  (xii) $Y^4$—$(C_{1-3}$ alkylene)$_y$-$C_{6-10}$ aryl optionally substituted with from 1-4 $R^d$, wherein y is 0 or 1; and $Y^4$ is a bond, $N(R^f)$, O, or S;
  (xiii) $Y^4$—$(C_{1-3}$ alkylene)$_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S;
  (xiv) —$N_3$;
  (xv) —$CO_2H$;
  (xvi) —OH;
  (xvii) —$SO_{1-2}(R^h)$;
  (xviii) —$NR^bR^c$;

(xvix) —$SO_{1-2}$(NR'R''); and
(xx) thioalkoxy;
$R^a$ is:
  (i) $C_{1-8}$ alkyl optionally substituted with from 1-2 independently selected R;
  (ii) —($C_{0-6}$ alkylene)-$C_{3-10}$ cycloalkyl, wherein the cycloalkyl is optionally substituted with from 1-4 independently selected $R^g$;
  (iii) —($C_{0-6}$ alkylene)-heterocyclyl including from 3-10 ring atoms, wherein from 1-3 ring atoms are each independently selected from N($R^f$), O, and S, wherein the heterocyclyl is optionally substituted with from 1-4 independently selected $R^g$;
  (iv) —($C_{0-6}$ alkylene)-($C_{6-10}$ aryl), wherein the aryl is optionally substituted with from 1-5 independently selected $R^d$; or
  (v) —($C_{0-6}$ alkylene)-heteroaryl including from 5-10 ring atoms, wherein from 1-4 ring atoms are each independently selected from N, N($R^f$), O, and S, wherein the heteroaryl is optionally substituted with from 1-3 independently selected $R^d$;
each occurrence of $R^b$ and $R^c$ is independently selected from: H; $R^a$; —C(O)($R^a$), —C(O)O($R^a$), —$S(O)_{1-2}$($R^h$), —C(O)NR'R'', —$S(O)_{1-2}$(NR'R''), —OH, and $C_{1-4}$ alkoxy;
each occurrence of $R^d$ is independently selected from:
(i) halo;
(ii) cyano;
(iii) $C_{1-6}$ alkyl optionally substituted with from 1-2 independently selected $R^e$;
(iv) $C_{2-6}$ alkenyl;
(v) $C_{2-6}$ alkynyl;
(vi) $C_{1-4}$ haloalkyl;
(vii) $C_{1-4}$ alkoxy;
(viii) $C_{1-4}$ haloalkoxy;
(ix) —($C_{0-3}$ alkylene)-$C_{3-6}$ cycloalkyl optionally substituted with from 1-4 independently selected $C_{1-4}$ alkyl;
(x) —($C_{0-3}$ alkylene)-heterocyclyl including from 3-10 ring atoms, wherein from 1-3 ring atoms are each independently selected from N($R^f$), O, and S, wherein the heterocyclyl is optionally substituted with from 1-4 independently selected $C_{1-4}$ alkyl;
(xi) —($C_{0-3}$ alkylene)-phenyl optionally substituted with from 1-3 $R^m$;
(xii) —($C_{0-3}$ alkylene)-heteroaryl including from 5-10 ring atoms, wherein from 1-4 ring atoms are each independently selected from N, N($R^f$), O, and S, wherein the heteroaryl is optionally substituted with from 1-3 $R^m$;
(xiii) —$S(O)_{1-2}$($R^h$); and
(xiv) —$NR^jR^k$;
(xv) —OH;
(xvi) —$S(O)_{1-2}$(NR'R'');
(xvii) —$C_{1-4}$ thioalkoxy;
(xviii) —$NO_2$;
(xix) —N($R^n$)(C(=O)$C_{1-3}$ alkyl);
(xx) —C(=O)($C_{1-4}$ alkyl);
(xxi) —C(=O)O($C_{1-4}$ alkyl);
(xxii) —C(=O)OH, and
(xxiii) —C(=O)N(R')(R'');
each occurrence of $R^e$ is independently selected from:
  —OH; F; —$NR^jR^k$; —N($R^n$)(C(=O)$C_{1-4}$ alkyl); —N($R^n$)(C(=O)O$C_{1-4}$ alkyl); $C_{1-4}$ alkoxy; $C_{1-4}$ haloalkoxy; —C(=O)O($C_{1-4}$ alkyl); —C(=O)($C_{1-4}$ alkyl); —C(=O)OH; —CON(R')(R''); —$S(O)_{1-2}$(NR'R''); —$S(O)_{1-2}$(C-4 alkyl); and cyano;

each occurrence of $R^f$ is independently selected from: H; $C_{1-4}$ alkyl; $C_{3-6}$ cycloalkyl; phenyl; —C(O)($C_{1-4}$ alkyl); —C(O)O($C_{1-4}$ alkyl); —CON(R')(R''); —$S(O)_{1-2}$(NR'R''); —$S(O)_{1-2}R^h$; —OH; and $C_{1-4}$ alkoxy; wherein each $C_{1-4}$ alkyl is optionally substituted with from 1-2 independently selected $R^e$; each $C_{3-6}$ cycloalkyl is optionally substituted with from 1-2 independently selected $R^g$; and each phenyl is optionally substituted with from 1-2 independently selected $R^d$.
each occurrence of $R^g$ is independently selected from: $C_{1-6}$ alkyl optionally substituted with from 1-2 independently selected $R^e$; $C_{1-4}$ haloalkyl; —OH; oxo; F; Cl; Br; —$NR^jR^k$; —N($R^n$)(C(=O)$C_{1-4}$ alkyl); $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N(R')(R''); —$S(O)_{1-2}$(NR'R''); —$S(O)_{1-2}$($C_{1-4}$ alkyl); cyano; $C_{3-6}$ cycloalkyl optionally substituted with from 1-4 independently selected $C_{1-4}$ alkyl; heteroaryl including from 5-10 ring atoms, wherein from 1-4 ring atoms are each independently selected from N, N($R^f$), O, and S, wherein the heteroaryl is optionally substituted with from 1-3 $R^m$; and phenyl optionally substituted with from 1-4 $R^m$;
each occurrence of $R^h$ is independently selected from: $C_{1-4}$ alkyl, $C_{1-4}$ haloalkyl, $C_{1-4}$ alkoxy, $C_{1-4}$ haloalkoxy, phenyl optionally substituted with from 1-3 $R^m$, and heteroaryl including from 5-6 ring atoms, wherein from 1-4 ring atoms are each independently selected from N, N($R^f$), O, and S, wherein the heteroaryl is optionally substituted with from 1-3 $R^m$;
each occurrence of $R^j$ and $R^k$ is independently selected from: H and $C_{1-4}$ alkyl, which is optionally substituted with from 1-2 independently selected $R^u$, wherein each occurrence of $R^u$ is independently selected from: —OH, —N($R^p$)($R^q$), —N($R^n$)(C(=O)$C_{1-4}$ alkyl), —N($R^n$)(C(=O)O$C_{1-4}$ alkyl), $C_{1-4}$ alkoxy, $C_{1-4}$ haloalkoxy, —C(=O)($C_{1-4}$ alkyl); —C(=O)O($C_{1-4}$ alkyl); —C(=O)OH; —C(=O)N($R^p$)($R^q$), —$S(O)_{1-2}$($C_{1-4}$ alkyl); —$S(O)_{1-2}$(N($R^p$)($R^q$)), and cyano;
each occurrence of $R^m$ is independently selected from: $C_{1-4}$ alkyl; $C_{1-4}$ haloalkyl; —OH, F, Cl, Br, —N($R^j$)($R^k$), —N($R^n$)(C(=O)$C_{1-4}$ alkyl), —N($R^n$)(C(=O)O$C_{1-4}$ alkyl), $C_{1-4}$ alkoxy, $C_{1-4}$ haloalkoxy, —C(=O)($C_{1-4}$ alkyl); —C(=O)O($C_{1-4}$ alkyl); —C(=O)OH, —C(=O)N($R^p$)($R^q$), —$S(O)_{1-2}$($C_{1-4}$ alkyl); —$S(O)_{1-2}$(N($R^p$)($R^q$)), and cyano;
each occurrence of $R^n$, $R^p$, and $R^q$ is independently selected from: H and $C_{1-4}$ alkyl;
each occurrence of R' and R'' is independently selected from: H and $C_{1-4}$ alkyl, which is optionally substituted with from 1-2 independently selected $R^u$; or R' and R'' together with the nitrogen atom to which each is attached forms a ring including from 3-8 ring atoms, wherein the ring includes: (a) from 1-7 ring carbon atoms, each of which is substituted with from 1-2 substituents independently selected from H and $R^s$; and (b) from 0-3 ring heteroatoms (in addition to the nitrogen atom attached to R' and R''), which are each independently selected from N($R^r$), O, and S;
each occurrence of $R^s$ is independently selected from: $C_{1-6}$ alkyl optionally substituted with from 1-2 independently selected $R^u$; $C_{1-4}$ haloalkyl; —OH; oxo; F; Cl; Br; —$NR^jR^k$; —N($R^n$)(C(=O)$C_{1-4}$ alkyl); $C_{1-4}$ alkoxy; $C_{1-4}$ haloalkoxy; —C(=O)($C_{1-4}$ alkyl); —C(=O)O($C_{1-4}$ alkyl); —C(=O)OH; —C(=O)N($R^p$)($R^q$); —$S(O)_{1-2}$(N($R^p$)($R^q$)); —$S(O)_{1-2}$($C_{1-4}$ alkyl); cyano; heteroaryl including from 5-10 ring atoms, wherein from 1-4 ring atoms are each independently selected from N, N(R$^f$), O, and S, wherein the heteroaryl is optionally substituted with from 1-3 R$^m$; phenyl optionally substituted with from 1-4 R$^m$; and C$_{3-6}$ cycloalkyl optionally substituted with from 1-4 independently selected R$^u$; and each occurrence of R$^t$ is independently selected from: H; C$_{1-4}$ alkyl; C$_{3-6}$ cycloalkyl; phenyl; —C(O)(C$_{1-4}$ alkyl); —C(O)O(C$_{1-4}$ alkyl); —CON(R$^p$)(R$^q$); —S(O)$_{1-2}$(N(R$^p$)(R$^q$)), —S(O)$_{1-2}$R$^h$; —OH; and C$_{1-4}$ alkoxy; wherein each C$_{1-4}$ alkyl is optionally substituted with from 1-2 independently selected R$^u$; each C$_{3-6}$ cycloalkyl is optionally substituted with from 1-4 independently selected R$^s$; and each phenyl is optionally substituted with from 1-2 independently selected R$^m$.

In another aspect, compounds of Formula (I), or a pharmaceutically acceptable salt thereof, wherein:

W' is R$^2$ or Q'-R$^2$;

Q' is NH, O, or S;

W is H, R$^2$, or Q-R$^2$;

Q is NR$^1$, CHR$^1$, O, or S;

R$^1$ is independently H or C$_{1-4}$ alkyl;

R$^2$ is independently R$^6$ or -Q$^2$-Y—R$^6$;

Q$^2$ is a bond or C(O);

Y is independently C$_{1-10}$ alkylene which is optionally substituted with from 1-4 R$^e$ and/or is optionally interrupted by one or more of the following:
 (i) O;
 (ii) N(R$^f$);
 (iii) C$_{3-6}$ cycloalkylene optionally substituted with from 1 to 2 R$^g$, (iv) C$_{6-10}$ arylene, optionally further substituted with from 1 to 2 R$^d$, (v) heteroarylene including from 5 to 6 ring atoms, wherein from 1 to 4 ring atoms are each independently selected from N, N(R$^f$), O, and S, and which is optionally substituted with from 1 to 2 R$^g$, or
 (vi) heterocycloalkylene including from 5 to 6 ring atoms, wherein from 1 to 2 ring atoms are each independently selected from N, N(R$^f$), O and S(O)$_{1-2}$, and which is optionally further substituted with from 1 to 2 R$^g$, R$^6$ is independently selected from: H, —OH, C$_{1-4}$ alkoxy, C$_{1-4}$ haloalkoxy, —C(O)R$^a$, —CO$_2$R$^a$, —CONR'R", —NR$^b$R$^c$, cyano; phenyl that is optionally substituted with from 1-3 independently selected R$^d$; and heteroaryl including from 5 to 10 ring atoms, wherein from 1 to 4 ring atoms are each independently selected from N, N(R$^f$), O, and S, wherein the heteroaryl is optionally substituted with from 1-3 R$^d$;

R$^3$ is independently —(C$_{0-3}$ alkylene)-heteroaryl including 5 ring atoms, wherein from 1 to 4 ring atoms are each independently selected from N, NH, N(C$_{1-4}$ alkyl), O, and S, wherein the heteroaryl is optionally substituted with from 1-3 R$^d$;

R$^4$ is independently selected from: hydrogen; halo; cyano; OH, —CO$_2$H; —CO$_2$R$^a$; —CONR'R"; C$_{1-4}$ haloalkyl; C$_{1-4}$ alkoxy; C$_{1-4}$ haloalkoxy; NR$^b$R$^c$; and C$_{1-4}$ alkyl optionally substituted with from 1-2 independently selected R$^e$;

R$^a$ is:
 (i) C$_{1-8}$ alkyl optionally substituted with from 1-2 independently selected R$^e$;
 (ii) —(C$_{0-3}$ alkylene)-C$_{3-10}$ cycloalkyl, wherein the cycloalkyl is optionally substituted with from 1-4 independently selected R$^g$;
 (iii) —(C$_{0-3}$ alkylene)-heterocyclyl including from 3-10 ring atoms, wherein from 1-3 ring atoms are each independently selected from N(R$^f$), O, and S, wherein the heterocyclyl is optionally substituted with from 1-4 independently selected R$^g$;
 (iv) —(C$_{0-3}$ alkylene)-(C$_{6-10}$ aryl), wherein the aryl is optionally substituted with from 1-5 independently selected R$^d$; or
 (v) —(C$_{0-3}$ alkylene)-heteroaryl including from 5-10 ring atoms, wherein from 1-4 ring atoms are each independently selected from N, N(R$^f$), O, and S, wherein the heteroaryl is optionally substituted with from 1-3 independently selected R$^d$;

each occurrence of R$^b$ and R$^c$ is independently selected from: H; R$^a$; —C(O)(R$^a$), —C(O)O(R$^a$), —S(O)$_{1-2}$(R$^h$), —C(O)NR'R", —S(O)$_{1-2}$(NR'R"), —OH, and C$_{1-4}$ alkoxy;

each occurrence of R$^d$ is independently selected from:
(i) halo;
(ii) cyano;
(iii) C$_{1-6}$ alkyl optionally substituted with from 1-2 independently selected R$^e$;
(iv) C$_{2-6}$ alkenyl;
(v) C$_{2-6}$ alkynyl;
(vi) C$_{1-4}$ haloalkyl;
(vii) C$_{1-4}$ alkoxy;
(viii) C$_{1-4}$ haloalkoxy;
(ix) —(C$_{0-3}$ alkylene)-C$_{3-6}$ cycloalkyl optionally substituted with from 1-4 independently selected C$_{1-4}$ alkyl;
(x) —(C$_{0-3}$ alkylene)-heterocyclyl including from 3-10 ring atoms, wherein from 1-3 ring atoms are each independently selected from N(R$^f$), O, and S, wherein the heterocyclyl is optionally substituted with from 1-4 independently selected C$_{1-4}$ alkyl;
(xi) —(C$_{0-3}$ alkylene)-phenyl optionally substituted with from 1-3 R$^m$;
(xii) —(C$_{0-3}$ alkylene)-heteroaryl including from 5-10 ring atoms, wherein from 1-4 ring atoms are each independently selected from N, N(R$^f$), O, and S, wherein the heteroaryl is optionally substituted with from 1-3 R$^m$;
(xiii) —NR$^j$R$^k$;
(xv) —OH;
(xvii) —C(=O)(C$_{1-4}$ alkyl);
(xviii) —C(=O)O(C$_{1-4}$ alkyl);
(xix) —C(=O)OH, and
(xx) —C(=O)N(R')(R");

each occurrence of R$^e$ is independently selected from: —OH; F; C$_{1-4}$ alkoxy; C$_{1-4}$ haloalkoxy; and cyano;

each occurrence of R$^f$ is independently selected from: H; C$_{1-4}$ alkyl; C$_{3-6}$ cycloalkyl; phenyl; and —C(O)(C$_{1-4}$ alkyl);

each occurrence of R$^g$ is independently selected from: C$_{1-6}$ alkyl optionally substituted with from 1-2 independently selected R$^e$; C$_{1-4}$ haloalkyl; —OH; oxo; F; Cl; Br; —NR$^j$R$^k$; C$_{1-4}$ alkoxy; C$_{1-4}$ haloalkoxy; —C(=O)(C$_{1-4}$ alkyl); —C(=O)O(C$_{1-4}$ alkyl); —C(=O)OH; —C(=O)N(R')(R"); —S(O)$_{1-2}$(NR'R"); —S(O)$_{1-2}$(C$_{1-4}$ alkyl); cyano; C$_{3-6}$ cycloalkyl optionally substituted with from 1-4 independently selected C$_{1-4}$ alkyl; heteroaryl including from 5-10 ring atoms, wherein from 1-4 ring atoms are each independently selected from N, N(R$^f$), O, and S, wherein the heteroaryl is optionally substituted with from 1-3 R$^m$; and phenyl optionally substituted with from 1-4 R$^m$;

each occurrence of R$^j$ and R$^k$ is independently H or C$_{1-4}$ alkyl;

each occurrence of $R^m$ is independently selected from: $C_{1-4}$ alkyl; $C_{1-4}$ haloalkyl; —OH, F, Cl, Br, —N($R^j$)($R^k$), $C_{1-4}$ alkoxy, $C_{1-4}$ haloalkoxy, and cyano;

each occurrence of R' and R" is independently selected from: H and $C_{1-4}$ alkyl; or R' and R" together with the nitrogen atom to which each is attached forms a ring including from 3-8 ring atoms, wherein the ring includes: (a) from 1-7 ring carbon atoms, each of which is substituted with from 1-2 substituents independently selected from H and $R^s$; and (b) from 0-3 ring heteroatoms (in addition to the nitrogen atom attached to R' and R"), which are each independently selected from NH, N($C_{1-4}$ alkyl), O, and S; and $R^s$ is independently selected from: $C_{1-6}$ alkyl; $C_{1-4}$ haloalkyl; —OH; oxo; F; Cl; Br; —NR$^j$R$^k$; $C_{1-4}$ alkoxy; $C_{1-4}$ haloalkoxy; and cyano.

In another aspect, compounds of Formula (I), or a pharmaceutically acceptable salt thereof, wherein:

W' is independently $R^6$ or -$Q^2$-Y—$R^6$;

W is independently H, $R^6$, -$Q^2$-Y—$R^6$, or -Q-$Q^2$-Y—$R^6$;

Q is independently selected from NH, N($C_{1-4}$ alkyl), O, and $CH_2$;

$Q^2$ is independently a bond or C(O);

Y is independently $C_{1-8}$ alkylene, which is optionally substituted with from 1-2 $R^e$ and/or is optionally interrupted by one or more of the following:
 (i) O;
 (ii) N($R^f$);
 (iii) $C_{3-6}$ cycloalkylene optionally substituted with from 1 to 2 $R^g$;
 (iv) phenylene optionally further substituted with from 1 to 2 $R^d$;
 (v) heteroarylene including from 5 to 6 ring atoms, wherein from 1 to 4 ring atoms are each independently selected from N, N($R^f$), O, and S, and the heteroarylene is optionally substituted with from 1 to 2 $R^g$; or
 (vi) heterocycloalkylene including from 3 to 7 ring atoms, wherein from 1 to 2 ring atoms are each independently selected from N, N($R^f$), O and S(O)$_{1-2}$, and the heterocycloalkylene is optionally further substituted with from 1 to 2 $R^g$;

$R^3$ is independently heteroaryl including 5 ring atoms, wherein from 1 to 4 ring atoms are each independently selected from N, NH, N($C_{1-4}$ alkyl), O, and S, wherein the heteroaryl is optionally substituted with from 1-3 $R^d$;

$R^4$ is independently selected from: H, halo, $C_{1-4}$ alkyl, $C_{1-4}$ haloalkyl; $C_{1-4}$ alkoxy; and $C_{1-4}$ haloalkoxy;

$R^6$ is independently selected from: H, OH, CN, $C_{1-4}$ alkoxy, OBn, —NR$^b$R$^c$, —NR$^b$COR$^a$, —NHC(O)O($C_{1-4}$ alkyl), —CONR'R", —NR$^b$C(O)NH($C_{1-4}$ alkyl), —NR$^b$C(O)N($C_{1-4}$ alkyl)$_2$, —NHS(O)$_2$($C_{1-4}$ alkyl), —S(O)$_2$($C_{1-4}$ alkyl); heterocyclyl including from 3-10 ring atoms, wherein from 1-3 ring atoms are each independently selected from N, N($R^f$) and O, wherein the heterocyclyl is optionally substituted with from 1-4 $R^g$; phenyl optionally substituted with from 1-3 $R^d$; and heteroaryl including from 5 to 10 ring atoms, wherein from 1 to 4 ring atoms are each independently selected from N, N($R^f$), O, and S, wherein the heteroaryl is optionally substituted with from 1-3 $R^d$;

$R^a$ is independently selected from: $C_{1-4}$ alkyl, phenyl substituted with 0 to 2 $R^d$, and heteroaryl including from 5 to 6 ring atoms, wherein from 1 to 4 ring atoms are each independently selected from N, N($R^f$), O, and S, wherein the heteroaryl is substituted 0 to 2 $R^d$;

$R^b$ is independently H or $C_{1-4}$ alkyl;

$R^c$ is independently H or $C_{1-4}$ alkyl;

$R^d$ is independently halo, $C_{1-4}$ alkoxy, —C(O)O($C_{1-4}$ alkyl), or $C_{1-4}$ alkyl substituted with from 0 to 2 $R^e$;

$R^e$ is independently F or OH;

$R^f$ is independently H, $C_{1-4}$ alkyl, —C(O)O($C_{1-4}$ alkyl), or —C(O)O($C_{1-4}$ alkyl);

$R^g$ is independently selected from: $C_{1-4}$ alkyl, $C_{1-4}$ haloalkyl, —OH, oxo, F, Cl, $C_{1-4}$ alkoxy, $C_{1-4}$ haloalkoxy, and N($C_{1-4}$ alkyl)$_2$;

each occurrence of R' and R" is independently selected from: H and $C_{1-4}$ alkyl; or R' and R" together with the nitrogen atom to which each is attached forms a ring including from 5 to 6 ring atoms, wherein the ring includes: (a) from 3 to 5 ring carbon atoms, each of which is substituted with from 1 to 2 substituents independently selected from H and $R^s$; and (b) from 0 to 2 ring heteroatoms (in addition to the nitrogen atom attached to R' and R"), which are each independently selected from NH, N($C_{1-4}$ alkyl), O, and S; and $R^s$ is independently selected from: $C_{1-4}$ alkyl, $C_{1-4}$ haloalkyl, —OH; oxo, F, Cl, $C_{1-4}$ alkoxy, $C_{1-4}$ haloalkoxy, and cyano.

In another aspect, compounds of Formula (I), or a pharmaceutically acceptable salt thereof, wherein:

W' is independently $R^6$ or -$Q^2$-Y—$R^6$;

W is independently H or -Q-$Q^2$-Y—R;

Q is independently selected from NH, N($C_{1-4}$ alkyl), O, and $CH_2$;

$Q^2$ is independently a bond or C(O);

Y is independently $C_{1-8}$ alkylene, which is optionally substituted with from 1-2 $R^e$ and/or is optionally interrupted by one or more of the following:
 (i) O;
 (ii) N($R^f$);
 (iii) $C_{3-6}$ cycloalkylene optionally substituted with from 1 to 2 $R^g$;
 (iv) phenylene optionally further substituted with from 1 to 2 $R^d$;
 (v) heteroarylene including from 5 to 6 ring atoms, wherein from 1 to 4 ring atoms are each independently selected from N, N($R^f$), O, and S, and the heteroarylene is optionally substituted with from 1 to 2 $R^g$; or
 (vi) heterocycloalkylene including from 5 to 6 ring atoms, wherein from 1 to 2 ring atoms are each independently selected from N, N($R^f$), O and S(O)$_{1-2}$, and the heterocycloalkylene is optionally further substituted with from 1 to 2 $R^g$;

$R^3$ is independently heteroaryl including 5 ring atoms, wherein from 1 to 4 ring atoms are each independently selected from N, NH, N($C_{1-4}$ alkyl), O, and S, wherein the heteroaryl is optionally substituted with from 1-3 $R^d$;

$R^4$ is independently selected from: H, halo, $C_{1-4}$ alkyl, $C_{1-4}$ haloalkyl; $C_{1-4}$ alkoxy; and $C_{1-4}$ haloalkoxy;

$R^6$ is independently selected from: H, OH, $C_{1-4}$ alkoxy, OBn, —NR$^b$R$^c$, —NR$^b$COR$^a$, —NHC(O)O($C_{1-4}$ alkyl), —CONR'R", —NR$^b$C(O)NH($C_{1-4}$ alkyl), —NR$^b$C(O)N($C_{1-4}$ alkyl)$_2$, —NHS(O)$_2$($C_{1-4}$ alkyl), —S(O)$_2$($C_{1-4}$ alkyl), and heteroaryl including from 5 to 10 ring atoms, wherein from 1 to 4 ring atoms are each independently selected from N, N($R^f$), O, and S, wherein the heteroaryl is optionally substituted with from 1-3 $R^d$;

$R^a$ is independently selected from: $C_{1-4}$ alkyl, phenyl substituted with 0 to 2 $R^d$, and heteroaryl including from 5 to 6 ring atoms, wherein from 1 to 4 ring atoms are each independently selected from N, N(R$^f$), O, and S, wherein the heteroaryl is substituted 0 to 2 R$^d$;

R$^b$ is independently H or C$_{1-4}$ alkyl;

R$^c$ is independently H or C$_{1-4}$ alkyl;

R$^d$ is independently C$_{1-4}$ alkoxy or C$_{1-4}$ alkyl substituted with from 0 to 2 R$^e$;

R$^e$ is independently F or OH;

R$^f$ is independently H or C$_{1-4}$ alkyl;

R$^g$ is independently selected from: C$_{1-4}$ alkyl, C$_{1-4}$ haloalkyl, —OH, oxo, F, Cl, C$_{1-4}$ alkoxy, C$_{1-4}$ haloalkoxy, and N(C$_{1-4}$ alkyl)$_2$;

each occurrence of R' and R'' is independently selected from: H and C$_{1-4}$ alkyl; or R' and R'' together with the nitrogen atom to which each is attached forms a ring including from 5 to 6 ring atoms, wherein the ring includes: (a) from 3 to 5 ring carbon atoms, each of which is substituted with from 1 to 2 substituents independently selected from H and R$^s$; and (b) from 0 to 2 ring heteroatoms (in addition to the nitrogen atom attached to R' and R''), which are each independently selected from NH, N(C$_{1-4}$ alkyl), O, and S; and R$^s$ is independently selected from: C$_{1-4}$ alkyl, C$_{1-4}$ haloalkyl, —OH; oxo, F, Cl, C$_{1-4}$ alkoxy, C$_{1-4}$ haloalkoxy, and cyano.

In some embodiments, it is provided that at least one of W' and W is a substituent other than H.

In another aspect, compounds of Formula (I), or a pharmaceutically acceptable salt thereof, wherein:

W' is H;

W is independently -Q-Y—R$^6$,

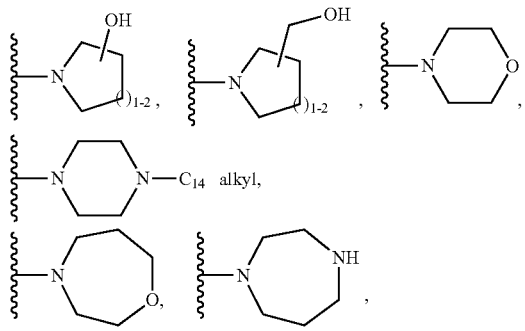

or heteroaryl including from 5 to 6 ring atoms, wherein from 1 to 4 ring atoms are each independently selected from N, NH, N(R$^f$), O, and S, wherein the heteroaryl is optionally substituted with from 1-2 R$^d$;

Q is independently selected from NH, N(C$_{1-4}$ alkyl), O, and CH$_2$;

Y is C$_{1-6}$ alkylene, which is optionally substituted with from 1-2 R$^e$ and/or is optionally interrupted by one or more of the following:

(i) O;

(ii) N(R$^f$);

(iii) C$_{3-6}$ cycloalkylene optionally substituted with from 1 to 2 R$^g$; or (iv) heterocycloalkylene including from 5 to 6 ring atoms, wherein from 1 to 2 ring atoms are each independently selected from N, N(R$^f$), O and S(O)$_{1-2}$, and the heterocycloalkylene is optionally further substituted with from 1 to 2 R$^g$, R$^3$ is independently pyrazolyl, thienyl or isothiazolyl;

R$^4$ is independently H or F;

R$^6$ is independently selected from: H, OH, CN, C$_{1-4}$ alkoxy, phenyl, —NR$^b$R$^c$, —NR$^b$COR$^a$, —NHC(O)O (C$_{1-4}$ alkyl), —C(O)NH(C$_{1-4}$ alkyl), —C(O)N(C$_{1-4}$ alkyl)$_2$, —NR$^b$C(O)NH(C$_{1-4}$ alkyl), —NR$^b$C(O)N (C$_{1-4}$ alkyl)$_2$, —S(O)$_2$(C$_{1-4}$ alkyl), —NHS(O)$_2$(C$_{1-4}$ alkyl),

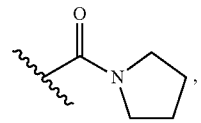

—CO-morpholinyl, phenyl, and heteroaryl including from 5 to 6 ring atoms, wherein from 1 to 3 ring atoms are each independently selected from N, N(R$^f$), O, and S, wherein said phenyl and heteroaryl are optionally substituted with from 1-2 R$^d$;

R$^a$ is independently selected from: C$_{1-4}$ alkyl, phenyl, and heteroaryl including from 5 to 6 ring atoms, wherein from 1 to 4 ring atoms are each independently selected from N, N(R$^f$), O, and S; wherein the phenyl and heteroaryl are substituted with 0 to 2 R$^d$;

R$^b$ is independently H or C$_{1-4}$ alkyl;

R$^c$ is independently H or C$_{1-4}$ alkyl;

R$^d$ is independently F, C$_{1-4}$ alkyl, C$_{1-4}$ alkoxy, or —NHSO$_2$(C$_{1-4}$ alkyl);

R$^e$ is independently F or OH;

R$^f$ is independently H, C$_{1-4}$ alkyl, —C(O)(C$_{1-4}$ alkyl) or —C(O)O(C$_{1-4}$ alkyl); and R$^g$ is independently selected from: F, Cl, C$_{1-4}$ alkyl, —OH, and oxo.

In another aspect, compounds of Formula (I), or a pharmaceutically acceptable salt thereof, wherein:

W' is H;

W is independently -Q-Y—R$^6$,

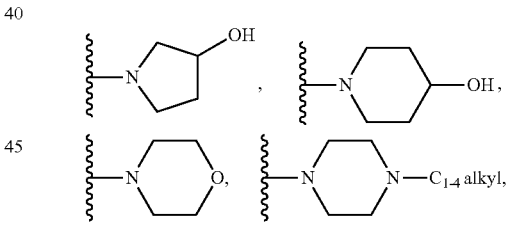

or heteroaryl including from 5 to 6 ring atoms, wherein from 1 to 4 ring atoms are each independently selected from N, NH, N(C$_{1-4}$ alkyl), O, and S, wherein the heteroaryl is optionally substituted with from 1-2 R$^d$;

Q is independently selected from NH, N(C$_{1-4}$ alkyl), O, and CH$_2$;

Y is C$_{1-6}$ alkylene, which is optionally substituted with from 1-2 R$^e$ and/or is optionally interrupted by one or more of the following:

(i) O;

(ii) N(R$^f$);

(iii) C$_{3-6}$ cycloalkylene optionally substituted with from 1 to 2 R$^g$; or (iv) heterocycloalkylene including from 5 to 6 ring atoms, wherein from 1 to 2 ring atoms are each independently selected from N, N(R$^f$), O and S(O)$_{1-2}$, and the heterocycloalkylene is optionally further substituted with from 1 to 2 R$^g$, R³ is independently pyrazolyl or isothiazolyl;
R⁴ is H;
R⁶ is independently selected from: H, OH, C₁₋₄ alkoxy, phenyl, —NR$^b$R$^c$, —NR$^b$COR$^a$, —NHC(O)O(C₁₋₄ alkyl), —C(O)NH(C₁₋₄ alkyl), —C(O)N(C₁₋₄ alkyl)₂, —NR$^b$C(O)NH(C₁₋₄ alkyl), —NR$^b$C(O)N(C₁₋₄ alkyl)₂, —NHS(O)₂(C₁₋₄ alkyl), —S(O)₂(C₁₋₄ alkyl),

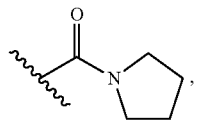 [SMILES: *C(=O)N1CCCC1]

and heteroaryl including from 5 to 6 ring atoms, wherein from 1 to 3 ring atoms are each independently selected from N, N(R$^f$), O, and S, wherein the heteroaryl is optionally substituted with from 1-2 R$^d$;

R$^a$ is independently selected from: C₁₋₄ alkyl, phenyl, heteroaryl including from 5 to 6 ring atoms, wherein from 1 to 4 ring atoms are each independently selected from N, N(R$^f$), O, and S; wherein the phenyl and heteroaryl are substituted with 0 to 2 R$^d$;

R$^b$ is independently H or C₁₋₄ alkyl;
R$^c$ is independently H or C₁₋₄ alkyl;
R$^d$ is independently C₁₋₄ alkyl or C₁₋₄ alkoxy;
R$^e$ is independently F or OH;
R$^f$ is independently H or C₁₋₄ alkyl; and
R$^g$ is independently selected from: F, Cl, C₁₋₄ alkyl, —OH, and oxo.

In another aspect, compounds of Formula (I), or a pharmaceutically acceptable salt thereof, wherein:
W' is H;
W is independently selected from: -Q-Y—R⁶, pyrazolyl, NR$^f$-pyrazolyl, imidazolyl, N(C₁₋₄ alkyl)₂, —O(CH₂)₂₋₃ CH₃, —(CH₂)₃-OBn,

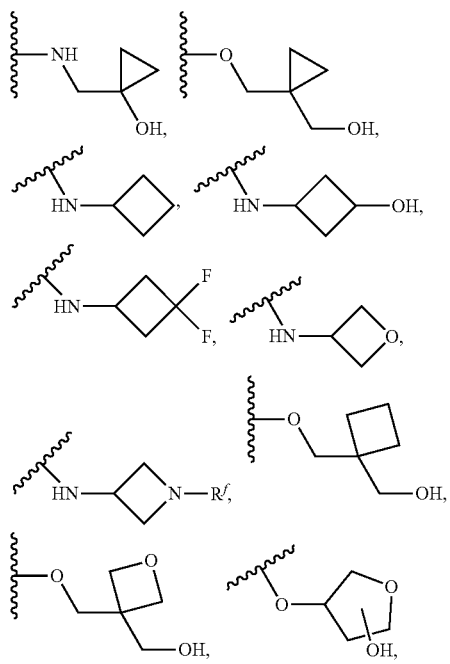

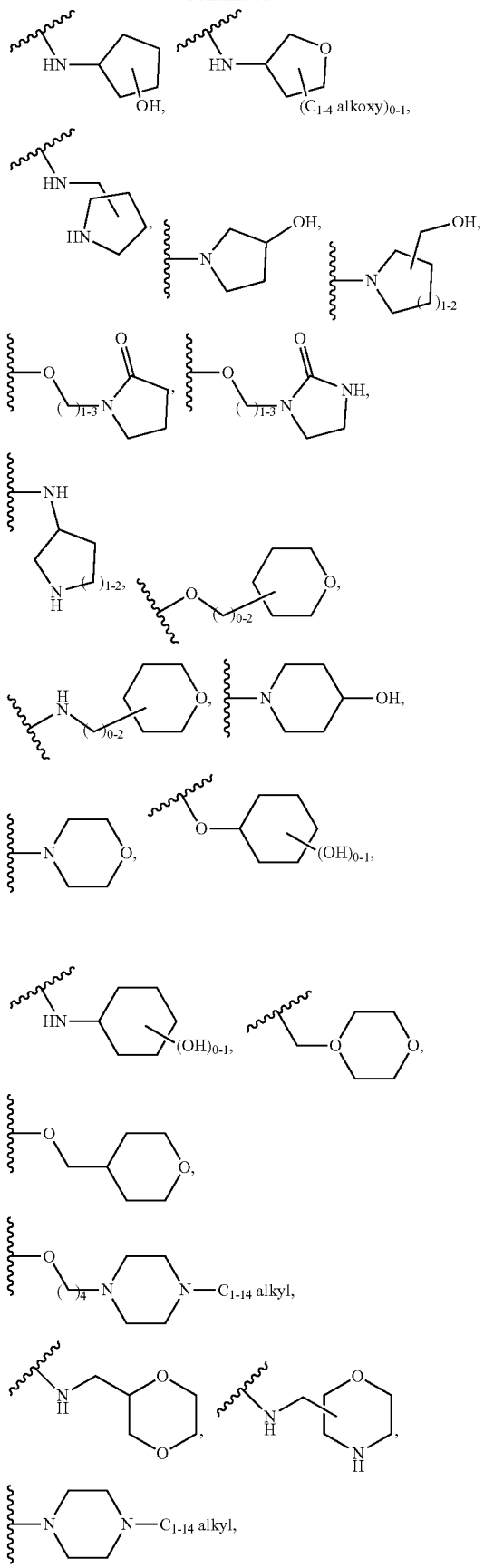

-continued

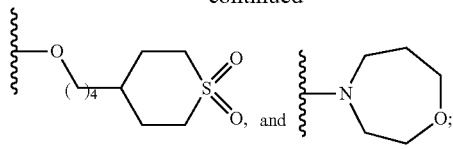

Q is independently selected from NH, N(C$_{1-4}$ alkyl), O, and CH$_2$;

Y is C$_{1-6}$ alkylene, which is optionally substituted with from 1-2 R$^e$ and/or is optionally interrupted by O;

R$^3$ is independently pyrazolyl or thienyl;

R$^4$ is independently H or F;

R$^6$ is independently selected from: H, OH, CN, C$_{1-4}$ alkoxy, —NR$^b$R$^c$, —NR$^b$COR$^a$, —NHC(O)O(C$_{1-4}$ alkyl), —C(O)NH(C$_{1-4}$ alkyl), —C(O)N(C$_{1-4}$ alkyl)$_2$, —NR$^b$C(O)NH(C$_{1-4}$ alkyl), —NR$^b$C(O)N(C$_{1-4}$ alkyl)$_2$, —S(O)$_2$(C$_{1-4}$ alkyl), —NHS(O)$_2$(C$_{1-4}$ alkyl),

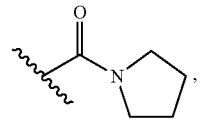 [SMILES: *C(=O)N1CCCC1]

morpholinyl, —CO-morpholinyl, phenyl and heteroaryl selected from thienyl, oxazolyl, thiazolyl, imidazolyl, N(C$_{1-4}$ alkyl)-imidazolyl, pyrazolyl, N(C$_{1-4}$ alkyl)-pyrazolyl, trizolyl, N(C$_{1-4}$ alkyl)-trizolyl, pyridyl, pyrimidinyl, and pyridazinyl, wherein said phenyl and heteroaryl are substituted with 0 to 2 R$^d$;

R$^a$ is independently C$_{1-4}$ alkyl, phenyl or heteroaryl selected from thiazolyl, N—(C$_{1-4}$ alkyl)-imidazolyl, and pyridyl; wherein the phenyl and heteroaryl are substituted with 0 to 2 R$^d$;

R$^b$ is independently H or C$_{1-4}$ alkyl;

R$^c$ is independently H or C$_{1-4}$ alkyl;

R$^d$ is independently selected from F, C$_{1-4}$ alkyl, C$_{1-4}$ alkoxy, and —NHSO$_2$(C$_{1-4}$ alkyl);

R$^e$ is independently F or OH; and

R$^f$ is independently H, CH$_2$CH$_2$OH, or —C(O)O(C$_{1-4}$ alkyl).

In another aspect, compounds of Formula (I), or a pharmaceutically acceptable salt thereof, wherein:

W' is H;

W is independently selected from: -Q-Y—R$^6$, imidazolyl, N(C$_{1-4}$ alkyl)$_2$, —O(CH$_2$)$_{2-3}$CH$_3$, —(CH$_2$)$_3$-OBn,

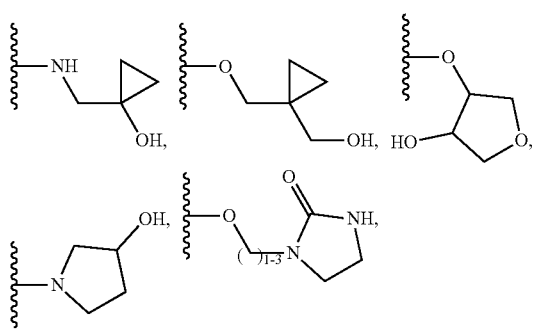

-continued

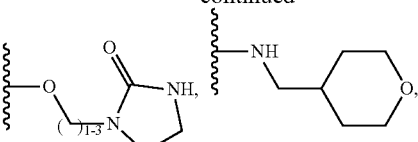

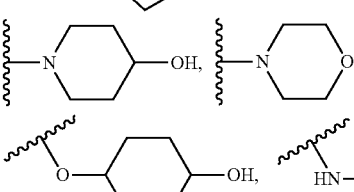

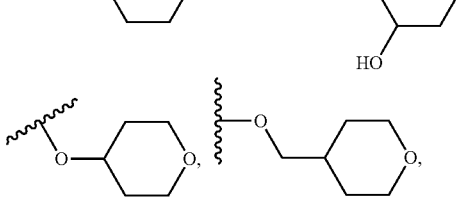

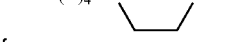

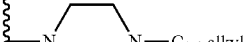

Q is independently selected from NH, N(C$_{1-4}$ alkyl), O, and CH$_2$;

Y is C$_{1-6}$ alkylene, which is optionally substituted with from 1-2 R$^e$ and/or is optionally interrupted by O;

R$^3$ is independently pyrazolyl;

R$^4$ is H;

R$^6$ is independently selected from: OH, C$_{1-4}$ alkoxy, —NR$^b$R$^c$, —NR$^b$COR$^a$, —NHC(O)O(C$_{1-4}$ alkyl), —C(O)NH(C$_{1-4}$ alkyl), —C(O)N(C$_{1-4}$ alkyl)$_2$, —NR$^b$C(O)NH(C$_{1-4}$ alkyl), —NR$^b$C(O)N(C$_{1-4}$ alkyl)$_2$, —NHS(O)$_2$(C$_{1-4}$ alkyl), —S(O)$_2$(C$_{1-4}$ alkyl),

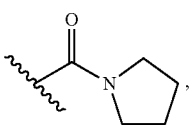

and heteroaryl selected from thiazolyl, imidazolyl, pyrazolyl, trizolyl, pyridyl, pyridazinyl, wherein the heteroaryl is substituted with 0 to 2 R$^d$;

R$^a$ is independently selected from: C$_{1-4}$ alkyl, phenyl, heteroaryl selected from thiazolyl, N—(C$_{1-4}$ alkyl)-imidazolyl, and pyridyl; wherein the phenyl and heteroaryl are substituted with 0 to 2 R$^d$;

R$^b$ is independently H or C$_{1-4}$ alkyl;

R$^c$ is independently H or C$_{1-4}$ alkyl;

R$^d$ is C$_{1-4}$ alkyl; and

R$^e$ is independently F or OH.

In another aspect, compounds of Formula (I), or a pharmaceutically acceptable salt thereof, wherein:

W' is H;

W is independently selected from: pyrazolyl, —(CH$_2$)$_{1-5}$—R$^6$, —O—(CH$_2$)$_{1-4}$—R$^6$, —NH—(CH$_2$)$_{1-4}$—R$^6$, —N(CH$_3$)—(CH$_2$)$_{1-4}$—R$^6$, —(CH$_2$)$_3$-OBn, —O—CH(CH$_2$OH)$_2$, —O—CH$_2$CH(OH)(CH$_2$OH), —O—(CH$_2$)$_{1-2}$—C(CH$_3$)$_2$OH, —O—(CH$_2$)$_{1-2}$—C(CH$_3$)CH$_2$OH, —O—CH$_2$C(CH$_3$)(CH$_2$OH)$_2$, —NH—(CH$_2$)$_{1-2}$—CH(OH)CH$_2$OH, —NH—CH(CH$_3$)CH$_2$OH, —NH—(CH$_2$)$_{1-2}$—CH(CH$_3$)OH, —NH—(CH$_2$)$_{1-2}$—C(CH$_3$)$_2$OH, —NH—(CH$_2$)$_{1-2}$—C(CH$_3$)$_2$CH$_2$OH, —NH—CH(CH$_2$OH)$_2$, —NH—(CH$_2$)$_{1-2}$—CH(OH)CH$_2$OH, —NH—(CH$_2$)$_{1-2}$—CH(OH)CH$_2$OCH$_3$, —NH—(CH$_2$)$_{1-2}$—C(CH$_3$)$_2$SO$_2$(CH$_3$), —NH—(CH$_2$)$_{1-2}$—CF$_2$(pyridyl), —NH—(CH$_2$)$_{1-2}$—CH(OH)(pyridyl),

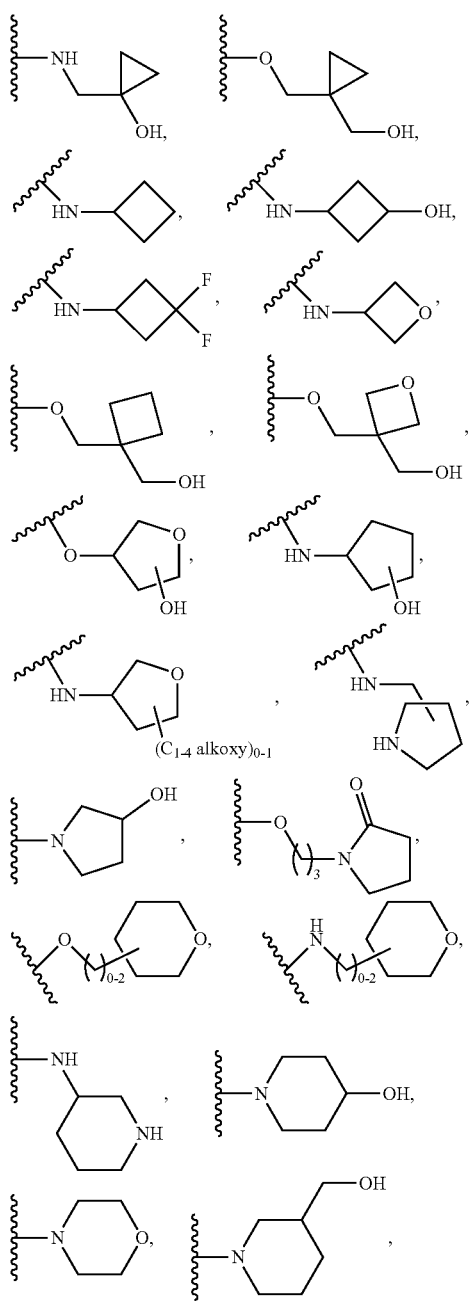

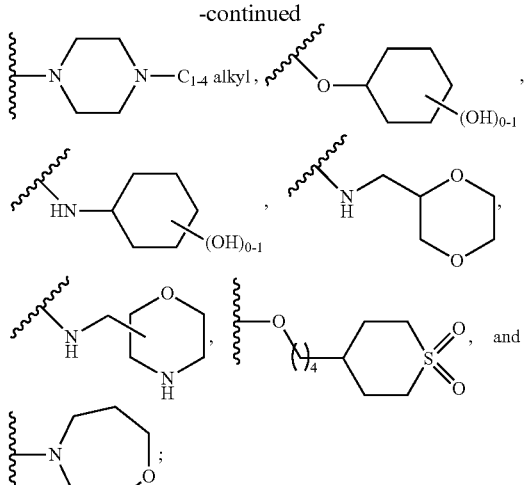

R$^3$ is independently

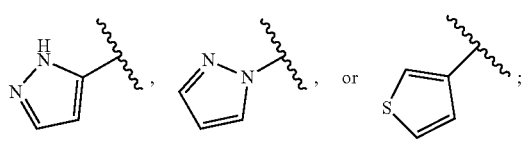 [SMILES: *c1ccn[nH]1 ; *n1cccn1 ; *c1ccsc1]

R$^4$ is independently H or F;
R$^6$ is independently selected from: H, OH, CN, C$_{1-4}$ alkoxy, —NR$^b$R$^c$, —NR$^b$COR$^a$, —NHC(O)O(C$_{1-4}$ alkyl), —C(O)NH(C$_{1-4}$ alkyl), —C(O)N(C$_{1-4}$ alkyl)$_2$, —NR$^b$C(O)N(C$_{1-4}$ alkyl)$_2$, —S(O)$_2$(C$_{1-4}$ alkyl), —NHS(O)$_2$(C$_{1-4}$ alkyl), phenyl, and heteroaryl selected from thienyl, oxazolyl, pyrazolyl, N(C$_{1-4}$ alkyl)-pyrazolyl, thiazolyl, imidazolyl, N(C$_{1-4}$ alkyl)-imidazolyl, trizolyl, N(C$_{1-4}$ alkyl)-trizolyl, pyridyl, pyrimidinyl, and pyridazinyl, wherein said phenyl and heteroaryl are substituted with 0 to 2 R$^d$;
R$^a$ is independently C$_{1-4}$ alkyl, phenyl or heteroaryl selected from thiazolyl, N—(C$_{1-4}$ alkyl)-imidazolyl, and pyridyl; wherein the heteroaryl is substituted with 0 to 2 R$^d$;
R$^b$ is independently H or C$_{1-4}$ alkyl;
R$^c$ is independently H or C$_{1-4}$ alkyl; and
R$^d$ is independently selected from F, C$_{1-4}$ alkyl, C$_{1-4}$ alkoxy, and —NHSO$_2$(C$_{1-4}$ alkyl).

In another aspect, compounds of Formula (I), or a pharmaceutically acceptable salt thereof, wherein:
W' is H;
W is independently selected from: —(CH$_2$)$_{1-5}$—R$^6$, —O—(CH$_2$)$_{2-4}$—R$^6$, —NH—(CH$_2$)$_{1-4}$—R$^6$, —(CH$_2$)$_3$-OBn, —O—CH(CH$_2$OH)$_2$, —NH—(CH$_2$)$_{1-2}$—C(OH)CH$_2$OH, —NH—C(CH$_3$)CH$_2$OH, —O—(CH$_2$)$_{1-2}$—C(CH$_3$)$_2$OH, —NH—(CH$_2$)$_{1-2}$—CH(CH$_3$)OH, —NH—(CH$_2$)$_{1-2}$—C(CH$_3$)$_2$OH, —NH—(CH$_2$)$_{1-2}$—CF$_2$(pyridyl), —NH—(CH$_2$)$_{1-2}$—CH(OH)(pyridyl),

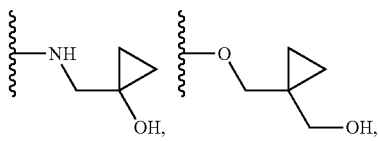

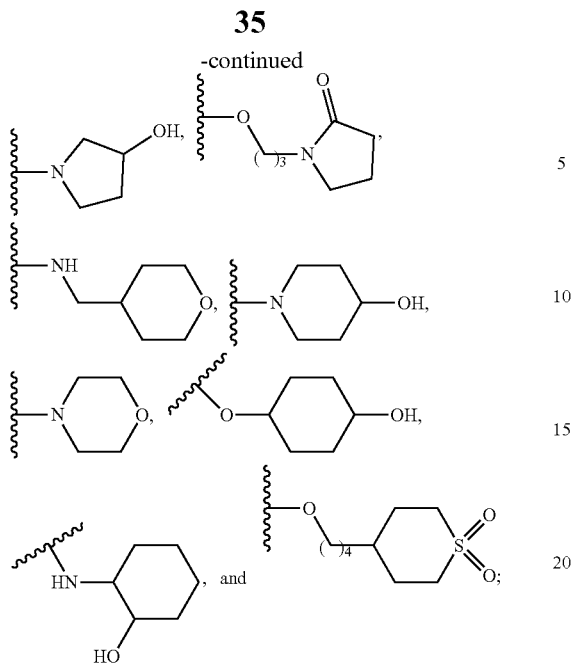

R³ is independently 1H-pyrazol-3-yl or pyrazol-1-yl;
R⁴ is H;
R⁶ is independently selected from: OH, $C_{1-4}$ alkoxy, —NR$^b$R$^c$, —NR$^b$COR$^a$, —NHC(O)O($C_{1-4}$ alkyl), —C(O)NH($C_{1-4}$ alkyl), —C(O)N($C_{1-4}$ alkyl)$_2$, —NR$^b$C(O)N($C_{1-4}$ alkyl)$_2$, —NHS(O)$_2$($C_{1-4}$ alkyl), —S(O)$_2$($C_{1-4}$ alkyl), and heteroaryl selected from pyrazolyl, thiazolyl, imidazolyl, trizolyl, pyridyl, and pyridazinyl, wherein the heteroaryl is substituted with 0 to 2 R$^d$;
R$^a$ is independently $C_{1-4}$ alkyl or heteroaryl selected from thiazolyl, N—($C_{1-4}$ alkyl)-imidazolyl, and pyridyl; wherein the heteroaryl is substituted with 0 to 2 R$^d$;
R$^b$ is independently H or $C_{1-4}$ alkyl;
R$^c$ is independently H or $C_{1-4}$ alkyl; and
R$^d$ is independently $C_{1-4}$ alkyl.

In another aspect, compounds of Formula (I), or a pharmaceutically acceptable salt thereof, wherein:
W' is H;
W is independently selected from: pyrazolyl, —(CH$_2$)$_{1-4}$—R⁶, —O—(CH$_2$)$_{1-4}$—R⁶, —NH—(CH$_2$)$_{1-4}$—R⁶, —(CH$_2$)$_3$—OBn, —O—CH(CH$_2$OH)$_2$, —O—CH$_2$CH(OH)(CH$_2$OH), —O—(CH$_2$)$_{1-2}$—C(CH$_3$)$_2$CH$_2$OH, —NH—(CH$_2$)$_{1-2}$—CH(CH$_3$)OH, —NH—CH(CH$_3$)CH$_2$OH, —NH—(CH$_2$)$_{1-2}$—C(CH$_3$)$_2$OH, —NH—(CH$_2$)$_{1-2}$—C(CH$_3$)$_2$CH$_2$OH, —NH—CH(CH$_2$OH)$_2$, —NH—(CH$_2$)$_{1-2}$—CH(OH)CH$_2$OH, —NH—(CH$_2$)$_{1-2}$—CH(OH)CH$_2$OCH$_3$, —NH—(CH$_2$)$_{1-2}$—C(CH$_3$)$_2$SO$_2$(CH$_3$), —NH—(CH$_2$)$_{1-2}$—CF$_2$(pyrid-1-yl), —NH—(CH$_2$)$_{1-2}$—CH(OH)(pyridyl),

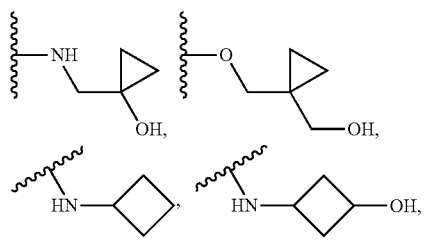

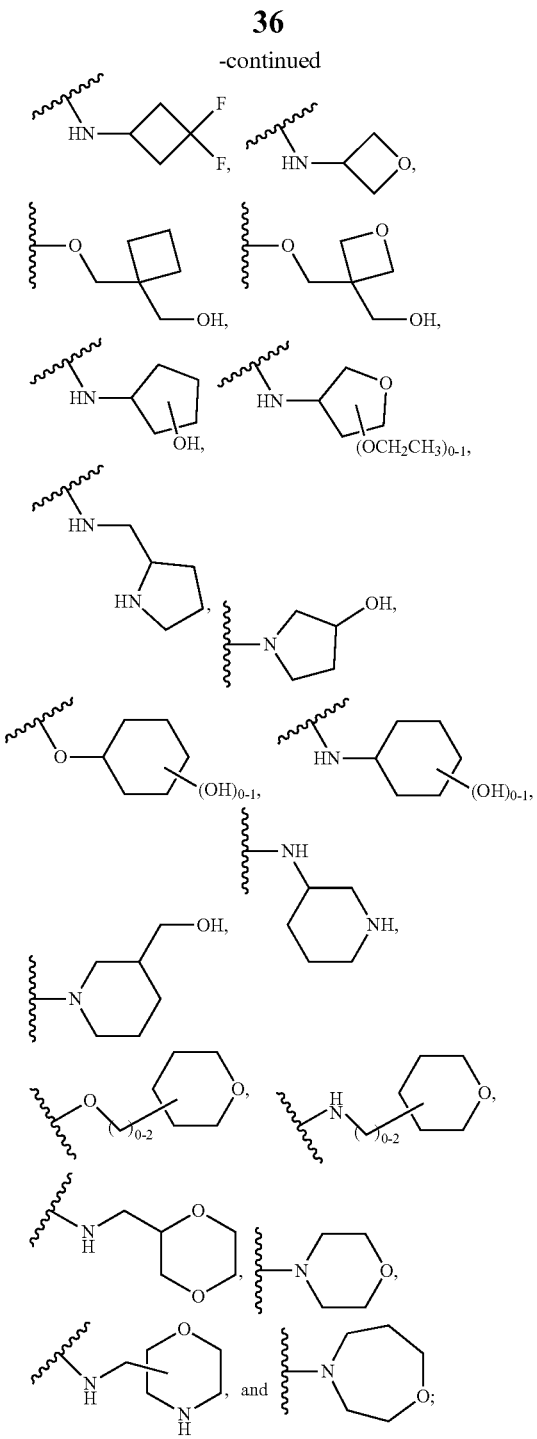

R³ is independently

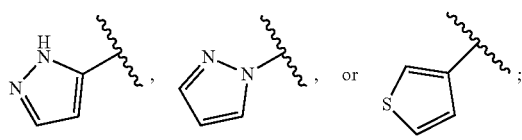 [SMILES: *c1ccn[nH]1 ; *n1cccn1 ; *c1ccsc1]

R⁴ is independently H or F;
R⁶ is independently selected from: H, OH, CN, $C_{1-4}$ alkoxy, —C(O)NHCH$_3$, —N(CH$_2$CH$_3$)C(O)CH$_3$, —NHC(O)(OCH$_3$), —NHC(O)NH$_2$CHCH$_3$, —NHC(O)N(CH$_3$)$_2$, —SO$_2$(CH$_3$), —NHS(O)$_2$CH$_3$, —NHCOR$^a$, phenyl and heteroaryl selected from thienyl, oxazolyl, pyrazolyl, N—CH$_3$-pyrazolyl, thiazolyl, imidazolyl, N—CH$_3$-imidazolyl, trizolyl, N—CH$_3$-trizolyl, pyridyl, pyrimidinyl, and pyridazinyl, wherein said phenyl and heteroaryl are substituted with 0 to 2 R$^d$;

R$^a$ is independently selected from C$_{1-4}$ alkyl, 2-(CH$_3$)-thiazol-4-yl and N—(CH$_3$)-imidazol-2-yl; and R$^d$ is independently selected from F, C$_{1-4}$ alkyl, C$_{1-4}$ alkoxy, and —NHSO$_2$(CH$_3$).

In another aspect, compounds of Formula (I), or a pharmaceutically acceptable salt thereof, wherein:

W' is H;

W is independently selected from: —(CH$_2$)$_{1-4}$—R$^6$, —O—(CH$_2$)$_{1-4}$—R$^6$, —NH—(CH$_2$)$_{1-4}$—R$^6$, —(CH$_2$)$_3$-OBn, —O—CH(CH$_2$OH)$_2$, —NH—(CH$_2$)$_{1-2}$—CH(CH$_3$)OH, —NH—(CH$_2$)$_{1-2}$—C(CH$_3$)$_2$OH, —NH—(CH$_2$)$_{1-2}$—CF$_2$(pyrid-1-yl), and

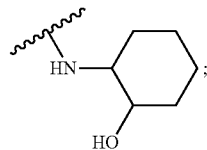 [SMILES: *NC1CCCCC1O]

R$^3$ is independently 1H-pyrazol-3-yl or pyrazol-1-yl;

R$^4$ is H;

R$^6$ is independently selected from: OH, —N(CH$_2$CH$_3$)C(O)CH$_3$, —NHC(O)N(CH$_3$)$_2$, —NHCOR$^a$ and heteroaryl selected from pyrazolyl, thiazolyl, imidazolyl, trizolyl, pyridyl, and pyridazinyl, wherein the heteroaryl is substituted with 0 to 2 R$^d$;

R$^a$ is independently selected from C$_{1-4}$ alkyl, 2-(CH$_3$)-thiazol-4-yl and N—(CH$_3$)-imidazol-2-yl; and R$^d$ is independently C$_{1-4}$ alkyl.

In another aspect, compounds of Formula (I), or a pharmaceutically acceptable salt thereof, wherein:

W' is independently selected from: —Y—R$^6$, —CONH(pyrid-3-yl),

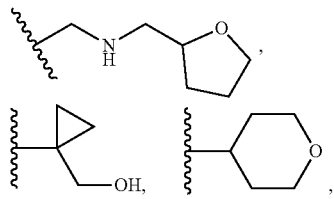

and heteroaryl selected from imidazolyl, pyrazolyl, trizolyl, pyridyl and indazolyl, wherein the heteroaryl is substituted with 0 to 2 R$^d$;

Y is —(CH$_2$)$_{1-5}$— or —(CH$_2$)$_{3-5}$—O—(CH$_2$)$_{1-2}$;

W is H;

R$^3$ is independently pyrazolyl;

R$^4$ is H; and

R$^6$ is independently selected from: OH, OBn, C$_{1-4}$ alkoxy, phenyl, —NH(C$_{1-4}$ alkyl), —NHC(O)(C$_{1-4}$ alkyl), —N(C$_{1-4}$ alkyl)C(O)(C$_{1-4}$ alkyl),

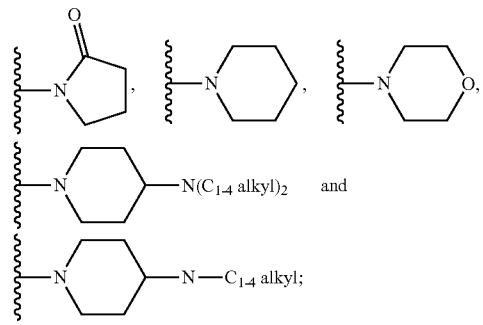

R$^d$ is independently CH$_2$OH or C$_{1-4}$ alkyl.

In another aspect, compounds of Formula (I), or a pharmaceutically acceptable salt thereof, wherein:

W' is independently selected from: —(CH$_2$)$_{3-5}$—OH, —(CH$_2$)$_{3-5}$-OBn, —(CH$_2$)$_{3-4}$—NHCH$_2$CH$_3$, —(CH$_2$)$_{3-4}$—NHC(O)CH$_3$, CH$_2$)$_{3-4}$—N(CH$_2$CH$_3$C(O)CH$_3$, 6-(CH$_2$OH)-pyrid-2-yl, imidazolyl,

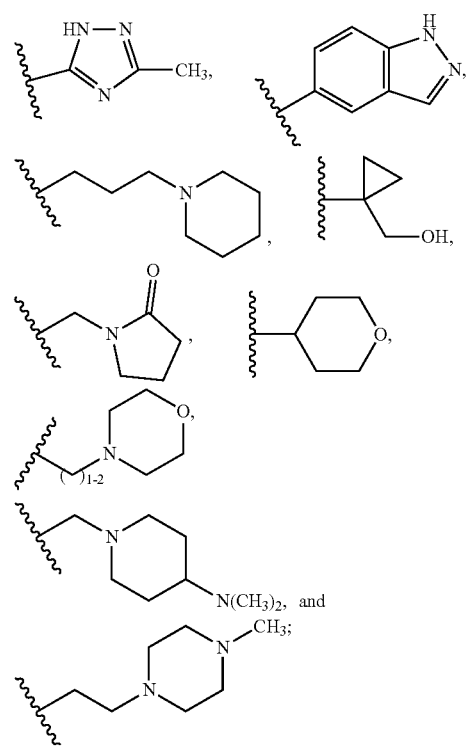

W is H;

R$^3$ is 1H-pyrazol-3-yl; and

R$^4$ is H.

In another aspect, compounds of Formula (I), or a pharmaceutically acceptable salt thereof, wherein:

W' is independently selected from: —Y—R$^6$, —CONH(pyrid-3-yl),

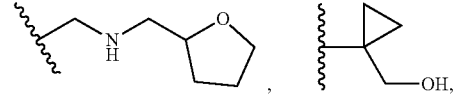

-continued

[structure: tetrahydropyran-4-yl]

and heteroaryl selected from imidazolyl, pyridyl and indazolyl, wherein the heteroaryl is substituted with 0 to 2 $R^d$;

Y is —$(CH_2)_{1-5}$— or —$(CH_2)_{3-5}$—O—$(CH_2)_{1-2}$;

W is H;

$R^3$ is independently pyrazolyl;

$R^4$ is H; and $R^6$ is independently selected from: OH, $C_{1-4}$ alkoxy, phenyl, —NH($C_{1-4}$ alkyl), —N($C_{1-4}$ alkyl)C(O($C_{1-4}$ alkyl),

[structures: 2-oxopyrrolidin-1-yl, piperidin-1-yl, morpholin-4-yl, 4-(N($C_{1-4}$ alkyl)$_2$)piperidin-1-yl, and 4-(N—$C_{1-4}$ alkyl)piperidin-1-yl]

and $R^d$ is independently $CH_2OH$ or $C_{1-4}$ alkyl.

In another aspect, compounds of Formula (I), or a pharmaceutically acceptable salt thereof, wherein:

W' is independently selected from: —$(CH_2)_{3-5}$—OH, —$(CH_2)_{3-5}$-OBn, —$(CH_2)_{3-4}$—NHCH$_2$CH$_3$, —$(CH_2)_{3-4}$—N(CH$_2$CH$_3$)C(O)CH$_3$, —CONH(pyrid-3-yl), 6-($CH_2OH$)-pyrid-2-yl,

[structures: 1-(hydroxymethyl)cyclopropyl, 2-oxopyrrolidin-1-ylmethyl, tetrahydropyran-4-yl, and morpholin-4-ylmethyl]

W is H;

$R^3$ is 1H-pyrazol-3-yl; and $R^4$ is H.

In another aspect, compounds of Formula (I), or a pharmaceutically acceptable salt thereof, wherein: (generalized from a list of 19 compounds)

W' is H;

W is independently selected from: —O—CH$_2$CH(OH)(CH$_2$OH), —NH—$(CH_2)_{3-4}$—OH, —NH—$(CH_2)_{1-2}$—CH(CH$_3$)OH, —NH—$(CH_2)_{1-2}$—C(CH$_3$)$_2$OH, —O—$(CH_2)_{1-2}$-(pyrazolyl), —NH—$(CH_2)_{1-2}$-(pyrimidinyl), —NH—$(CH_2)_{1-2}$-(pyridazinyl), —NH—$(CH_2)_{1-2}$—CF$_2$(pyridyl),

[structures: (3-hydroxymethyl-oxetan-3-yl)methoxy, (3-hydroxycyclopentyl)amino, (tetrahydrofuran-3-yl)amino, (pyrrolidin-2-ylmethyl)amino, and (4-hydroxycyclohexyl)amino]

$R^3$ is independently

[structures: 1H-pyrazol-3-yl or 1H-pyrazol-1-yl];

and $R^4$ is independently H or F.

In another aspect, compounds of Formula (I), or a pharmaceutically acceptable salt thereof, wherein: (generalized from a list of 12 compounds)

W' is H;

W is independently selected from: —O—CH$_2$CH(OH)(CH$_2$OH), —NH—$(CH_2)_{3-4}$—OH, —NH—$(CH_2)_{1-2}$—CH(CH$_3$)OH, —NH—$(CH_2)_{1-2}$—C(CH$_3$)$_2$OH, —NH—$(CH_2)_{1-2}$-(pyrazolyl), and

[structures: (3-hydroxymethyl-oxetan-3-yl)methoxy, and (3-hydroxycyclopentyl)amino]

$R^3$ is independently

[structures: 1H-pyrazol-3-yl or 1H-pyrazol-1-yl];

and $R^4$ is independently H or F.

In another aspect, compounds of Formula (I), or a pharmaceutically acceptable salt thereof, wherein: (generalized from a short list of 7 compounds)

W' is H;

W is independently selected from: —O—CH$_2$CH(OH)(CH$_2$OH), —NH—$(CH_2)_{3-4}$—OH, —NH—$(CH_2)_{1-2}$—CH(CH$_3$)OH, —NH—$(CH_2)_{1-2}$—C(CH$_3$)$_2$OH, —NH—$(CH_2)_{1-2}$-(pyrazolyl), and

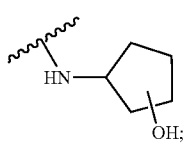
R³ is
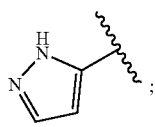 [SMILES: *c1ccn[nH]1]
and
R⁴ is independently H or F.
In another aspect, a compound is selected from:
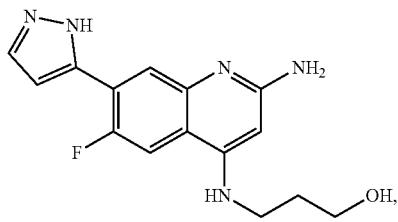
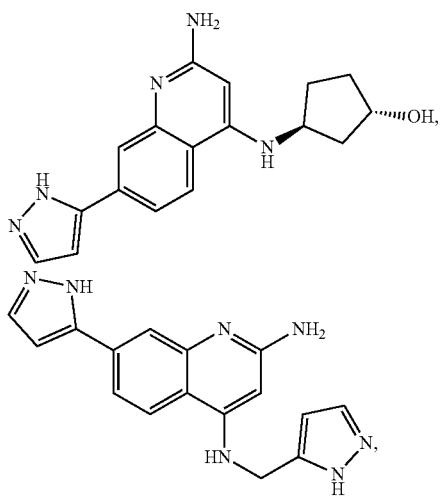
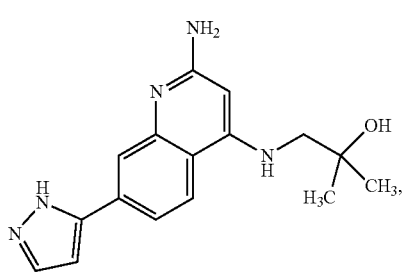
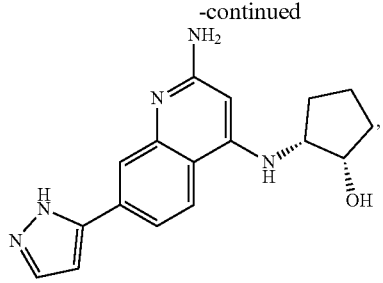
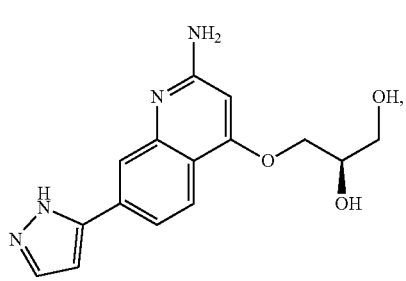
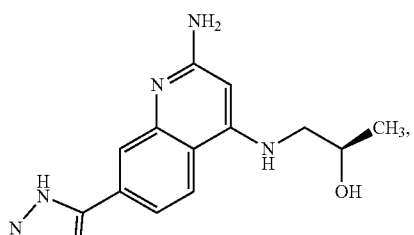
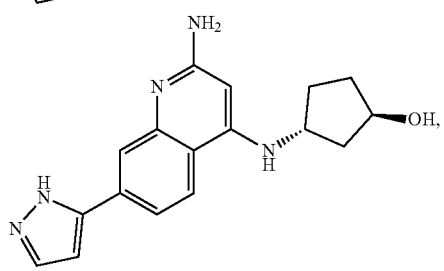
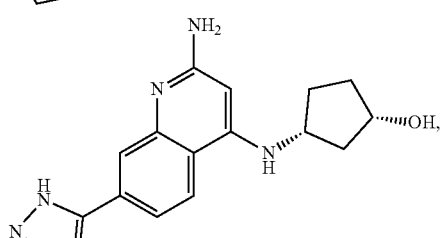
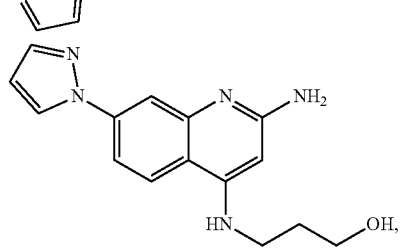

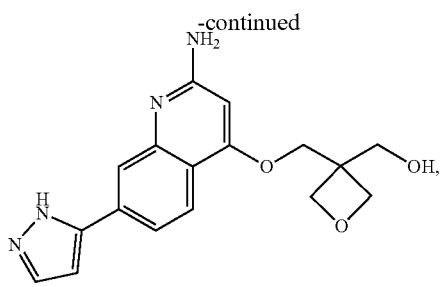
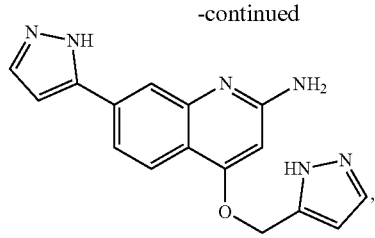
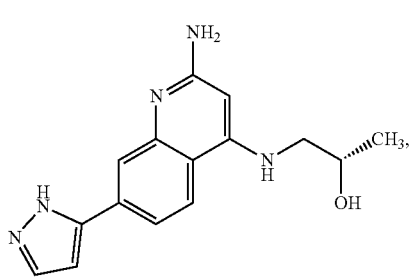
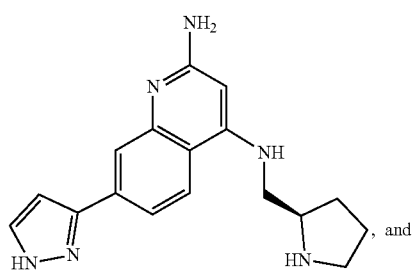
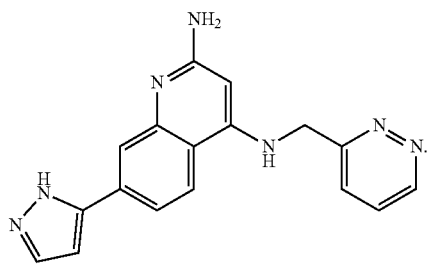
, and
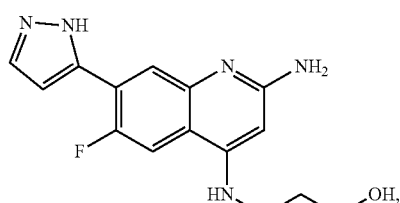
or a pharmaceutically acceptable salt thereof.
In another aspect, a compound is selected from:
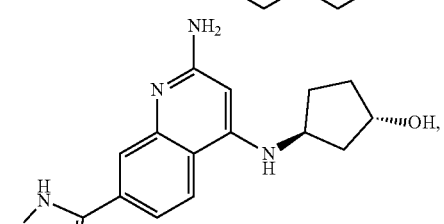
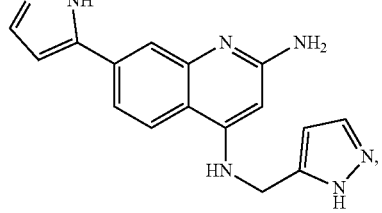

-continued
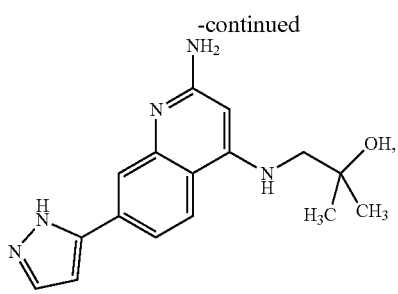
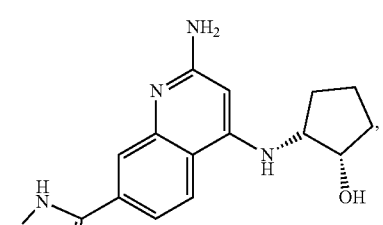
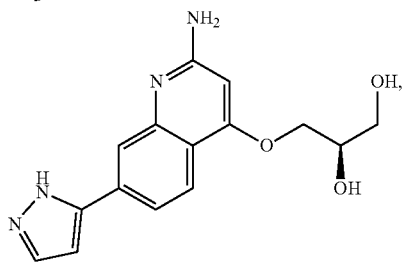
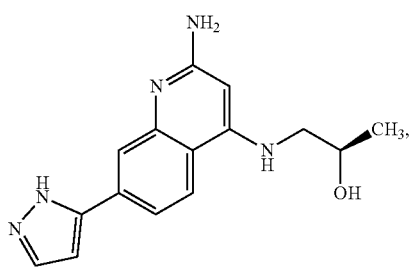
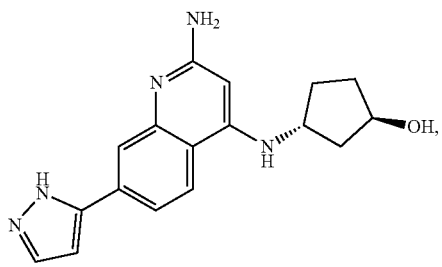
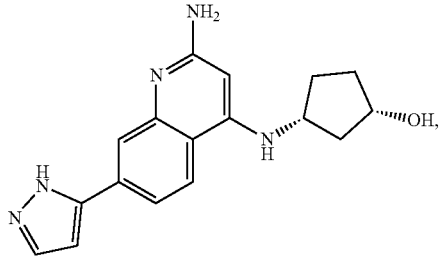
-continued
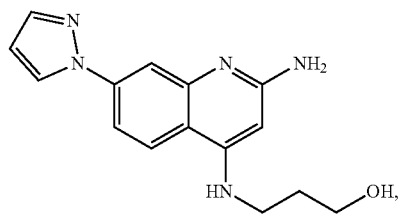
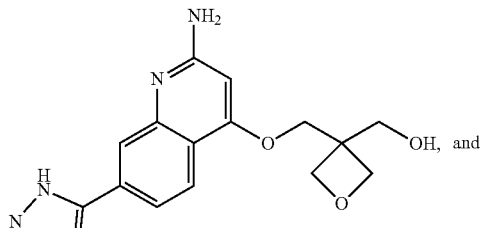
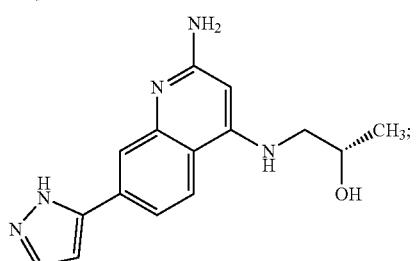
or a pharmaceutically acceptable salt thereof.
In another aspect, a compound is selected from:
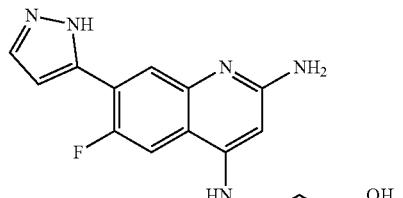
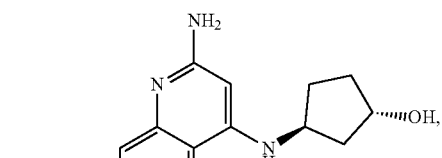
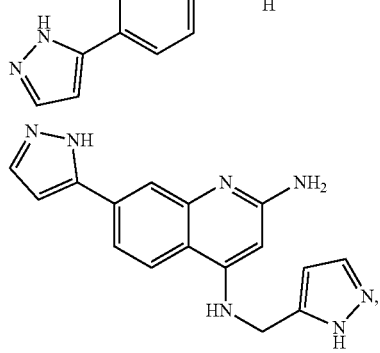

-continued

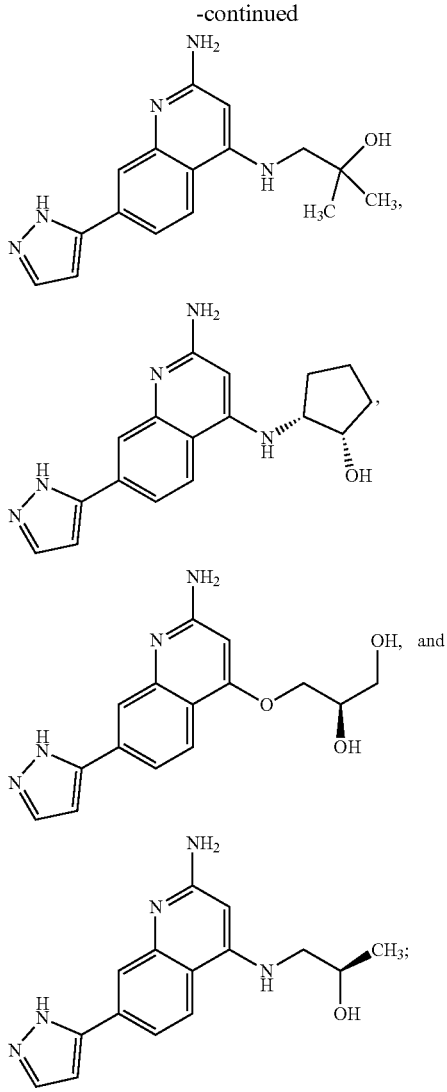

or a pharmaceutically acceptable salt thereof.

In another aspect, a compound is selected from:

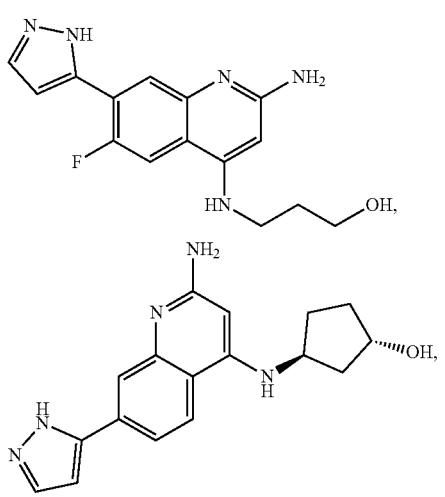

-continued

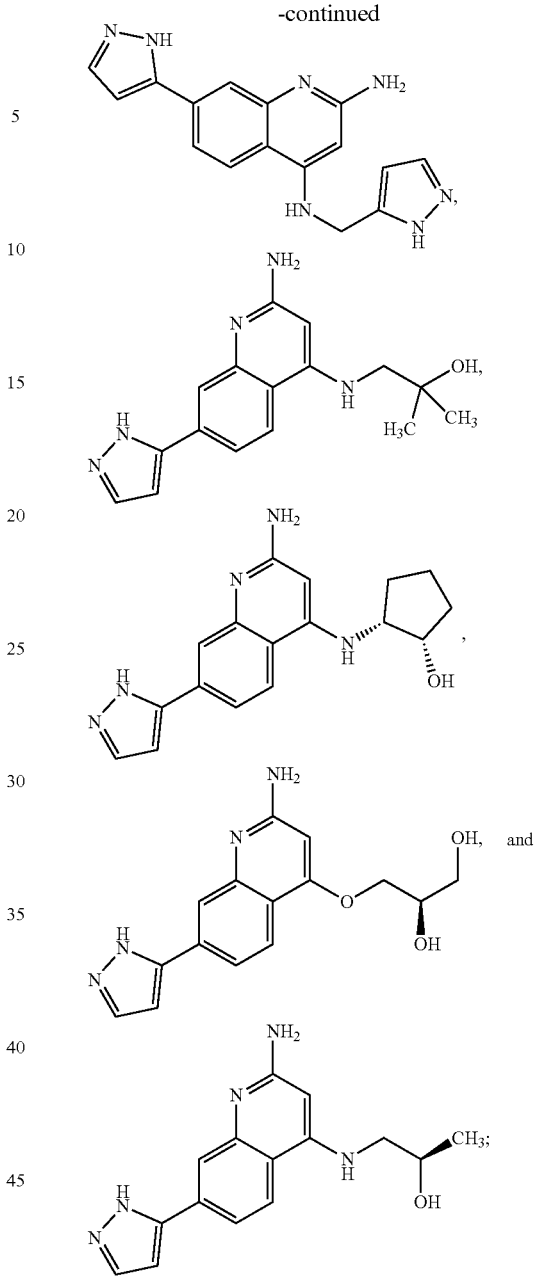

or a pharmaceutically acceptable salt thereof.

Variables W, W', Q, and Q'

In some embodiments, W' is $R^2$.
In some embodiments, W' is Q'-$R^2$.
In some embodiments, Q' is NH.
In some embodiments, Q' is O.
In some embodiments, Q' is S.
In some embodiments, W is H.
In some embodiments, W is $R^2$.
In some embodiments, W is Q-$R^2$.
In some embodiments, Q is $NR^1$.
In some embodiments, Q is $CHR^1$.
In some embodiments, Q is O.
In some embodiments, Q is S.
In some embodiments, W' is $R^2$ (e.g., Y—$R^6$, e.g., hydroxyalkyl) and W is H.
In some embodiments, W' is $R^2$ (e.g., H) and W is $R^2$ (e.g., Y—$R^6$, e.g., hydroxyalkyl).

In some embodiments, W' is $R^2$; W is Q-$R^2$; and Q is CH$R^1$.

In some embodiments, W' is $R^2$; W is Q-$R^2$; and Q is N$R^1$.

In some embodiments, W' is $R^2$; W is Q-$R^2$; and Q is O.

In some embodiments, W' is $R^2$; W is Q-$R^2$; and Q is S.

In some embodiments, W' is $R^2$ and W is H.

In some embodiments, W is $R^2$ and W' is H.

Variable $R^2$

In some embodiments, $R^2$ is selected from: H, $R^6$, and $Q^2$-Y—$R^6$. In certain embodiments, $R^2$ is selected from: $R^6$ and $Q^2$-Y—$R^6$.

In certain embodiments, $R^2$ is H.

In certain embodiments, $R^2$ is $Q^2$-Y—$R^6$.

In certain of these embodiments, $Q^2$ is bond. In other embodiments, $Q^2$ is O or S (e.g., O).

In certain of these embodiments, Y is selected from: $C_{1-10}$ alkylene, $C_{2-10}$ alkenylene, and $C_{2-10}$ alkynylene, each of which is optionally substituted with from 1-4 $R^e$. In certain of these embodiments, Y is selected from: $C_{1-10}$ alkylene, $C_{2-10}$ alkenylene, and $C_{2-10}$ alkynylene, each of which is unsubstituted. For example, Y can be unsubstituted $C_{1-10}$ alkylene. As another example, Y can be $C_{1-10}$ alkylene, which is substituted with from 1-4 $R^e$. In certain of the foregoing embodiments, Y is unbranched. In other of the foregoing embodiments, Y is branched. In other of the foregoing embodiments, Y is interrupted by one or more (e.g., one) of the following:

(i) O;

(ii) S;

(iii) N($R^f$);

(iv) $C_{3-6}$ cycloalkylene optionally substituted with from 1-4 $R^g$, (v) $C_{6-10}$ arylene, optionally further substituted with from 1-4 $R^d$, (vi) heteroarylene including from 5-10 ring atoms, wherein from 1-4 ring atoms are each independently selected from N, N($R^f$), O, and S, and which is optionally substituted with from 1-4 $R^g$, or (vii) heterocycloalkylene including from 3-10 ring atoms, wherein from 1-3 ring atoms are each independently selected from N, N($R^f$) and O, and which is optionally further substituted with from 1-4 $R^g$.

For example, Y can be interrupted by a heteroatom (e.g., one or more of O, S, and N($R^f$)). As another example, Y can be interrupted by any of (iv), (v), (vi), or (vii).

In certain embodiments, $R^2$ is $R^6$.

In any of the foregoing embodiments, $R^6$ can be as defined anywhere herein.

In some embodiments, $R^2$ is:

(i) —Y—$R^6$, wherein:

Y is $C_{1-8}$ alkylene, which is optionally substituted with from 1-4 $R^e$; and $R^6$ is —OH; -OBn; —O($C_{1-4}$ alkyl), —C(O)$R^a$; —CO$_2R^a$; —CONR'R''; —N$R^bR^c$; cyano; -OBn, wherein the phenyl portion is optionally substituted with from 1-3 $R^d$; or heteroaryl including from 5-6 ring atoms, wherein from 1-4 ring atoms are each independently selected from N, N($R^f$), O, and S, wherein the heteroaryl is optionally substituted with from 1-3 $R^d$;

OR (ii) —C(O)—Y—$R^6$;

OR (iii) —$R^6$;

OR (iv) —($Y^1$)$_n$—$Y^2$—($Y^3$)$_p$—$R^{6'}$, wherein:

each of n and p is independently 0 or 1;

each of $Y^1$ and $Y^3$ is, independently, $C_{1-3}$ alkylene, which is optionally substituted with from 1-2 $R^e$, $Y^2$ is:

(a) $C_{3-6}$ cycloalkylene optionally substituted with from 1-4 $R^g$, (b) $C_{6-10}$ arylene, optionally further substituted with from 1-4 $R^d$, (c) heteroarylene including from 5-10 ring atoms, wherein from 1-4 ring atoms are each independently selected from N, N($R^f$), O, and S, and which is optionally further substituted with from 1-4 $R^g$, or (d) heterocycloalkylene including from 3-10 ring atoms, wherein from 1-3 ring atoms are each independently selected from N, N($R^f$) and O, and wherein $Y^2$ is optionally further substituted with from 1-4 $R^g$, and $R^{6'}$ is H, —OH, —C(O)$R^a$, —CO$_2R^a$; —CONR'R'', —N$R^bR^c$, cyano, or heteroaryl including from 5-6 ring atoms, wherein from 1-4 ring atoms are each independently selected from N, N($R^f$), O, and S, wherein $R^{6'}$ cannot be H when $Y^2$ is $C_{3-6}$ cycloalkylene optionally substituted with from 1-4 $R^g$ or when $Y^2$ is $C_{6-10}$ arylene, optionally substituted with from 1-4 $R^d$,

OR (v) —$Z^1$—$Z^2$—$Z^3$—$R^7$, wherein:

$Z^1$ is $C_{1-3}$ alkylene, which is optionally substituted with from 1-6 F, $Z^2$ is —N($R^f$)—, —O—, or —S—;

$Z^3$ is $C_{2-5}$ alkylene, which is optionally substituted with from 1-6 F, and $R^7$ is —OH, —C(O)$R^a$, CO$_2R^a$; —CONR'R'', —N$R^bR^c$, or heteroaryl including from 5-10 ring atoms, wherein from 1-4 ring atoms are each independently selected from N, N($R^f$), O, and S, wherein the heteroaryl is optionally substituted with from 1-3 $R^d$.

In some embodiments, $R^2$ is:

(i) —Y—$R^6$, wherein:

Y is $C_{1-8}$ alkylene, which is optionally substituted with from 1-4 $R^e$; and $R^6$ is —OH; -OBn; —O($C_{1-4}$ alkyl), —C(O)$R^a$; —CO$_2R^a$; —CONR'R''; —N$R^bR^c$; cyano; -OBn, wherein the phenyl portion is optionally substituted with from 1-3 $R^d$; or heteroaryl including from 5-6 ring atoms, wherein from 1-4 ring atoms are each independently selected from N, N($R^f$), O, and S, wherein the heteroaryl is optionally substituted with from 1-3 $R^d$;

OR (ii) —C(O)—Y—$R^6$;

OR (iii) —$R^6$;

OR (iv) —($Y^1$)$_n$—$Y^2$—($Y^3$)$_p$—$R^{6'}$, wherein:

each of n and p is independently 0 or 1;

each of $Y^1$ and $Y^3$ is, independently, $C_{1-3}$ alkylene, which is optionally substituted with from 1-2 $R^e$, $Y^2$ is:
(a) $C_{3-6}$ cycloalkylene optionally substituted with from 1-4 $R^g$,
(b) $C_{6-10}$ arylene, optionally further substituted with from 1-4 $R^d$,
(c) heteroarylene including from 5-10 ring atoms, wherein from 1-4 ring atoms are each independently selected from N, N($R^f$), O, and S, and which is optionally further substituted with from 1-4 $R^g$, or
(d) heterocycloalkylene including from 3-10 ring atoms, wherein from 1-3 ring atoms are each independently selected from N, N($R^f$) and O, and wherein $Y^2$ is optionally further substituted with from 1-4 $R^g$, and $R^{6'}$ is H, —OH, —C(O)$R^a$, —CO$_2R^a$; —CONR'R'', —NR$^b$R$^c$, cyano, or heteroaryl including from 5-6 ring atoms, wherein from 1-4 ring atoms are each independently selected from N, N($R^f$), O, and S, wherein $R^{6'}$ cannot be H when $Y^2$ is $C_{3-6}$ cycloalkylene optionally substituted with from 1-4 $R^g$ or when $Y^2$ is $C_{6-10}$ arylene, optionally substituted with from 1-4 $R^d$.

In some embodiments, $R^2$ is:
(i) —Y—$R^6$, wherein:
  Y is $C_{1-8}$ alkylene, which is optionally substituted with from 1-4 $R^e$; and
  $R^6$ is —OH; -OBn; —O($C_{1-4}$ alkyl), —C(O)$R^a$; —CO$_2R^a$; —CONR'R''; —NR$^b$R$^c$; cyano; -OBn, wherein the phenyl portion is optionally substituted with from 1-3 $R^d$; or heteroaryl including from 5-6 ring atoms, wherein from 1-4 ring atoms are each independently selected from N, N($R^f$), O, and S, wherein the heteroaryl is optionally substituted with from 1-3 $R^d$;
OR
(ii) —C(O)—Y—$R^6$;
OR
(iii) —$R^6$;

In some embodiments, $R^2$ is:
(i) —Y—$R^6$, wherein:
  Y is $C_{1-8}$ alkylene, which is optionally substituted with from 1-4 $R^e$; and
  $R^6$ is —OH, C(O)$R^a$, CO$_2R^a$, —CONR$^b$R$^c$, —NR$^b$R$^c$, or heteroaryl including from 5-6 ring atoms, wherein from 1-4 ring atoms are each independently selected from N, N($R^f$), O, and S, wherein the heteroaryl is optionally substituted with from 1-3 $R^d$.
OR
(ii) —C(O)—Y—$R^6$, wherein Y and $R^6$ are as defined above in (i);
OR
(iii) —$R^6$.

In some embodiments, $R^2$ is:
(i) —Y—$R^6$, wherein:
  Y is $C_{1-8}$ alkylene, which is optionally substituted with from 1-4 $R^e$; and
  $R^6$ is —OH, C(O)$R^a$, CO$_2R^a$, —CONR$^b$R$^c$, —NR$^b$R$^c$, or heteroaryl including from 5-6 ring atoms, wherein from 1-4 ring atoms are each independently selected from N, N($R^f$), O, and S, wherein the heteroaryl is optionally substituted with from 1-3 $R^d$;
OR
(ii) —C(O)—Y—$R^6$, wherein Y and $R^6$ are as defined above in (i).

—Y—$R^6$

In some embodiments, $R^2$ is:
(i) —Y—$R^6$, wherein:
  Y is $C_{1-8}$ alkylene, which is optionally substituted with from 1-4 $R^e$; and
  $R^6$ is —OH, C(O)$R^a$, CO$_2R^a$, —CON$^b$R$^c$, —NR$^b$R$^c$, or heteroaryl including from 5-6 ring atoms, wherein from 1-4 ring atoms are each independently selected from N, N($R^f$), O, and S, wherein the heteroaryl is optionally substituted with from 1-3 $R^d$;

In some embodiments, $R^2$ is Y—$R^6$, wherein:
Y is $C_{2-8}$ alkylene, which is optionally substituted with from 1-4 $R^e$; and
$R^6$ is —OH, C(O)$R^a$, CO$_2R^a$; —CONR$^b$R$^c$, —NR$^b$R$^c$, or heteroaryl including from 5-6 ring atoms, wherein from 1-4 ring atoms are each independently selected from N, N($R^f$), O, and S.

In some embodiments, Y is an unbranched $C_{1-8}$ alkylene (e.g., $C_{1-4}$ alkylene), which is optionally substituted with from 1-4 (e.g., 1-2, 1) $R^e$.

In some embodiments, Y is an unbranched $C_{1-8}$ alkylene, which is unsubstituted.

In some embodiments, Y is $CH_2$.

In some embodiments, Y is an unbranched $C_{2-6}$ (e.g., $C_{2-4}$, $C_{2-3}$, $C_2$) alkylene, which is optionally substituted with from 1-4 (e.g., 1-2, 1) $R^e$. In certain embodiments, Y is an unbranched $C_{2-6}$ (e.g., $C_{2-4}$, $C_{2-3}$, $C_2$) alkylene, which is unsubstituted (e.g., $C_2$ alkylene or $C_3$ alkylene; e.g., $C_3$ alkylene).

In other embodiments, Y is branched $C_{3-6}$ (e.g., $C_{4-6}$, $C_{5-6}$) alkylene, which is optionally substituted with from 1-4 (e.g., 1-2, 1) $R^e$. In certain embodiments, Y has the formula, R—CH(CH$_3$)—$R^6$, in which R is $C_{1-4}$ alkylene. In certain embodiments, Y is a branched $C_{2-3}$ alkylene. In certain embodiments, Y is a $C_2$ alkylene with the formula —CH(CH$_3$)—. In certain embodiments, Y is a $C_3$ alkylene with the formula —C(CH$_3$)$_2$—.

In some embodiments, $R^6$ is —OH, CO$_2R^a$; -or —NR$^b$R$^c$.
In some embodiments, $R^6$ is —OH or —NR$^b$R$^c$.
In certain embodiments, $R^6$ is —OH. In certain embodiments, $R^6$ is -OBn. In certain embodiments, $R^6$ is —O($C_{1-4}$ alkyl).

In certain embodiments, $R^6$ is —NR$^b$R$^c$.

In certain of these embodiments, each occurrence of $R^b$ and $R^c$ is independently selected from: H; $R^a$; —C(O)($R^a$), —C(O)O($R^a$), —S(O)$_{1-2}$($R^h$), —C(O)NR'R'', and —S(O)$_{1-2}$(NR'R'').

In certain of these embodiments, each occurrence of $R^b$ and $R^c$ is independently selected from: H; $R^a$; —C(O)($R^a$), —C(O)O($R^a$), and —C(O)NR'R''.

In certain of these embodiments, each occurrence of $R^b$ and $R^c$ is independently selected from: H; $R^a$; —S(O)$_{1-2}$($R^h$), and —S(O)$_{1-2}$(NR'R'').

In certain of these embodiments, each occurrence of $R^b$ and $R^c$ is independently selected from: H; $R^a$; and —C(O)($R^a$).

In certain of these embodiments, one of $R^b$ and $R^c$ is —C(O)($R^a$); and the other is H or $R^a$.

In certain of these embodiments, each occurrence of $R^b$ and $R^c$ is independently selected from: H, $C_{1-4}$ alkyl, and —C(O)($C_{1-4}$ alkyl).

In certain of these embodiments, one of $R^b$ and $R^c$ is —C(O)($C_{1-4}$ alkyl) (e.g., —C(O)CH$_3$); and the other is H or $C_{1-4}$ alkyl (e.g., CH$_2$CH$_3$).

In certain of these embodiments, each occurrence of $R^b$ and $R^c$ is independently selected from: H, $C_{1-4}$ alkyl, —C(O)($C_{1-4}$ alkyl), —C(O)O($C_{1-4}$ alkyl), —S(O)$_{1-2}$($R^h$), —C(O)NR$^j$R$^k$, —OH, and $C_{1-4}$ alkoxy.

In certain of these embodiments, each occurrence of $R^b$ and $R^c$ is independently selected from: H, $C_{1-4}$ alkyl, —C(O)($C_{1-4}$ alkyl), —C(O)O($C_{1-4}$ alkyl), —S(O)$_{1-2}$($R^h$), and —C(O)N$R^j R^k$.

In certain of these embodiments, each occurrence of $R^b$ and $R^c$ is independently selected from: H, $C_{1-4}$ alkyl, and —C(O)($C_{1-4}$ alkyl).

In certain of these embodiments, each occurrence of $R^b$ and $R^c$ is independently selected from: H and $C_{1-4}$ alkyl. For example, $R^6$ can be —NH$_2$, —N(H)($C_{1-4}$ alkyl) (e.g., —NHCH$_3$) or —N($C_{1-4}$ alkyl)$_2$ (e.g., —N(CH$_3$)$_2$).

In certain of these embodiments, each occurrence of $R^b$ and $R^c$ is independently selected from: H and —C(O)($C_{1-4}$ alkyl). For example, one of $R^b$ and $R^c$ is H, and the other is —C(O)($C_{1-4}$ alkyl) (e.g., —C(O)(CH$_3$).

In certain of these embodiments, each occurrence of $R^b$ and $R^c$ is independently selected from: $C_{1-4}$ alkyl and —C(O)($C_{1-4}$ alkyl). For example, one of $R^b$ and $R^c$ is $C_{1-4}$ alkyl (e.g., CH$_3$), and the other is —C(O)($C_{1-4}$ alkyl) (e.g., —C(O)(CH$_3$).

In certain embodiments, $R^6$ is CO$_2 R^a$.

In certain of these embodiments, $R^a$ is $C_{1-6}$ alkyl optionally substituted with —OH, —NH$_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-6}$ alkyl (e.g., CH$_3$ or CH$_2$CH$_3$).

In certain embodiments, $R^6$ is —OH (in certain embodiments, $R^2$ is —CH$_2$CH$_2$CH$_2$OH).

In some embodiments, $R^2$ has formula (R2-A)

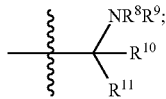

wherein:
$R^8$ and $R^9$, are defined according to (1) or (2) below:
(1):
$R^8$ is independently selected from: H; $C_{1-8}$ (e.g., $C_{1-6}$) alkyl optionally substituted with from 1-2 independently selected $R^e$; —C(O)($R^a$); —C(O)O($R^a$); —S(O)$_{1-2}$($R^h$); —C(O)NR'R"; and —S(O)$_{1-2}$(NR'R");
$R^9$ is independently selected from: H and $C_{1-6}$ alkyl optionally substituted with from 1-2 independently selected $R^e$; and
OR
(2):
$R^8$ and $R^9$, together with the nitrogen atom to which each is attached forms a saturated ring including from 3-10 ring atoms, wherein the ring includes:
(a) from 1-9 ring carbon atoms, each of which is substituted with from 1-2 substituents independently selected from H and $R^g$, and
(b) from 0-3 ring heteroatoms (in addition to the nitrogen atom attached to $R^8$ and $R^9$), each of which is independently selected from N, N($R^f$), O, and S; and
each of $R^{10}$ and $R^{11}$ is independently selected from: H and unsubstituted $C_{1-2}$ alkyl; or $R^{10}$ and $R^{11}$ together with the carbon atom to which each is attached, forms a $C_3$-$C_5$ cycloalkyl, optionally substituted with from 1-4 independently selected $R^g$.

In some embodiments, $R^8$ and $R^9$ are defined according to (1).

In some embodiments, $R^8$ is independently selected from: —C(O)($R^a$); —C(O)O($R^a$); —S(O)$_{1-2}$($R^h$); —C(O)NR'R"; and —S(O)$_{1-2}$(NR'R").

In some embodiments, $R^a$ is $C_{1-6}$ alkyl optionally substituted with from 1-2 independently selected $R^e$.

In certain embodiments, $R^a$ is unsubstituted $C_{1-6}$ alkyl.

In some embodiments, $R^a$ is selected from CH$_3$, CH$_2$CH$_3$, and unsubstituted, unbranched $C_{3-6}$ alkyl. In some embodiments, $R^a$ is CH$_3$ or CH$_2$CH$_3$.

In some embodiments, $R^a$ is unsubstituted, branched $C_{3-6}$ alkyl. In some embodiments, $R^a$ is iso-propyl.

In some embodiments, $R^a$ is —($C_{0-6}$ alkylene)-$C_{3-10}$ cycloalkyl, wherein the cycloalkyl is optionally substituted with from 1-4 independently selected $R^g$;

In some embodiments, $R^a$ is $C_{3-10}$ (e.g., $C_{3-8}$ or $C_{3-6}$) cycloalkyl, wherein the cycloalkyl is optionally substituted with from 1-4 independently selected $R^g$;

In some embodiments, $R^a$ is unsubstituted $C_{3-10}$ (e.g., $C_{3-8}$ or $C_{3-6}$) cycloalkyl. In some embodiments, the cycloalkyl is cyclopropyl.

In some embodiments, $R^a$ is —($C_{0-6}$ alkylene)-heteroaryl including from 5-10 ring atoms, wherein from 1-4 ring atoms are each independently selected from N, N($R^f$), O, and S, wherein the heteroaryl is optionally substituted with from 1-3 independently selected $R^d$.

In some embodiments, $R^a$ is heteroaryl including from 5-10 ring atoms, wherein from 1-4 ring atoms are each independently selected from N, N($R^f$), O, and S, wherein the heteroaryl is optionally substituted with from 1-3 independently selected $R^d$.

In some embodiments, $R^8$ is —S(O)$_{1-2}$($R^h$). In some embodiments, $R^h$ is $C_{1-6}$ alkyl. In some embodiments, $R^h$ is CH$_3$.

In some embodiments, $R^8$ is —C(O)NR'R".

In some embodiments, each of R' and R" is independently selected from: H and $C_{1-4}$ alkyl.

In some embodiments, $R^g$ is unsubstituted $C_{1-6}$ alkyl. In some embodiments, $R^8$ is selected from CH$_3$, CH$_2$CH$_3$, and unsubstituted, unbranched $C_{3-6}$ alkyl. In some embodiments, $R^8$ is CH$_3$ or CH$_2$CH$_3$.

In some embodiments, $R^8$ is H.

In some embodiments, $R^9$ is unsubstituted $C_{1-8}$ alkyl. In some embodiments, $R^9$ is selected from CH$_3$, CH$_2$CH$_3$, and unsubstituted, unbranched $C_{3-6}$ alkyl. In some embodiments, $R^9$ is CH$_3$ or CH$_2$CH$_3$.

In some embodiments, $R^9$ is H.

In some embodiments, $R^8$ and $R^9$ are defined according to (2).

In some embodiments, $R^8$ and $R^9$, together with the nitrogen atom to which each is attached forms a saturated ring including from 4-7 (e.g., 5-6) ring atoms, wherein the ring includes:
(a) from 1-6 (e.g., 1-5) ring carbon atoms, each of which is substituted with from 1-2 substituents independently selected from H and $R^g$, and
(b) from 0-2 ring heteroatoms, each of which is independently selected from N, N($R^f$), O, and S; and
provided that one ring atom is —C(O)—.

In some embodiments, —C($R^{10}$)($R^{11}$)—N$R^8 R^9$ has the following formula:

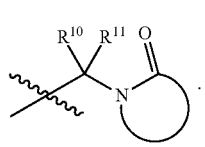

(AA)

In some embodiments, —C(R$^{10}$)(R$^{11}$)—NR$^8$R$^9$ has the following formula:

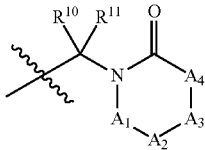

(BB)

wherein:
A$_1$ is a bond, C(O), CH$_2$, CHR$^g$, or C(R$^g$)$_2$;
A$_2$ is C(O), CH$_2$, CHR$^g$, or C(R$^g$)$_2$;
A$_3$ is C(O), CH$_2$, CHR$^g$, or C(R$^g$)$_2$; or N(R$^f$);
A$_4$ is CH$_2$, CHR$^g$, or C(R$^g$)$_2$; or N(R$^f$); provided that both A$_3$ and A$_4$ cannot both be N(R$^f$).

In some embodiments, —C(R$^{10}$)(R$^{11}$)—NR$^8$R$^9$ has the following formula:

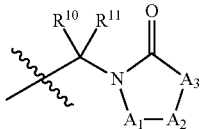

(CC)

wherein:
A$_1$ is a bond, C(O), CH$_2$, CHR$^g$, or C(R$^g$)$_2$;
A$_2$ is C(O), CH$_2$, CHR$^g$, or C(R$^g$)$_2$; and
A$_3$ is CH$_2$, CHR$^g$, or C(R$^g$)$_2$; or N(R$^f$).

In some embodiments, A$_1$ is a bond.
In some embodiments, each of A$_2$ and A$_4$ is independently selected from CH$_2$, CHR$^g$, and C(R$^g$)$_2$.
In some embodiments, each of A$_2$ and A$_4$ is CH$_2$.
In some embodiments, A$_3$ is CH$_2$ or CHR$^g$.
In some embodiments, R$^g$ is C$_{1-4}$ alkyl, —OH, C$_{1-4}$ alkoxy, C$_{1-4}$ haloalkoxy, heteroaryl including from 5-10 ring atoms, wherein from 1-4 ring atoms are each independently selected from N, N(R$^f$), O, and S, wherein the heteroaryl is optionally substituted with from 1-3 R$^m$; and phenyl optionally substituted with from 1-4 R$^m$.
In some embodiments, each of R$^{10}$ and R$^{11}$ is H.
In some embodiments:
R$^8$ is independently selected from: —C(O)(R$^a$); —C(O)O(R$^a$); —S(O)$_{1-2}$(R$^h$); —C(O)NR'R''; and —S(O)$_{1-2}$(NR'R'') (as defined anywhere herein); and R$^9$ is unsubstituted C$_{1-6}$ alkyl (as defined anywhere herein; e.g., CH$_3$, CH$_2$CH$_3$, and unsubstituted, unbranched C$_{3-6}$ alkyl; e.g., CH$_3$, CH$_2$CH$_3$); or
R$^8$ is independently selected from: —C(O)(R$^a$); —C(O)O(R$^a$); —S(O)$_{1-2}$(R$^h$); —C(O)NR'R''; and —S(O)$_{1-2}$(NR'R'') (as defined anywhere herein); and R$^9$ is H; or
R$^8$ is unsubstituted C$_{1-6}$ alkyl (as defined anywhere herein); and R$^9$ is unsubstituted C$_{1-6}$ alkyl (as defined anywhere herein; e.g., CH$_3$, CH$_2$CH$_3$, and unsubstituted, unbranched C$_{3-6}$ alkyl; e.g., CH$_3$, CH$_2$CH$_3$); or
R$^8$ is unsubstituted C$_{1-6}$ alkyl (as defined anywhere herein; e.g., CH$_3$, CH$_2$CH$_3$, and unsubstituted, unbranched C$_{3-6}$ alkyl; e.g., CH$_3$, CH$_2$CH$_3$); and R$^9$ is H; or
R$^8$ is H; and R$^9$ is H.
In some embodiments, R$^8$ is —C(O)(R$^a$) (e.g., R$^a$ is C$_{1-6}$ alkyl optionally substituted with from 1-2 independently selected R$^e$ e.g., R$^e$ is unsubstituted C$_{1-6}$ alkyl; e.g., R$^e$ is selected from CH$_3$, CH$_2$CH$_3$, and unsubstituted, unbranched C$_{3-6}$ alkyl; e.g., R$^e$ is CH$_3$ or CH$_2$CH$_3$).
In some embodiments, each of R$^{10}$ and R$^{11}$ is H.
In some embodiments, R$^2$ is

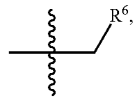

wherein:
R$^6$ is independently selected from: —OH, —O(C$_{1-4}$ alkyl), —CO$_2$R$^a$, —C(O)NR'R'; and heteroaryl including from 5-6 ring atoms, wherein from 1-3 ring atoms are each independently selected from N, N(R$^f$), O, and S, wherein the heteroaryl is optionally substituted with from 1-3 R$^d$;

In certain embodiments, R$^6$ is —OH.
In certain embodiments, R$^6$ is —O(C$_{1-4}$ alkyl). For example, R$^{12}$ is methoxy or ethoxy.
In certain embodiments, R$^6$ is —C(O)R$^a$.
In certain embodiments, R$^a$ is C$_{1-6}$ alkyl optionally substituted with from 1-2 independently selected R$^e$. In certain embodiments, R$^a$ is unsubstituted C$_{1-6}$ alkyl. For example, R$^a$ can be selected from CH$_3$, CH$_2$CH$_3$, and unsubstituted, unbranched C$_{3-6}$ alkyl (e.g., CH$_3$ or CH$_2$CH$_3$). As another example, R$^a$ can be unsubstituted, branched C$_{3-6}$ alkyl (e.g., iso-propyl).
In other embodiments, R$^a$ is —(C$_{0-6}$ alkylene)-C$_{3-10}$ cycloalkyl, wherein the cycloalkyl is optionally substituted with from 1-4 independently selected R$^g$. For example, R$^a$ can be C$_{3-10}$ (e.g., C$_{3-8}$ or C$_{3-6}$) cycloalkyl, wherein the cycloalkyl is optionally substituted with from 1-4 independently selected R$^g$; e.g., R$^a$ can be unsubstituted C$_{3-10}$ (e.g., C$_{3-8}$ or C$_{3-6}$ or C$_{3-5}$ or C$_{3-4}$) cycloalkyl. In each of the foregoing embodiments, the cycloalkyl is cyclopropyl.
In still other embodiments, R$^a$ is —(C$_{0-6}$ alkylene)-heteroaryl including from 5-10 ring atoms, wherein from 1-4 ring atoms are each independently selected from N, N(R$^f$), O, and S, wherein the heteroaryl is optionally substituted with from 1-3 independently selected R$^d$. For example, R$^a$ can be heteroaryl including from 5-10 ring atoms, wherein from 1-3 ring atoms are each independently selected from N, N(R$^f$), O, and S, wherein the heteroaryl is optionally substituted with from 1-3 independently selected R$^d$.
In certain embodiments, R$^6$ is —C(O)NR'R'. In certain of these embodiments, each of R' and R' is independently selected from: H and C$_{1-4}$ alkyl.

—(Y$^1$)$_n$—Y$^2$—(Y$^3$)$_p$—R$^{6'}$

In some embodiments, R$^2$ is —(Y$^1$)$_n$—Y$^2$—(Y$^3$)$_p$—R$^{6'}$, wherein:
each of n and p is independently 0 or 1;
each of Y$^1$ and Y$^3$ is, independently, C$_{1-3}$ alkylene, which is optionally substituted with from 1-2 R$^e$,
Y$^2$ is:
(a) C$_{3-6}$ cycloalkylene optionally substituted with from 1-4 R$^g$,
(b) C$_{6-10}$ arylene, optionally further substituted with from 1-4 R$^d$,
(c) heteroarylene including from 5-10 ring atoms, wherein from 1-4 ring atoms are each independently selected from N, N(R$^f$), O, and S, and which is optionally further substituted with from 1-4 R$^g$, or (d) heterocycloalkylene including from 3-8 ring atoms, wherein from 1-2 ring atoms are each independently selected from N, N($R^f$) and O, and wherein $Y^2$ is optionally further substituted with from 1-4 $R^g$, and $R^{6'}$ is H, —OH, —C(O)$R^a$, —CO$_2R^a$; —CONR'R'', —N$R^bR^c$, or heteroaryl including from 5-6 ring atoms, wherein from 1-4 ring atoms are each independently selected from N, N($R^f$), O, and S, wherein $R^{6'}$ cannot be H when $Y^2$ is $C_{3-6}$ cycloalkylene optionally substituted with from 1-4 $R^g$ or when $Y^2$ is $C_{6-10}$ arylene, optionally substituted with from 1-4 $R^d$.

In some embodiments, $R^2$ is —$(Y^1)_n$—$Y^2$—$(Y^3)_p$—$R^{6'}$, wherein:
each of n and p is independently 0 or 1;
each of $Y^1$ and $Y^3$ is, independently, $C_{1-3}$ alkylene, which is optionally substituted with from 1-2 $R^e$,
$Y^2$ is $C_{3-6}$ cycloalkylene $C_{6-10}$ aryl, heteroaryl including from 5-10 ring atoms, wherein from 1-4 ring atoms are each independently selected from N, N($R^e$), O, and S, or heterocycloalkylene including from 3-8 ring atoms, wherein from 1-2 ring atoms are each independently selected from N, N($R^f$) and oxygen, and wherein $Y^2$ is optionally further substituted with from 1-4 $R^g$, and
$R^{6'}$ is H, —OH, CO$_2R^a$; —CONR$^bR^c$, —N$R^bR^c$, or heteroaryl including from 5-6 ring atoms, wherein from 1-4 ring atoms are each independently selected from N, N($R^f$), O, and S.

In some embodiments, $R^2$ is —$(Y^1)_n$—$Y^2$—$(Y^3)_p$—$R^{6'}$, wherein:
each of n and p is independently 0 or 1;
each of $Y^1$ and $Y^3$ is, independently, $C_{1-3}$ alkylene, which is optionally substituted with from 1-2 $R^e$,
$Y^2$ is $C_{3-6}$ cycloalkylene or heterocycloalkylene including from 3-8 ring atoms, wherein from 1-2 ring atoms are each independently selected from N, N($R^f$) and oxygen, and wherein $Y^2$ is optionally further substituted with from 1-4 R, and
$R^{6'}$ is H, —OH, CO$_2R^a$; —CONR$^bR^c$, —N$R^bR^c$, or heteroaryl including from 5-6 ring atoms, wherein from 1-4 ring atoms are each independently selected from N, N($R^f$), O, and S, wherein $R^{6'}$ cannot be H when $Y^2$ is $C_{3-6}$ cycloalkylene optionally substituted with from 1-4 $R^g$;

In some embodiments, n is 0.

In some embodiments, n is 1. In certain of these embodiments, $Y^1$ is CH$_2$.

In some embodiments, $Y^2$ is $C_{3-6}$ (e.g., $C_{3-5}$, $C_{3-4}$) cycloalkylene optionally substituted with from 1-4 $R^g$. In certain embodiments, p is 0. In certain embodiments, p is 1; in certain of these embodiments, $Y^3$ is $C_{1-2}$ alkylene.

In some embodiments, $Y^2$ is $C_{6-10}$ aryl (e.g., phenyl).

In some embodiments, $Y^2$ is heteroaryl including from 5-10 ring atoms, wherein from 1-4 ring atoms are each independently selected from N, N($R^e$), O, and S.

In some embodiments, $Y^2$ is pyrrole, pyrazole, 1,2,3-triazole, thiophene, or thiazole.

In some embodiments, $Y^2$ is heterocycloalkylene including from 3-8 (e.g., 5-8, 6-8, 7-8, 4-6, 5-6) ring atoms, wherein from 1-2 (e.g., 1) ring atoms are each independently selected from N, N($R^f$), and oxygen, and wherein $Y^2$ is optionally further substituted with from 1-4 $R^g$.

In some embodiments, $Y^2$ is heterocycloalkylene including from 3-8 ring atoms, wherein from 1-2 ring atoms are each independently selected from N and N($R^f$), and wherein $Y^2$ is optionally further substituted with from 1-4 $R^g$.

In some embodiments, $Y^2$ is heterocycloalkylene including from 3-8 ring atoms, wherein 1 ring atom is N($R^f$), and wherein $Y^2$ is optionally further substituted with from 1-4 $R^g$.

In some embodiments, $Y^2$ is heterocycloalkylene including from 3-8 ring atoms, wherein 1 ring atom is N, and wherein $Y^2$ is optionally further substituted with from 1-4 $R^g$.

In some embodiments, $Y^2$ is heterocycloalkylene including from 3-6 (e.g., 4-6, 5-6) ring atoms, wherein from 1-2 (e.g., 1) ring atoms are each independently selected from N, N($R^f$), and oxygen, and wherein $Y^2$ is optionally further substituted with from 1-4 $R^g$.

In certain embodiments, $Y^2$ is heterocycloalkylene including from 3-6 (e.g., 4-6, 5-6) ring atoms, wherein from 1-2 ring atoms are each independently selected from N and N($R^f$), and wherein $Y^2$ is optionally further substituted with from 1-4 $R^g$.

In certain embodiments, $Y^2$ is heterocycloalkylene including from 3-6 (e.g., 4-6, 5-6) ring atoms, wherein 1 ring atom is N($R^f$), and wherein $Y^2$ is optionally further substituted with from 1-4 $R^g$.

In certain embodiments, $Y^2$ is heterocycloalkylene including from 3-6 (e.g., 4-6, 5-6) ring atoms, wherein 1 ring atom is N, and wherein $Y^2$ is optionally further substituted with from 1-4 $R^g$. In certain of these embodiments, the ring atom N is attached to Y, when present, or the 5-membered heteroaromatic ring of formula (I). In other of these embodiments, the ring atom N is attached to $Y^3$, when present, or $R^6$. In certain embodiments, p is 0. In certain embodiments, p is 1; in certain of these embodiments, $Y^3$ is $C_{2-3}$ alkylene. In still other embodiments, the ring atom N is attached to the imidazole ring of formula (I). In still other embodiments, the ring atom N is attached to $R^6$. In another embodiment, n is 0, p is 0, and the ring atom N is attached to $R^6$.

In some embodiments, each occurrence of $R^f$ is independently selected from H; $C_{1-4}$ alkyl; $C_{3-6}$ cycloalkyl; and phenyl; wherein each $C_{1-4}$ alkyl is optionally substituted with from 1-2 independently selected $R^e$; each $C_{3-6}$ cycloalkyl is optionally substituted with from 1-2 independently selected $R^g$; and each phenyl is optionally substituted with from 1-2 independently selected $R^d$.

In some —$(Y^1)_n$—$Y^2$—$(Y^3)_p$—$R^{6'}$ embodiments, $R^{6'}$ can be as defined above in conjunction with variable Y. In certain embodiments, $R^{6'}$ can be H.

In some embodiments, $Y^2$ is further substituted with from 1-4 $R^g$.

In some embodiments, $Y^2$ is further substituted with from 1-2 $R^g$.

In some embodiments, each occurrence of $R^9$ is independently selected from: $C_{1-6}$ alkyl optionally substituted with from 1-2 independently selected $R^e$; $C_{1-4}$ haloalkyl; oxo; heteroaryl including from 5-10 ring atoms, wherein from 1-4 ring atoms are each independently selected from N, N($R^f$), O, and S, wherein the heteroaryl is optionally substituted with from 1-3 $R^m$; and phenyl optionally substituted with from 1-4 $R^m$.

In some embodiments, one $R^g$ is oxo.

In certain embodiments, p is 0.

In certain embodiments, p is 1.

In some embodiments, $Y^3$ is $C_{2-3}$ alkylene.

In some embodiments, $Y^2$ is $C_{3-6}$ cycloalkylene optionally substituted with from 1-4 $R^g$.

In certain embodiments, p is 0.

In certain embodiments, p is 1.

In some embodiments, $Y^3$ is $C_{1-2}$ alkylene.

In some embodiments, $Y^2$ is $C_{6-10}$ arylene (e.g., phenylene).

In certain embodiments, p is 0.

In certain embodiments, p is 1.

In some embodiments, $Y^3$ is $C_{2-3}$ alkylene.

In some embodiments, $Y^2$ is heteroarylene including from 5-10 ring atoms, wherein from 1-4 ring atoms are each independently selected from N, $N(R^e)$, O, and S.

In some embodiments, $Y^2$ is pyrrolylene, pyrazolylene, 1,2,3-triazolylene, thienylene, or thiazolylene.

In certain embodiments, p is 0.

In certain embodiments, p is 1.

In some embodiments, $Y^3$ is $C_{2-3}$ alkylene.

In some embodiments, $R^{6'}$ is H, —OH, $CO_2R^a$; -or —$NR^bR^c$.

In some embodiments, $R^{6'}$ is H.

In some embodiments, $R^{6'}$ is $CO_2R'$.

In some embodiments, $R^a$ is $C_{1-6}$ alkyl optionally substituted with —OH, —$NH_2$, —$NH(C_{1-3}$ alkyl), —$N(C_{1-3}$ alkyl$)_2$, —N(H)(C(=O)$C_{1-3}$ alkyl), or cyano.

In some embodiments, $R^a$ is unsubstituted $C_{1-6}$ alkyl.

In some embodiments, $R^a$ is $CH_3$ or $CH_2CH_3$.

In some embodiments, $R^{6'}$ is —OH.

In some embodiments, $R^{6'}$ is —$NR^bR^c$.

In some embodiments, each occurrence of $R^b$ and $R^c$ is independently selected from: H; $R^a$; and —C(O)($R^a$).

In some embodiments, one of $R^b$ and $R^c$ is —C(O)($R^a$); and the other is H or $R^a$.

In some embodiments, each occurrence of $R^b$ and $R^c$ is independently selected from: H, $C_{1-4}$ alkyl, and —C(O)($C_{1-4}$ alkyl).

In some embodiments, one of $R^b$ and $R^c$ is —C(O)($C_{1-4}$ alkyl) (e.g., —C(O)$CH_3$); and the other is H or $C_{1-4}$ alkyl (e.g., $CH_2CH_3$).

In some embodiments, $R^{6'}$ is —OH.

In some embodiments, $R^{6'}$ is —$NR^bR^c$.

In some embodiments, each occurrence of $R^b$ and $R^c$ is independently selected from: H; $R^a$; and —C(O)($R^a$).

In some embodiments, one of $R^b$ and $R^c$ is —C(O)($R^a$); and the other is H or $R^a$.

In some embodiments, each occurrence of $R^b$ and $R^c$ is independently selected from: H, $C_{1-4}$ alkyl, and —C(O)($C_{1-4}$ alkyl).

In some embodiments, one of $R^b$ and $R^c$ is —C(O)($C_{1-4}$ alkyl) (e.g., —C(O)$CH_3$); and the other is H or $C_{1-4}$ alkyl (e.g., $CH_2CH_3$).

—$Z^1$—$Z^2$—$Z^3$—$R^7$

In some embodiments, $R^2$ is —$Z^1$—$Z^2$—$Z^3$—$R^7$, wherein:

$Z^1$ is $C_{1-3}$ alkylene, which is optionally substituted with from 1-6 F, $Z^2$ is —N($R^f$)—, —O—, or —S—;

$Z^3$ is $C_{2-5}$ alkylene, which is optionally substituted with from 1-6 F, and $R^7$ is —OH, —C(O)$R^a$, $CO_2R^a$; —CONR'R", —$NR^bR^c$, or heteroaryl including from 5-10 ring atoms, wherein from 1-4 ring atoms are each independently selected from N, $N(R^f)$, O, and S, wherein the heteroaryl is optionally substituted with from 1-3 $R^d$.

In some embodiments, $R^2$ is —$Z^1$—$Z^2$—$Z^3$—$R^7$, wherein:

$Z^1$ is an unbranched or branched $C_{1-3}$ alkylene, which is optionally substituted with from 1-6 F, $Z^2$ is —N($R^f$)—, —O—, or —S—;

$Z^3$ is an unbranched or branched $C_{2-5}$ alkylene, which is optionally substituted with from 1-6 F, and $R^7$ is —OH, —C(O)$R^a$, $CO_2R^a$; —CONR$^b$R$^c$, —$NR^bR^c$, or heteroaryl including from 5-6 ring atoms, wherein from 1-4 ring atoms are each independently selected from N, $N(R^f)$, O, and S;

In some embodiments, $Z^1$ is $CH_2$.

In some embodiments, $Z^2$ is —O—, or —S— (e.g., —O—).

In some embodiments, $Z^2$ is —N($R^f$)—. For example, $Z^2$ can be —NH—, —N($C_{1-4}$ alkyl)-, or —NC(O)($C_{1-4}$ alkyl)- (e.g., —NC(O)($CH_3$)—).

In some embodiments, $Z^3$ is $C_{2-3}$ alkylene.

In some embodiments, $R^7$ is —OH, $CO_2R^a$; -or —$NR^bR^c$.

In certain embodiments, $R^7$ is —$NR^bR^c$.

In certain of these embodiments, each occurrence of $R^b$ and $R^c$ is independently selected from: H; $R^a$; —C(O)($R^a$), —C(O)O($R^a$), —S(O)$_{1-2}$($R^h$), —C(O)NR'R", and —S(O)$_{1-2}$(NR'R").

In certain of these embodiments, each occurrence of $R^b$ and $R^c$ is independently selected from: H; $R^a$; —C(O)($R^a$), —C(O)O($R^a$), and —C(O)NR'R".

In certain of these embodiments, each occurrence of $R^b$ and $R^c$ is independently selected from: H; $R^a$; —S(O)$_{1-2}$($R^h$), and —S(O)$_{1-2}$(NR'R").

In certain of these embodiments, each occurrence of $R^b$ and $R^c$ is independently selected from: H; $R^a$; and —C(O)($R^a$).

In certain of these embodiments, one of $R^b$ and $R^c$ is —C(O)($R^a$); and the other is H or $R^a$.

In certain of these embodiments, each occurrence of $R^b$ and $R^c$ is independently selected from: H, $C_{1-4}$ alkyl, and —C(O)($C_{1-4}$ alkyl).

In certain of these embodiments, one of $R^b$ and $R^c$ is —C(O)($C_{1-4}$ alkyl) (e.g., —C(O)$CH_3$); and the other is H or $C_{1-4}$ alkyl (e.g., $CH_2CH_3$).

In certain of these embodiments, each occurrence of $R^b$ and $R^c$ is independently selected from: $C_{1-4}$ alkyl and —C(O)($C_{1-4}$ alkyl). For example, one of $R^b$ and $R^c$ is $C_{1-4}$ alkyl (e.g., $CH_3$), and the other is —C(O)($C_{1-4}$ alkyl) (e.g., —C(O)($CH_3$)).

In certain embodiments, $R^7$ is $CO_2R^a$.

In certain of these embodiments, $R^a$ is $C_{1-6}$ alkyl optionally substituted with —OH, —$NH_2$, —$NH(C_{1-3}$ alkyl), —$N(C_{1-3}$ alkyl$)_2$, —N(H)(C(=O)$C_{1-3}$ alkyl), or cyano.

In certain of these embodiments, $R^a$ is unsubstituted $C_{1-6}$ alkyl (e.g., $CH_3$ or $CH_2CH_3$).

In certain embodiments, $R^7$ is —OH.

Variables $R^3$ and $R^4$

In some embodiments, one of $R^3$ and $R^4$ is hydrogen, and the other is a substituent other than hydrogen.

In some embodiments, $R^3$ is hydrogen, and $R^4$ is hydrogen.

In some embodiments, one of $R^3$ and $R^4$ (e.g., $R^3$) is:

(ii) halo;

(iii) cyano;

(vi) $C_{1-4}$ alkyl, optionally substituted with from 1-2 independently selected $R^e$;

(vii) $C_{1-4}$ haloalkyl;

(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, $N(R^f)$, O, or S;

(xi) $Y^4$—($C_{1-3}$ alkylene)$_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;

(xii) $Y^4$—$(C_{1-3}$ alkylene$)_y$-$C_{6-10}$ aryl optionally substituted with from 1-4 $R^d$, wherein y is 0 or 1; and $Y^4$ is a bond, N($R^f$), O, or S;

(xiii) $Y^4$—$(C_{1-3}$ alkylene$)_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$)O, or S;

and the other (e.g., $R^4$) is H.

In some embodiments, one of $R^3$ and $R^4$ (e.g., $R^3$) is $Y^4$—$(C_{1-3}$ alkylene$)_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S; and the other (e.g., $R^4$) is H.

In some embodiments, $Y^4$ is a bond.
In some embodiments, $Y^4$ is S.
In some embodiments, y is 0.
In some embodiments, y is 1.

In some embodiments, one of $R^3$ and $R^4$ (e.g., $R^3$) is heteroaryl including from 5-10 ring atoms, wherein from 1-4 ring atoms are each independently selected from N, N($R^f$), O, and S, wherein the heteroaryl is optionally substituted with from 1-3 $R^d$;
and the other (e.g., $R^4$) is H.

In some embodiments, one of $R^3$ and $R^4$ (e.g., $R^3$) is heteroaryl including from 5-6 ring atoms, wherein from 1-4 ring atoms are each independently selected from N, N($R^f$), O, and S, wherein the heteroaryl is optionally substituted with from 1-2 $R^d$; and the other (e.g., $R^4$) is H.

In some embodiments, one of $R^3$ and $R^4$ (e.g., $R^3$) is heteroaryl including from 5-6 ring atoms, wherein from 1-4 ring atoms are each independently selected from N and N($R^f$), wherein the heteroaryl is optionally substituted with from 1-2 $R^d$; and the other (e.g., $R^4$) is H.

In some embodiments, one of $R^3$ and $R^4$ (e.g., $R^3$) is pyrrolyl, imidazolyl, pyrazolyl, triazolyl, pyridyl, pyrimidinyl, or pyrazinyl, wherein each is optionally substituted with from 1-2 $R^g$; and the other (e.g., $R^4$) is H.

In some embodiments, one of $R^3$ and $R^4$ (e.g., $R^3$) is pyrrolyl, imidazolyl, pyrazolyl, or triazolyl, wherein each is optionally substituted with from 1-2 $R^g$; and the other (e.g., $R^4$) is H.

In some embodiments, one of $R^3$ and $R^4$ (e.g., $R^3$) is pyrazolyl, optionally substituted with from 1-2 $R^g$; and the other (e.g., $R^4$) is H.

In some embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^g$; and the other (e.g., $R^4$) is H.

In some embodiments, one of $R^3$ and $R^4$ (e.g., $R^3$) is C-linked-pyrazolyl, C-linked pyrrolyl (e.g., 3-pyrrolyl), C-linked imidazolyl, C-linked triazolyl, or C-linked tetrazolyl, optionally substituted with from 1-2 $R^g$; and the other (e.g., $R^4$) is H.

In some embodiments, one of $R^3$ and $R^4$ (e.g., $R^3$) is $Y^4$—$(C_{1-3}$ alkylene$)_y$-$C_{6-10}$ aryl optionally substituted with from 1-4 $R^d$, wherein y is 0 or 1; and $Y^4$ is a bond, N($R^f$), O, or S; and the other (e.g., $R^4$) is H.

In some embodiments, one of $R^3$ and $R^4$ (e.g., $R^3$) is $Y^4$—$(C_{1-3}$ alkylene$)_y$-heterocyclyl including from 5-8 ring atoms, wherein from 1-3 ring atoms are each independently selected from N($R^f$), O, and S, wherein the heterocyclyl is optionally substituted with from 1-4 independently selected $R^d$, wherein y is 0 or 1; and $Y^4$ is a bond, N($R^f$), O, or S Variable $R^1$ In some embodiments, $R^1$ is hydrogen.
In some embodiments, $R^1$ is X—$R^5$.

In certain embodiments, X is optionally substituted $C_{1-10}$ alkylene. In other embodiments, X is unsubstituted $C_{1-10}$ alkylene. In certain of the foregoing embodiments, X is unbranched. In other of the foregoing embodiments, X is branched.

In certain embodiments, X is an unbranched $C_{1-6}$ alkylene, and $R^5$ is hydrogen, —OH, $C_{1-4}$ alkoxy, —$C_{1-4}$ haloalkoxy, $CO_2R^a$; —CONR'R', cyano, or —$NR^bR^c$.

In certain embodiments, X is an unbranched chain $C_{2-4}$ alkylene. In some embodiments, X is an unbranched chain $C_{5-6}$ alkylene.

In some embodiments, $R^5$ is —OH, $C_{1-4}$ alkoxy, —$C_{1-4}$ haloalkoxy, $CO_2R^a$; or —$NR^bR^c$.

In certain embodiments, $R^5$ is —OH, $C_{1-4}$ alkoxy, —$C_{1-4}$ haloalkoxy, or $CO_2R^a$.

In certain embodiments, $R^5$ is $C_{1-4}$ alkoxy or —$C_{1-4}$ haloalkoxy (e.g., $C_{1-4}$ alkoxy, e.g., $OCH_3$).

In certain embodiments, $R^5$ is $CO_2R^a$.

In some embodiments, $R^5$ is H. In certain of these embodiments, $R^1$ is unsubstituted $C_{1-2}$ alkyl (e.g., $CH_3$).

In certain of these embodiments, $R^a$ is $C_{1-6}$ alkyl optionally substituted with —OH, —$NH_2$, —NH($C_{1-3}$ alkyl), —N($C_{1-3}$ alkyl)$_2$, —N(H)(C(=O)$C_{1-3}$ alkyl), or cyano.

In certain of these embodiments, $R^a$ is unsubstituted $C_{1-6}$ alkyl (e.g., $CH_3$ or $CH_2CH_3$).

In some embodiments, $R^1$ is:
(iii) ($C_{1-3}$ alkylene)-aryl, wherein the aryl is optionally substituted with from 1-3 $R^d$; or
(iv) ($C_{1-3}$ alkylene)heteroaryl including from 5-6 ring atoms, wherein from 1-4 ring atoms are each independently selected from N, N($R^f$), O, and S, and wherein the heteroaryl is optionally substituted with from 1-3 $R^d$.

In certain embodiments, $R^1$ is ($C_{1-3}$ alkylene)aryl, wherein the aryl is optionally substituted with from 1-3 (e.g., 2, 1) $R^d$.

In certain embodiments, $R^1$ is ($C_{1-3}$ alkylene)phenyl, wherein the phenyl is optionally substituted with from 1-3 (e.g., 2, 1) $R^d$.

In certain embodiments, $R^1$ is ($C_{1-3}$ alkylene)aryl, wherein the aryl is substituted with from 1-3 (e.g., 2, 1) $R^d$.

In certain embodiments, $R^1$ is ($C_{1-3}$ alkylene)phenyl, wherein the phenyl is substituted with from 1-3 (e.g., 2, 1) $R^d$.

In certain embodiments, $R^1$ is ($C_{1-3}$ alkylene)phenyl, wherein the phenyl is substituted with 1 $R^d$.

In certain of these embodiments, $R^d$, or at least one $R^d$ is $C_{1-6}$ (e.g., $C_{1-4}$, $C_{1-3}$, $C_{1-2}$, $C_1$) alkyl optionally substituted with from 1-2 substituents independently selected from —OH, $C_{1-4}$ alkoxy, $C_{1-4}$ haloalkoxy, —C(=O)O($C_{1-4}$ alkyl); —CON(R')(R''), cyano, and —$NR^jR^k$.

In certain of these embodiments, $R^d$, or at least one $R^d$ is $C_{1-6}$ (e.g., $C_{1-4}$, $C_{1-3}$, $C_{1-2}$, $C_1$) alkyl substituted with from 1-2 substituents independently selected from —OH, $C_{1-4}$ alkoxy, $C_{1-4}$ haloalkoxy, —C(=O)O($C_{1-4}$ alkyl); —CONR'R', cyano, and —$NR^jR^k$. By way of example, $R^d$ can be —$CH_2NR^jR^k$, e.g., —$CH_2NH_2$.

Non-Limiting Combinations

[1] In some embodiments:
W' is $R^2$;
$R^2$ is Y—$R^6$, wherein:
Y is $C_{1-8}$ alkylene, which is optionally substituted with from 1-4 $R^e$; and $R^6$ is —OH, $CO_2R^a$; —CONR'R", —$NR^bR^c$, or heteroaryl including from 5-6 ring atoms, wherein from 1-4 ring atoms are each independently selected from N, $N(R^f)$, O, and S, wherein the heteroaryl is optionally substituted with from 1-3 $R^d$; and W is hydrogen.

In some of these embodiments, each of $R^3$ and R is independently selected from:
(i) H;
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, $N(R^f)$, O, or S;
(xi) $Y^4$—($C_{1-3}$ alkylene)$_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, $N(R^f)$, O, or S;
(xiii) $Y^4$—($C_{1-3}$ alkylene)$_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S; and
(vii) $C_{1-4}$ haloalkyl.

In some embodiments, one of $R^3$ and $R^4$ (e.g., $R^3$) is:
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, $N(R^f)$, O, or S;
(xi) $Y^4$—($C_{1-3}$ alkylene)$_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, $N(R^f)$, O, or S;
(xiii) $Y^4$—($C_{1-3}$ alkylene)$_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S; and
(vii) $C_{1-4}$ haloalkyl; and the other (e.g., $R^4$) is H.

In some embodiments, one of $R^3$ and $R^4$ (e.g., $R^3$) is —($C_{1-3}$ alkylene)$_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline.

In certain embodiments, one of $R^3$ and $R^4$ (e.g., $R^3$) is heteroaryl including from 5-6 ring atoms, wherein from 1-4 ring atoms are each independently selected from N, $N(R^f)$, O, and S, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from N and $N(R^f)$, wherein the heteroaryl is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^d$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^d$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^d$; and the other (e.g., $R^4$) is H. In certain embodiments, one of $R^3$ and $R^4$ (e.g., $R^3$) is pyrazolyl, optionally substituted with from 1-2 $R^d$; and the other (e.g., $R^4$) is H.

In certain embodiments, one of $R^3$ and $R^4$ (e.g., $R^3$) is C-linked pyrazolyl, optionally substituted with from 1-2 $R^d$; and the other (e.g., $R^4$) is H.

In certain embodiments, one of $R^3$ and $R^4$ (e.g., $R^3$) is N-linked pyrazolyl, optionally substituted with from 1-2 $R^d$; and the other (e.g., $R^4$) is H.

In some embodiments, one of $R^3$ and $R^4$ (e.g., $R^3$) is —($C_{1-3}$ alkylene)$_y$-$C_{6-10}$ aryl, wherein the aryl is optionally substituted with from 1-3 $R^d$, wherein y is 0 or 1; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^d$, wherein y is 0 or 1; and the other (e.g., $R^4$) is H.

In some embodiments, one of $R^3$ and $R^4$ (e.g., $R^3$) is —($C_{1-3}$ alkylene)$_y$-heterocyclyl including from 3-10 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from $N(R^f)$, O, and S, wherein the heterocyclyl is optionally substituted with from 1-4 independently selected $R^g$ (e.g., oxo), and the other (e.g., $R^4$) is H.

[2] In some embodiments:

W is $R^2$;

$R^2$ is Y—$R^6$, wherein:
  Y is $C_{1-8}$ alkylene, which is optionally substituted with from 1-4 $R^e$; and
  $R^6$ is —OH, $CO_2R^a$; —CONR'R", —$NR^bR^c$, or heteroaryl including from 5-6 ring atoms, wherein from 1-4 ring atoms are each independently selected from N, N($R^f$), O, and S; and W' is H.

In some embodiments, each of $R^3$ and $R^4$ is independently selected from:
(i) H;
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, N($R^f$), O, or S;
(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;
(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;
and
(vii) $C_{1-4}$ haloalkyl.

In some embodiments, one of $R^3$ and $R^4$ (e.g., $R^3$) is:
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, N($R^f$), O, or S;
(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;
(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;
and
(vii) $C_{1-4}$ haloalkyl; and the other (e.g., $R^4$) is H.

In some embodiments, one of $R^3$ and $R^4$ (e.g., $R^3$) is —($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from N, N($R^f$), O, and S, wherein the heteroaryl is optionally substituted with from 1-3 $R^d$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline.

In certain embodiments, one of $R^3$ and $R^4$ (e.g., $R^3$) is heteroaryl including from 5-6 ring atoms, wherein from 1-4 ring atoms are each independently selected from N, N($R^f$), O, and S, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from N and N($R^f$), wherein the heteroaryl is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^d$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^d$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^d$; and the other (e.g., $R^4$) is H. In certain embodiments, one of $R^3$ and $R^4$ (e.g., $R^3$) is pyrazolyl, optionally substituted with from 1-2 $R^d$; and the other (e.g., $R^4$) is H.

In certain embodiments, one of $R^3$ and $R^4$ (e.g., $R^3$) is C-linked pyrazolyl, optionally substituted with from 1-2 $R^d$; and the other (e.g., $R^4$) is H.

In certain embodiments, one of $R^3$ and $R^4$ (e.g., $R^3$) is N-linked pyrazolyl, optionally substituted with from 1-2 $R^d$; and the other (e.g., $R^4$) is H.

In some embodiments, one of $R^3$ and $R^4$ (e.g., $R^3$) is —($C_{1-3}$ alkylene)$_y$-$C_{6-10}$ aryl, wherein the aryl is optionally substituted with from 1-3 $R^d$, wherein y is 0 or 1; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^d$; and the other (e.g., $R^4$) is H.

In some embodiments, one of $R^3$ and $R^4$ (e.g., $R^3$) is —($C_{1-3}$ alkylene)$_y$-heterocyclyl including from 3-10 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from $N(R^f)$, O, and S, wherein the heterocyclyl is optionally substituted with from 1-4 independently selected $R^g$ (e.g., oxo), and the other (e.g., $R^4$) is H.

[3] In some embodiments:
W' is $R^2$;
$R^2$ is $-(Y^1)_n-Y^2-(Y^3)_p-R^{6'}$, wherein:
  each of n and p is independently 0 or 1;
  each of $Y^1$ and $Y^3$ is, independently, $C_{1-3}$ alkylene, which is optionally substituted with from 1-2 $R^e$,
  $Y^2$ is $C_{3-6}$ cycloalkylene or heterocycloalkylene including from 3-8 ring atoms, wherein from 1-2 ring atoms are each independently selected from N, $N(R^f)$ and O, and wherein $Y^2$ is optionally further substituted with from 1-4 $R^g$, and
  $R^{6'}$ is $-OH$, $CO_2R^a$; $-CONR'R''$, $-NR^bR^c$, or heteroaryl including from 5-6 ring atoms, wherein from 1-4 ring atoms are each independently selected from N, $N(R^f)$, O, and S;
and W is hydrogen.

[4] In some embodiments:
W is $R^2$;
$R^2$ is $-(Y^1)_n-Y^2-(Y^3)_p-R^{6'}$, wherein:
  each of n and p is independently 0 or 1;
  each of $Y^1$ and $Y^3$ is, independently, $C_{1-3}$ alkylene, which is optionally substituted with from 1-2 $R^e$,
  $Y^2$ is $C_{3-6}$ cycloalkylene or heterocycloalkylene including from 3-8 ring atoms, wherein from 1-2 ring atoms are each independently selected from N, $N(R^f)$ and oxygen, and wherein $Y^2$ is optionally further substituted with from 1-4 $R^g$, and
  $R^{6'}$ is H, $-OH$, $CO_2R^a$; $-CONR'R''$, $-NR^bR^c$, or heteroaryl including from 5-6 ring atoms, wherein from 1-4 ring atoms are each independently selected from N, $N(R^f)$, O, and S, wherein $R^{6'}$ cannot be H when $Y^2$ is $C_{3-6}$ cycloalkylene optionally substituted with from 1-4 $R^g$;
and W' is hydrogen.

In some embodiments of combination [3] and [4], each of $R^3$ and $R^4$ is independently selected from:
(i) H;
(ii) halo;
(iii) cyano;
(x) $Y^4-(C_{1-3}$ alkylene$)_y-C_{5-8}$ cycloalkyl, wherein the cycloalkyl is optionally substituted with from 1-4 independently selected $R^g$ wherein y is 0 or 1; and $Y^4$ is a bond, $N(R^f)$, O, or S;
(xi) $Y^4-(C_{1-3}$ alkylene$)_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
(xii) $Y^4-(C_{1-3}$ alkylene$)_y-C_{6-10}$ aryl optionally substituted with from 1-4 $R^d$, wherein y is 0 or 1; and $Y^4$ is a bond, $N(R^f)$, O, or S;
(xiii) $Y^4-(C_{1-3}$ alkylene$)_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S;
and
(vii) $C_{1-4}$ haloalkyl.

In some embodiments, one of $R^3$ and $R^4$ (e.g., $R^3$) is:
(ii) halo;
(iii) cyano;
(x) $Y^4-(C_{1-3}$ alkylene$)_y-C_{5-8}$ cycloalkyl, wherein the cycloalkyl is optionally substituted with from 1-4 independently selected $R^g$ wherein y is 0 or 1; and $Y^4$ is a bond, $N(R^f)$, O, or S;
(xi) $Y^4-(C_{1-3}$ alkylene$)_y$-heterocyclyl including from 5-8 ring atoms, wherein from 1-3 ring atoms are each independently selected from $N(R^f)$, O, and S, wherein the heterocyclyl is optionally substituted with from 1-4 independently selected $R^g$, wherein y is 0 or 1; and $Y^4$ is a bond, $N(R^f)$, O, or S;
(xii) $Y^4-(C_{1-3}$ alkylene$)_y-C_{6-10}$ aryl optionally substituted with from 1-4 $R^d$, wherein y is 0 or 1; and $Y^4$ is a bond, $N(R^f)$, O, or S;
(xiii) $Y^4-(C_{1-3}$ alkylene$)_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and $Y^4$ is a bond, $N(R^f)$, O, or S;
and
(vii) $C_{1-4}$ haloalkyl; and the other (e.g., $R^4$) is H.

In some embodiments, one of $R^3$ and $R^4$ (e.g., $R^3$) is $-(C_{1-3}$ alkylene$)_y$-heteroaryl including from 5-10 ring atoms, wherein from 1-4 ring atoms are each independently selected from N, $N(R^f)$, O, and S, wherein the heteroaryl is optionally substituted with from 1-3 $R^d$, wherein y is 0 or 1; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from N, $N(R^f)$, O, and S, wherein the heteroaryl is optionally substituted with from 1-3 $R^d$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline.

In certain embodiments, one of $R^3$ and $R^4$ (e.g., $R^3$) is heteroaryl including from 5-6 ring atoms, wherein from 1-4 ring atoms are each independently selected from N, $N(R^f)$, O, and S, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from N and $N(R^f)$, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including 5 ring atoms, wherein from 1 ring atom is independently selected from O and S (e.g., S), wherein the heteroaryl is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^d$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^d$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^d$; and the other (e.g., $R^4$) is H. In certain embodiments, one of $R^3$ and $R^4$ (e.g., $R^3$) is pyrazolyl, optionally substituted with from 1-2 $R^d$; and the other (e.g., $R^4$) is H.

In certain embodiments, one of $R^3$ and $R^4$ (e.g., $R^3$) is C-linked pyrazolyl, optionally substituted with from 1-2 $R^d$; and the other (e.g., $R^4$) is H.

In certain embodiments, one of $R^3$ and $R^4$ (e.g., $R^3$) is N-linked pyrazolyl, optionally substituted with from 1-2 $R^d$; and the other (e.g., $R^4$) is H.

In certain embodiments, one of $R^3$ and $R^4$ (e.g., $R^3$) is furyl or thienyl, optionally substituted with from 1-2 $R^d$; and the other (e.g., $R^4$) is H.

In certain embodiments, one of $R^3$ and $R^4$ (e.g., $R^3$) is thienyl, optionally substituted with from 1-2 $R^d$; and the other (e.g., $R^4$) is H.

In some embodiments, one of $R^3$ and $R^4$ (e.g., $R^3$) is —($C_{1-3}$ alkylene)$_y$-$C_{6-10}$ aryl, wherein the aryl is optionally substituted with from 1-3 $R^d$, wherein y is 0 or 1; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^d$; and the other (e.g., $R^4$) is H.

In some embodiments, one of $R^3$ and $R^4$ (e.g., $R^3$) is —($C_{1-3}$ alkylene)$_y$-heterocyclyl including from 3-10 ring atoms, wherein from 1-3 ring atoms are each independently selected from N($R^f$), O, and S, wherein the heterocyclyl is optionally substituted with from 1-4 independently selected $R^g$, wherein y is 0 or 1; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from N($R^1$), O, and S, wherein the heterocyclyl is optionally substituted with from 1-4 independently selected $R^g$ (e.g., oxo), and the other (e.g., $R^4$) is H.

[5] In some embodiments:
W' is $R^2$;
$R^2$ has formula ($R^2$-A)

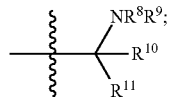

wherein:
$R^8$ and $R^9$, are defined according to (1) or (2) below:
(1):
$R^8$ is independently selected from: H; $C_{1-8}$ (e.g., $C_{1-6}$) alkyl optionally substituted with from 1-2 independently selected $R^e$; —C(O)($R^a$); —C(O)O($R^a$); —S(O)$_{1-2}$($R^h$); —C(O)NR'R"; and —S(O)$_{1-2}$(NR'R");

$R^9$ is independently selected from: H and $C_{1-6}$ alkyl optionally substituted with from 1-2 independently selected $R^e$; and

OR (2):
$R^8$ and $R^9$, together with the nitrogen atom to which each is attached forms a saturated ring including from 3-10 ring atoms, wherein the ring includes:
(a) from 1-9 ring carbon atoms, each of which is substituted with from 1-2 substituents independently selected from H and $R^g$, and
(b) from 0-3 ring heteroatoms (in addition to the nitrogen atom attached to $R^8$ and $R^9$), each of which is independently selected from N, N($R^f$), O, and S; and each of $R^{10}$ and $R^{11}$ is independently selected from: H and unsubstituted $C_{1-2}$ alkyl; or $R^{10}$ and $R^{11}$ together with the carbon atom to which each is attached, forms a $C_3$-$C_5$ cycloalkyl, optionally substituted with from 1-4 independently selected $R^g$;
and W is hydrogen.

[6] In some embodiments:
W is $R^2$;
$R^2$ has formula ($R^2$-A)

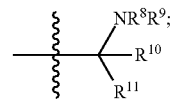

wherein:
$R^8$ and $R^9$, are defined according to (1) or (2) below:
(1):
$R^8$ is independently selected from: H; $C_{1-8}$ (e.g., $C_{1-6}$) alkyl optionally substituted with from 1-2 independently selected R; —C(O)($R^a$); —C(O)O($R^a$); —S(O)$_{1-2}$($R^h$); —C(O)NR'R"; and —S(O)$_{1-2}$(NR'R");

$R^9$ is independently selected from: H and $C_{1-6}$ alkyl optionally substituted with from 1-2 independently selected $R^e$; and

OR (2):
$R^8$ and $R^9$, together with the nitrogen atom to which each is attached forms a saturated ring including from 3-10 ring atoms, wherein the ring includes:
(a) from 1-9 ring carbon atoms, each of which is substituted with from 1-2 substituents independently selected from H and $R^g$, and
(b) from 0-3 ring heteroatoms (in addition to the nitrogen atom attached to $R^8$ and $R^9$), each of which is independently selected from N, N($R^f$), O, and S; and each of $R^{10}$ and $R^{11}$ is independently selected from: H and unsubstituted $C_{1-2}$ alkyl; or $R^{10}$ and $R^{11}$ together with the carbon atom to which each is attached, forms a $C_3$-$C_5$ cycloalkyl, optionally substituted with from 1-4 independently selected $R^g$;
and W' is hydrogen.

In some embodiments of combination [5] and [6], each of $R^3$ and $R^4$ is independently selected from:
(i) H;
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, N($R^f$), O, or S;

(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;

(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;

(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;

and (vii) $C_{1-4}$ haloalkyl.

In some embodiments, one of $R^3$ and $R^4$ (e.g., $R^3$) is:

(ii) halo;

(iii) cyano;

(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, N($R^f$), O, or S;

(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;

(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;

(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;

and (vii) $C_{1-4}$ haloalkyl; and the other (e.g., $R^4$) is H.

In some embodiments, one of $R^3$ and $R^4$ (e.g., $R^3$) is —($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from N, N($R^f$), O, and S, wherein the heteroaryl is optionally substituted with from 1-3 R; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline.

In certain embodiments, one of $R^3$ and $R^4$ (e.g., $R^3$) is heteroaryl including from 5-6 ring atoms, wherein from 1-4 ring atoms are each independently selected from N, N($R^f$), O, and S, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from N and N($R^f$), wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including 5 ring atoms, wherein from 1 ring atom is independently selected from O and S (e.g., S), wherein the heteroaryl is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^d$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^d$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^d$; and the other (e.g., $R^4$) is H. In certain embodiments, one of $R^3$ and $R^4$ (e.g., $R^3$) is pyrazolyl, optionally substituted with from 1-2 $R^d$; and the other (e.g., $R^4$) is H.

In certain embodiments, one of $R^3$ and $R^4$ (e.g., $R^3$) is C-linked pyrazolyl, optionally substituted with from 1-2 $R^d$; and the other (e.g., $R^4$) is H.

In certain embodiments, one of $R^3$ and $R^4$ (e.g., $R^3$) is N-linked pyrazolyl, optionally substituted with from 1-2 $R^d$; and the other (e.g., $R^4$) is H.

In certain embodiments, one of $R^3$ and $R^4$ (e.g., $R^3$) is furyl or thienyl, optionally substituted with from 1-2 $R^d$; and the other (e.g., $R^4$) is H.

In certain embodiments, one of $R^3$ and $R^4$ (e.g., $R^3$) is thienyl, optionally substituted with from 1-2 $R^d$; and the other (e.g., $R^4$) is H.

In some embodiments, one of $R^3$ and $R^4$ (e.g., $R^3$) is —($C_{1-3}$ alkylene)$_y$-$C_{6-10}$ aryl, wherein the aryl is optionally substituted with from 1-3 $R^d$, wherein y is 0 or 1; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^d$; and the other (e.g., $R^4$) is H.

In some embodiments, one of $R^3$ and $R^4$ (e.g., $R^3$) is —($C_{1-3}$ alkylene)$_y$-heterocyclyl including from 3-10 ring atoms, wherein from 1-3 ring atoms are each independently selected from N($R^f$), O, and S, wherein the heterocyclyl is optionally substituted with from 1-4 independently selected $R^g$, wherein y is 0 or 1; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from N($R^f$), O, and S, wherein the heterocyclyl is optionally substituted with from 1-4 independently selected $R^g$ (e.g., oxo), and the other (e.g., $R^4$) is H.

[7] In some embodiments:
In some embodiments, one of W and W' is $R^2$, and the other is H;
In some embodiments, $R^2$ is

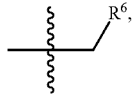

wherein:
$R^6$ is independently selected from: —OH, —O($C_{1-4}$ alkyl), —$CO_2R^a$, —C(O)NR'R'; and heteroaryl including from 5-6 ring atoms, wherein from 1-3 ring atoms are each independently selected from N, N($R^f$), O, and S, wherein the heteroaryl is optionally substituted with from 1-3 $R^d$.

In some embodiments of combination [7], each of $R^3$ and $R^4$ is independently selected from:
(i) H;
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$, wherein y is 0 or 1; and $Y^4$ is a bond, N($R^f$), O, or S;
(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;
(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;
and
(vii) $C_{1-4}$ haloalkyl.

In some embodiments, one of $R^3$ and $R^4$ (e.g., $R^3$) is:
(ii) halo;
(iii) cyano;
(x) $Y^4$—($C_{1-3}$ alkylene)$_y$-$C_{5-8}$ cycloalkyl, wherein the cycloalkyl is optionally substituted with from 1-4 independently selected $R^g$ wherein y is 0 or 1; and $Y^4$ is a bond, N($R^f$), O, or S;
(xi) $Y^4$—($C_{1-3}$ alkylene)$_y$-heterocyclyl including from 5-8 ring atoms, wherein from 1-3 ring atoms are each independently selected from N($R^f$), O, and S, wherein the heterocyclyl is optionally substituted with from 1-4 independently selected $R^g$, wherein y is 0 or 1; and $Y^4$ is a bond, N($R^f$), O, or S;
(xii) $Y^4$—($C_{1-3}$ alkylene)$_y$-$C_{6-10}$ aryl optionally substituted with from 1-4 $R^d$, wherein y is 0 or 1; and $Y^4$ is a bond, N($R^f$), O, or S;
(xiii) $Y^4$—($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and $Y^4$ is a bond, N($R^f$), O, or S;

and
(vii) $C_{1-4}$ haloalkyl; and the other (e.g., $R^4$) is H.

In some embodiments, one of $R^3$ and $R^4$ (e.g., $R^3$) is —($C_{1-3}$ alkylene)$_y$-heteroaryl including from 5-10 ring atoms, wherein from 1-4 ring atoms are each independently selected from N, N($R^f$), O, and S, wherein the heteroaryl is optionally substituted with from 1-3 $R^d$, wherein y is 0 or 1; and the other (e.g., $R^4$) is H.

In certain embodiments, one of $R^3$ and $R^4$ (e.g., $R^3$) is heteroaryl including from 5-10 ring atoms, wherein from 1-4 ring atoms are each independently selected from N, N($R^f$), O, and S, wherein the heteroaryl is optionally substituted with from 1-3 $R^d$; and the other (e.g., $R^4$) is H.

Representative heteroaryl groups include, without limitation, thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline.

In certain embodiments, one of $R^3$ and $R^4$ (e.g., $R^3$) is heteroaryl including from 5-6 ring atoms, wherein from 1-4 ring atoms are each independently selected from N, N($R^f$), O, and S, wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including from 5-6 ring atoms, wherein from 1-4 ring atoms are each independently selected from N and N($R^f$), wherein the heteroaryl is optionally substituted with from 1-2 $R^d$; and the other (e.g., $R^4$) is H.

In certain embodiments, one of $R^3$ and $R^4$ (e.g., $R^3$) is heteroaryl including 5 ring atoms, wherein from 1 ring atom is independently selected from O and S (e.g., S), wherein the heteroaryl is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, tetrazolyl, pyridyl, pyrimidinyl, or pyrazinyl, wherein each is optionally substituted with from 1-2 $R^d$; and the other (e.g., $R^4$) is H.

In certain embodiments, one of $R^3$ and $R^4$ (e.g., $R^3$) is pyrrolyl, imidazolyl, pyrazolyl, triazolyl, or tetrazolyl, wherein each is optionally substituted with from 1-2 $R^d$; and the other (e.g., $R^4$) is H.

In certain embodiments, one of $R^3$ and $R^4$ (e.g., $R^3$) is N-linked-pyrazolyl, N-linked pyrrolyl, N-linked imidazolyl, N-linked triazolyl, or N-linked tetrazolyl, optionally substituted with from 1-2 $R^d$; and the other (e.g., $R^4$) is H.

In certain embodiments, one of $R^3$ and $R^4$ (e.g., $R^3$) is C-linked-pyrazolyl, C-linked pyrrolyl, C-linked imidazolyl, C-linked triazolyl, or C-linked tetrazolyl, optionally substituted with from 1-2 $R^d$; and the other (e.g., $R^4$) is H. In certain embodiments, one of $R^3$ and $R^4$ (e.g., $R^3$) is pyrazolyl, optionally substituted with from 1-2 $R^d$; and the other (e.g., $R^4$) is H.

In certain embodiments, one of $R^3$ and $R^4$ (e.g., $R^3$) is C-linked pyrazolyl, optionally substituted with from 1-2 $R^d$; and the other (e.g., $R^4$) is H.

In certain embodiments, one of $R^3$ and $R^4$ (e.g., $R^3$) is N-linked pyrazolyl, optionally substituted with from 1-2 $R^d$; and the other (e.g., $R^4$) is H.

In certain embodiments, one of $R^3$ and $R^4$ (e.g., $R^3$) is furyl or thienyl, optionally substituted with from 1-2 $R^d$; and the other (e.g., $R^4$) is H.

In certain embodiments, one of $R^3$ and $R^4$ (e.g., $R^3$) is thienyl, optionally substituted with from 1-2 $R^d$; and the other (e.g., $R^4$) is H.

In some embodiments, one of $R^3$ and $R^4$ (e.g., $R^3$) is —($C_{1-3}$ alkylene)$_y$-$C_{6-10}$ aryl, wherein the aryl is optionally substituted with from 1-3 $R^d$, wherein y is 0 or 1; and the other (e.g., $R^4$) is H.

In certain embodiments, one of $R^3$ and $R^4$ (e.g., $R^3$) is $C_{6-10}$ aryl (e.g., phenyl), optionally substituted with from 1-3 $R^d$; and the other (e.g., $R^4$) is H.

In some embodiments, one of $R^3$ and $R^4$ (e.g., $R^3$) is —($C_{1-3}$ alkylene)$_y$-heterocyclyl including from 3-10 ring atoms, wherein from 1-3 ring atoms are each independently selected from N($R^f$), O, and S, wherein the heterocyclyl is optionally substituted with from 1-4 independently selected $R^g$, wherein y is 0 or 1; and the other (e.g., $R^4$) is H.

In some embodiments, one of $R^3$ and $R^4$ (e.g., $R^3$) is heterocyclyl including from 3-10 ring atoms, wherein from 1-3 ring atoms are each independently selected from N($R^f$), O, and S, wherein the heterocyclyl is optionally substituted with from 1-4 independently selected $R^g$ (e.g., oxo), and the other (e.g., $R^4$) is H.

Embodiments of any one of combinations [1]-[11] can include one or more of the following features.

Y can be $C_{1-6}$ (e.g., $C_{2-4}$, $C_{2-3}$, $C_2$) alkylene, which is optionally substituted with from 1-4 (e.g., 1-2, 1) $R^e$. In certain embodiments, Y is $C_{2-6}$ (e.g., $C_{2-4}$, $C_{2-3}$, $C_2$) alkylene, which is unsubstituted (e.g., $C_2$ alkylene or $C_3$ alkylene; e.g., $C_3$ alkylene).

$R^6$ can be —OH, $CO_2R^a$, -or —NR$^b$R$^c$. For example, $R^6$ can be —NH$_2$, —N(H)(C$_{1-4}$ alkyl) (e.g., —NHCH$_3$) or —N(C$_{1-4}$ alkyl)$_2$ (e.g., —N(CH$_3$)$_2$). $R^6$ can be —NR$^b$R$^c$.

Each occurrence of R$^b$ and R$^c$ can be independently selected from: H, C$_{1-4}$ alkyl, —C(O)(C$_{1-4}$ alkyl), —C(O)O (C$_{1-4}$ alkyl), —S(O)$_{1-2}$(R$^h$), —C(O)NR'R', —OH, and C$_{1-4}$ alkoxy.

Each occurrence of R$^b$ and R$^c$ can be independently selected from: H, C$_{1-4}$ alkyl, —C(O)(C$_{1-4}$ alkyl), —C(O)O (C$_{1-4}$ alkyl), —S(O)$_{1-2}$(R$^h$), and —C(O)NR'R'.

Each occurrence of R$^b$ and R$^c$ can be independently selected from: H, C$_{1-4}$ alkyl, and —C(O)(C$_{1-4}$ alkyl).

Each occurrence of R$^b$ and R$^c$ can be independently selected from: H and C$_{1-4}$ alkyl.

Each occurrence of R$^b$ and R$^c$ can be independently selected from: H and —C(O)(C$_{1-4}$ alkyl). For example, one of R$^b$ and R$^c$ is H, and the other is —C(O)(C$_{1-4}$ alkyl) (e.g., —C(O)(CH$_3$).

Each occurrence of R$^b$ and R$^c$ can be independently selected from: C$_{1-4}$ alkyl and —C(O)(C$_{1-4}$ alkyl). For example, one of R$^b$ and R$^c$ is C$_{1-4}$ alkyl (e.g., CH$_3$), and the other is —C(O)(C$_{1-4}$ alkyl) (e.g., —C(O)(CH$_3$).

$R^6$ can be CO$_2$R$^a$. R$^a$ can be C$_{1-8}$ alkyl optionally substituted with —OH, —NH$_2$, —NH(C$_{1-3}$ alkyl), —N(C$_{1-3}$ alkyl)$_2$, —N(H)(C(=O)C$_{1-4}$ alkyl), or cyano; e.g., R$^a$ can be unsubstituted C$_{1-6}$ alkyl (e.g., CH$_3$ or CH$_2$CH$_3$).

$R^6$ can be —OH (in certain embodiments, $R^2$ is —CH$_2$CH$_2$CH$_2$OH).

X can be unbranched chain C$_{2-4}$ alkylene. In some embodiments, X is an unbranched chain C$_{5-6}$ alkylene.

One of R$^3$ and R$^4$ (e.g., R$^4$) can be hydrogen, and the other (e.g., R$^3$) can be a substituent other than hydrogen.

One of R$^3$ and R$^4$ (e.g., R$^4$) can be hydrogen, and the other (e.g., R$^3$) can be halo or CO$_2$R$^a$.

One of R$^3$ and R$^4$ (e.g., R$^4$) can be hydrogen, and the other (e.g., R$^3$) can be halo (e.g., Br).

One of R$^3$ and R$^4$ (e.g., R$^4$) can be hydrogen, and the other (e.g., R$^3$) can be CO$_2$R$^a$. R$^a$ can be C$_{1-8}$ alkyl optionally substituted with —OH, —NH$_2$, —NH(C$_{1-3}$ alkyl), —N(C$_{1-3}$ alkyl)$_2$, —N(H)(C(=O)C$_{1-4}$ alkyl), or cyano; e.g., R$^a$ can be unsubstituted C$_{1-6}$ alkyl (e.g., CH$_3$ or CH$_2$CH$_3$).

$R^3$ can be 3-pyrazolyl, and $R^4$ can be hydrogen.

$R^3$ can be hydrogen, and $R^4$ can be hydrogen.

In another aspect, the invention provides a compound selected from the exemplified examples or a pharmaceutically acceptable salt thereof.

In another aspect, the present invention provides a compound selected from any subset list of compounds or a single compound from the exemplified examples within the scope of any of the above aspects.

Pharmaceutical Compositions and Administration

In some embodiments, a chemical entity (e.g., a compound that modulates (e.g., agonizes or partially agonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, a pharmaceutical composition comprising a compound of the present invention or a salt thereof, and one or more pharmaceutically acceptable excipients. In certain embodiments, a pharmaceutical composition comprising a compound of the present invention or a pharmaceutically acceptable salt thereof, and one or more pharmaceutically acceptable excipients. In certain embodiments, a pharmaceutical composition comprising a therapeutically effective amount of a compound of the present invention or a pharmaceutically acceptable salt thereof, and one or more pharmaceutically acceptable excipients.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy*, 22$^{nd}$ Edition (Pharmaceutical Press, London, UK. 2012).

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral). In certain embodiments, a preferred route of administration is systemic.

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., *"Effect of Intratumoral Injection on the Biodistribution and the Therapeutic Potential of HPMA Copolymer-Based Drug Delivery Systems" Neoplasia*. 10:788-795 (2006).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry.* 2013, 13, 776-802.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradeable poly(D,L-lactic-co-glycolic acid) [PLGA]-based or poly anhydride-based nanoparticles or microparticles, and nanoporous particle-supported lipid bilayers.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

Indications

In any of the methods described herein, the subject can have a cancer. In some examples of any of the methods described herein, the mammal has been identified as having a cancer, or has been diagnosed as having a cancer.

Non-limiting examples of cancer include: acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

In certain embodiments, non-limiting examples of cancer include: breast cancer, colon cancer, rectal cancer, colorectal cancer, pancreatic cancer, and prostate cancer.

Methods for diagnosing a subject as having a cancer or identifying a mammal as having a cancer are well known in the art. For example, a medical professional (e.g., a physician, a physician's assistant, or a technician) can diagnose cancer in a mammal by observing one or more symptoms of cancer in a mammal. Non-limiting examples of symptoms of cancer include: fatigue, lump or area of thickening felt under the skin, weight change, jaundice, darkening or redness of the skin, sores that won't heal, changes to existing moles, changes in bowel or bladder habits, persistent cough or trouble breathing, difficulty swallowing, hoarseness, persistent indigestion or discomfort after eating, persistent, unexplained muscle or joint pain, persistent, unexplained fevers or night sweats, and unexplained bleeding or bruising. Methods of diagnosing a subject as having a cancer or identifying a subject as having a cancer can further include performing one or more diagnostic tests (e.g., performing one or more diagnostic tests on a biopsy or a blood sample).

In some examples of any of the methods described herein, a subject can be a subject having a cancer, a subject diagnosed as having a cancer, or a subject identified as having a cancer that has been unresponsive to a previously administered treatment for cancer. Diagnostic tests for diagnosing a subject as having a cancer or identifying a mammal as having a cancer are known in the art.

In some embodiments, methods for treating a subject having condition, disease or disorder in which an increase in NLRP3 signaling may correct a deficiency in innate immune activity (e.g., a condition, disease or disorder associated with an insufficient immune response) that contributes to the pathology and/or symptoms and/or progression of the condition, disease or disorder (e.g., cancer) are provided.

In some embodiments, the present invention provides a method of treating cancer, wherein the cancer can be any cancer that does not elicit an optimal innate immune system response.

Innate immune system refers to a part of the immune system consisting of cells that react to threats for the organism like infections or cancer in an antigen-non-specific way and stimulate the adaptive, antigen-specific immune system. In general, complete removal of the threat and long-lasting protection (=immunity) requires activity of the adaptive, antigen-specific immune system that in turn depends on stimulation by the innate immune system.

In some embodiments, the present invention provides a method of treating case, the cancer is selected based on resistance to T-cell checkpoint inhibition, either independent of cancer type and based on failure to respond to previous T-cell checkpoint inhibitor therapy or based on cancer type that is generally resistant to T-cell checkpoint inhibitor therapy such as hormone receptor positive breast cancer, microsatellite stable colon or rectal cancer, pancreatic cancer and prostate cancer.

In certain other embodiments, the present invention provides a method of treating cancer comprising an NLPR3 agonist of the present invention to treat non-inflamed tumors with low CD8+ T-cell infiltration to enhance tumor immunogenicity and promote inflammatory responses. For example, the combination may be used to treat a solid tumor based on results of a biopsy that demonstrated low CD8+ T-cell infiltration or low expression of genes produced by CD8+ T-cells.

Resistance to T-cell checkpoint inhibition refers to cancer progression on therapy or lack of response within 6 months of therapy according to consensus response criteria for the respective cancer, such as RECIST1.1 for most solid tumors.

T-cell infiltration refers to percent of T-cells of all nucleated cells by immunohistochemistry of tumor biopsy specimens.

CD8+ T-cell infiltration refers to percent of CD8+ cells of all nucleated cells by immunohistochemistry of tumor biopsy specimens.

In addition to immunohistochemistry for quantifying CD8+ T-cells in biopsy specimens, expression of genes produced by CD8+ T-cells like interferon-γ can be measured by quantifying mRNA using for example next generation sequencing and inform about CD8+ T-cell infiltration. Thresholds for low and high CD8+ T-cell infiltration by immunohistochemistry of mRNA quantifying techniques are being developed by various groups and take the spectrum of CD8+ T-cell infiltration across cancers as well as for specific cancers into account.

In any of the methods described herein, the subject can have an infectious disease. In some examples of any of the methods described herein, the subject has been identified as having an infectious disease, or has been diagnosed as having an infectious disease. For example, an infectious disease can be caused by a bacterium, virus, fungus, parasite, or a *mycobacterium*.

Non-limiting examples of infectious disease include: Acinobacter infection, actinomycosis, African sleeping sickness, acquired immunodeficiency syndrome, amebiasis, anaplasmosis, anthrax, *Arcanobacterium haemolyticum* infection, Argentine hemorrhagic fever, ascariasis, aspergillosis, astrovirus infection, babesiosis, *Bacillus cereus* infection, bacterial pneumonia, bacterial vaginosis, *Bacteroides* infection, balantidiasis, *Baylisascaris* infection, BK virus infection, black piedra, *Blastocystic hominis* infection, blastomycosis, Bolivian hemorrhagic fever, botulism, Brazilian hemorrhagic fever, brucellosis, bubonic plaque, Burkholderi infection, Buruli ulcer, Calicivirus infection, camptobacteriosis, candidiasis, cat-scratch disease, cellulitis, Chagas disease, chancroid, chickenpox, chikungunya, chlamydia, *Chlamydophila pneumoniae* infection, cholera, chromoblastomycosis, clonorchiasis, *Clostridium difficile* infection, coccidioidomycosis, Colorado tick fever, common cold, Creutzfeldt-Jakob disease, Crimean-Congo hemorrhagic fever, crytococcosis, cryptosporidiosis, cutaneous larva migrans, cyclosporiasis, cysticercosis, cytomegalovirus infection, dengue fever, Desmodesmus infection, deintamoebiasis, diphtheria, diphyllobothriasis, dracunculiasis, ebola hemorrhagic fever, echinococcosis, ehrlichiosis, enterobiasis, *Enterococcus* infection, Enterovirus infection, epidemic typhus, erythema infection, exanthema subitum, fasciolopsiasis, fasciolosis, fatal familial insomnia, filariasis, food poisoning by *Clostridium* myonecrosis, free-living amebic infection, *Fusobacterium* infection, gas gangrene, geotrichosis, Gerstmann-Straussler-Scheinker syndrome, giardiasis, glanders, gnathostomiasis, gonorrhea, granuloma inguinale, Group A streptococcal infection, Group B streptococcal infection, *Haemophilus influenzae* infection, hand foot and mouth disease, hantavirus pulmonary syndrome, Heartland virus disease, *Heliobacter pylori* infection, hemolytic-uremic syndrome, hemorrhagic fever with renal syndrome, hepatitis A, hepatitis B, hepatitis C, hepatitis D, hepatitis E, herpes simplex, histoplasmosis, hookworm infection, human bocavirus infection, human ewingii ehrlichiosis, human granulocyte anaplasmosis, human metapneuomovirus infection, human monocytic ehrlichiosis, human papillomavirus infection, human parainfluenza virus infection, hymenolepiasis, Epstein-Barr virus infectious mononucleosis, influenza, isosporiasis, Kawasaki disease, keratitis, Kingella kingae infection, kuru, lassa fever, Legionnaires' disease, Pontiac fever, leishmaniasis, leprosy, leptospirosis, listeriosis, lyme disease, lymphatic filariasis, lymphocytic choriomeningitis, malaria, Marburg hemorrhagic fever, measles, Middle East respiratory syndrome, melioidosis, meningitis, meningococcal disease, metagonimiasis, microsporidiosis, molluscum contagiosum, monkeypox, mumps, murine typhus, mycoplasma pneumonia, mycetoma, myiasis, neonatal conjunctivitis, variant Creutzfeldt-Jakob disease, nocardiosis, onchocerciasis, paracoccidioidomycosis, paragonimiasis, pasteurellosis, pediculosis capitis, pediculosis corporis, pediculosis pubis, pelvic inflammatory disease, pertussis, plague, pneumonia, poliomyelitis, *Prevotella* infection, primary amoebic meningoencephalitis, progressive multifocal leukoencephalopathy, psittacosis, Q fever, rabies, relapsing fever, respiratory syncytial virus infection, rhinosporidiosis, rhinovirus infection, rickettsial infection, rickettsialpox, Rift Valley Fever, Rocky Mountain spotted fever, rotavirus infection, rubella, salmonellosis, severe acute respiratory syndrome, scabies, schistosomiasis, sepsis, shigellosis, shingles, smallpox, sporothrichosis, staphylococcal food poisoning, staphylococcal infection, strongyloidiasis, subacute sclerosing panencephalitis, syphilis, taeniasis, tetanus, tinea barabe, tinea capitis, tinea corporis, tinea cruris, tinea manum, tinea nigra, tinea pedis, tinea unguium, tinea versicolor, toxocariasis, trachoma, toxoplasmosis, trichinosis, trichomoniasis, trichuriasis, tuberculosis, tularemia, typhoid fever, *Ureaplasma urealyticum* infection, valley fever, Venezuelan hemorrhagic fever, viral pneumonia, West Nile fever, white piedra, *Yersinia psuedotuberculosis* infection, yersiniosis, yellow fever, and zygomycosis.

Methods for diagnosing a subject as having an infectious disease, or identifying a subject as having an infectious disease are well known in the art. For example, a medical professional (e.g., a physician, a physician's assistant, or a technician) can diagnose infectious disease in a subject by observing one or more symptoms of infectious disease in a subject. Non-limiting examples of symptoms of infectious disease include: fever, diarrhea, fatigue, and muscle aches. Methods of diagnosing a mammal as having an infectious disease or identifying a subject as having an infectious disease can further include performing one or more diagnostic tests (e.g., performing one or more diagnostic tests on a biopsy or a blood sample). Diagnostic tests for diagnosing a subject as having an infectious disease or identifying a subject as having an infectious disease are known in the art.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the methods described herein can further include administering one or more additional cancer therapies.

The one or more additional cancer therapies can include, without limitation, surgery, radiotherapy, chemotherapy, toxin therapy, immunotherapy, cryotherapy, cancer vaccines (e.g., HPV vaccine, hepatitis B vaccine, Oncophage, Provenge) and gene therapy, as well as combinations thereof. Immunotherapy, including, without limitation, adoptive cell therapy, the derivation of stem cells and/or dendritic cells, blood transfusions, lavages, and/or other treatments, including, without limitation, freezing a tumor.

In some embodiments, the one or more additional cancer therapies is chemotherapy, which can include administering one or more additional chemotherapeutic agents.

In certain embodiments, the additional cancer therapy comprises (chemotherapeutic agent) an immunomodulatory moiety, e.g., an immune checkpoint inhibitor. In certain of these embodiments, the immune checkpoint inhibitor targets an immune checkpoint receptor selected from CTLA-4, PD-1, PD-L1, PD-1-PD-L1, PD-1-PD-L2, T cell immunoglobulin and mucin 3 (TIM3 or HAVCR2), Galectin 9-TIM3, Phosphatidylserine-TIM3, lymphocyte activation gene 3 protein (LAG3), MHC class II-LAG3, 4-1BB-4-1BB ligand, OX40-OX40 ligand, GITR, GITR ligand-GITR, CD27, CD70-CD27, TNFRSF25, TNFRSF25-TL1A, CD40L, CD40-CD40 ligand, HVEM-LIGHT-LTA, HVEM, HVEM-BTLA, HVEM-CD160, HVEM-LIGHT, HVEM-BTLA-CD160, CD80, CD80-PDL-1, PDL2-CD80, CD244, CD48-CD244, CD244, ICOS, ICOS-ICOS ligand, B7-H3, B7-H4, VISTA, TMIGD2, HHLA2-TMIGD2, Butyrophilins, including BTNL2, Siglec family, TIGIT and PVR family members, KIRs, ILTs and LIRs, NKG2D and NKG2A, MICA and MICB, CD244, CD28, CD86-CD28, CD86-CTLA, CD80-CD28, Phosphatidylserine, TIM3, Phosphatidylserine-TIM3, SIRPA-CD47, VEGF, Neuropilin, CD160, CD30, and CD155 (e.g., CTLA-4 or PD1 or PD-L1) and other immunomodulatory agents, such as interleukin-2 (IL-2), indoleamine 2,3-dioxygenase (IDO), IL-10, transforming growth factor-$\beta$ (TGF$\beta$), CD39, CD73 Adenosine-CD39-CD73, and CXCR4-CXCL12. See, e.g., Postow, M. *J. Clin. Oncol.* 33, 1 (2015).

In certain embodiments, the immune checkpoint inhibitor targets an immune checkpoint receptor selected from CTLA-4, PD-1, PD-L1, PD-1-PD-L1, and PD-1-PD-L2.

In certain embodiments, the immune checkpoint inhibitor is selected from: nivolumab (also known as "OPDIVO"; formerly designated 5C4, BMS-936558, MDX-1106, or ONO-4538), pembrolizumab (also known as "KEYTRUDA", lambrolizumab, and MK-3475. See WO 2008/156712), PDR001 (Novartis; see WO 2015/112900), MEDI-0680 (AstraZeneca; AMP-514; see WO 2012/145493), cemiplimab (REGN-2810) (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J. Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGD013 (Macrogenics); IBI308 (Innovent; see WO 2017/024465, WO 2017/025016, WO 2017/132825, WO2017/133540); BMS-936559 (formerly 12A4 or MDX-1105; see. e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) *J Clin Oncol* 31(suppl):3000), durvalumab (IMFINZI; MEDI-4736; AstraZeneca; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), CK-301 (Checkpoint Therapeutics; see Gorelik et al., AACR:Abstract 4606 (April 2016)); urelumab, PF-05082566, MEDI6469, TRX518, varlilumab, CP-870893, BMS-986016, MGA271, lirilumab, IPH2201, emactuzumab, INCB024360, galunisertib, ulocuplumab, BKT140, Bavituximab, CC-90002, bevacizumab, MNRP1685A, ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; AstraZeneca; see, e.g., WO 2000/037504 and Ribas, *Update Cancer Ther.* 2(3): 133-39 (2007)).

In certain embodiments, the immune checkpoint inhibitor is selected from: nivolumab, pembrolizumab, JS001, BGB-A317, INCSHR1210, TSR-042, GLS-010, STI-1110, MGD013, IBI308, BMS-936559, atezolizumab, durvalumab, avelumab, STI-1014, CX-072, KN035, LY3300054, CK-301, urelumab, PF-05082566, MEDI6469, TRX518, varlilumab, BMS-986016, ipilimumab, AGEN-1884, and tremelimumab.

In certain of these embodiments, the immune checkpoint inhibitor is selected from: Urelumab, PF-05082566, MEDI6469, TRX518, Varlilumab, CP-870893, Pembrolizumab (PD1), Nivolumab (PD1), Atezolizumab (formerly MPDL3280A) (PDL1), MEDI4736 (PD-L1), Avelumab (PD-L1), PDR001 (PD1), BMS -986016, MGA271, Lirilumab, IPH2201, Emactuzumab, INCB024360, Galunisertib, Ulocuplumab, BKT140, Bavituximab, CC-90002, bevacizumab, and MNRP1685A.

In certain embodiments, the immune checkpoint inhibitor is selected from: nivolumab, ipilimumab, pembrolizumab, atezolizumab, durvalumab and avelumab.

In certain embodiments, the immune checkpoint inhibitor is selected from: nivolumab and ipilimumab.

In certain embodiments, the additional anti-cancer agent (chemotherapeutic agent) is a STING agonist. For example, the STING agonist can include cyclic di-nucleotides, such as cAMP, cGMP, and cGAMP as well as modified cyclic di-nucleotides that include one or more of the following modification features (2'-O/3'-O linkage, phosphorothioate linkage, adenine and/or guanine analogue, 2'-OH modification (e.g., $-OCH_3$ or replacement, e.g., $-F$ or $N_3$). See, e.g., WO 2014/189805.

In certain embodiments, the additional chemotherapeutic agent is an alkylating agent. Alkylating agents are so named because of their ability to alkylate many nucleophilic functional groups under conditions present in cells, including, but not limited to cancer cells. In a further embodiment, an alkylating agent includes, but is not limited to, Cisplatin, carboplatin, mechlorethamine, cyclophosphamide, chlorambucil, ifosfamide and/or oxaliplatin. In an embodiment, alkylating agents can function by impairing cell function by forming covalent bonds with the amino, carboxyl, sulfhydryl, and phosphate groups in biologically important molecules or they can work by modifying a cell's DNA. In a further embodiment an alkylating agent is a synthetic, semi-synthetic or derivative.

In certain embodiments, the additional chemotherapeutic agent is an anti-metabolite. Anti-metabolites masquerade as purines or pyrimidines, the building-blocks of DNA and in general, prevent these substances from becoming incorporated in to DNA during the "S" phase (of the cell cycle), stopping normal development and division. Anti-metabolites can also affect RNA synthesis. In an embodiment, an antimetabolite includes, but is not limited to azathioprine and/or mercaptopurine. In a further embodiment an anti-metabolite is a synthetic, semisynthetic or derivative.

In certain embodiments, the additional chemotherapeutic agent is a plant alkaloid and/or terpenoid. These alkaloids are derived from plants and block cell division by, in general, preventing microtubule function. In an embodiment, a plant alkaloid and/or terpenoid is a vinca alkaloid, a podophyllotoxin and/or a taxane. *Vinca* alkaloids, in general, bind to specific sites on tubulin, inhibiting the assembly of tubulin into microtubules, generally during the M phase of the cell cycle. In an embodiment, a vinca alkaloid is derived, without limitation, from the Madagascar periwinkle, *Catharanthus roseus* (formerly known as *Vinca rosea*). In an embodiment, a vinca alkaloid includes, without limitation, Vincristine, Vinblastine, Vinorelbine and/or Vindesine. In an embodiment, a taxane includes, but is not limited, to Taxol, Paclitaxel and/or Docetaxel. In a further embodiment a plant alkaloid or terpemoid is a synthetic, semisynthetic or derivative. In a further embodiment, a podophyllotoxin is, without limitation, an etoposide and/or teniposide. In an embodiment, a taxane is, without limitation, docetaxel and/or ortataxel. In an embodiment, a cancer therapeutic is a topoisomerase. Topoisomerases are essential enzymes that maintain the topology of DNA. Inhibition of type I or type II topoisomerases interferes with both transcription and replication of DNA by upsetting proper DNA supercoiling. In a further embodiment, a topoisomerase is, without limitation, a type I topoisomerase inhibitor or a type II topoisomerase inhibitor. In an embodiment a type I topoisomerase inhibitor is, without limitation, a camptothecin. In another embodiment, a camptothecin is, without limitation, exatecan, irinotecan, lurtotecan, topotecan, BNP 1350, CKD 602, DB 67 (AR67) and/or ST 1481. In an embodiment, a type II topoisomerase inhibitor is, without limitation, epipodophyllotoxin. In a further embodiment an epipodophyllotoxin is, without limitation, an amsacrine, etoposid, etoposide phosphate and/or teniposide. In a further embodiment a topoisomerase is a synthetic, semisynthetic or derivative, including those found in nature such as, without limitation, epipodophyllotoxins, substances naturally occurring in the root of American Mayapple (*Podophyllum peltatum*).

In certain embodiments, the additional chemotherapeutic agent is a stilbenoid. In a further embodiment, a stilbenoid includes, but is not limited to, Resveratrol, Piceatannol, Pinosylvin, Pterostilbene, Alpha-Viniferin, Ampelopsin A, Ampelopsin E, Diptoindonesin C, Diptoindonesin F, Epsilon-Vinferin, Flexuosol A, Gnetin H, Hemsleyanol D, Hopeaphenol, Trans-Diptoindonesin B, Astringin, Piceid and Diptoindonesin A. In a further embodiment a stilbenoid is a synthetic, semisynthetic or derivative.

In certain embodiments, the additional chemotherapeutic agent is a cytotoxic antibiotic. In an embodiment, a cytotoxic antibiotic is, without limitation, an actinomycin, an anthracenedione, an anthracycline, thalidomide, dichloroacetic acid, nicotinic acid, 2-deoxyglucose and/or chlofazimine. In an embodiment, an actinomycin is, without limitation, actinomycin D, bacitracin, colistin (polymyxin E) and/or polymyxin B. In another embodiment, an antracenedione is, without limitation, mitoxantrone and/or pixantrone. In a further embodiment, an anthracycline is, without limitation, bleomycin, doxorubicin (Adriamycin), daunorubicin (daunomycin), epirubicin, idarubicin, mitomycin, plicamycin and/or valrubicin. In a further embodiment a cytotoxic antibiotic is a synthetic, semisynthetic or derivative.

In certain embodiments, the additional chemotherapeutic agent is selected from endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-β), vasculostatin, vasostatin (calreticulin fragment) and the like.

In certain embodiments, the additional chemotherapeutic agent is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In certain embodiments, the additional chemotherapeutic agent is platinum, cisplatin, carboplatin, oxaliplatin, mechlorethamine, cyclophosphamide, chlorambucil, azathioprine, mercaptopurine, vincristine, vinblastine, vinorelbine, vindesine, etoposide and teniposide, paclitaxel, docetaxel, irinotecan, topotecan, amsacrine, etoposide, etoposide phosphate, teniposide, 5-fluorouracil, leucovorin, methotrexate, gemcitabine, taxane, leucovorin, mitomycin C, tegafir-uracil, idarubicin, fludarabine, mitoxantrone, ifosfamide and doxorubicin. Additional agents include inhibitors of mTOR (mammalian target of rapamycin), including but not limited to rapamycin, everolimus, temsirolimus and deforolimus.

In still other embodiments, the additional chemotherapeutic agent can be selected from those delineated in U.S. Pat. No. 7,927,613.

In yet another embodiment, the methods can further include administering one or both of: (i) one or more anti-fungal agents (e.g., selected from the group of bifonazole, butoconazole, clotrimazole, econazole, ketoconazole, luliconazole, miconazole, omoconazole, oxiconazole, sertaconazole, sulconazole, tioconazole, albaconazole, efinaconazole, epoziconazole, fluconazole, isavuconazole, itraconazole, posaconazole, propiconazole, ravusconazole, terconazole, voriconazole, abafungin, amorolfin, butenafine, naftifine, terbinafine, anidulafungin, caspofungin, micafungin, benzoic acid, ciclopirox, flucytosine, 5-fluorocytosine, griseofulvin, haloprogin, tolnaflate, undecylenic acid, and balsam of peru) and (ii) one or more antibiotics (e.g., selected from the group of amikacin, gentamicin, kanamycin, neomycin, netilmicin, tobramycin, paromomycin, streptomycin, spectinomycin, geldanamycin, herbimycin, rifaximin, loracarbef, ertapenem, doripenem, imipenem, cilastatin, meropenem, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, teicoplanin, vancomycin, telavancin, dalbavancin, oritavancin, clindamycin, lincomycin, daptomycin, azithromycin, clarithromycin, dirithromycin, erythromycin, roxithromycin, troleandomycin, telithromycin, spiramycin, aztreonam, furazolidone, nitrofurantoin, linezolid, posizolid, radezolid, torezolid, amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, penicillin G, temocillin, ticarcillin, amoxicillin, calvulanate, ampicillin, subbactam, piperacillin, tazobactam, ticarcillin, clavulanate, bacitracin, colistin, polymyxin B, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, mafenide, sulfacetamide, sulfadiazine, silver sulfadiazine, sulfadimethoxine, sulfamethoxazole, sulfanilimide, sulfasalazine, sulfisoxazole, trimethoprim-sulfamethoxazole, sulfonamideochrysoidine, demeclocycline, minocycline, oytetracycline, tetracycline, clofazimine, dapsone, dapreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin, dalopristin, thiamphenicol, tigecycyline, tinidazole, trimethoprim, and teixobactin).

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of such treatment (e.g., by way of biopsy, endoscopy, or other conventional method known in the art). In certain embodiments, the NLRP3 protein can serve as a biomarker for certain types of cancer.

In some embodiments, the chemical entities, methods, and compositions described herein can be administered to certain treatment-resistant patient populations (e.g., patients resistant to checkpoint inhibitors).

In some embodiments, the compounds of the present invention may be used in therapy. In certain embodiments, the present invention provides a combined preparation of a compound of the present invention, or a pharmaceutically acceptable salt thereof, and additional therapeutic agent(s) for simultaneous, separate or sequential use in therapy.

In some embodiments, a compound of the present invention, or a pharmaceutically acceptable salt thereof, or a pharmaceutical composition containing the same, may be used as a medicament. In certain embodiments, the compounds of the invention may be used for the manufacture of a medicament for the treatment of cancer. In certain embodiments, the compounds of the invention may be used for the manufacture of a medicament for modulating NLRP3 activity. In certain embodiments, the modulating comprises agonizing NLRP3.

Methods of Preparation

As can be appreciated by the skilled artisan, methods of synthesizing the compounds of the formulae herein will be evident to those of ordinary skill in the art. For example, the compounds described herein can be synthesized, e.g., using one or more of the methods described herein and/or using methods described in, e.g., US 2015/0056224. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and RGM. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof. The starting materials used in preparing the compounds of the invention are known, made by known methods, or are commercially available. The skilled artisan will also recognize that conditions and reagents described herein that can be interchanged with alternative art-recognized equivalents. For example, in many reactions, triethylamine can be interchanged with other bases, such as non-nucleophilic bases (e.g. diisopropylamine, 1,8-diazabicycloundec-7-ene, 2,6-di-tert-butylpyridine, or tetrabutylphosphazene).

The skilled artisan will recognize a variety of analytical methods that can be used to characterize the compounds described herein, including, for example, $^1$H NMR, heteronuclear NMR, mass spectrometry, liquid chromatography, and infrared spectroscopy. The foregoing list is a subset of characterization methods available to a skilled artisan and is not intended to be limiting.

To further illustrate the foregoing, the following non-limiting, exemplary synthetic schemes are included. Variations of these examples within the scope of the claims are within the purview of one skilled in the art and are considered to fall within the scope of the invention as described, and claimed herein. The reader will recognize that the skilled artisan, provided with the present disclosure, and skill in the art is able to prepare and use the invention without exhaustive examples.

The following abbreviations have the indicated meanings:
ACN=acetonitrile
Ac$_2$O=acetic anhydride
AcOH=acetic acid
BnOH=benzyl alcohol
CDCl$_3$=chloroform-d
CD$_3$OD=methanol-d
CH$_2$Cl$_2$=dichloromethane
CH$_3$ReO$_3$=methyltrioxorhenium
conc.=concentrated
Cs$_2$CO$_3$=cesium carbonate
CuI=copper (I) iodide
d=doublet
DCM=dichloromethane
DCE=1,2-dichloroethane
DIAD=diisopropyl azodicarboxylate
DIPEA=N,N-diisopropylethylamine
DMF=N,N-dimethylformamide
DMSO=dimethylsulfoxide ES=electrospray ionization
Et$_2$O=diethyl ether
EtOAc=ethyl acetate
EtOH=ethanol
equiv=equivalents
g=grams
h=hours
HCl=hydrogen chloride (usually as a solution)
H$_2$O=water
H$_2$O$_2$=hydrogen peroxide
HATU=1-[Bis(dimethylamino)methylene]-1H-1,2,3-triazolo[4,5-b]pyridinium 3-oxide hexafluorophosphate
HCl=hydrogen chloride or hydrochloric acid
HPLC=high-performance liquid chromatography
I$_2$=iodine
K$_2$CO$_3$=potassium carbonate
K$_2$HPO$_4$=potassium phosphate, dibasic
KI=potassium iodide
L=liter
LC/MS=liquid chromatography mass spectrometer
LiBH$_4$=lithium borohydride
m=multiplet
m/z=mass to charge ratio
M=molar
m-CPBA=meta-chloroperoxybenzoic acid
mg=milligram(s)
MeOH=methanol
MHz=megahertz
mL=milliliter(s)
mmol=millimole(s)
NaH=sodium hydride
NaHCO$_3$=sodium hydrogen carbonate
Na$_2$CO$_3$=sodium carbonate
NaOH=sodium hydroxide
Na$_2$SO$_4$=sodium sulfate
NEt$_3$ and TEA=trimethylamine
NH$_4$OH and NH$_3$H$_2$O=ammonium hydroxide
NH$_4$HCO$_3$=ammonium hydrogen carbonate
nm=nanometer
PBr$_3$=phosphorus tribromide
PdCl$_2$(PPh$_3$)$_2$=bis(triphenylphosphine)palladium (II) dichloride
Pd(dppf)Cl$_2$=1,1'-Bis(diphenylphosphino)ferrocene
Pd(dppf)Cl$_2$DCM=1,1'-Bis(diphenylphosphino)ferrocene-dichloromethane complex
Pd(OH)$_2$=palladium hydroxide
PMB=para-methoxybenzyl
POCl$_3$=phosphorous oxychloride
ppm=parts per million
Pt=platinum
Pt/C=platinum on carbon
RP=reverse phase
s=singlet
t=triplet
T3P=1-propanephosphonic anhydride
t-BuOK=potassium tert-butoxide
TFA=trifluoroacetic acid
TLC=thin layer chromatography
TsCl and TosCl=para-toluenesulfonyl chloride
° C.=degrees Celsius
μm and um=micrometer
μmol and umol=micromole(s)

General Procedures for Compounds of the Invention:

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be effected using the methods summarized in Schemes 1 and 2.

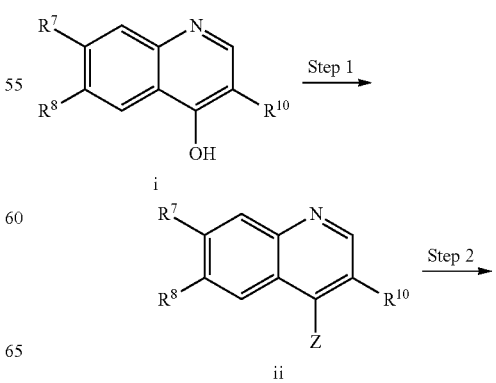

Scheme 1

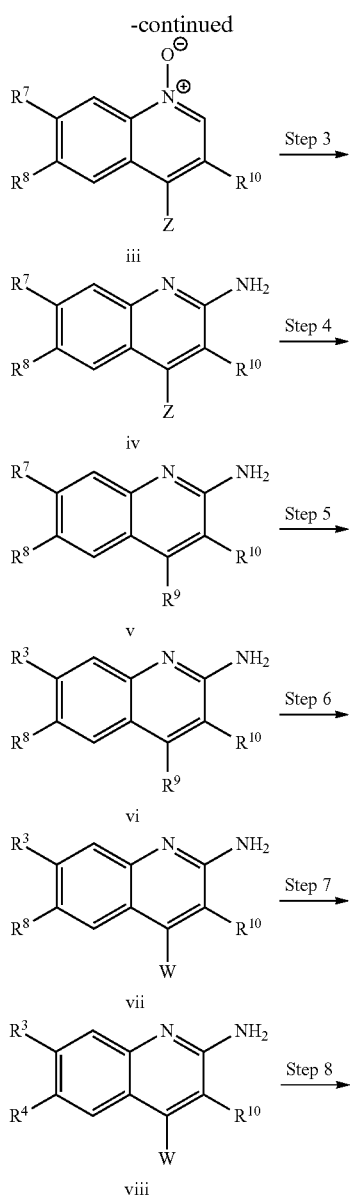

Step 1

The first step of Scheme 1 begins with a suitably functionalized quinolinol (i). If desired, the groups $R^7$, $R^8$, and $R^{10}$ may be the groups $R^3$, $R^4$, and W' found in the final product. Alternatively, one or more of these groups may be groups that can be modified at a later stage of the synthesis, such as bromo. This quinolinol may be purchased commercially, or may be synthesized by methods known to one skilled in the art. In step 1, the alcohol group of compound (i) may be transformed into a halogen group or sulfonate ester, such as chloro, bromo, or triflate. If the desired group Z is chloro, this transformation may be effected by treating compound (i) with a reagent such as phosphoryl chloride in a solvent such as toluene. Alternatively, if the desired group Z is bromo, this transformation may be effected by treating compound (i) with a reagent such as phosphorous tribromide in a solvent such as DMF. Alternatively, if the desired group Z is triflate, this transformation may be effected by treating compound (i) with a reagent such as trifluoromethanesulfonyl chloride, a reagent such as 4-dimethylaminopyridine, and a base such as Hunig's base in a solvent such as dichloromethane.

Step 2

In step 2 of Scheme 1, compound (ii) is transformed into N-oxide (iii) by treatment with an appropriate oxidant, such as meta-chloroperoxybenzoic acid, in a solvent such as DCM.

Step 3

In step 3 of Scheme 1, compound (iii) is transformed into amine (iv) by treatment with an appropriate activating reagent, such as tosyl chloride, and a source of ammonia, such as ammonium chloride and triethylamine, in an appropriate solvent, such as DCM.

Step 4

In step 4 of Scheme 1, the halogen Z of compound (iv) is transformed into group $R^9$ of compound (v). The group $R^9$ may be the group W desired in the final compound; alternatively, it may be a group that can be transformed into group W at a later stage of the synthesis. One skilled in the art will recognize that the means to effect this transformation will depend on the nature of the groups R and Z. For example, if Z is chloro and the desired group $R^9$ is an amine, this transformation may be effected by heating compound (iv) to a suitable temperature, such as 120° C. with an appropriate amine and a base such as Hunig's base in a solvent such as DMSO. Alternatively, if Z is chloro and the desired group $R^9$ is an ether, this transformation may be effected by heating compound (iv) to a suitable temperature, such as 100° C. with an appropriate alcohol and a base such as potassium tert-butoxide in a solvent such as NMP. Alternatively, if Z is bromo and the desired group $R^9$ is an alkyne, this transformation may be effected by heating compound (iv) to a suitable temperature, such as 70° C., with an appropriate alkyne, copper (I) iodide, an appropriate base, such as Hunig's base, and a suitable palladium source, such as tetrakis(triphenylphosphine)palladium(0), in a suitable solvent, such as THF. Alternatively, if Z is a triflate and the desired group $R^9$ is a optionally substituted alkyl group, this step may be accomplished by treating compound (iv) with an appropriate alkyl boronic acid or ester, a catalyst such as $PdCl_2(dppf)$-DCM complex, and a base such as cesium carbonate in a solvent such as dioxane.

Steps 5 through 8 of Scheme 1 consist of a series of optional functional group manipulations to convert the substituents $R^7$, $R^8$, $R^9$, and $R^{10}$ in intermediate (v) to the substituents $R^3$, R, W, and W' desired in the final compound (ix). One skilled in the art will recognize that some or all of these steps may not be necessary depending on the groups found in compounds (v) and (ix). One skilled in the art will also recognize that, for some substrates, these steps may be performed in alternative order.

Step 5

Step 5 of Scheme 1 is an optional step or series of steps to transform the group $R^7$ in intermediate (v) to the group $R^3$ found in molecule (vi). For example, if $R^7$ is bromo and the desired group $R^3$ is an aromatic or heteroaromatic group, this transformation may be effected by reacting intermediate (v) with an optionally protected aromatic or heteroaromatic boronic acid or boronic ester, a catalyst such as PdCl$_2$(dppf)-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrohydropyran protecting group, the tetrohydropyran may be removed by reaction with an acid such as trifluoroacetic acid in a solvent such as dichloromethane. Alternatively, if $R^7$ is bromo and the desired group $R^3$ is an aromatic or heteroaromatic group, this transformation may be effected by reacting intermediate (v) first with a compound such as PdCl$_2$(dppf)-DCM complex bis(pinacolato)diboron, a reagent such as potassium acetate, and a catalyst such as PdCl$_2$(dppf)-DCM complex in a solvent such as dioxane, then reacting the resulting boronic ester with an appropriate aryl or heteroaryl halide, a base such as sodium carbonate, and a catalyst such as tetrakis(triphenylphosphine)palladium(0) in an appropriate solvent mixture such as dioxane and water. Alternatively, if $R^7$ is bromo and the desired group $R^3$ is a heterocycle linked through a nitrogen atom, this step may be effected by reaction of intermediate (v) with the appropriate heterocycle in the presence of a copper source such as copper (I) iodide, a base such as sodium carbonate, and a ligand such as N,N'-dimethylethane-1,2-diamine in an appropriate solvent such as DMSO.

Step 6

Step 6 of Scheme 1 is an optional step or series of steps to transform the group $R^9$ in intermediate (vi) to the group W found in molecule (vii). For example, if the group $R^9$ contains a Boc-protected amine and the desired group W contains an amide, this transformation may be accomplished by first removing the Boc group with a suitable combination of acid and solvent, such as hydrochloric acid and dioxane, then forming the desired amide by reaction with the appropriate carboxylic acid, a coupling agent such as T3P, and a base such as triethylamine in a solvent such as DMF. Alternatively, if the group $R^9$ contains an unsaturated group such as an alkyne, and the desired group W is fully saturated, this transformation may be effected by reaction with hydrogen and a suitable catalyst such as palladium on carbon.

Step 7

Step 7 of Scheme 1 is an optional step or series of steps to transform the group R' in intermediate (vii) to the group R found in molecule (viii).

Step 8

Step 8 of Scheme 1 is an optional step or series of steps to transform the group $R^{10}$ in intermediate (vii) to the group W' found in molecule (ix). For example, if the group $R^{10}$ contains an alcohol protected with a benzyl ether, and the desired group W' is the corresponding alcohol, this transformation may be effected by reaction with a suitable acid, such as hydrochloric acid. If group $R^{10}$ contains an alcohol, and the desired group W' contains an amine at the same location, this transformation may be effected by first reacting intermediate (vii) with a reagents such as thionyl chloride in a solvent such as dichloromethane, then by reacting the resulting chloride with an amine such as ethylamine, sodium iodide, and a base such as potassium carbonate in a solvent such as acetonitrile.

One skilled in the art will recognize that a number of these steps may be performed in alternative order, depending on the groups desired in the final molecule (ix). For example, for some molecules, the transformation of the group $R^7$ to $R^3$ described in Step 5 may be conducted prior to the transformation of the group Z to the group $R^9$ described in Step 4.

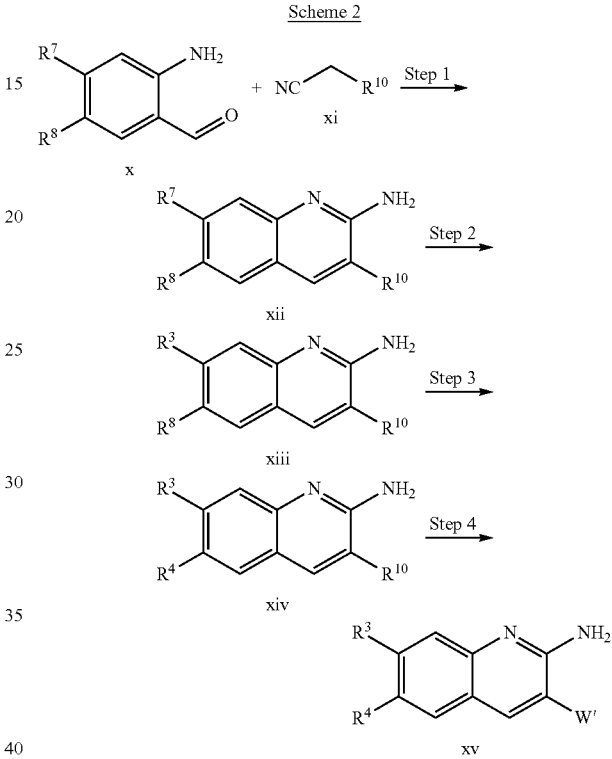

Scheme 2

As an alternative to the route described in Scheme 1, some compounds of Formula (I) may be accessed by the route described in Scheme 2.

Step 1

Step 1 of Scheme 2 begins with a suitably functionalized amino benzaldehyde (x) and a suitably functionalized nitrile (xi). If desired, the groups $R^7$, $R^8$, and $R^{10}$ may be the groups $R^3$, $R^4$, and W' found in the final product. Alternatively, one or more of these groups may be groups that can be modified at a later stage of the synthesis, such as bromo. These compounds may be purchased commercially, or may be synthesized by methods known to one skilled in the art. Step 1 of Scheme X involves reaction of (x) and (xi) in the presence of a suitable combination of base and solvent, such as potassium tert-butoxide in DMSO or sodium hydroxide in ethanol, to form aminoquinoline (xii).

Steps 2 through 4 of Scheme 2 consist of a series of optional functional group manipulations to convert the substituents $R^7$, $R^8$, and $R^{10}$ in intermediate (xii) to the substituents $R^3$, $R^4$, and W' desired in the final compound (xv). One skilled in the art will recognize that some or all of these steps may not be necessary, depending on the groups found in compounds (v) and (x). One skilled in the art will also recognize that, for some substrates, these steps may be performed in alternative order.

Step 2

Step 2 of Scheme 2 is an optional step or series of steps to transform the group $R^7$ in intermediate (xii) to the group $R^3$ found in molecule (xiii). For example, if $R^7$ is bromo and the desired group $R^3$ is an aromatic or heteroaromatic group, this transformation may be effected by reacting intermediate (xii) with an optionally protected aromatic or heteroaromatic boronic acid or boronic ester, a catalyst such as $PdCl_2(dppf)$-DCM complex, and a base such as tripotassium phosphate in a solvent mixture such as dioxane and water. If the group installed contains a protecting group, a further optional step may be conducted to remove that protecting group under appropriate conditions if desired. For example, if the group installed was a pyrazole with a tetrohydropyran protecting group, the tetrohydropyran may be removed by reaction with an acid such as trifluoroacetic acid in a solvent such as dichloromethane.

Step 3

Step 3 of Scheme 2 is an optional step or series of steps to transform the group $R_8$ in intermediate (xiii) to the group $R^4$ found in molecule (xiv).

Step 4

Step 4 of Scheme 2 is an optional step or series of steps to transform the group $R^{10}$ in intermediate (xiv) to the group W' found in molecule (xv). For example, if the group $R^{10}$ contains an alcohol protected with a benzyl ether, and the desired group W' is the corresponding alcohol, this transformation may be effected by reaction with a suitable acid, such as hydrochloric acid. If group $R^{10}$ contains an alcohol, and the desired group W' is an amine, this transformation may be effected by first reacting intermediate (xiv) with a reagents such as thionyl chloride in a solvent such as dichloromethane, then by reacting the resulting chloride with an amine such as ethylamine, sodium iodide, and a base such as potassium carbonate in a solvent such as acetonitrile.

Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities. In some cases, NMR spectra are obtained using water peak suppression, which may result in overlapping peaks not being visible or having altered shape and/or integration.

Example 1. Synthesis of Compound 101

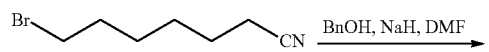

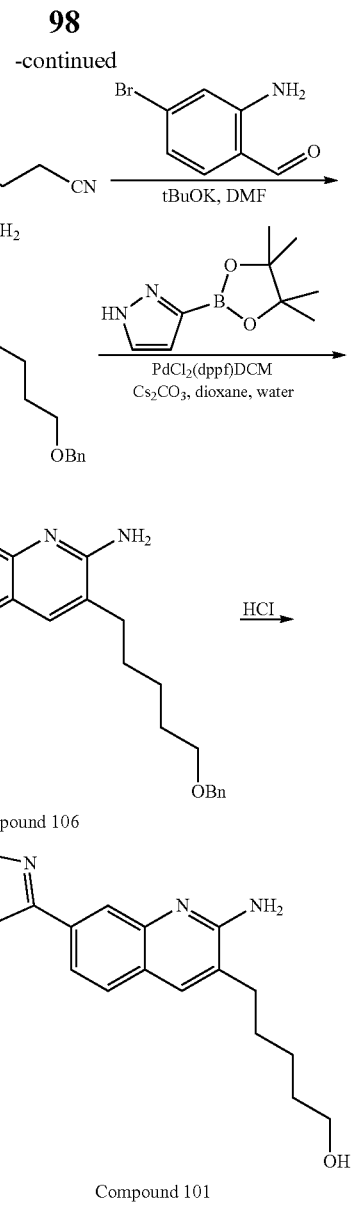

Compound 106

Compound 101

Step 1: Synthesis of 7-(benzyloxy)heptanenitrile

In a 250-mL round-bottom flask purged and maintained with an inert atmosphere of nitrogen was placed a solution of BnOH (1.6 g, 14.80 mmol, 1.00 equiv) in N,N-dimethylformamide (60 mL). This was followed by the addition of sodium hydride (1.02 g, 29.75 mmol, 2.00 equiv) in several batches at 0° C. The resulting solution was stirred for 30 minutes at 0° C. in a water/ice bath. To this was added 7-bromoheptanenitrile (2.8 g, 14.73 mmol, 1.00 equiv), in portions at 0° C. The resulting solution was allowed to react, with stirring, for an additional 16 hours at room temperature. The reaction was then quenched by the addition of 500 mL of water. The resulting solution was extracted with ethyl acetate (2×500 mL) and the combined organic layers were concentrated under vacuum. The residue was applied onto a silica gel column with ethyl acetate/petroleum ether (50:1). This resulted in 1.87 g (58%) of 7-(benzyloxy)heptanenitrile as a yellow solid.

Step 2: Synthesis of 3-[5-(benzyloxy)pentyl]-7-bromoquinolin-2-amine

In a 250-mL round-bottom flask purged and maintained with an inert atmosphere of nitrogen was placed a solution of 7-(benzyloxy)heptanenitrile (3.05 g, 14.04 mmol, 1.00 equiv) in N,N-dimethylformamide (50 mL). This was followed by the addition of t-BuOK (4.73 g, 42.15 mmol, 3.00 equiv) in several batches at 0° C. The resulting solution was stirred for 15 minutes at 0° C. in a water/ice bath. To this was added 2-amino-4-bromobenzaldehyde (2.8 g, 14.00 mmol, 1.00 equiv) in several batches at 0° C. The resulting solution was allowed to react, with stirring, for an additional 3 hours at room temperature. The reaction was then quenched by the addition of 200 mL of water. The resulting solution was extracted with ethyl acetate (2×300 mL) and the combined organic layers were concentrated under vacuum. The residue was applied onto a silica gel column with ethyl acetate/petroleum ether (40:1). This resulted in 1.87 g (33%) of 3-[5-(benzyloxy)pentyl]-7-bromoquinolin-2-amine as a yellow solid. LC-MS: (ES, m/z): [M+H]$^+$=399.1.

Step 3: Synthesis of 3-[5-(benzyloxy)pentyl]-7-(1H-pyrazol-3-yl)quinolin-2-amine (Compound 106)

Into a 30-mL sealed tube purged and maintained with an inert atmosphere of nitrogen, was placed a solution of 3-[5-(benzyloxy)pentyl]-7-bromoquinolin-2-amine (850 mg, 2.13 mmol, 1.00 equiv) in dioxane/H$_2$O (10:1) (15 mL). To the solution were added 3-(tetramethyl-1,3,2-dioxaborolan-2-yl)-1H-pyrazole (828.6 mg, 4.27 mmol, 2.00 equiv), Cs$_2$CO$_3$ (2.78 g, 8.53 mmol, 4.00 equiv) and PdCl$_2$(dppf) DCM adduct (349 mg, 0.43 mmol, 0.20 equiv). The resulting solution was stirred for 16 hours at 90° C. in an oil bath. The resulting mixture was concentrated under vacuum. The residue was applied onto a silica gel column with dichloromethane/methanol (30:1). This resulted in 559 mg (68%) of 3-[5-(benzyloxy)pentyl]-7-(1H-pyrazol-3-yl)quinolin-2-amine as a yellow solid. LC-MS: (ES, m/z): [M+H]+=387.2.

Step 4: Synthesis of 5-[2-amino-7-(1H-pyrazol-3-yl)quinolin-3-yl]pentan-1-ol (Compound 101)

Into a 50-mL round-bottom flask, was placed a solution of 3-[5-(benzyloxy)pentyl]-7-(1H-pyrazol-3-yl)quinolin-2-amine (350 mg, 0.91 mmol, 1.00 equiv) in concentrated hydrogen chloride (8 mL). The resulting solution was stirred for 1 h at 50° C. in an oil bath. The resulting mixture was concentrated under vacuum. The crude product was purified by Prep-HPLC with the following conditions (HPLC-10): Column, XBridge Shield RP18 OBD Column, 19*250 mm, 10 um; mobile phase, Water (10 mmol/L NH$_4$HCO$_3$) and MeCN (27.0% MeCN up to 60.0% in 8 min); Detector, UV 254/210 nm. This resulted in 59.8 mg (22%) of 5-[2-amino-7-(1H-pyrazol-3-yl)quinolin-3-yl]pentan-1-ol as a white solid. LC-MS: (ES, m/z): [M+H]$^+$=297.2. H-NMR: $^1$H NMR (300 MHz, CD$_3$OD-d$_4$) δ 7.85 (br s, 1H), 7.73 (s, 1H), 7.65-7.62 (m, 3H), 6.71 (d, J=2.1 Hz, 1H), 3.55 (t, J=6.3 Hz, 2H), 2.63 (t, J=7.5 Hz, 2H), 1.78-1.67 (m, 2H), 1.64-1.53 (m, 2H), 1.51-1.46 (m, 2H).

Example 2: Preparation of 3-[2-amino-7-(1H-pyrazol-3-yl)quinolin-3-yl]propan-1-ol (Compound 103)

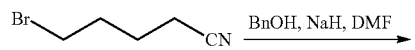

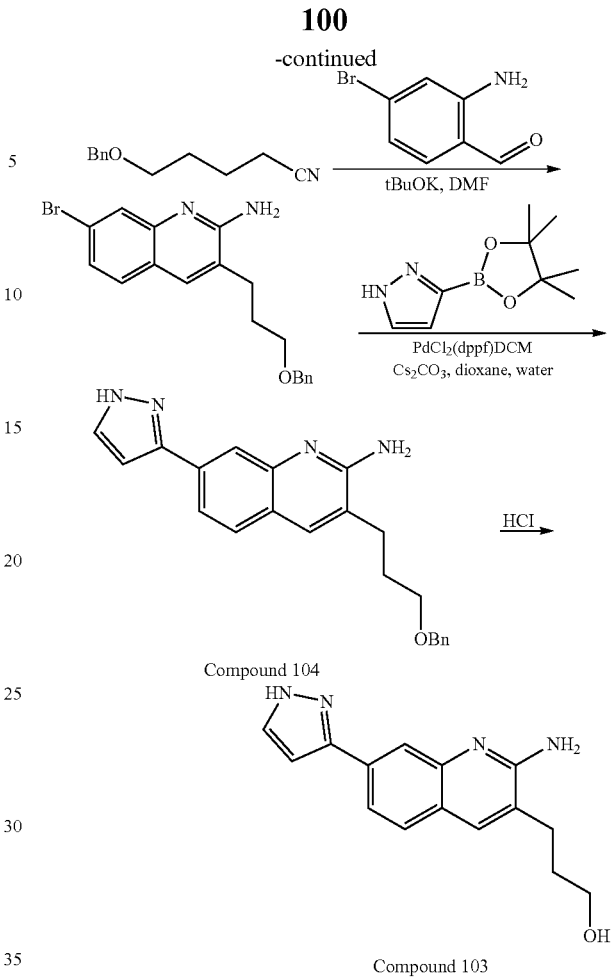

Compound 104

Compound 103

Step 1: Synthesis of 5-(benzyloxy)pentanenitrile

In a 250-mL round-bottom flask purged and maintained with an inert atmosphere of nitrogen was placed a solution of phenylmethanol (3.02 g, 27.93 mmol, 1.00 equiv) in N,N-dimethylformamide (50 mL). This was followed by the addition of sodium hydride (1.92 g, 56.00 mmol, 2.00 equiv, 70%) in several batches at 0° C. The resulting solution was stirred for 30 minutes at 0° C. in an ice water bath. To this was added 5-bromopentanenitrile (4.5 g, 27.77 mmol, 1.00 equiv), in portions at 0° C. The resulting solution was allowed to react, with stirring, for an additional 3 h at room temperature. The reaction was then quenched by the addition of 200 mL of water. The resulting solution was extracted with ethyl acetate (2×300 mL) and the combined organic layers were concentrated under vacuum. The residue was applied onto a silica gel column with ethyl acetate/petroleum ether (50:1). This resulted in 700 mg (13%) of 5-(benzyloxy)pentanenitrile as a yellow oil.

Step 2: Synthesis of 3-[3-(benzyloxy)propyl]-7-bromoquinolin-2-amine

In a 250-mL round-bottom flask purged and maintained with an inert atmosphere of nitrogen was placed a solution of 5-(benzyloxy)pentanenitrile (2.05 g, 10.83 mmol, 1.00 equiv) in N,N-dimethylformamide (50 mL). This was followed by the addition of t-BuOK (3.641 g, 32.45 mmol, 3.00 equiv) in several batches at 0° C. The resulting solution was stirred for 15 min at 0° C. in a water/ice bath. To this was added 2-amino-4-bromobenzaldehyde (2.15 g, 10.75 mmol, 1.00 equiv) in several batches at 0° C. The resulting solution was allowed to react, with stirring, for an additional 3 hours at room temperature. The reaction was then quenched by the addition of 200 mL of water. The resulting solution was extracted with ethyl acetate (2×300 mL) and the combined organic layers were concentrated under vacuum. The residue was applied onto a silica gel column with ethyl acetate/petroleum ether (30:1). This resulted in 1.3 g (32%) of 3-[3-(benzyloxy)propyl]-7-bromoquinolin-2-amine as yellow oil. LC-MS: (ES, m/z): [M+H]$^+$=371.3

Step 3: Synthesis of 3-[3-(benzyloxy)propyl]-7-(1H-pyrazol-3-yl)quinolin-2-amine (Compound 104)

In a 15-mL sealed tube purged and maintained with an inert atmosphere of nitrogen was placed a solution of 3-[3-(benzyloxy)propyl]-7-bromoquinolin-2-amine (360 mg, 0.97 mmol, 1.00 equiv) in Dioxane/H$_2$O (10:1) (8 mL). To the solution were added 3-(tetramethyl-1,3,2-dioxaborolan-2-yl)-1H-pyrazole (377.6 mg, 1.95 mmol, 2.00 equiv), Cs$_2$CO$_3$ (1.26 g, 3.87 mmol, 4.00 equiv) and pdCl$_2$(dppf) DCM adduct (159 mg, 0.19 mmol, 0.20 equiv). The resulting solution was stirred for 16 hours at 90° C. in an oil bath. The resulting mixture was concentrated under vacuum. The residue was applied onto a silica gel column with dichloromethane/methanol (25:1). This resulted in 249 mg (72%) of 3-[3-(benzyloxy)propyl]-7-(1H-pyrazol-3-yl)quinolin-2-amine as a yellow solid. LC-MS: (ES, m/z): [M+H]$^+$=359.2

Step 4. Synthesis of 3-[2-amino-7-(1H-pyrazol-3-yl)quinolin-3-yl]propan-1-ol (Compound 103)

In a 50-mL round-bottom flask was placed a solution of 3-[3-(benzyloxy)propyl]-7-(1H-pyrazol-3-yl)quinolin-2-amine (400 mg, 1.12 mmol, 1.00 equiv) in concentrated hydrogen chloride (10 mL). The resulting solution was stirred for 40 minutes at 50° C. in an oil bath. The resulting mixture was concentrated under vacuum. The crude product was purified by Prep-HPLC with the following conditions (HPLC-10): Column, X Bridge Shield RP18 OBD Column, 19*250 mm, 10 um; mobile phase, Water (10 mmol/L NH$_4$HCO$_3$) and MeCN (6.0% meCN up to 55.0% in 8 min); Detector, UV 254/210 nm. This resulted in 41.4 mg (14%) of 3-[2-amino-7-(1H-pyrazol-3-yl)quinolin-3-yl]propan-1-ol as a yellow solid. LC-MS: (ES, m/z): [M+H]$^+$=269.2. $^1$H NMR (300 MHz, DMSO-d$_6$) δ 12.86 (s, 1H), 7.82-7.79 (m, 2H), 7.66-7.59 (m, 3H), 6.74 (s, 1H), 6.21 (br s, 2H), 4.52 (t, J=5.1 Hz, 1H), 3.49-3.43 (m, 2H), 2.57 (t, J=7.5 Hz, 2H), 1.77-1.72 (m, 2H).

Example 3: Preparation of 4-[2-amino-7-(1H-pyrazol-3-yl)quinolin-3-yl]butan-1-ol (Compound 102)

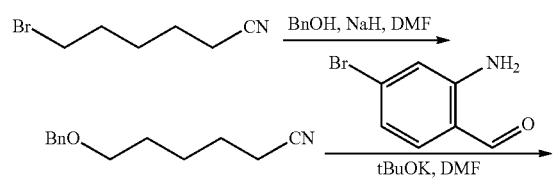

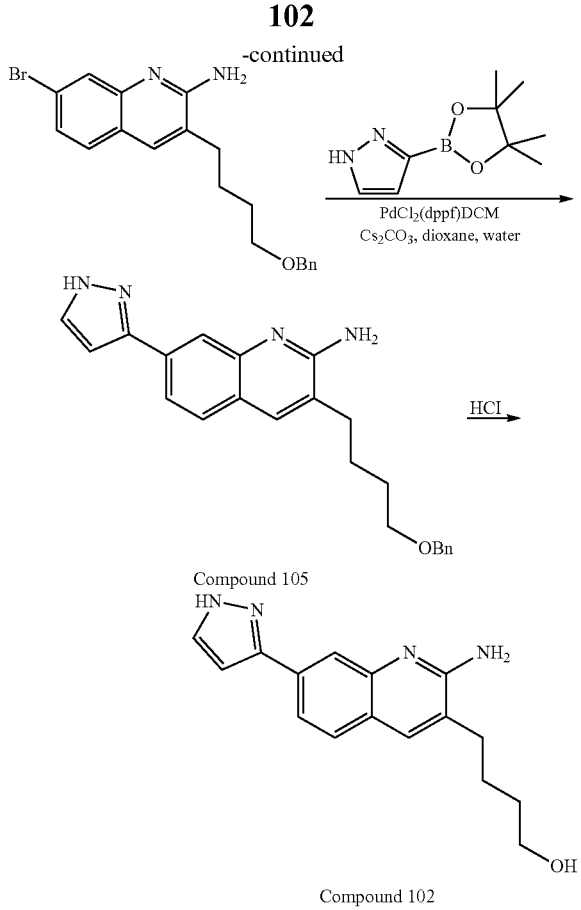

Compound 102

Step 1: Synthesis of 6-(benzyloxy)hexanenitrile

In a 250-mL round-bottom flask purged and maintained with an inert atmosphere of nitrogen was placed a solution of BnOH (3.22 g, 29.78 mmol, 1.00 equiv) in N,N-dimethylformamide (80 mL). This was followed by the addition of sodium hydride (2.05 g, 59.79 mmol, 2.00 equiv) in several batches at 0° C. The resulting solution was stirred for 30 minutes at 0° C. in a water/ice bath. To this was added 6-bromohexanenitrile (5.2 g, 29.54 mmol, 1.00 equiv) in portions at 0° C. The resulting solution was allowed to react, with stirring, for an additional 3 hours at room temperature. The reaction was then quenched by the addition of 500 mL of water. The resulting solution was extracted with ethyl acetate (3×500 mL) and the combined organic layers were concentrated under vacuum. The residue was applied onto a silica gel column with ethyl acetate/petroleum ether (60:1). This resulted in 1.06 g (18%) of 6-(benzyloxy)hexanenitrile as yellow oil.

Step 2. Synthesis of 3-[4-(benzyloxy)butyl]-7-bromoquinolin-2-amine

In a 250-mL round-bottom flask purged and maintained with an inert atmosphere of nitrogen, was placed a solution of 6-(benzyloxy)hexanenitrile (2.3 g, 11.31 mmol, 1.00 equiv) in N,N-dimethylformamide (50 mL). This was followed by the addition of t-BuOK (3.81 g, 33.95 mmol, 3.00 equiv) in several batches at 0° C. The resulting solution was stirred for 15 minutes at 0° C. in a water/ice bath. To this was added 2-amino-4-bromobenzaldehyde (2.25 g, 11.25 mmol, 1.00 equiv) in several batches at 0° C. The resulting solution was allowed to react, with stirring, for an additional 3 hours at room temperature. The reaction was then quenched by the addition of 200 mL of water. The resulting solution was extracted with ethyl acetate (2×300 mL) and the combined organic layers were concentrated under vacuum. The residue was applied onto a silica gel column with ethyl acetate/petroleum ether (40:1). This resulted in 1.8 g (41%) of 3-[4-(benzyloxy)butyl]-7-bromoquinolin-2-amine as yellow oil. LC-MS: (ES, m/z): [M+H]$^+$=385.1.

Step 3: Synthesis of 3-[4-(benzyloxy)butyl]-7-(1H-pyrazol-3-yl)quinolin-2-amine (Compound 105)

In a 30-mL sealed tube purged and maintained with an inert atmosphere of nitrogen was placed a solution of 3-[4-(benzyloxy)butyl]-7-bromoquinolin-2-amine (1.37 g, 3.56 mmol, 1.00 equiv) in dioxane/H$_2$O (10:1) (15 mL). To the solution were added 3-(tetramethyl-1,3,2-dioxaborolan-2-yl)-1H-pyrazole (1.38 g, 7.11 mmol, 2.00 equiv), Cs$_2$CO$_3$ (4.64 g, 14.24 mmol, 4.00 equiv) and PdCl$_2$(dppf)Cl$_2$ DCM adduct (583 mg, 0.71 mmol, 0.20 equiv). The resulting solution was stirred for 16 hours at 90° C. in an oil bath. The resulting mixture was concentrated under vacuum. The residue was applied onto a silica gel column with dichloromethane/methanol (35:1). This resulted in 1 g (76%) of 3-[4-(benzyloxy)butyl]-7-(1H-pyrazol-3-yl)quinolin-2-amine as a yellow solid. LC-MS: (ES, m/z): [M+H]$^+$=373.2.

Step 4: Synthesis of 4-[2-amino-7-(1H-pyrazol-3-yl)quinolin-3-yl]butan-1-ol (Compound 102)

In a 100-mL round-bottom flask was placed a solution of 3-[4-(benzyloxy)butyl]-7-(1H-pyrazol-3-yl)quinolin-2-amine (400 mg, 1.07 mmol, 1.00 equiv) in concentrated hydrogen chloride (10 mL). The resulting solution was stirred for 40 minutes at 50° C. in an oil bath. The pH value of the solution was adjusted to 8 with NH$_4$OH. The resulting mixture was concentrated under vacuum. The crude product was purified by Prep-HPLC with the following conditions (HPLC-10): Column, XBridge Shield RP18 OBD Column, 19*250 mm, 10 um; mobile phase, Water (10 mmol/L NH$_4$HCO$_3$) and MeCN (18.0% MeCN up to 40.0% in 9 min); Detector, UV 254/210 nm. This resulted in 64.7 mg (21%) of 4-[2-amino-7-(1H-pyrazol-3-yl)quinolin-3-yl]butan-1-ol as a white solid. LC-MS: (ES, m/z): [M+H]$^+$=283.2.
$^1$H NMR (300 MHz, DMSO-d$_6$) δ 12.89 (br s, 1H), 7.82 (s, 1H), 7.68-7.58 (m, 4H), 6.74 (s, 1H), 6.24 (s, 2H), 4.38 (t, J=5.1 Hz, 1H), 3.45-3.50 (m, 2H), 2.54 (t, J=7.5 Hz, 2H), 1.67-1.45 (m, 4H).

Example 4: Preparation of 3-[4-amino-7-(1H-pyrazol-3-yl)-[1,3]oxazolo[4,5-c]quinolin-2-yl]propan-1-ol (Compound 107)

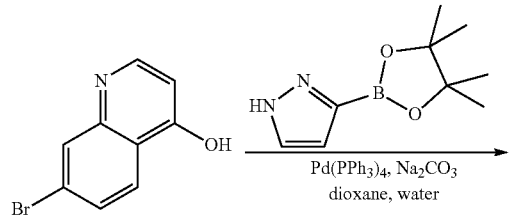

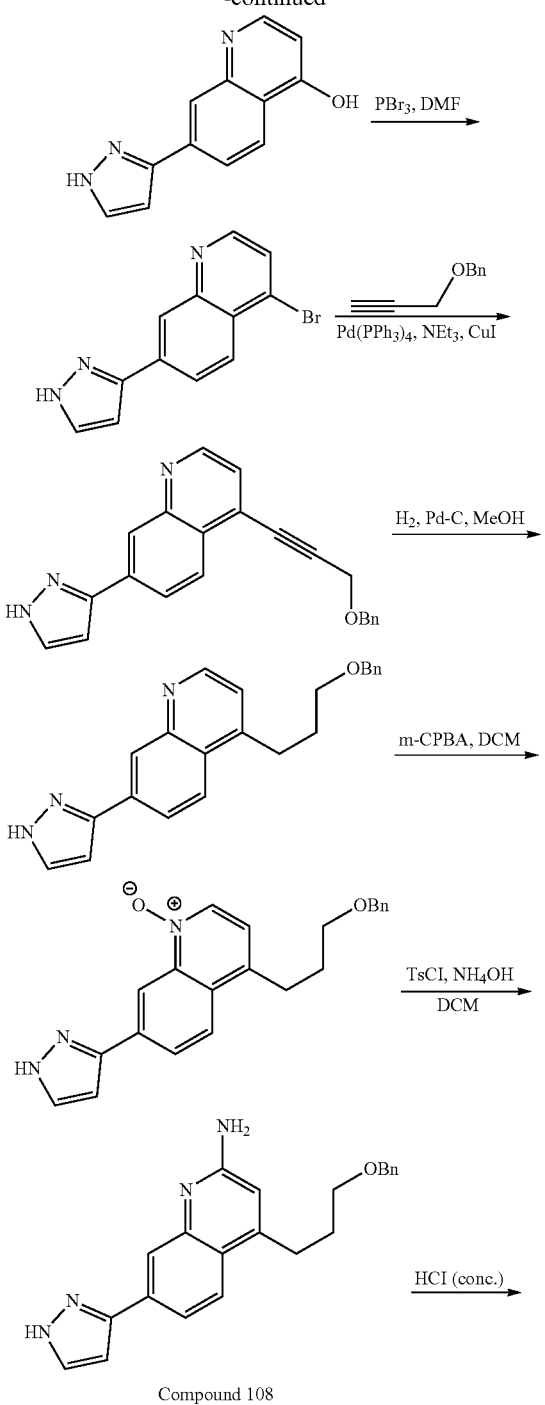

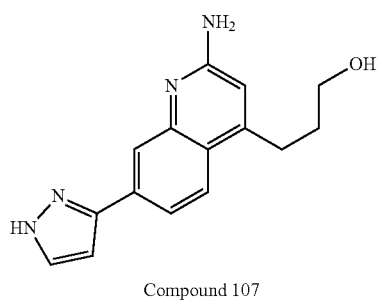

Compound 107

Step 1: Synthesis of 7-(1H-pyrazol-3-yl)quinolin-4-ol

In a 500-ml, round-bottom flask purged and maintained with an inert atmosphere of nitrogen was placed a solution of 7-bromoquinolin-4-ol (11.2 g, 49.99 mmol, 1.00 equiv) in dioxane (250 mL) and water (50 mL). To the solution were added sodium carbonate (15.9 g, 150.01 mmol, 3.00 equiv), 3-(tetramethyl-1,3,2-dioxaborolan-2-yl)-1H-pyrazole (19.4 g, 99.98 mmol, 2.00 equiv), and Pd(PPh$_3$)$_4$ (5 g, 4.33 mmol, 0.10 equiv). The resulting solution was stirred for 16 hours at 90° ° C. in an oil bath. The resulting mixture was concentrated under vacuum. The residue was applied onto a silica gel column with DCM/MeOH (0-10%). This resulted in 8.44 g (76%) of 7-(1H-pyrazol-3-yl)quinolin-4-ol as a light yellow solid. LC-MS: (ES, m/z): [M+H]$^+$=212.2.

Step 2: Synthesis of 4-bromo-7-(1H-pyrazol-3-yl)quinoline

In a 500-ml, round-bottom flask purged and maintained with an inert atmosphere of nitrogen, was placed a solution of 7-(1H-pyrazol-3-yl)quinolin-4-ol (8.44 g, 39.96 mmol, 1.00 equiv) in N,N-dimethylformamide (200 mL). This was followed by the addition of PBr$_3$ (21.6 g, 79.80 mmol, 2.00 equiv) dropwise with stirring at 0° C. The resulting solution was stirred for 30 minutes at room temperature. The reaction was then quenched by the addition of ice water. The pH of the solution was adjusted to 10 with sodium hydroxide. The resulting solution was extracted with ethyl acetate (3×500 mL) and the organic layers combined. The solution was washed with brine (3×200 mL), dried over anhydrous sodiumسulfate, and concentrated under vacuum. The residue was applied onto a silica gel column with ethyl acetate/petroleum ether (0-80%). This resulted in 5.3 g (48%) of 4-bromo-7-(1H-pyrazol-3-yl)quinoline as a light yellow solid. LC-MS: (ES, m/z): [M+H]$^+$=275.1.

Step 3: Synthesis of 4-[3-(benzyloxy)prop-1-yn-1-yl]-7-(1H-pyrazol-3-yl)quinolone In a 30-mL round-bottom flask purged and maintained with an inert atmosphere of nitrogen was placed a solution of 4-bromo-7-(1H-pyrazol-3-yl)quinoline (548 mg, 2.00 mmol, 1.00 equiv) in tetrahydrofuran (20 mL). To the solution were added Hunig's base (1.29 g, 10.00 mmol, 5.00 equiv), [(prop-2-yn-1-yloxy)methyl]benzene (584 mg, 3.99 mmol, 2.00 equiv), CuI (7.4 mg, 0.04 mmol, 0.20 equiv), and Pd(PPh$_3$)$_4$(231 mg, 0.20 mmol, 0.10 equiv). The resulting solution was stirred for 16 hours at 70° C. in an oil bath. The resulting mixture was concentrated under vacuum. The residue was applied onto a silica gel column with ethyl acetate/petroleum ether (0-70%). This resulted in 500 mg (74%) of 4-[3-(benzyloxy)prop-1-yn-1-yl]-7-(1H-pyrazol-3-yl)quinoline as a light yellow solid. LC-MS: (ES, m/z): [M+H]$^+$=340.4.

Step 4: Synthesis of 4-[3-(benzyloxy)propyl]-7-(1H-pyrazol-3-yl)quinoline

In a 100-mL round-bottom flask was placed a solution of 4-[3-(benzyloxy)prop-1-yn-1-yl]-7-(1H-pyrazol-3-yl)quinoline (420 mg, 1.24 mmol, 1.00 equiv) in methanol (20 mL). To the solution was added palladium on carbon (210 mg). The resulting solution was degassed and back filled with hydrogen. Then the solution was stirred for 16 hours at room temperature. The solids were filtered out. The resulting mixture was concentrated under vacuum. The residue was applied onto a silica gel column with ethyl acetate/petroleum ether (0-80%). This resulted in 343 mg (81%) of 4-[3-(benzyloxy)propyl]-7-(1H-pyrazol-3-yl)quinoline as a light yellow solid. LC-MS: (ES, m/z): [M+H]$^+$=344.4.

Step 5: Synthesis of 4-[3-(benzyloxy)propyl]-7-(1H-pyrazol-3-yl)quinolin-1-ium-1-olate Into a 50-mL round-bottom flask purged and maintained with an inert atmosphere of nitrogen, was placed a solution of 4-[3-(benzyloxy)propyl]-7-(1H-pyrazol-3-yl)quinoline (343 mg, 1.00 mmol, 1.00 equiv) in dichloromethane (10 mL). To the solution was added m-CPBA (344 mg, 1.99 mmol, 2.00 equiv). The resulting solution was stirred for 5 h at room temperature. The reaction was then quenched by the addition of 10 mL of Na$_2$S$_2$O$_4$ aqueous. The resulting solution was extracted with DCM:MeOH (10:1, 3×10 mL) and the organic layers combined. The solution was dried over anhydrous sodium sulfate and concentrated under vacuum. The residue was applied onto a silica gel column with dichloromethane/methanol (0-5%). This resulted in 240 mg (67%) of 4-[3-(benzyloxy)propyl]-7-(1H-pyrazol-3-yl)quinolin-1-ium-1-olate as a light yellow solid. LC-MS: (ES, m/z): [M+H]$^+$=360.4.

Step 6: Synthesis of 4-[3-(benzyloxy)propyl]-7-(1H-pyrazol-3-yl)quinolin-2-amine (Compound 108)

Into a 50-mL round-bottom flask purged and maintained with an inert atmosphere of nitrogen, was placed 4-[3-(benzyloxy)propyl]-7-(1H-pyrazol-3-yl)quinolin-1-ium-1-olate (240 mg, 0.67 mmol, 1.00 equiv) in dichloromethane (6 mL). To the solution were added NH$_4$OH (3 mL) and TsCl (176 mg, 2.00 equiv). The resulting solution was stirred for 16 h at room temperature. The resulting mixture was concentrated under vacuum. The residue was applied onto a silica gel column with dichloromethane/methanol (0-10%). This resulted in 220 mg (92%) of 4-[3-(benzyloxy)propyl]-7-(1H-pyrazol-3-yl)quinolin-2-amine as a light yellow solid. LC-MS: (ES, m/z): [M+H]$^+$=359.4.

Step 7: Synthesis of 3-[4-amino-7-(1H-pyrazol-3-yl)-[1,3]oxazolo[4,5-c]quinolin-2-yl]propan-1-ol (Compound 107)

In a 25-mL round-bottom flask was placed a solution of 4-[3-(benzyloxy)propyl]-7-(1H-pyrazol-3-yl)quinolin-2-amine (180 mg, 0.50 mmol, 1.00 equiv) in concentrated hydrogen chloride (5 mL). The resulting solution was stirred for 5 hours at room temperature. The resulting mixture was concentrated under vacuum. The pH of the solution was adjusted to 10 with NH$_4$OH. The resulting solution was extracted with DCM:MeOH (10:1, 5×10 mL) and the organic layers combined. The solution was dried over anhydrous sodium sulfate and concentrated under vacuum. The residue was purified by Prep-HPLC with the following conditions (HPLC-10): Column, X Bridge Shield RP18 OBD Column, 19*250 mm, 10 µm; mobile phase, Water (10 mmol/L NH$_4$HCO$_3$) and MeCN (5.0% MeCN up to 50.0% in 7 min); Detector, UV 254/210 nm. This resulted in 45 mg (29%) of 3-[4-amino-7-(1H-pyrazol-3-yl)-[1,3]oxazolo[4,5-c]quinolin-2-yl]propan-1-ol as a white solid. LC-MS: (ES, m/z): [M+H]$^+$=269.3.

H-NMR: (DMSO-d$_6$, 300 MHz, ppm): δ 13.38-12.91 (m, 1H), 7.84-7.81 (m, 2H), 7.67-7.64 (m, 2H), 6.78 (s, 1H), 6.58 (s, 1H), 6.30 (br s, 2H), 4.60 (t, J=5.4 Hz, 2H), 3.54-3.49 (m, 2H), 2.91 (t, J=7.8 Hz, 2H), 1.84-1.75 (m, 2H).

Example 5: Preparation of N-[3-[2-amino-7-(1H-pyrazol-3-yl)quinolin-3-yl]propyl]-N-ethylacetamide (Compound 112)

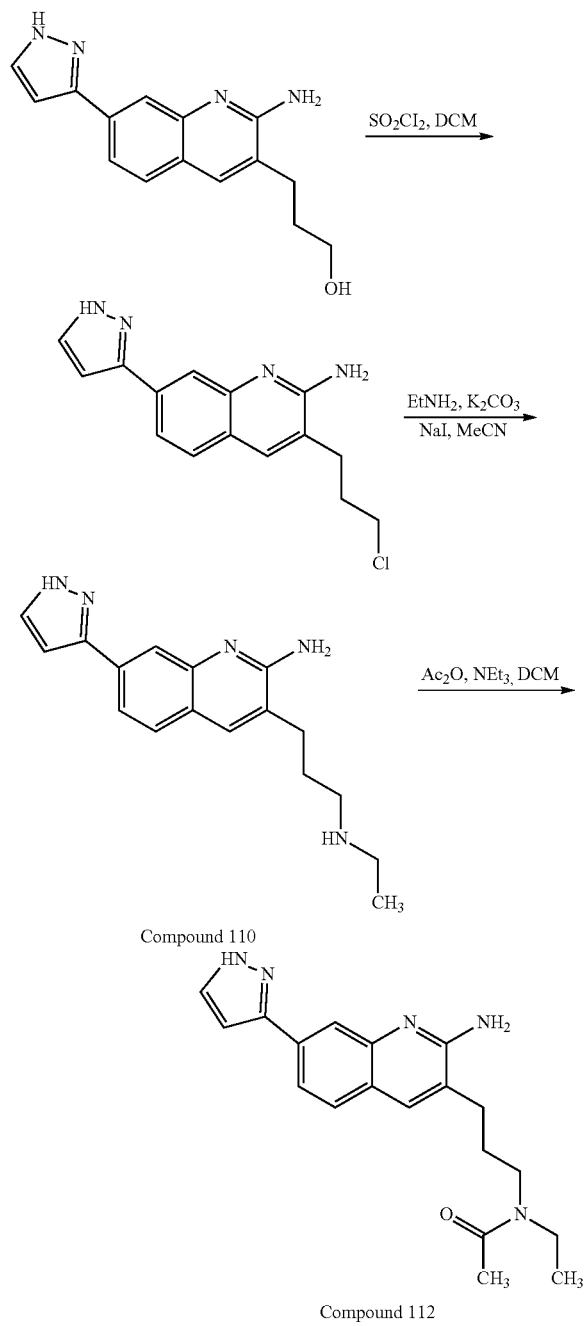

Compound 110

Compound 112

Step 1: Synthesis of 3-(3-chloropropyl)-7-(1H-pyrazol-3-yl)quinolin-2-amine

In a 100-mL round-bottom flask was placed a solution of 3-[2-amino-7-(1H-pyrazol-3-yl)quinolin-3-yl]propan-1-ol (380 mg, 1.42 mmol, 1.00 equiv) in dichloromethane (30 mL). To the solution was added $SO_2Cl_2$ (15 mL). The resulting solution was stirred overnight at room temperature. The resulting mixture was concentrated under vacuum. This resulted in 574 mg (crude) of 3-(3-chloropropyl)-7-(1H-pyrazol-3-yl)quinolin-2-amine as a yellow solid. LC-MS: (ES, m/z): $[M+H]^+$=287.1.

Step 2: Synthesis of 3-[3-(ethylamino)propyl]-7-(1H-pyrazol-3-yl)quinolin-2-amine (Compound 110)

In a 100-mL round-bottom flask, was placed a solution of 3-(3-chloropropyl)-7-(1H-pyrazol-3-yl)quinolin-2-amine (574 mg, 2.00 mmol, 1.00 equiv) in MeCN (20 mL). To the solution were added ethanamine (453 mg, 6.83 mmol, 5.00 equiv, 68%), potassium carbonate (554 mg, 4.01 mmol, 2.00 equiv), and NaI (301 mg, 2.01 mmol, 1.00 equiv). The resulting solution was stirred for 2 days at 70° C. in an oil bath. The resulting mixture was concentrated under vacuum. The residue was applied onto a silica gel column with dichloromethane/methanol (40:1). This resulted in 754 mg (crude) of 3-[3-(ethylamino)propyl]-7-(1H-pyrazol-3-yl)quinolin-2-amine as a yellow solid.
LC-MS: (ES, m/z): $[M+H]^+$=296.2.

Step 3: Synthesis of N-[3-[2-amino-7-(1H-pyrazol-3-yl)quinolin-3-yl]propyl]-N-ethylacetamide (Compound 112)

In a 100-mL round-bottom flask was placed a solution of 3-[3-(ethylamino)propyl]-7-(1H-pyrazol-3-yl)quinolin-2-amine (400 mg, 1.35 mmol, 1.00 equiv) and triethylamine (411 mg, 4.06 mmol, 3.00 equiv) in dichloromethane (20 mL). To the solution was added acetic anhydride (211 mg, 2.07 mmol, 1.50 equiv). The resulting solution was stirred for 3 hours at room temperature. The resulting mixture was concentrated under vacuum. The crude product was purified by Prep-HPLC with the following conditions: Column, XBridge Shield RP18 OBD Column, 19*250 mm, 10 μm; mobile phase, Water (10 mmol/L $NH_4HCO_3$) and MeCN (17.0% MeCN up to 55.0% in 8 min); Detector, UV 254/210 nm. This resulted in 30.9 mg (7%) of N-[3-[2-amino-7-(1H-pyrazol-3-yl)quinolin-3-yl]propyl]-N-ethylacetamide as a white solid. H-NMR: $^1$H NMR (300 MHz, DMSO-$d_6$) δ 13.38-12.90 (m, 1H), 7.87-7.63 (m, 5H), 6.79 (s, 1H), 6.45-6.28 (m, 2H), 2.60-2.55 (m, 6H), 2.00 (d, J=5.1 Hz, 3H), 1.87-1.82 (m, 2H), 1.13 (t, J=6.9 Hz, 2H), 1.03 (t, J=6.9 Hz, 2H). LC-MS: (ES, m/z): $[M+H]^+$=338.2.

Example II-1. Synthesis of 3-substituted Quinolines

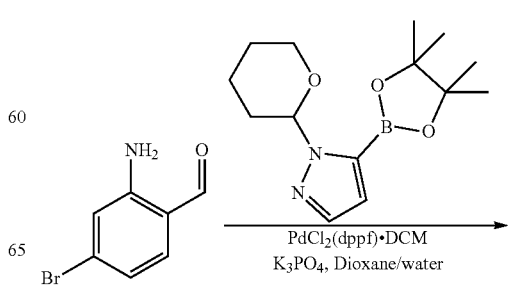

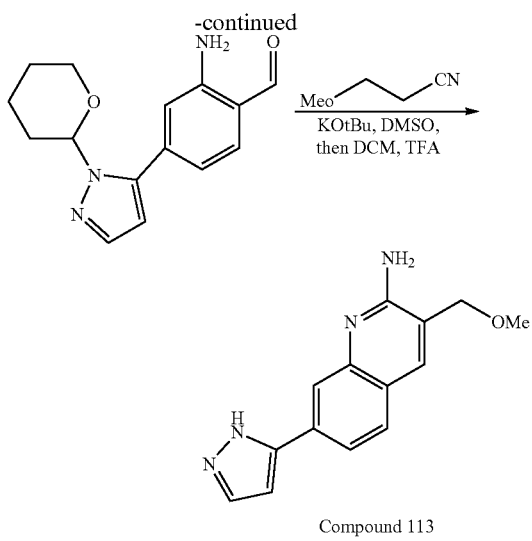

Compound 113

Step 1. Preparation of 2-amino-4-(1-(tetrahydro-2H-pyran-2-yl)-1H-pyrazol-5-yl)benzaldehyde 2-amino-4-bromobenzaldehyde (250 mg, 1.250 mmol), 1-(tetrahydro-2H-pyran-2-yl)-5-(4,4,5,5-tetramethyl-1,3,2-dioxaborolan-2-yl)-1H-pyrazole (521 mg, 1.875 mmol), and PdCl$_2$(dppf)-CH$_2$Cl$_2$ adduct (102 mg, 0.125 mmol) were placed in a vial. The vial was placed under vacuum and backfilled with nitrogen. Tripotassium phosphate (2M aqueous) (1875 µl, 3.75 mmol) and dioxane (6249 µl) were added, nitrogen was bubbled through the solution, and then the vial was capped and the reaction was heated to 100° C. overnight. The reaction was cooled, diluted with water, and extracted three times with EtOAc. The organic layers were dried with sodium sulfate and concentrated. The residue was purified via ISCO (24 g column; Hex/EtOAc; 0 to 50% gradient) to give 2-amino-4-(1-(tetrahydro-2H-pyran-2-yl)-1H-pyrazol-5-yl)benzaldehyde (207 mg, 0.763 mmol, 61.0% yield).

Step 2. Preparation of 3-(methoxymethyl)-7-(1H-pyrazol-5-yl)quinolin-2-amine. (Compound 113)

To a solution of 3-methoxypropanenitrile (12.55 mg, 0.147 mmol) and 2-amino-4-(1-(tetrahydro-2H-pyran-2-yl)-1H-pyrazol-5-yl)benzaldehyde (20 mg, 0.074 mmol) in DMSO (400 µl) was added KOtBu (16.54 mg, 0.147 mmol). The reaction was heated to 60° C. After 5 hours, the reaction was complete by LC/MS. The reaction was cooled, diluted with water, and extracted twice with EtOAc. The organic layers were concentrated. The residue was dissolved in 0.4 mL DCM and 0.4 mL TFA. After 2 hours, the reaction was complete by LC/MS. The reaction was concentrated and azeotroped with DCM. The residue was dissolved in DMF, filtered through a syringe filter, and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 7% B, 7-47% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 3-(methoxymethyl)-7-(1H-pyrazol-5-yl)quinolin-2-amine (3.2 mg, 16%). $^1$H NMR (500 MHz, DMSO-d$_6$) δ 8.33 (s, 1H), 8.06 (s, 1H), 7.98-7.88 (m, 2H), 7.82 (s, 1H), 6.87 (d, J=1.5 Hz, 1H), 4.50 (s, 2H), 3.36 (s, 3H). LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC RT: 0.99 min. M/Z=255.2.

Unless otherwise specified, the same analytical LC/MS conditions applied to the compounds characterized.

Compound 114 to Compound 122 were prepared according to synthetic procedures similar to those described for Compound 113 from the appropriate starting materials.

| Compd No. | Structure | LC/MS [M + H]$^+$ | RT (min) | $^1$H NMR (500 MHz, DMSO-d$_6$) |
|---|---|---|---|---|
| 114 | 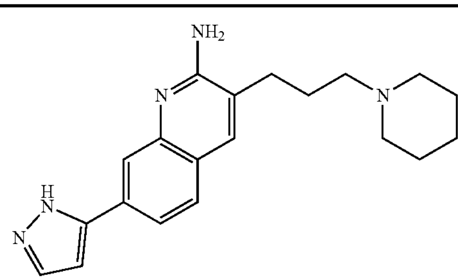 | 336.2 | 0.96 | δ 7.84 (s, 1H), 7.71 (br s, 2H), 7.65-7.55 (m, 2H), 6.76 (s, 1H), 2.61-2.54 (m, 2H), 2.45-2.26 (m, 6H), 1.82-1.70 (m, 2H), 1.57-1.45 (m, 4H), 1.38 (br s, 2H) |

| Compd No. | Structure | LC/MS [M + H]+ | RT (min) | ¹H NMR (500 MHz, DMSO-d$_6$) |
|---|---|---|---|---|
| 115 | 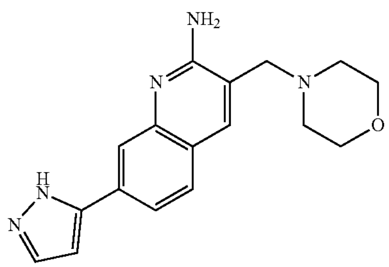 [SMILES: Nc1nc2cc(-c3ccn[nH]3)ccc2cc1CN1CCOCC1] | 310.1 | 1.44 | δ 7.88 (s, 1H), 7.81 (s, 1H), 7.72 (br s, 1H), 7.68-7.60 (m, 2H), 6.78 (s, 1H), 6.53 (br s, 1H), 3.60 (br s, 2H), 2.40 (br s, 4H) 4 protons from morpholine are not visible in NMR. |
| 116 | 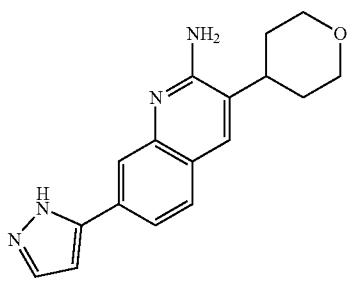 [SMILES: Nc1nc2cc(-c3ccn[nH]3)ccc2cc1C1CCOCC1] | 295.0 | 1.12 | δ 7.84 (s, 1H), 7.76 (s, 1H), 7.74-7.65 (m, 2H), 7.60 (br d, J = 7.9 Hz, 1H), 6.77 (s, 1H), 6.32 (br s, 1H), 4.03-3.89 (m, 2H), 2.91 (br t, J = 11.3 Hz, 1H), 1.81 (br d, J = 13.1 Hz, 2H), 1.71-1.58 (m, 2H) one methylene of THP ring is not visible, likely due to overlap with suppressed water peak. |
| 117 | 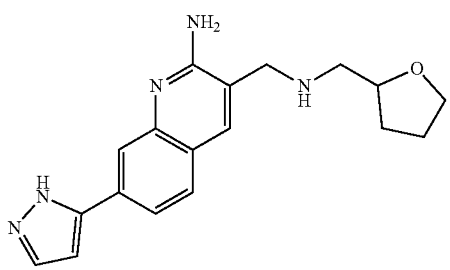 [SMILES: Nc1nc2cc(-c3ccn[nH]3)ccc2cc1CNCC1CCCO1] | 324.2 | 1.24 | δ 7.87 (s, 1H), 7.79 (s, 1H), 7.72-7.59 (m, 3H), 6.75 (d, J = 1.9 Hz, 1H), 6.42 (br s, 1H), 3.91 (dt, J = 12.4, 6.2 Hz, 1H), 3.81-3.77 (m, 1H), 3.77-3.70 (m, 1H), 3.64-3.57 (m, 1H), 2.59-2.56 (m, 1H), 1.95-1.73 (m, 4H), 1.55-1.41 (m, 2H) |
| 118 | 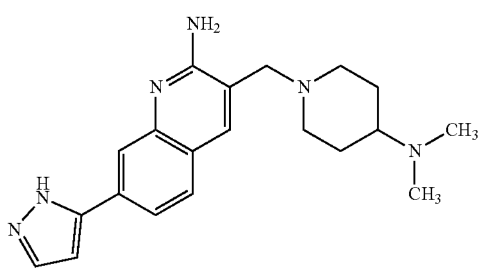 [SMILES: CN(C)C1CCN(Cc2cc3ccc(-c4ccn[nH]4)cc3nc2N)CC1] | 351.3 | 0.93 | δ 8.38 (s, 1H), 8.11 (s, 1H), 7.98-7.89 (m, 2H), 7.86 (s, 1H), 6.87 (d, J = 1.5 Hz, 1H), 4.02-3.86 (m, 1H), 3.26 (br s, 1H), 2.80-2.70 (m, 6H), 2.06 (br d, J = 10.4 Hz, 2H), 1.83-1.63 (m, 2H) several protons from piperidine ring are not visible, likely due to overlap with water/DMSO. |
| 119 | 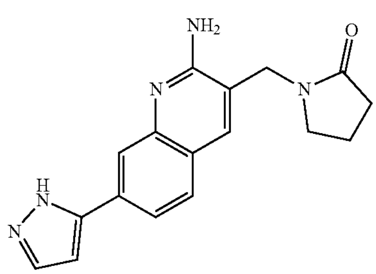 [SMILES: Nc1nc2cc(-c3ccn[nH]3)ccc2cc1CN1CCCC1=O] | 308.2 | 0.99 | δ 8.28 (s, 1H), 8.08 (s, 1H), 8.00-7.90 (m, 2H), 7.84 (br s, 1H), 6.87 (d, J = 1.5 Hz, 1H), 4.43 (s, 2H), 3.49-3.37 (m, 2H) (overlaps suppressed water peak), 2.38 (br t, J = 8.1 Hz, 2H), 2.07-1.92 (m, 2H) |

-continued

| Compd No. | Structure | LC/MS [M + H]+ | RT (min) | 1H NMR (500 MHz, DMSO-d6) |
|---|---|---|---|---|
| 120 | 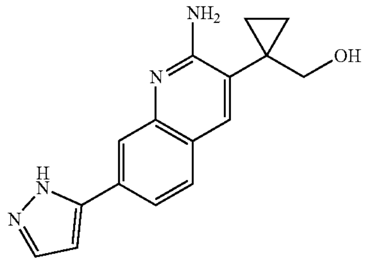 [SMILES: Nc1nc2cc(-c3ccn[nH]3)ccc2cc1C1(CO)CC1] | 280.9 | 1.14 | δ 7.86 (s, 1H), 7.79 (s, 1H), 7.74-7.68 (m, 1H), 7.67-7.57 (m, 2H), 6.78 (s, 1H), 6.20 (br s, 1H), 0.94 (br s, 2H), 0.72 (br s, 2H) Methylene adjacent to alcohol is not visible, possibly due to overlap with suppressed water peak. |
| 121 | 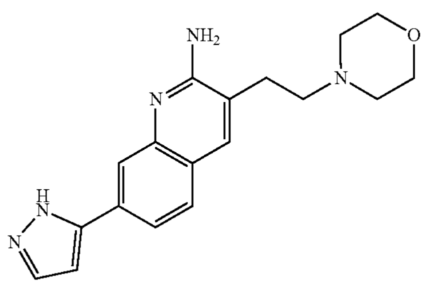 [SMILES: Nc1nc2cc(-c3ccn[nH]3)ccc2cc1CCN1CCOCC1] | 324.2 | 0.96 | δ 8.30 (br s, 1H), 8.11 (br s, 1H), 7.98-7.81 (m, 3H), 6.86 (s, 1H), 4.16-3.66 (m, 2H), 3.11 (br s, 1H). Peaks for morpholino ethyl chain are broadened and have low integration |
| 122 | 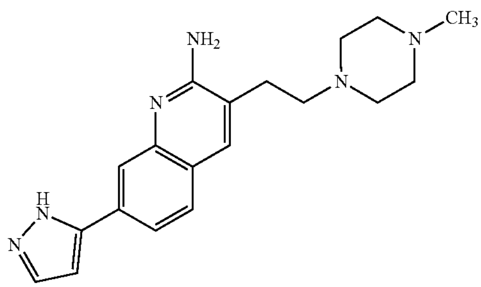 [SMILES: CN1CCN(CCc2cc3ccc(-c4ccn[nH]4)cc3nc2N)CC1] | 337.06 | 0.99 | δ 7.84 (s, 1H), 7.76-7.68 (m, 2H), 7.65-7.57 (m, 2H), 6.76 (d, J = 1.8 Hz, 1H), 2.78-2.69 (m, 2H), 2.60 (br t, J = 7.0 Hz, 2H), 2.47-2.25 (m, 4H), 2.17 (s, 3H) |

Step 2A. Alternative Procedure for Quinoline Formation: Preparation of 3-(1H-imidazol-5-yl)-7-(1H-pyrazol-5-yl)quinolin-2-amine (Compound 123)

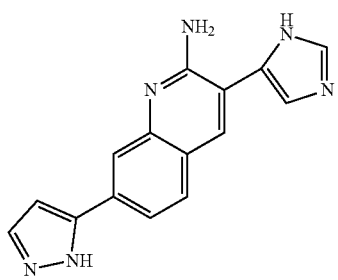 [SMILES: Nc1nc2cc(-c3ccn[nH]3)ccc2cc1-c1cnc[nH]1]

To a solution of 2-(1H-imidazol-5-yl)acetonitrile (11.84 mg, 0.111 mmol) and 2-amino-4-(1-(tetrahydro-2H-pyran-2-yl)-1H-pyrazol-5-yl)benzaldehyde (20 mg, 0.074 mmol) in EtOH (369 µl) was added sodium hydroxide (1M in EtOH) (14.74 µl, 0.015 mmol). The reaction was heated to 70° C. After 1 hour, 75 µL of 1M sodium hydroxide in EtOH was added, and heating was continued overnight. LC/MS showed that the reaction was complete. The reaction was cooled and concentrated. The residue was dissolved in 0.4 mL DCM and 0.4 mL TFA was added. After 45 minutes, LC/MS showed that the reaction was complete. The reaction was concentrated and azeotroped with DCM. The residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile: water with 10-mM. ammnonium acetate; Gradient: a 0-minute hold at 0% B, 0-40% B over minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 3-(1H-imidazol-5-yl)-7-(1H-pyrazol-5-yl)quinolin-2-amine (6.4 mg, 31%). 1H NMR (500 MHz, DMSO-d6) δ 8.27 (s, 1H), 7.86 (d, J=8.3 Hz, 2H), 7.81 (s, 1H), 7.73-7.59 (m, 3H), 6.77 (d, J=1.8 Hz, 1H). LC RT: 0.86 min. M/Z=277.2.

Compound 124 to Compound 127 were prepared according to the synthetic procedures described for Compound 123 from the appropriate starting materials.

| Compd. No. | Structure | LC/MS [M + H]+ | RT (min) | 1H NMR (500 MHz, DMSO-d6) |
|---|---|---|---|---|
| 124 | 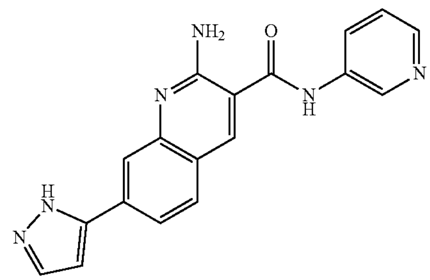 [SMILES: Nc1nc2cc(-c3ccn[nH]3)ccc2cc1C(=O)Nc1cccnc1] | 331.1 | 1.19 | δ 8.90 (s, 1H), 8.56 (s, 1H), 8.34 (br d, J = 4.5 Hz, 1H), 8.15 (br d, J = 7.7 Hz, 1H), 7.91 (s, 1H), 7.84-7.79 (m, 1H), 7.75 (br s, 1H), 7.42 (dd, J = 8.1, 4.7 Hz, 1H), 6.93-6.75 (m, 2H) |
| 125 | 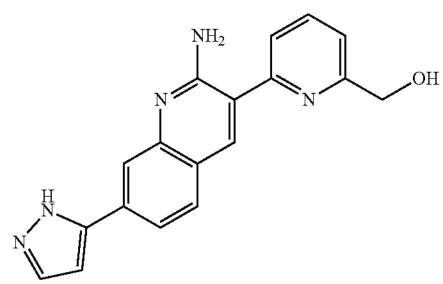 [SMILES: Nc1nc2cc(-c3ccn[nH]3)ccc2cc1-c1cccc(CO)n1] | 318.1 | 1.10 | δ 8.48 (s, 1H), 8.01-7.95 (m, 1H), 7.91 (br d, J = 4.8 Hz, 2H), 7.80 (d, J = 8.3 Hz, 1H), 7.73 (s, 1H), 7.68 (br d, J = 8.4 Hz, 1H), 7.48 (br d, J = 7.5 Hz, 2H), 6.81 (d, J = 1.9 Hz, 1H), 4.67 (br s, 2H) |
| 126 | 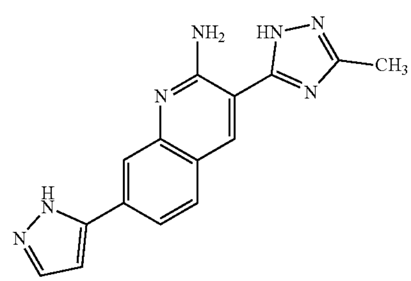 [SMILES: Cc1n[nH]c(-c2cc3ccc(-c4ccn[nH]4)cc3nc2N)n1] | 292.1 | 0.95 | δ 8.77 (br s, 1H), 7.96-7.52 (m, 5H), 6.84 (br s, 1H), 2.48 (br s, 3H) |
| 127 | 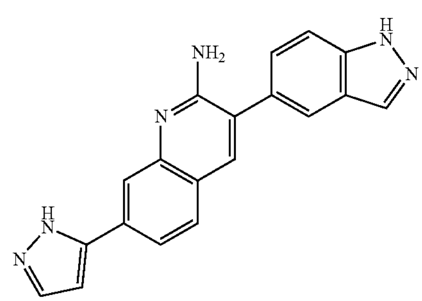 [SMILES: Nc1nc2cc(-c3ccn[nH]3)ccc2cc1-c1ccc2[nH]ncc2c1] | 326.9 | 1.36 | δ 8.33 (s, 1H), 8.23-8.14 (m, 2H), 7.98 (br d, J = 7.6 Hz, 3H), 7.87 (br s, 1H), 7.73 (d, J = 8.5 Hz, 1H), 7.50 (br d, J = 8.5 Hz, 1H), 6.89 (s, 1H) |

Example II-2: Synthesis of 4-amino Substituted Quinolines

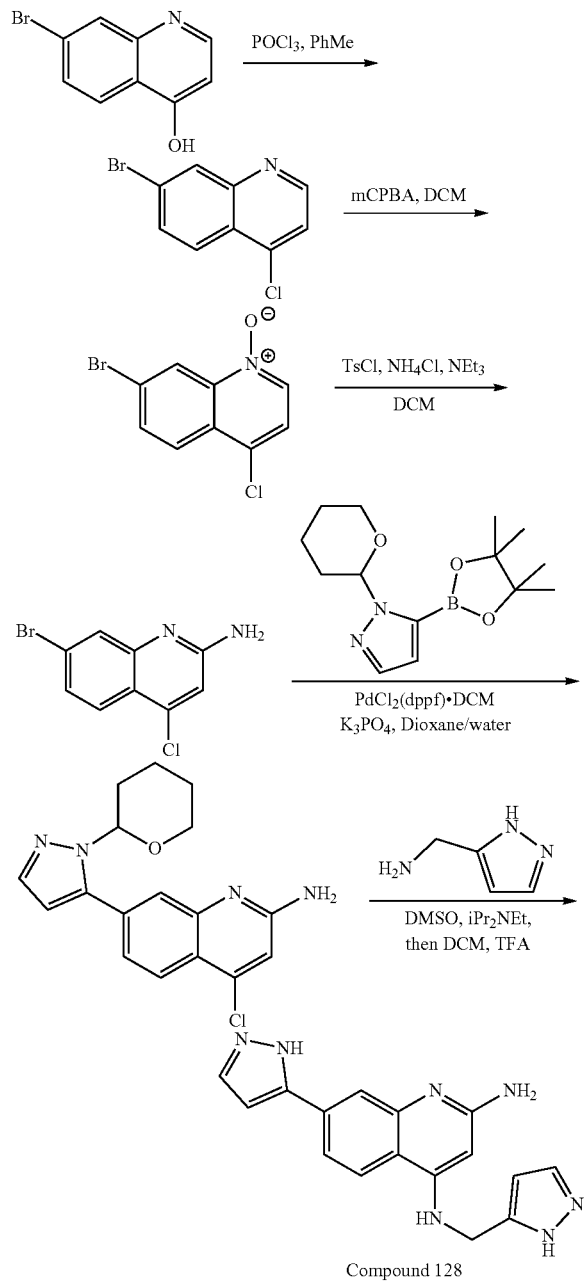

Compound 128

Step 1. Preparation of 7-bromo-4-chloroquinoline

To a suspension of 7-bromoquinolin-4-ol (2.5 g, 11.16 mmol) in toluene (20 mL) was added POCl₃ (2.080 mL, 22.32 mmol). The reaction was heated to 100° C. After 1.5 hours, the reaction was cooled, and then ice was added. The reaction was stirred vigorously for ca. 30 min, then water was added. The reaction was extracted twice with DCM. The organic layers were washed with saturated aqueous NaHCO₃ and brine, then dried over sodium sulfate and concentrated. LC/MS shows that some product remains in the initial aqueous layer. The aqueous layer was stirred and saturated aqueous NaHCO₃ solution was added carefully. The precipitated solid was filtered off, washed with water, and dried. Material from organic layer and the filtered solid were combined and dried under high vacuum to give 7-bromo-4-chloroquinoline (2.46 g, 10.14 mmol, 91% yield). $^1$H NMR (400 MHz, CHLOROFORM-d) δ 8.80 (d, J=4.7 Hz, 1H), 8.33 (d, J=1.9 Hz, 1H), 8.12 (d, J=9.0 Hz, 1H), 7.75 (dd, J=9.0, 2.0 Hz, 1H), 7.52 (d, J=4.8 Hz, 1H).

Step 2. Preparation of 7-bromo-4-chloroquinoline 1-oxide

To a solution of 7-bromo-4-chloroquinoline (2.0 g, 8.25 mmol) in DCM (55.0 ml) was added mCPBA (6.10 g, 24.74 mmol). The reaction was stirred overnight, then quenched with saturated sodium thiosulfate solution. The reaction was stirred for 0.5 hours, then saturated aqueous sodium bicarbonate was added. The reaction was extracted twice with DCM. The organic layers were washed with brine, dried with sodium sulfate, and concentrated to give 7-bromo-4-chloroquinoline 1-oxide (2.16 g, 8.36 mmol, quantitative yield). $^1$H NMR (400 MHz, CHLOROFORM-d) δ 8.99 (d, J=1.9 Hz, 1H), 8.43 (d, J=6.6 Hz, 1H), 8.10 (d, J=9.0 Hz, 1H), 7.86 (dd, J=9.0, 2.0 Hz, 1H), 7.40 (d, J=6.6 Hz, 1H).

Step 3. Preparation of 7-bromo-4-chloroquinolin-2-amine

In one round-bottomed flask, 7-bromo-4-chloroquinoline 1-oxide (9400 mg, 36.4 mmol) was suspended in DCM (150 mL). Ts-Cl (7626 mg, 40.0 mmol) was added. This mixture was stirred for one hour. In a second round-bottomed flask, ammonium chloride (9725 mg, 182 mmol) (dried in an oven at 110° C. overnight) was suspended in DCM (150 mL). Triethylamine (25.3 mL, 182 mmol) was added and the mixture was stirred for 0.5 hours, then the contents of the first roundbottom flask were added to the second. The reaction was stirred overnight, then filtered and concentrated. The residue was dissolved in 100 ml of hot DCM. The solution was cooled to room temperature and the solid was filtered off. The filter cake was washed with 100 mL of −20° C. DCM. The filter cake was suspended in water (50 mL) and filtered. The solid is the desired product 7-bromo-4-chloroquinolin-2-amine. The DCM filtrate was evaporated, suspended in water (100 mL), and filtered. The filter cake was washed with 100 mL of −20° C. DCM to give additional product. The combined solids were dried under high vacuum to give 7-bromo-4-chloroquinolin-2-amine (6.52 g, 69.6%). $^1$H NMR (400 MHz, DMSO-d₆) δ 7.79 (d, J=8.7 Hz, 1H), 7.65 (d, J=1.9 Hz, 1H), 7.39 (dd, J=8.8, 2.0 Hz, 1H), 6.98 (s, 1H), 6.88 (s, 2H).

Step 4. Preparation of 4-chloro-7-(1-(tetrahydro-2H-pyran-2-yl)-1H-pyrazol-5-yl)quinolin-2-amine In each of two 40 mL pressure vials was placed (1-(tetrahydro-2H-pyran-2-yl)-1H-pyrazol-5-yl)boronic acid (0.714 g, 3.64 mmol), 7-bromo-4-chloroquinolin-2-amine (0.750 g, 2.91 mmol), and PdCl₂(dppf)-DCM adduct (0.238 g, 0.291 mmol). The vials were placed under vacuum and backfilled with nitrogen three times. Dioxane (14.56 ml) and tripotassium phosphate (2M aqueous) (4.37 ml, 8.74 mmol)

were added to each vial, nitrogen was bubbled through the solution, then the reaction was heated to 100° C. overnight. The vials were cooled, diluted with EtOAc and water, and combined. The reaction was extracted three times with EtOAc, and then the organic layers were washed with brine, dried with sodium sulfate, and concentrated. The residue was purified via ISCO (80 g column; DCM/MeOH; 0 to 10% gradient) to give 4-chloro-7-(1-(tetrahydro-2H-pyran-2-yl)-1H-pyrazol-5-yl)quinolin-2-amine (1.14 g, 59.5% yield). $^1$H NMR (400 MHz, CHLOROFORM-d) δ 8.11 (d, J=8.6 Hz, 1H), 7.82 (d, J=1.4 Hz, 1H), 7.65 (d, J=1.5 Hz, 1H), 7.52 (dd, J=8.5, 1.7 Hz, 1H), 6.90 (s, 1H), 6.45 (d, J=1.8 Hz, 1H), 5.38-5.26 (m, 1H), 4.90 (br s, 1H), 4.22-4.09 (m, 2H), 3.65 (td, J=11.7, 2.3 Hz, 1H), 2.68-2.51 (m, 1H), 2.14-1.51 (m, 5H).

Step 5: Preparation of N4-((1H-pyrazol-3-yl)methyl)-7-(1H-pyrazol-5-yl)quinoline-2,4-diamine (Compound 128)

To a solution of 4-chloro-7-(1-(tetrahydro-2H-pyran-2-yl)-1H-pyrazol-5-yl)quinolin-2-amine (20 mg, 0.061 mmol) and (1H-pyrazol-3-yl)methanamine (59.1 mg, 0.608 mmol) in DMSO (0.5 mL) was added Hunig's Base (0.032 mL, 0.182 mmol). The reaction was heated to 120° C. overnight. The reaction was cooled, diluted with water, and extracted three times with EtOAc. The organic layers were concentrated, then dissolved in 0.4 mL DCM and 0.4 mL TFA. After 1 hour, the reaction was complete by LCMS. The reaction was concentrated and azeotroped with DCM. The residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 3-minute hold at 0% B, 0-32% B over 25 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give N4-((1H-pyrazol-3-yl)methyl)-7-(1H-pyrazol-5-yl)quinoline-2,4-diamine (4.6 mg, 24.7%). $^1$H NMR (500 MHz, DMSO-d$_6$) δ 8.00 (br d, J=8.2 Hz, 1H), 7.75 (s, 1H), 7.72 (br s, 1H), 7.58 (br s, 1H), 7.54 (br d, J=7.9 Hz, 1H), 7.43 (br s, 1H), 6.76 (s, 1H), 6.62-6.41 (m, 1H), 6.20 (s, 1H), 5.76 (s, 1H), 4.42 (br d, J=5.2 Hz, 2H).

LC RT: 0.99 min. M/Z=306.18.

Step 5b: Procedure for use of amine salts. Preparation of N4-(1-(6-methoxypyridin-2-yl)ethyl)-7-(1H-pyrazol-5-yl)quinoline-2,4-diamine, 7 TFA (Compound 129)

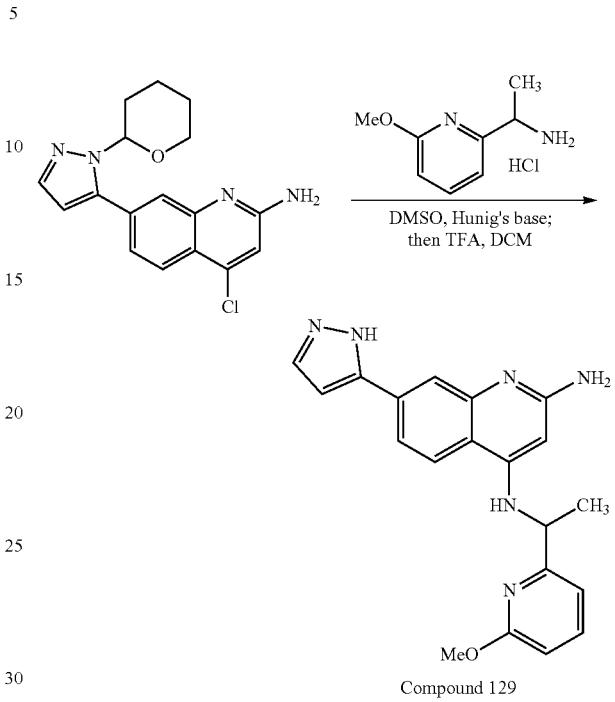

Compound 129

To a solution of 4-chloro-7-(1-(tetrahydro-2H-pyran-2-yl)-1H-pyrazol-5-yl)quinolin-2-amine (20 mg, 0.061 mmol) and 1-(6-methoxypyridin-2-yl)ethan-1-amine, HCl (115 mg, 0.608 mmol) in DMSO (0.5 mL) was added Hunig's Base (0.159 mL, 0.912 mmol). The reaction was heated to 100° C. overnight. Then, the reaction temperature was increased to 120° C. for 5.5 hours. The reaction was cooled, diluted with water, and extracted three times with EtOAc. The organic layers were concentrated. The residue was dissolved in 0.4 mL DCM and 0.4 mL TFA. After ca. 1 hour, the reaction was complete by LCMS. The reaction was concentrated and azeotroped with DCM. The residue was dissolved in DMF, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 9% B, 9-46% B over 23 minutes, then a 6-minute hold at 100% B; Flow Rate: 20 mL/min; Column Temperature: 25° C. Fraction collection was triggered by MS signals. Fractions containing the desired product were combined and dried via centrifugal evaporation to give N4-(1-(6-methoxypyridin-2-yl)ethyl)-7-(1H-pyrazol-5-yl)quinoline-2,4-diamine, 2 TFA (4.4 mg, 12%). $^1$H NMR (500 MHz, DMSO-d$_6$) δ 8.51 (br d, J=8.5 Hz, 1H), 8.18 (br d, J=6.4 Hz, 1H), 8.01-7.81 (m, 3H), 7.68 (br t, J=N7.6 Hz, 1H), 7.58 (br s, 2H), 6.96 (br d, J=7.3 Hz, 1H), 6.86 (br s, 1H), 6.71 (br d, J=7.9 Hz, 1H), 5.63 (s, 1H), 4.70 (br t, J=6.6 Hz, 1H), 3.88 (s, 3H), 1.68 (br d, J=6.7 Hz, 3H). LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 1.46 min. M/Z=361.31.

Compound 130 to Compound 166, Compound 222 to Compound 290 and Compound 351 were prepared according to the synthetic procedures described for Compound 129 from the appropriate starting materials.

| Compd. No. | Structure | LC/MS [M + H]+ | RT (min) | 1H NMR (500 MHz, DMSO-d6) |
|---|---|---|---|---|
| 130 | 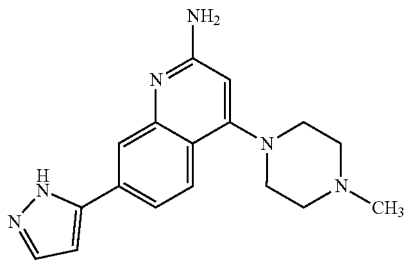 [SMILES: CN1CCN(c2cc(N)nc3cc(-c4ccn[nH]4)ccc23)CC1] | 309.2 | 1.21 | δ 7.81 (s, 1H), 7.76-7.67 (m, 2H), 7.58 (br d, J = 8.2 Hz, 1H), 6.75 (s, 1H), 6.31 (br s, 1H), 6.24 (s, 1H), 3.08 (br s, 4H), 2.60 (br s, 4H), 2.29 (s, 3H) |
| 131 | 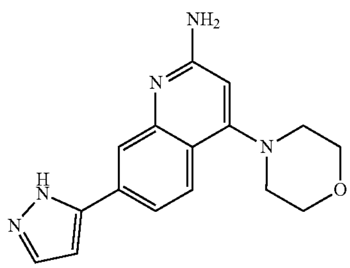 [SMILES: Nc1cc(N2CCOCC2)c2ccc(-c3ccn[nH]3)cc2n1] | 296.3 | 1.12 | δ 8.11 (br s, 1H), 8.02 (br s, 1H), 7.96-7.90 (m, 1H), 7.89-7.80 (m, 2H), 6.81 (d, J = 2.0 Hz, 2H), 6.34 (s, 2H), 3.88 (m, 4H), 3.36-3.29 (m, 2H) 2 protons from morpholine ring are not visible, likely due to overlap with water/water suppression. |
| 132 | 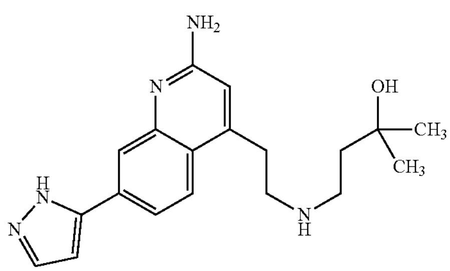 [SMILES: CC(C)(O)CCNCCc1cc(N)nc2cc(-c3ccn[nH]3)ccc12] | 311.9 | 1.05 | δ 7.89 (br d, J = 8.5 Hz, 1H), 7.76-7.66 (m, 2H), 7.51 (br s, 1H), 6.81 (br d, J = 4.0 Hz, 1H), 6.75 (s, 1H), 6.32-6.11 (m, 1H), 5.70 (s, 1H), 3.25 (br s, 1H), 1.80 (br t, J = 7.5 Hz, 2H), 1.20 (s, 6H) One proton from sidechain is missing in NMR, likely due to overlap with suppressed water peak. |
| 133 | 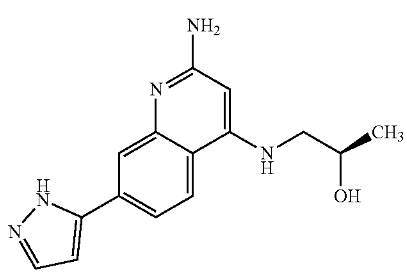 [SMILES: C[C@@H](O)CNc1cc(N)nc2cc(-c3ccn[nH]3)ccc12] | 284.3 | 0.69 | δ 8.04 (br d, J = 8.6 Hz, 1H), 7.80 (br s, 1H), 7.72 (br s, 1H), 7.67-7.56 (m, 1H), 6.76 (s, 1H), 5.80 (s, 1H), 4.04-3.95 (m, 1H), 3.89 (s, 2H), 1.18 (d, J = 6.1 Hz, 3H) |
| 134 | 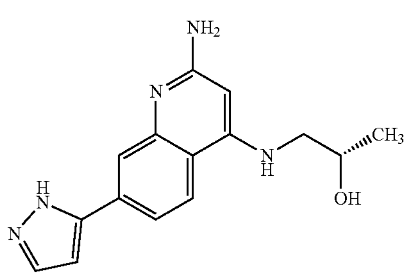 [SMILES: C[C@H](O)CNc1cc(N)nc2cc(-c3ccn[nH]3)ccc12] | 283.9 | 1.09 | δ 8.26 (d, J = 8.7 Hz, 1H), 8.00-7.91 (m, 2H), 7.88-7.78 (m, 2H), 7.47 (br s, 2H), 6.83 (d, J = 2.1 Hz, 1H), 5.89 (s, 1H), 4.05-3.98 (m, 1H), 3.89 (s, 2H), 1.18 (d, J = 6.2 Hz, 3H) |

-continued

| Compd. No. | Structure | LC/MS [M + H]⁺ | RT (min) | ¹H NMR (500 MHz, DMSO-d₆) |
|---|---|---|---|---|
| 135 | 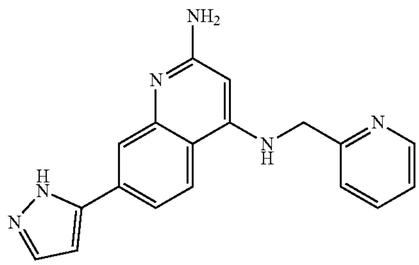 [SMILES: Nc1cc(NCc2ccccn2)c2ccc(-c3ccn[nH]3)cc2n1] | 317.0 | 1.06 | δ 8.56 (br d, J = 4.3 Hz, 1H), 8.07 (br d, J = 8.5 Hz, 1H), 7.81-7.68 (m, 4H), 7.65-7.56 (m, 1H), 7.33 (br d, J = 7.6 Hz, 1H), 7.31-7.24 (m, 1H), 6.78 (s, 1H), 5.59 (s, 1H), 4.55 (br d, J = 5.5 Hz, 2H) |
| 136 | 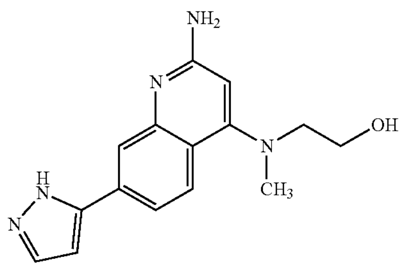 [SMILES: CN(CCO)c1cc(N)nc2cc(-c3ccn[nH]3)ccc12] | 284.3 | 0.99 | δ 8.02 (br d, J = 8.5 Hz, 1H), 7.84 (s, 1H), 7.74 (br s, 1H), 7.61 (br d, J = 4.9 Hz, 1H), 6.78 (s, 1H), 6.59 (br d, J = 12.2 Hz, 1H), 6.20 (s, 1H), 3.74 (br s, 2H), 2.91 (s, 3H). One methylene from sidechain is not visible, likely due to overlap with suppressed water peak. |
| 137 | 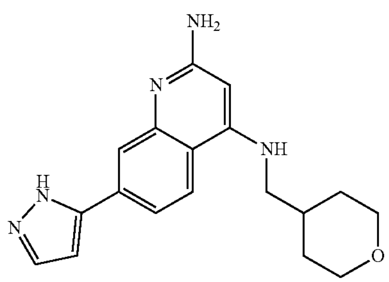 [SMILES: Nc1cc(NCC2CCOCC2)c2ccc(-c3ccn[nH]3)cc2n1] | 323.9 | 1.13 | δ 8.15 (br d, J = 8.5 Hz, 1H), 7.91-7.68 (m, 4H), 6.83 (s, 1H), 5.80 (s, 1H), 3.86 (br d, J = 10.7 Hz, 2H), 3.68-3.53 (m, 2H), 3.28 (br t, J = 11.6 Hz, 2H), 1.98 (br s, 1H), 1.66 (br d, J = 12.2 Hz, 2H), 1.33-1.19 (m, 2H) |
| 138 | 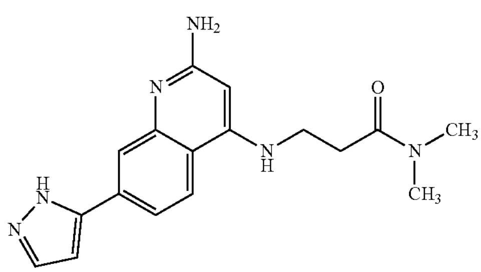 [SMILES: CN(C)C(=O)CCNc1cc(N)nc2cc(-c3ccn[nH]3)ccc12] | 325.1 | 1.08 | δ 8.16 (br d, J = 8.5 Hz, 1H), 8.01-7.74 (m, 4H), 7.49-7.29 (m, 1H), 6.84 (br s, 1H), 5.82 (s, 1H), 3.36 (br s, 2H), 2.98 (s, 3H), 2.85 (s, 3H), 2.76 (br t, J = 6.9 Hz, 2H) |
| 139 | 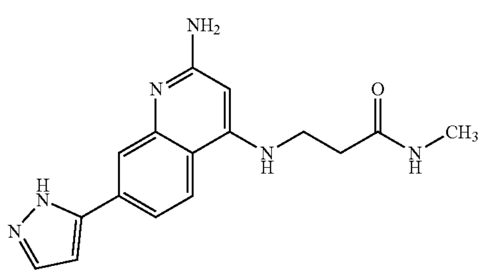 [SMILES: CNC(=O)CCNc1cc(N)nc2cc(-c3ccn[nH]3)ccc12] | 311.2 | 1.03 | δ 7.91 (br d, J = 8.5 Hz, 2H), 7.78-7.66 (m, 2H), 7.51 (br d, J = 7.6 Hz, 1H), 6.85 (br s, 1H), 6.75 (s, 1H), 6.36 (br s, 1H), 5.73 (s, 1H), 2.60 (br d, J = 4.3 Hz, 3H) methylenes of sidechains are not visible in NMR, likely due to overlap with suppressed water peak. |

-continued

| Compd. No. | Structure | LC/MS [M + H]+ | RT (min) | 1H NMR (500 MHz, DMSO-d6) |
|---|---|---|---|---|
| 140 | 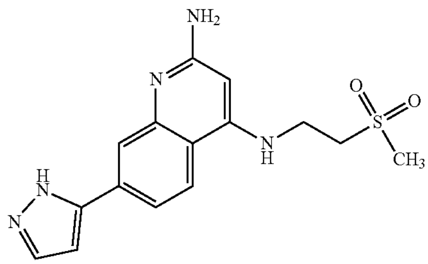 [SMILES: CS(=O)(=O)CCNc1cc(N)nc2cc(-c3ccn[nH]3)ccc12] | 332.2 | 0.87 | δ 8.25-8.09 (m, 2H), 7.99 (br s, 1H), 7.88 (br s, 2H), 7.75 (br s, 2H), 6.86 (br s, 1H), 5.87 (s, 1H), 3.76 (br d, J = 5.5 Hz, 2H), 3.56 (br t, J = 6.3 Hz, 2H), 3.10 (s, 3H) |
| 141 | 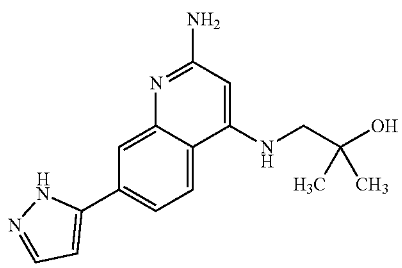 [SMILES: CC(C)(O)CNc1cc(N)nc2cc(-c3ccn[nH]3)ccc12] | 296.2 | 1.06 | δ 8.01 (br d, J = 8.5 Hz, 1H), 7.77 (s, 1H), 7.73 (br s, 1H), 7.56 (br d, J = 7.9 Hz, 1H), 6.76 (s, 1H), 6.60 (br d, J = 17.4 Hz, 1H), 6.45 (br s, 1H), 5.82 (s, 1H), 3.13 (br d, J = 5.2 Hz, 2H), 1.22 (s, 6H) |
| 142 | 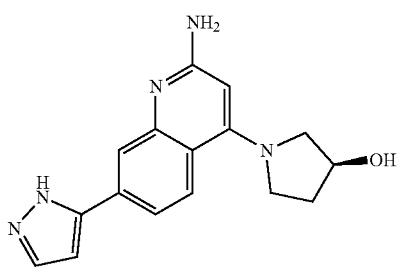 [SMILES: Nc1cc(N2CC[C@H](O)C2)c2ccc(-c3ccn[nH]3)cc2n1] | 296.0 | 0.75 | δ 8.28 (br d, J = 8.5 Hz, 1H), 7.97 (br s, 1H), 7.88 (br s, 1H), 7.79 (br d, J = 8.5 Hz, 1H), 7.53 (br s, 2H), 6.83 (br s, 1H), 5.82 (s, 1H), 4.46 (br s, 1H), 4.02-3.94 (m, 1H), 3.94-3.84 (m, 1H), 3.77-3.67 (m, 1H), 3.54 (br d, J = 10.7 Hz, 1H), 2.12-1.93 (m, 2H) |
| 143 | 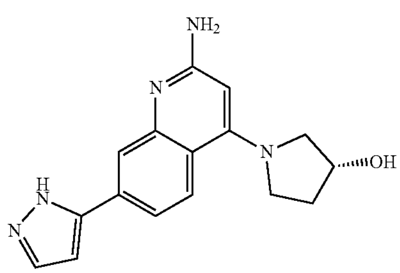 [SMILES: Nc1cc(N2CC[C@@H](O)C2)c2ccc(-c3ccn[nH]3)cc2n1] | 296.3 | 1.05 | δ 8.06 (br d, J = 8.5 Hz, 1H), 7.81 (br s, 1H), 7.75 (br s, 1H), 7.55 (br d, J = 3.1 Hz, 1H), 6.76 (s, 1H), 6.48 (br d, J = 5.5 Hz, 1H), 5.83 (s, 1H), 4.41 (br s, 1H), 3.85 (br dd, J = 10.1, 4.0 Hz, 1H), 3.75 (br d, J = 7.6 Hz, 1H), 2.12-1.99 (m, 1H), 1.97-1.91 (m, 1H) Two protons from pyrrolidine ring are not visible, likely due to overlap with suppressed water peak. |
| 144 | 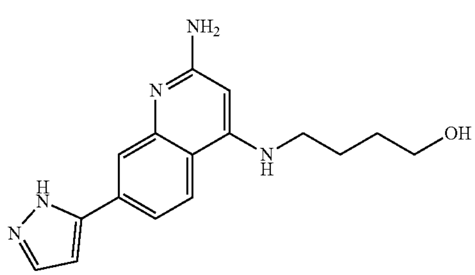 [SMILES: Nc1cc(NCCCCO)c2ccc(-c3ccn[nH]3)cc2n1] | 298.1 | 1.07 | δ 8.23 (br d, J = 8.2 Hz, 1H), 8.12 (br s, 1H), 7.96 (br s, 1H), 7.89-7.78 (m, 2H), 7.62 (br s, 2H), 6.85 (br s, 1H), 5.80 (s, 1H), 3.47 (br d, J = 4.9 Hz, 1H), 3.28 (br d, J = 10.4 Hz, 1H), 1.76-1.67 (m, 2H), 1.60-1.46 (m, 2H). Two protons from sidechain are not visible, likely due to low integration or overlap with suppressed water peak. |

-continued

| Compd. No. | Structure | LC/MS [M + H]+ | RT (min) | 1H NMR (500 MHz, DMSO-d6) |
|---|---|---|---|---|
| 145 | 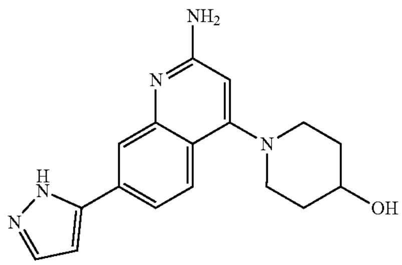 [SMILES: Nc1cc(N2CCC(O)CC2)c2ccc(-c3ccn[nH]3)cc2n1] | 310.2 | 1.07 | δ 8.14-7.97 (m, 2H), 7.91-7.80 (m, 3H), 6.83 (br s, 1H), 3.87-3.77 (m, 1H), 3.55 (br d, J = 8.5 Hz, 1H), 3.13 (br t, J = 11.4 Hz, 1H), 2.98-2.87 (m, 1H), 1.96 (br s, 2H), 1.67 (br d, J = 8.5 Hz, 2H). One proton from piperidine is missing, likely due to overlap with suppressed water peak or low integration. |
| 146 | 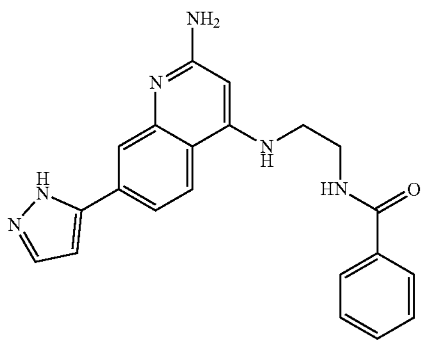 [SMILES: Nc1cc(NCCNC(=O)c2ccccc2)c2ccc(-c3ccn[nH]3)cc2n1] | 373.2 | 1.21 | δ 8.76 (br s, 1H), 8.12 (br d, J = 7.3 Hz, 1H), 7.96-7.71 (m, 7H), 7.57-7.41 (m, 5H), 6.83 (br s, 1H), 5.85 (s, 1H), 3.61 (br d, J = 5.2 Hz, 2H), 3.48 (br d, J = 4.3 Hz, 1H). one proton from sidechain is missing, likely due to overlap with suppressed water peak or low integration. |
| 147 | 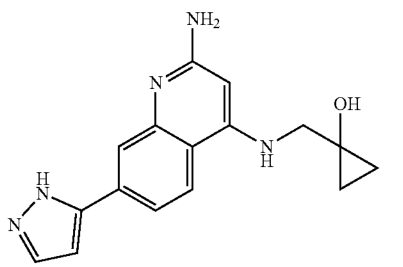 [SMILES: Nc1cc(NCC2(O)CC2)c2ccc(-c3ccn[nH]3)cc2n1] | 296.3 | 1.07 | δ 8.04 (br d, J = 8.5 Hz, 1H), 7.79 (br s, 1H), 7.77-7.69 (m, 1H), 7.61 (br s, 1H), 6.78 (br s, 1H), 5.79 (s, 1H), 2.99 (s, 1H), 0.66 (br s, 2H), 0.61 (br s, 2H). One proton from sidechain is not visible, possibly due to overlap with suppressed water peak or low integration. |
| 148 | 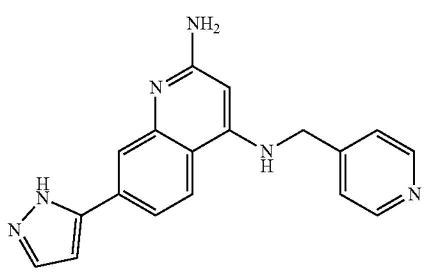 [SMILES: Nc1cc(NCc2ccncc2)c2ccc(-c3ccn[nH]3)cc2n1] | 317.3 | 0.92 | δ 8.50 (br d, J = 4.6 Hz, 2H), 8.04 (br d, J = 8.5 Hz, 1H), 7.79-7.65 (m, 3H), 7.59 (br d, J = 6.7 Hz, 1H), 7.35 (br d, J = 4.6 Hz, 2H), 6.78 (s, 1H), 4.51 (br d, J = 5.5 Hz, 2H) |
| 149 | 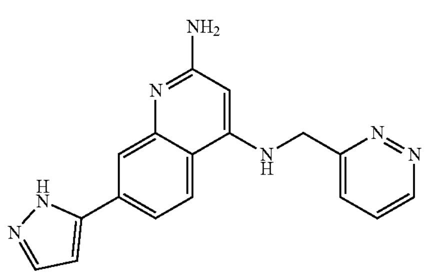 [SMILES: Nc1cc(NCc2cccnn2)c2ccc(-c3ccn[nH]3)cc2n1] | 318.3 | 1.01 | δ 9.20 (br s, 1H), 8.88 (br s, 1H), 8.29 (br d, J = 8.2 Hz, 1H), 7.98-7.79 (m, 4H), 7.74-7.64 (m, 4H), 6.86 (br s, 1H), 5.75 (s, 1H), 4.87 (br d, J = 5.8 Hz, 2H) |

| Compd. No. | Structure | LC/MS [M + H]+ | RT (min) | 1H NMR (500 MHz, DMSO-d6) |
|---|---|---|---|---|
| 150 | 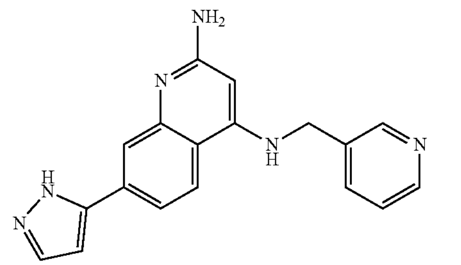 [SMILES: Nc1cc(NCc2cccnc2)c2ccc(-c3ccn[nH]3)cc2n1] | 317.3 | 1.11 | δ 12.50 (br s, 1H), 8.78 (br s, 1H), 8.66 (br s, 1H), 8.53 (br s, 1H), 8.26 (br d, J = 8.5 Hz, 1H), 7.94 (s, 1H), 7.90-7.79 (m, 3H), 7.65 (br s, 2H), 7.50-7.43 (m, 1H), 6.86 (s, 1H), 5.74 (s, 1H), 4.62 (br d, J = 5.2 Hz, 2H) |
| 151 | 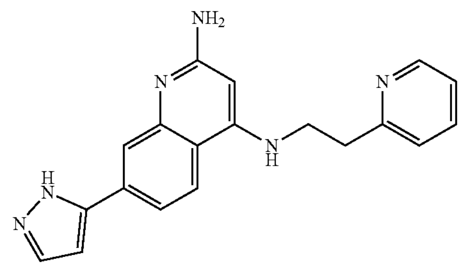 [SMILES: Nc1cc(NCCc2ccccn2)c2ccc(-c3ccn[nH]3)cc2n1] | 331.2 | 1.06 | δ 12.50 (br s, 1H), 8.62 (br d, J = 4.9 Hz, 1H), 8.20 (br s, 1H), 8.15 (br d, J = 8.5 Hz, 1H), 7.99-7.90 (m, 2H), 7.86-7.79 (m, 2H), 7.69 (br s, 2H), 7.54 (br d, J = 7.6 Hz, 1H), 7.48-7.40 (m, 1H), 6.84 (s, 1H), 5.89 (s, 1H), 3.71 (br d, J = 6.1 Hz, 1H), 3.23 (br t, J = 7.0 Hz, 1H). Two protons are missing from sidechain, either due to overlap with suppressed water peak or low integration. |
| 152 | 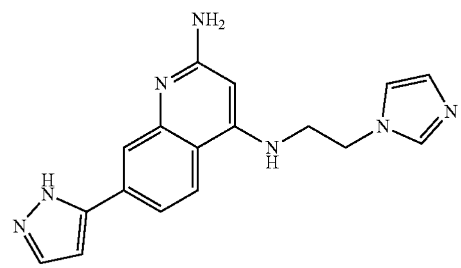 [SMILES: Nc1cc(NCCn2ccnc2)c2ccc(-c3ccn[nH]3)cc2n1] | 320.3 | 0.77 | δ 8.68-8.53 (m, 1H), 8.11-7.98 (m, 2H), 7.90 (br s, 1H), 7.85-7.76 (m, 2H), 7.56 (br s, 2H), 7.39 (br s, 1H), 6.85 (s, 1H), 5.78 (s, 1H), 4.43 (br s, 2H), 2.94-2.83 (m, 1H) One proton from sidechain is missing, likely due to low integration or overlap with suppressed water peak. |
| 153 | 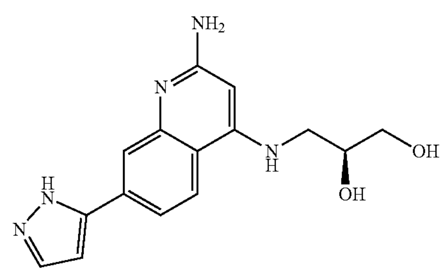 [SMILES: Nc1cc(NC[C@H](O)CO)c2ccc(-c3ccn[nH]3)cc2n1] | 300.3 | 0.64 | δ 7.92 (br d, J = 8.2 Hz, 1H), 7.73 (br s, 2H), 7.52 (br s, 1H), 6.76 (s, 1H), 6.65 (br s, 1H), 6.24-6.10 (m, 1H), 5.74 (s, 1H), 3.85-3.77 (m, 1H), 3.33-3.26 (m, 1H), 3.14-3.05 (m, 2H). One proton from sidechain is not visible, likely due to overlap with water peak. |
| 154 | 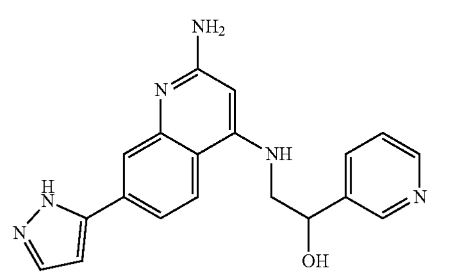 [SMILES: Nc1cc(NCC(O)c2cccnc2)c2ccc(-c3ccn[nH]3)cc2n1] | 347.1 | 1.06 | δ 8.64 (br s, 1H), 8.49 (br s, 1H), 8.20 (br d, J = 7.6 Hz, 2H), 7.96-7.79 (m, 4H), 7.61 (br s, 2H), 7.46-7.34 (m, 1H), 6.85 (s, 1H), 5.92 (s, 1H), 4.99 (br s, 1H). The sidechain methylene is not visible in the NMR, likely due to overlap with the suppressed water peak. |

| Compd. No. | Structure | LC/MS [M + H]+ | RT (min) | 1H NMR (500 MHz, DMSO-d6) |
|---|---|---|---|---|
| 155 | 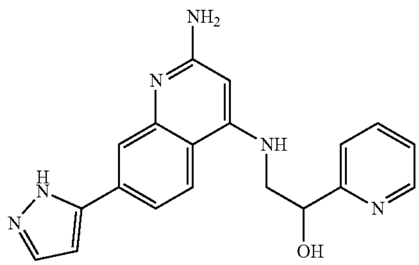 [SMILES: Nc1cc(NCC(O)c2ccccn2)c2ccc(-c3ccn[nH]3)cc2n1] | 347.0 | 1.05 | δ 8.55 (br d, J = 4.0 Hz, 1H), 8.00 (br d, J = 8.5 Hz, 1H), 7.87-7.80 (m, 1H), 7.79 (br s, 1H), 7.74 (br s, 1H), 7.60 (br d, J = 7.6 Hz, 2H), 7.34-7.25 (m, 1H), 7.11 (br s, 1H), 6.79 (s, 2H), 5.83 (s, 1H), 4.98 (br dd, J = 8.1, 3.5 Hz, 1H), 3.68-3.58 (m, 1H), 3.49-3.30 (m, 1H) |
| 156 | 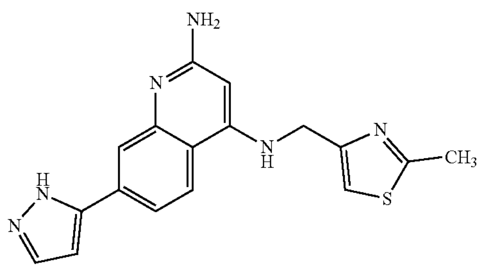 [SMILES: Cc1nc(CNc2cc(N)nc3cc(-c4ccn[nH]4)ccc23)cs1] | 337.2 | 0.92 | δ 8.74 (br s, 1H), 8.27 (br d, J = 8.5 Hz, 1H), 7.97 (br s, 1H), 7.87 (br s, 2H), 7.62 (br s, 2H), 7.33 (s, 1H), 6.86 (br s, 1H), 5.82 (s, 1H), 4.59 (br d, J = 5.5 Hz, 2H), 2.65 (s, 3H) |
| 157 | 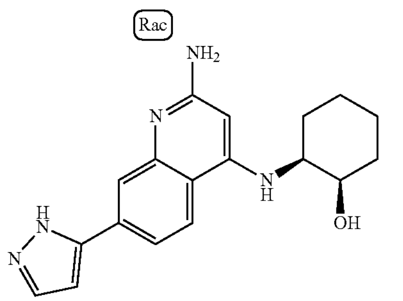 [SMILES: Nc1cc(N[C@H]2CCCC[C@H]2O)c2ccc(-c3ccn[nH]3)cc2n1] | 324.0 | 0.96 | δ 8.35 (br d, J = 7.6 Hz, 1H), 8.01-7.90 (m, 1H), 7.88-7.74 (m, 2H), 7.57 (br s, 2H), 7.27 (br d, J = 6.7 Hz, 1H), 6.85 (br s, 1H), 5.87 (s, 1H), 4.99 (br d, J = 3.4 Hz, 1H), 4.05 (br s, 1H), 3.55-3.33 (m, 1H), 1.96-1.29 (m, 8H) |
| 158 | 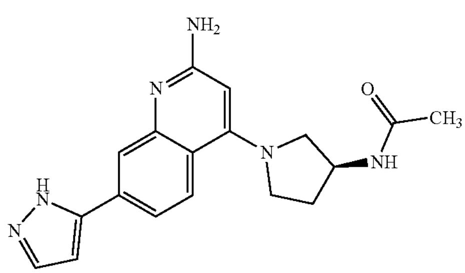 [SMILES: CC(=O)N[C@H]1CCN(c2cc(N)nc3cc(-c4ccn[nH]4)ccc23)C1] | 337.3 | 0.74 | δ 8.21 (br d, J = 5.2 Hz, 1H), 8.08 (br d, J = 7.9 Hz, 1H), 7.91-7.72 (m, 2H), 7.68-7.54 (m, 1H), 6.78 (br s, 1H), 6.75-6.55 (m, 1H), 5.84 (br s, 1H), 4.34 (br s, 1H), 3.89 (br s, 1H), 3.79-3.57 (m, 1H), 2.18 (br d, J = 6.1 Hz, 1H), 1.95 (br d, J = 5.5 Hz, 1H), 1.82 (s, 3H) Two protons from pyrrolidine ring are not visible, due to overlap with suppressed water peak or low integration. |
| 159 | 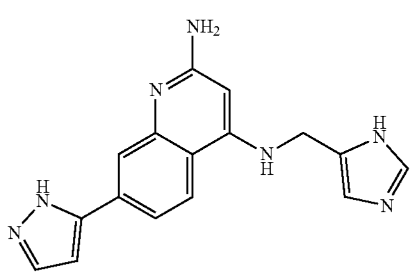 [SMILES: Nc1cc(NCc2cnc[nH]2)c2ccc(-c3ccn[nH]3)cc2n1] | 306.1 | 0.66 | δ 8.81 (br s, 1H), 8.56 (br s, 1H), 8.22 (br d, J = 8.2 Hz, 1H), 7.96 (br s, 1H), 7.91-7.82 (m, 2H), 7.75 (br s, 2H), 7.55 (br s, 1H), 6.86 (s, 1H), 5.83 (s, 1H), 4.60 (br d, J = 4.3 Hz, 1H) One proton from methylene is not visible, likely due to overlap with suppressed water peak or low integration. |

-continued

| Compd. No. | Structure | LC/MS [M + H]+ | RT (min) | 1H NMR (500 MHz, DMSO-d6) |
|---|---|---|---|---|
| 160 | 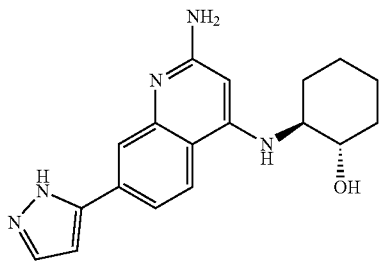 [SMILES: Nc1cc(N[C@H]2CCCC[C@@H]2O)c2ccc(-c3ccn[nH]3)cc2n1] | 324.1 | 0.97 | δ 8.33 (br d, J = 8.5 Hz, 1H), 7.98-7.90 (m, 1H), 7.90-7.75 (m, 2H), 7.65 (br d, J = 7.6 Hz, 1H), 7.49 (br s, 2H), 6.85 (br s, 1H), 5.91 (s, 1H), 4.97 (br d, J = 4.9 Hz, 1H), 3.60 (br d, J = 4.6 Hz, 1H), 3.46-3.22 (m, 2H), 2.03-1.92 (m, 2H), 1.71 (br d, J = 5.2 Hz, 2H), 1.43-1.19 (m, 4H) |
| 161 | 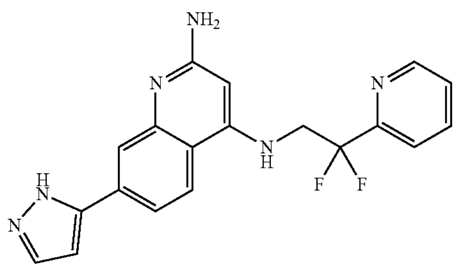 [SMILES: Nc1cc(NCC(F)(F)c2ccccn2)c2ccc(-c3ccn[nH]3)cc2n1] | 367.2 | 1.20 | δ 8.75 (br d, J = 4.3 Hz, 1H), 8.29-8.22 (m, 2H), 8.01 (br t, J = 7.6 Hz, 1H), 7.95 (br s, 1H), 7.88-7.79 (m, 2H), 7.75 (d, J = 7.9 Hz, 1H), 7.69 (br s, 1H), 7.63-7.57 (m, 1H), 6.83 (d, J = 1.8 Hz, 1H), 6.07 (s, 1H), 4.27 (td, J = 14.9, 6.1 Hz, 2H) |
| 162 | 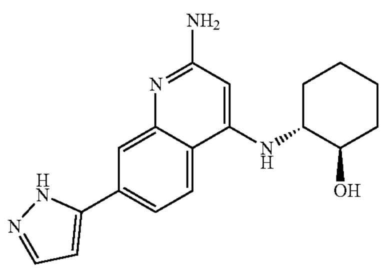 [SMILES: Nc1cc(N[C@@H]2CCCC[C@H]2O)c2ccc(-c3ccn[nH]3)cc2n1] | 324.3 | 1.11 | δ 8.23 (br d, J = 8.2 Hz, 1H), 7.92-7.69 (m, 3H), 7.40-7.04 (m, 2H), 6.82 (br s, 1H), 5.87 (s, 1H), 3.65-3.53 (m, 1H), 3.31-3.19 (m, 1H), 1.96 (br s, 2H), 1.70 (br s, 3H), 1.41-1.18 (m, 6H) |
| 163 | 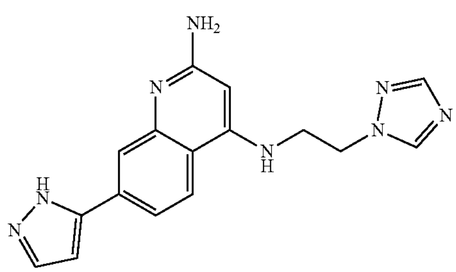 [SMILES: Nc1cc(NCCn2cncn2)c2ccc(-c3ccn[nH]3)cc2n1] | 321.3 | 0.93 | δ 8.49 (s, 1H), 8.03-7.89 (m, 2H), 7.82 (br s, 1H), 7.76 (br s, 1H), 7.66 (br d, J = 7.0 Hz, 1H), 7.43 (br s, 1H), 6.98-6.83 (m, 1H), 6.80 (s, 1H), 5.75 (s, 1H), 4.50 (br t, J = 5.6 Hz, 2H), 3.68 (br d, J = 4.9 Hz, 1H) One proton from sidechain is not visible, likely due to low integration or overlap with suppressed water peak. |
| 164 | 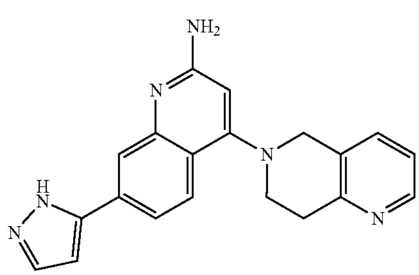 [SMILES: Nc1cc(N2CCc3ncccc3C2)c2ccc(-c3ccn[nH]3)cc2n1] | 343.2 | 1.20 | δ 8.43 (br d, J = 4.0 Hz, 1H), 7.95 (br s, 1H), 7.90 (br d, J = 8.5 Hz, 1H), 7.80 (br s, 2H), 7.64 (br d, J = 7.6 Hz, 1H), 7.27 (br dd, J = 7.5, 4.7 Hz, 1H), 6.82 (s, 1H), 6.38 (s, 1H), 4.49 (br s, 2H), 3.21 (br s, 2H), 3.16 (s, 2H) |

-continued

| Compd. No. | Structure | LC/MS [M + H]+ | RT (min) | ¹H NMR (500 MHz, DMSO-d₆) |
|---|---|---|---|---|
| 165 | 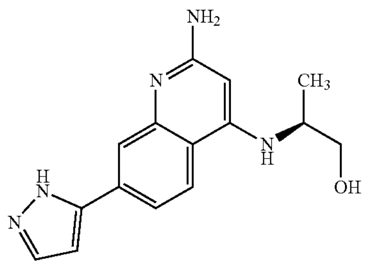 [SMILES: C[C@@H](CO)Nc1cc(N)nc2cc(-c3ccn[nH]3)ccc12] | 284.0 | 0.94 | δ 8.29 (br d, J = 8.5 Hz, 1H), 7.90 (br s, 1H), 7.80 (br d, J = 7.1 Hz, 2H), 7.40 (br s, 1H), 7.30 (br s, 1H), 6.82 (d, J = 1.9 Hz, 1H), 5.90 (s, 1H), 3.76-3.67 (m, 1H), 3.65-3.50 (m, 2H), 1.27 (d, J = 6.5 Hz, 3H) |
| 166 | 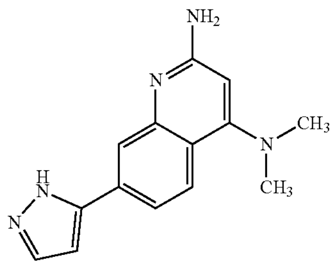 [SMILES: CN(C)c1cc(N)nc2cc(-c3ccn[nH]3)ccc12] | 254.4 | 1.02 | δ 8.05 (br d, J = 8.5 Hz, 1H), 7.95 (br s, 1H), 7.87-7.65 (m, 4H), 6.83 (s, 1H), 6.04 (s, 1H), 3.15 (s, 6H) |
| 222 | 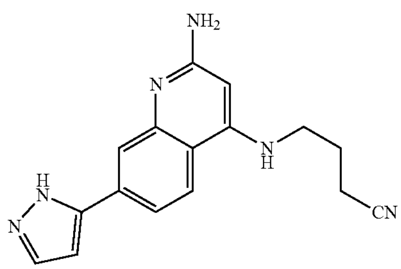 [SMILES: N#CCCCNc1cc(N)nc2cc(-c3ccn[nH]3)ccc12] | 292.9 | 0.79 | δ 8.23 (br d, J = 8.2 Hz, 1H), 8.12-8.05 (m, 1H), 7.96 (br s, 1H), 7.91-7.81 (m, 1H), 7.57 (br dd, J = 5.3, 4.1 Hz, 2H), 6.91-6.83 (m, 1H), 5.81 (s, 1H), 3.44-3.33 (m, 2H), 2.65 (br t, J = 6.9 Hz, 2H), 2.03-1.94 (m, 2H) |
| 223 | 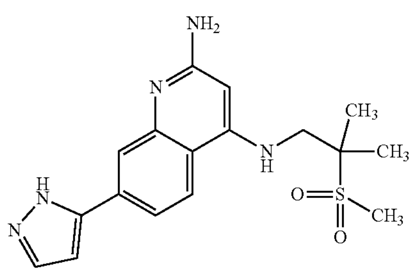 [SMILES: CC(C)(CNc1cc(N)nc2cc(-c3ccn[nH]3)ccc12)S(C)(=O)=O] | 360.3 | 0.84 | δ 8.21 (br d, J = 8.2 Hz, 1H), 8.02-7.95 (m, 1H), 7.93-7.84 (m, 3H), 7.83-7.69 (m, 2H), 6.86 (s, 1H), 6.05 (s, 1H), 3.71 (br d, J = 6.4 Hz, 2H), 3.05 (s, 3H), 1.40 (s, 6H) |
| 224 | 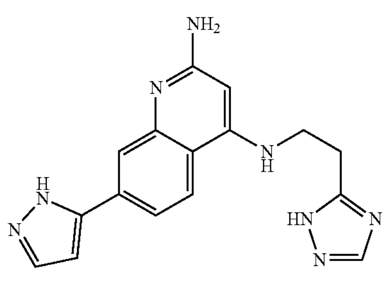 [SMILES: Nc1cc(NCCc2ncn[nH]2)c2ccc(-c3ccn[nH]3)cc2n1] | 321.0 | 0.66 | δ 8.24-8.11 (m, 2H), 7.94 (br s, 1H), 7.83 (br d, J = 9.2 Hz, 2H), 7.72 (br s, 1H), 6.84 (d, J = 2.1 Hz, 1H), 5.87 (s, 1H), 3.72-3.61 (m, 2H), 3.15-3.06 (m, 2H) |

-continued

| Compd. No. | Structure | LC/MS [M + H]+ | RT (min) | 1H NMR (500 MHz, DMSO-d6) |
|---|---|---|---|---|
| 225 | 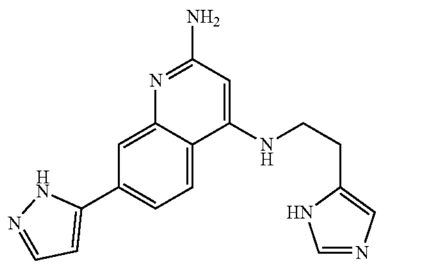 [SMILES: Nc1cc(NCCc2cnc[nH]2)c2ccc(-c3ccn[nH]3)cc2n1] | 320.1 | 0.71 | δ 8.86 (s, 1H), 8.22-8.10 (m, 2H), 7.95 (br s, 1H), 7.83 (br d, J = 8.5 Hz, 2H), 7.78 (br s, 2H), 7.46 (s, 1H), 6.84 (d, J = 2.2 Hz, 1H), 5.89 (s, 1H), 3.66-3.56 (m, 2H), 3.06 (t, J = 6.8 Hz, 2H) |
| 226 | 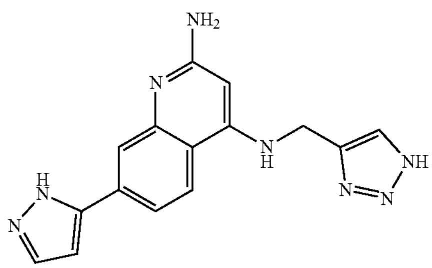 [SMILES: Nc1cc(NCc2c[nH]nn2)c2ccc(-c3ccn[nH]3)cc2n1] | 307.1 | 0.71 | δ 8.74-8.61 (m, 1H), 8.21 (br d, J = 8.2 Hz, 1H), 7.99-7.90 (m, 1H), 7.89-7.77 (m, 3H), 7.65 (br s, 2H), 6.85 (br s, 1H), 5.86 (s, 1H), 4.63 (br d, J = 5.2 Hz, 2H) |
| 227 | 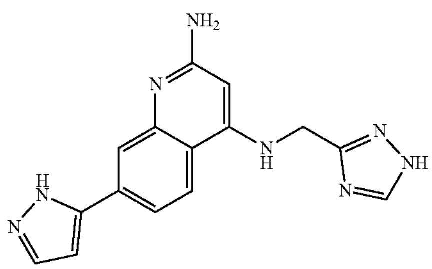 [SMILES: Nc1cc(NCc2nc[nH]n2)c2ccc(-c3ccn[nH]3)cc2n1] | 307.0 | 0.92 | δ 8.73 (br s, 1H), 8.55 (br s, 1H), 8.25 (br d, J = 7.6 Hz, 1H), 8.03-7.92 (m, 1H), 7.87 (br s, 2H), 7.73-7.57 (m, 2H), 6.86 (br s, 1H), 5.88 (br s, 1H), 4.76-4.50 (m, 2H) |
| 228 | 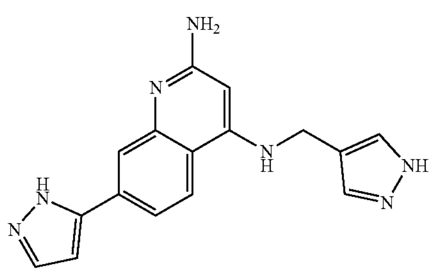 [SMILES: Nc1cc(NCc2cn[nH]c2)c2ccc(-c3ccn[nH]3)cc2n1] | 306.1 | 0.76 | δ 7.98 (d, J = 8.9 Hz, 1H), 7.76 (s, 1H), 7.72 (br s, 1H), 7.60 (br s, 2H), 7.56 (br d, J = 7.6 Hz, 1H), 7.44-7.34 (m, 1H), 6.78 (d, J = 1.8 Hz, 1H), 6.69-6.51 (m, 1H), 5.79 (s, 1H), 4.31 (br d, J = 5.5 Hz, 2H) |
| 229 | 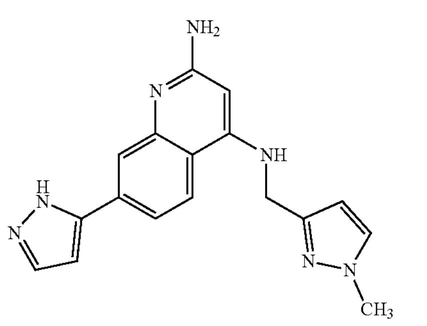 [SMILES: Cn1ccc(CNc2cc(N)nc3cc(-c4ccn[nH]4)ccc23)n1] | 320.1 | 1.00 | δ 8.62 (br s, 1H), 8.23 (d, J = 8.8 Hz, 1H), 7.98-7.92 (m, 1H), 7.84 (br d, J = 8.2 Hz, 2H), 7.63 (d, J = 1.8 Hz, 1H), 7.58 (br d, J = 1.6 Hz, 1H), 6.85 (d, J = 1.9 Hz, 1H), 6.21 (d, J = 2.2 Hz, 1H), 5.86 (s, 1H), 4.46 (d, J = 6.0 Hz, 2H), 3.80 (s, 3H) |

| Compd. No. | Structure | LC/MS [M + H]⁺ | RT (min) | ¹H NMR (500 MHz, DMSO-d₆) |
|---|---|---|---|---|
| 230 | 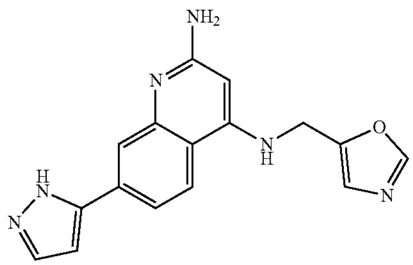 [SMILES: Nc1cc(NCc2cnco2)c2ccc(-c3ccn[nH]3)cc2n1] | 307.2 | 0.98 | δ 12.74 (s, 1H), 8.64 (br t, J = 5.0 Hz, 1H), 8.37 (s, 1H), 8.22 (d, J = 8.5 Hz, 1H), 7.96 (s, 1H), 7.88-7.75 (m, 4H), 7.23 (s, 1H), 6.85 (d, J = 2.1 Hz, 1H), 5.92 (s, 1H), 4.64 (br d, J = 5.2 Hz, 2H) |
| 231 | 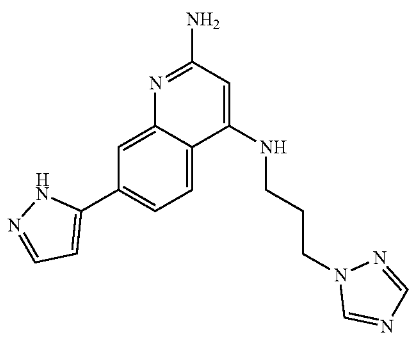 [SMILES: Nc1cc(NCCCn2cncn2)c2ccc(-c3ccn[nH]3)cc2n1] | 335.3 | 0.97 | δ 8.55 (s, 1H), 8.28-8.18 (m, 1H), 8.11-8.04 (m, 1H), 8.00 (s, 1H), 7.95 (br t, J = 5.1 Hz, 1H), 7.85 (br d, J = 8.7 Hz, 2H), 7.63 (br d, J = 1.3 Hz, 2H), 6.86 (d, J = 1.9 Hz, 1H), 5.76 (s, 1H), 4.34 (t, J = 6.9 Hz, 2H), 3.29 (q, J = 6.1 Hz, 1H), 2.28-2.18 (m, 2H). One proton is not visible in NMR, likely due to overlap with suppressed water peak. |
| 232 | 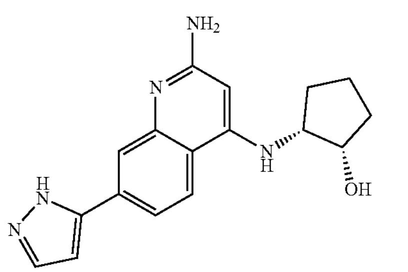 [SMILES: Nc1cc(N[C@@H]2CCC[C@@H]2O)c2ccc(-c3ccn[nH]3)cc2n1] | 310.3 | 1.08 | δ 12.46 (br s, 1H), 8.31 (br d, J = 8.8 Hz, 1H), 7.93 (br d, J = 4.0 Hz, 1H), 7.87-7.80 (m, 2H), 7.67-7.57 (m, 2H), 7.42 (br d, J = 6.4 Hz, 1H), 6.85 (d, J = 2.3 Hz, 1H), 5.90 (s, 1H), 4.31-4.23 (m, 1H), 3.77-3.67 (m, 1H), 2.09-1.98 (m, 1H), 1.95-1.76 (m, 3H), 1.72-1.64 (m, 1H), 1.60-1.49 (m, 1H) |
| 233 | 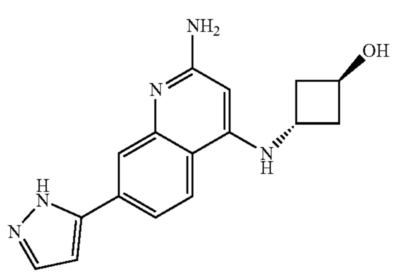 [SMILES: Nc1cc(N[C@H]2C[C@H](O)C2)c2ccc(-c3ccn[nH]3)cc2n1] | 296.0 | 0.74 | δ 8.07 (d, J = 8.8 Hz, 1H), 7.81-7.69 (m, 2H), 7.57 (br d, J = 7.6 Hz, 1H), 7.09-6.94 (m, 1H), 6.78 (d, J = 1.8 Hz, 1H), 5.51 (s, 1H), 4.36 (br t, J = 6.5 Hz, 1H), 4.04-3.91 (m, 1H), 2.43-2.32 (m, 2H), 2.30-2.20 (m, 2H) |
| 234 | 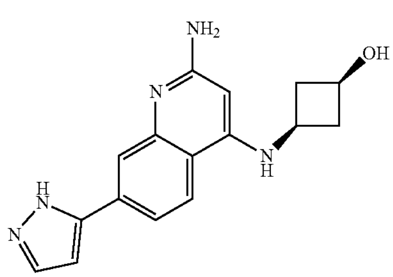 [SMILES: Nc1cc(N[C@H]2C[C@@H](O)C2)c2ccc(-c3ccn[nH]3)cc2n1] | 296.0 | 0.73 | δ 8.05 (d, J = 8.5 Hz, 1H), 7.77-7.73 (m, 1H), 7.73-7.68 (m, 1H), 7.54 (br d, J = 8.2 Hz, 1H), 7.03-6.93 (m, 1H), 6.77 (d, J = 1.8 Hz, 1H), 6.57-6.43 (m, 1H), 5.61 (s, 1H), 3.99-3.88 (m, 1H), 2.80-2.71 (m, 2H), 1.96-1.87 (m, 2H) One proton is not visible in NMR, likely due to overlap with suppressed water peak. |

-continued

| Compd. No. | Structure | LC/MS [M + H]+ | RT (min) | ¹H NMR (500 MHz, DMSO-d$_6$) |
|---|---|---|---|---|
| 235 | 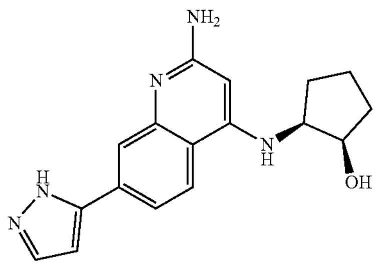 [SMILES: Nc1cc(N[C@H]2CCC[C@H]2O)c2ccc(-c3ccn[nH]3)cc2n1] | 310.3 | 1.13 | δ 8.31 (br d, J = 7.9 Hz, 2H), 7.93 (br s, 1H), 7.84 (br d, J = 8.5 Hz, 2H), 7.57 (br s, 2H), 7.41 (br d, J = 6.7 Hz, 1H), 6.85 (d, J = 1.8 Hz, 1H), 5.90 (s, 1H), 4.28 (br s, 1H), 3.78-3.67 (m, 1H), 2.09-1.98 (m, 1H), 1.95-1.76 (m, 3H), 1.75-1.63 (m, 1H), 1.61-1.48 (m, 1H) |
| 236 | 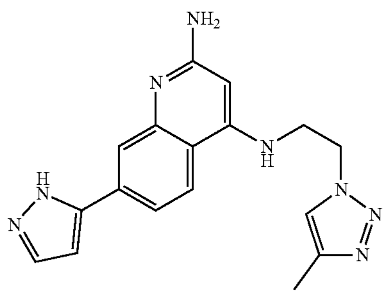 [SMILES: Cc1cn(CCNc2cc(N)nc3cc(-c4ccn[nH]4)ccc23)nn1] | 335.0 | 1.00 | δ 8.20-8.13 (m, 1H), 8.11 (br d, J = 8.8 Hz, 1H), 8.00-7.92 (m, 1H), 7.90-7.78 (m, 3H), 7.72-7.62 (m, 2H), 6.85 (d, J = 1.9 Hz, 1H), 5.81 (s, 1H), 4.64 (t, J = 6.1 Hz, 2H), 3.80-3.73 (m, 2H), 2.21 (s, 3H) |
| 237 | 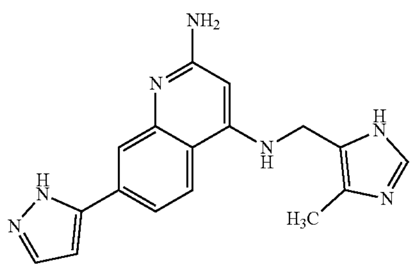 [SMILES: Cc1nc[nH]c1CNc1cc(N)nc2cc(-c3ccn[nH]3)ccc12] | 320.0 | 0.95 | δ 8.01 (br d, J = 8.5 Hz, 1H), 7.80-7.75 (m, 1H), 7.73 (br s, 1H), 7.54 (br d, J = 8.2 Hz, 1H), 7.45 (s, 1H), 7.30-7.16 (m, 1H), 6.77 (d, J = 1.9 Hz, 1H), 5.78 (s, 2H), 4.26 (br d, J = 4.8 Hz, 1H), 2.19 (s, 3H) |
| 238 | 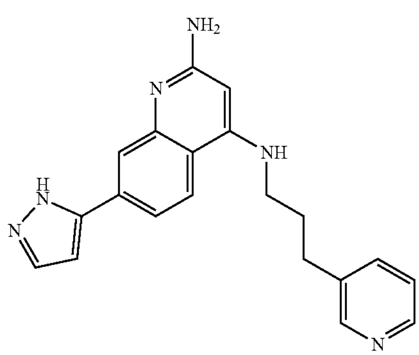 [SMILES: Nc1cc(NCCCc2cccnc2)c2ccc(-c3ccn[nH]3)cc2n1] | 345.3 | 1.14 | δ 12.46 (s, 1H), 8.72-8.65 (m, 1H), 8.60 (br d, J = 5.0 Hz, 1H), 8.21 (d, J = 8.6 Hz, 1H), 8.17-8.07 (m, 2H), 7.93 (d, J = 1.4 Hz, 1H), 7.87-7.80 (m, 2H), 7.73-7.58 (m, 3H), 6.85 (d, J = 2.2 Hz, 1H), 5.80 (s, 1H), 3.39-3.28 (m, 2H), 2.87-2.80 (m, 2H), 2.10-1.98 (m, 2H) |
| 239 | 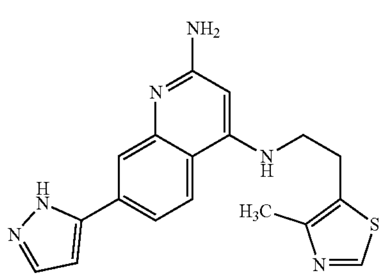 [SMILES: Cc1ncsc1CCNc1cc(N)nc2cc(-c3ccn[nH]3)ccc12] | 351.0 | 1.09 | δ 12.42 (s, 1H), 8.83 (s, 1H), 8.21 (br t, J = 5.6 Hz, 1H), 8.15 (d, J = 8.7 Hz, 1H), 7.93 (s, 1H), 7.87-7.81 (m, 2H), 7.69-7.59 (m, 1H), 6.85 (d, J = 2.3 Hz, 1H), 5.82 (s, 1H), 3.21-3.13 (m, 2H), 2.30 (s, 3H) Two protons are not visible in NMR, likely due to overlap with suppressed water peak. |

-continued

| Compd. No. | Structure | LC/MS [M + H]+ | RT (min) | ¹H NMR (500 MHz, DMSO-d₆) |
|---|---|---|---|---|
| 240 | 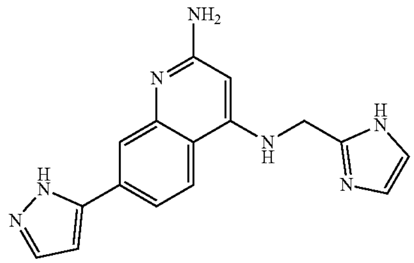 [SMILES: Nc1cc(NCc2ncc[nH]2)c2ccc(-c3ccn[nH]3)cc2n1] | 306.0 | 0.94 | δ 8.73 (br t, J = 5.6 Hz, 1H), 8.42-8.29 (m, 1H), 8.21 (d, J = 8.7 Hz, 1H), 7.98 (s, 1H), 7.94-7.82 (m, 4H), 7.58 (s, 2H), 6.87 (d, J = 2.3 Hz, 1H), 5.70 (s, 1H), 4.89 (d, J = 5.5 Hz, 2H) |
| 241 | 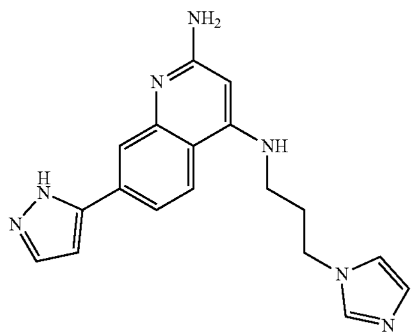 [SMILES: Nc1cc(NCCCn2ccnc2)c2ccc(-c3ccn[nH]3)cc2n1] | 334.0 | 0.99 | δ 8.72 (br s, 1H), 8.21 (br d, J = 8.6 Hz, 1H), 8.08-8.01 (m, 1H), 7.98-7.91 (m, 1H), 7.85 (br d, J = 8.4 Hz, 2H), 7.70-7.60 (m, 3H), 7.47 (s, 1H), 6.86 (d, J = 1.9 Hz, 1H), 5.77 (s, 1H), 4.27 (br t, J = 6.9 Hz, 2H), 3.35-3.25 (m, 1H), 2.23 (quin, J = 6.9 Hz, 2H) One proton is not visible in NMR, likely due to overlap with suppressed water peak. |
| 242 | 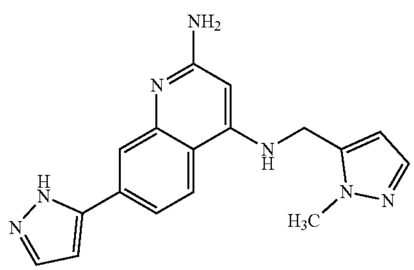 [SMILES: Cn1nccc1CNc1cc(N)nc2cc(-c3ccn[nH]3)ccc12] | 320.3 | 1.00 | δ 8.69-8.59 (m, 1H), 8.27 (br d, J = 8.1 Hz, 1H), 8.01-7.93 (m, 1H), 7.86 (br d, J = 7.6 Hz, 2H), 7.77-7.61 (m, 2H), 7.35 (s, 1H), 6.86 (s, 1H), 6.27 (s, 1H), 5.82 (s, 1H), 4.61 (br d, J = 5.3 Hz, 2H), 3.87 (s, 3H) |
| 243 | 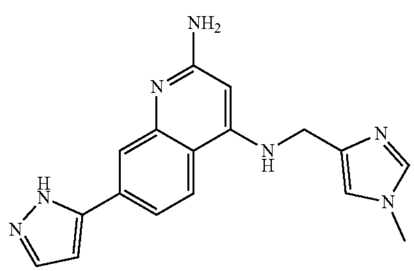 [SMILES: Cn1cnc(CNc2cc(N)nc3cc(-c4ccn[nH]4)ccc23)c1] | 320.1 | 0.87 | δ 8.61 (br d, J = 4.6 Hz, 1H), 8.52 (br s, 1H), 8.23 (br d, J = 8.5 Hz, 1H), 7.97 (br s, 1H), 7.87 (br d, J = 8.9 Hz, 2H), 7.79 (br d, J = 1.3 Hz, 2H), 7.45 (br s, 1H), 6.86 (s, 1H), 5.85 (s, 1H), 4.55 (br d, J = 4.4 Hz, 2H), 3.76 (s, 3H) |
| 244 | 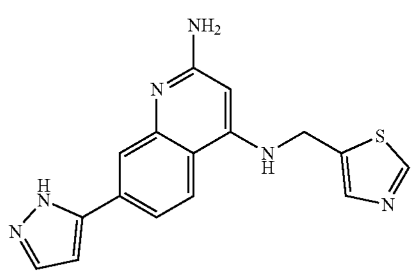 [SMILES: Nc1cc(NCc2cncs2)c2ccc(-c3ccn[nH]3)cc2n1] | 323.2 | 0.88 | δ 9.03 (s, 1H), 8.78 (br s, 1H), 8.18 (br d, J = 8.4 Hz, 1H), 7.94 (br d, J = 9.5 Hz, 2H), 7.90-7.80 (m, 2H), 7.75-7.60 (m, 1H), 6.86 (br s, 1H), 5.88 (br s, 1H), 4.81 (br d, J = 4.5 Hz, 2H) |

| Compd. No. | Structure | LC/MS [M + H]+ | RT (min) | 1H NMR (500 MHz, DMSO-d6) |
|---|---|---|---|---|
| 245 | 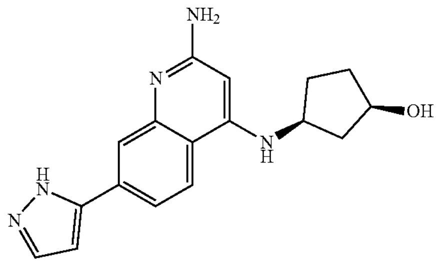 [SMILES: Nc1cc(N[C@H]2CC[C@@H](O)C2)c2ccc(-c3ccn[nH]3)cc2n1] | 310.0 | 0.89 | δ 8.05 (br d, J = 8.4 Hz, 1H), 7.81-7.76 (m, 1H), 7.75-7.70 (m, 1H), 7.63-7.54 (m, 1H), 6.96-6.84 (m, 1H), 6.80 (br s, 1H), 5.72 (s, 1H), 4.23-4.13 (m, 1H), 2.35-2.24 (m, 1H), 2.08-1.96 (m, 1H), 1.81 (br s, 1H), 1.81-1.70 (m, 1H), 1.70-1.57 (m, 2H) One proton is not visible in NMR, likely due to overlap with suppressed water peak. |
| 246 | 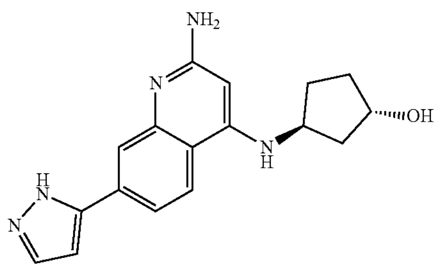 [SMILES: Nc1cc(N[C@H]2CC[C@H](O)C2)c2ccc(-c3ccn[nH]3)cc2n1] | 310.0 | 0.89 | δ 8.32 (br d, J = 8.4 Hz, 1H), 7.97-7.89 (m, 1H), 7.87-7.79 (m, 2H), 7.76 (br d, J = 6.3 Hz, 1H), 7.68-7.54 (m, 2H), 6.85 (s, 1H), 5.85 (s, 1H), 4.35-4.24 (m, 1H), 4.12-4.03 (m, 1H), 2.30-2.18 (m, 1H), 2.10-2.00 (m, 1H), 1.99-1.82 (m, 2H), 1.74-1.61 (m, 1H), 1.61-1.51 (m, 1H) |
| 247 | 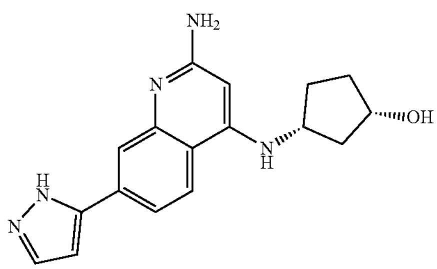 [SMILES: Nc1cc(N[C@@H]2CC[C@H](O)C2)c2ccc(-c3ccn[nH]3)cc2n1] | 310.1 | 0.83 | δ 8.02 (d, J = 8.5 Hz, 1H), 7.78-7.75 (m, 1H), 7.74-7.68 (m, 1H), 7.60-7.50 (m, 1H), 6.81-6.72 (m, 2H), 5.72 (s, 1H), 4.22-4.14 (m, 1H), 3.86-3.78 (m, 1H), 2.30 (dt, J = 13.8, 7.0 Hz, 1H), 2.07-1.96 (m, 1H), 1.84-1.71 (m, 2H), 1.70-1.56 (m, 2H) |
| 248 | 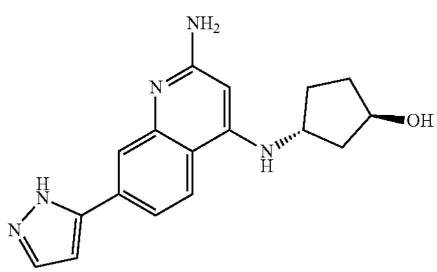 [SMILES: Nc1cc(N[C@@H]2CC[C@@H](O)C2)c2ccc(-c3ccn[nH]3)cc2n1] | 310.2 | 0.89 | δ 8.13 (d, J = 8.5 Hz, 1H), 7.79 (s, 1H), 7.76-7.71 (m, 1H), 7.67 (br d, J = 7.9 Hz, 1H), 7.17 (br dd, J = 7.9, 5.2 Hz, 1H), 6.82 (d, J = 1.8 Hz, 1H), 5.78 (s, 1H), 4.32-4.23 (m, 1H), 4.05 (br d, J = 6.4 Hz, 1H), 2.27-2.20 (m, 1H), 2.05-1.91 (m, 2H), 1.88-1.82 (m, 1H), 1.64-1.49 (m, 2H) |
| 249 | 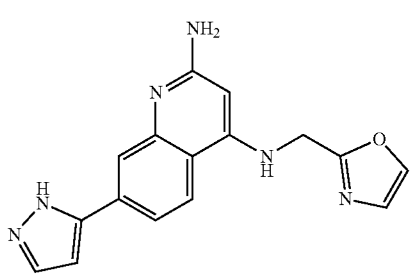 [SMILES: Nc1cc(NCc2ncco2)c2ccc(-c3ccn[nH]3)cc2n1] | 307.2 | 0.86 | δ 8.05 (s, 1H), 7.97 (d, J = 8.5 Hz, 1H), 7.75 (s, 1H), 7.71 (br s, 1H), 7.55 (br d, J = 7.3 Hz, 2H), 7.18 (s, 1H), 6.77 (d, J = 1.8 Hz, 1H), 6.31 (br s, 1H), 5.74 (s, 1H), 4.56 (br d, J = 5.5 Hz, 2H) |

-continued

| Compd. No. | Structure | LC/MS [M + H]+ | RT (min) | 1H NMR (500 MHz, DMSO-d6) |
|---|---|---|---|---|
| 250 | 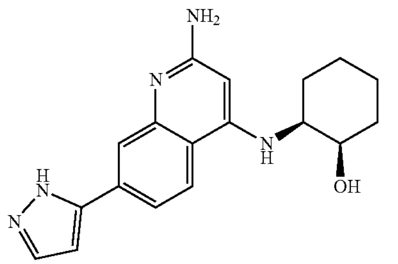 [SMILES: Nc1cc(N[C@H]2CCCC[C@H]2O)c2ccc(-c3ccn[nH]3)cc2n1] | 324.1 | 0.94 | δ 8.00 (d, J = 8.9 Hz, 1H), 7.77 (s, 1H), 7.73 (br s, 1H), 7.59-7.51 (m, 1H), 6.76 (d, J = 1.8 Hz, 1H), 6.71-6.56 (m, 1H), 6.16 (br d, J = 3.7 Hz, 1H), 5.77 (s, 1H), 4.02 (br s, 1H), 1.85-1.65 (m, 4H), 1.64-1.47 (m, 2H), 1.44-1.30 (m, 2H) One proton is not visible in NMR, likely due to overlap with suppressed water peak. |
| 251 | 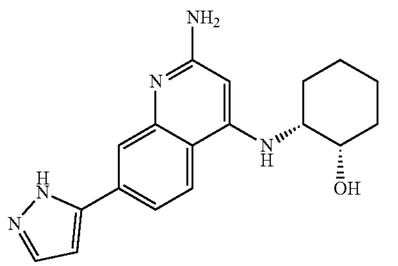 [SMILES: Nc1cc(N[C@@H]2CCCC[C@@H]2O)c2ccc(-c3ccn[nH]3)cc2n1] | 324.1 | 1.13 | δ 8.35 (br d, J = 8.5 Hz, 1H), 7.94 (br s, 1H), 7.89-7.79 (m, 2H), 7.71 (br s, 2H), 7.27 (br d, J = 7.0 Hz, 1H), 6.84 (s, 1H), 5.89 (s, 1H), 4.05 (br s, 1H), 3.56-3.47 (m, 1H), 1.95-1.47 (m, 6H), 1.42-1.30 (m, 2H) |
| 252 | 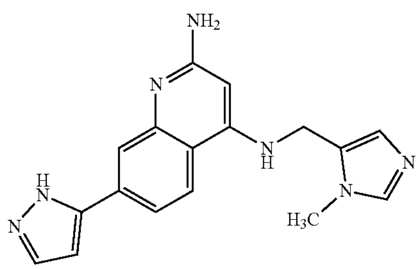 [SMILES: Cn1cncc1CNc1cc(N)nc2cc(-c3ccn[nH]3)ccc12] | 320.2 | 0.82 | δ 8.87 (s, 1H), 8.51 (br t, J = 4.9 Hz, 1H), 8.23 (d, J = 8.5 Hz, 1H), 7.96 (br s, 1H), 7.89-7.75 (m, 4H), 7.60 (s, 1H), 6.86 (d, J = 2.4 Hz, 1H), 5.91 (s, 1H), 4.66 (br d, J = 4.6 Hz, 2H), 3.86 (s, 3H) |
| 253 | 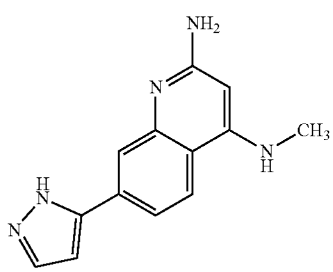 [SMILES: CNc1cc(N)nc2cc(-c3ccn[nH]3)ccc12] | 240.2 | 0.72 | δ 8.10 (d, J = 8.8 Hz, 1H), 8.06-7.98 (m, 1H), 7.95-7.74 (m, 3H), 7.48-7.30 (m, 1H), 6.83 (s, 1H), 5.70 (s, 1H), 2.91 (d, J = 4.6 Hz, 3H) |
| 254 | 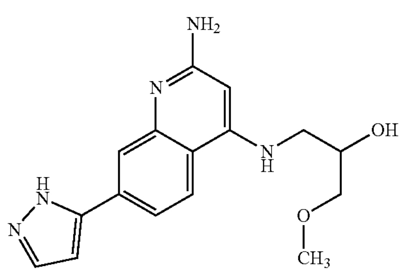 [SMILES: COCC(O)CNc1cc(N)nc2cc(-c3ccn[nH]3)ccc12] | 314.1 | 0.73 | δ 7.97 (d, J = 8.5 Hz, 1H), 7.80-7.75 (m, 1H), 7.73 (br s, 1H), 7.59-7.52 (m, 1H), 6.82 (br d, J = 2.1 Hz, 1H), 6.77 (d, J = 1.8 Hz, 1H), 6.62-6.47 (m, 1H), 5.74 (s, 1H), 4.01-3.90 (m, 1H), 3.38 (br d, J = 5.2 Hz, 1H), 3.29 (s, 3H), 3.28-3.21 (m, 1H), 3.18-3.10 (m, 1H) One proton is not visible in NMR, likely due to overlap with suppressed water peak. |

| Compd. No. | Structure | LC/MS [M + H]⁺ | RT (min) | ¹H NMR (500 MHz, DMSO-d₆) |
|---|---|---|---|---|
| 255 | 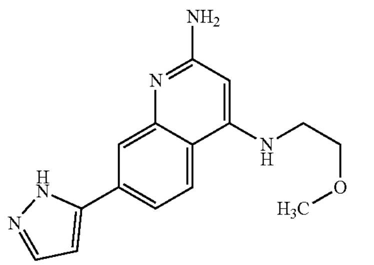 [SMILES: COCCNc1cc(N)nc2cc(-c3ccn[nH]3)ccc12] | 284.0 | 0.89 | δ 8.26-8.21 (m, 1H), 8.13 (br t, J = 5.3 Hz, 1H), 7.94 (br s, 1H), 7.84 (br d, J = 7.3 Hz, 2H), 7.58 (br s, 1H), 6.85 (d, J = 2.1 Hz, 1H), 5.85 (s, 1H), 3.62 (t, J = 5.5 Hz, 2H) Five protons are not visible in NMR, likely due to overlap with suppressed water peak |
| 256 | 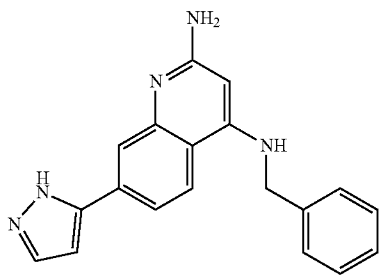 [SMILES: Nc1cc(NCc2ccccc2)c2ccc(-c3ccn[nH]3)cc2n1] | 316.2 | 1.10 | δ 8.11-8.05 (m, 1H), 7.78 (s, 1H), 7.74 (br s, 1H), 7.67 (br s, 1H), 7.59 (br d, J = 8.5 Hz, 1H), 7.41-7.33 (m, 5H), 7.31-7.12 (m, 1H), 6.78 (d, J = 1.8 Hz, 1H), 6.49 (br s, 2H), 5.62 (s, 1H), 4.49 (br d, J = 5.9 Hz, 2H) |
| 257 | 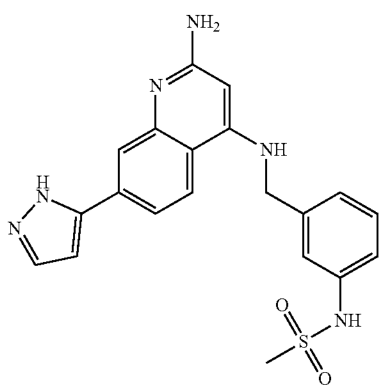 [SMILES: CS(=O)(=O)Nc1cccc(CNc2cc(N)nc3cc(-c4ccn[nH]4)ccc23)c1] | 409.2 | 1.10 | δ 8.83-8.75 (m, 1H), 8.29 (br d, J = 8.4 Hz, 1H), 7.96 (br s, 1H), 7.90 (br d, J = 8.1 Hz, 2H), 7.59 (br s, 2H), 7.47-7.26 (m, 2H), 7.26-7.16 (m, 1H), 7.12 (br d, J = 7.4 Hz, 2H), 6.88 (s, 1H), 5.68 (s, 1H), 4.57 (br d, J = 5.6 Hz, 2H), 2.96 (s, 3H) |
| 258 | 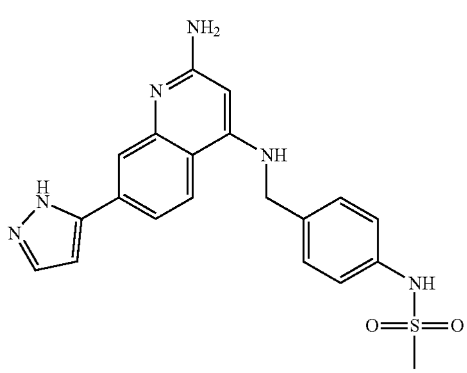 [SMILES: CS(=O)(=O)Nc1ccc(CNc2cc(N)nc3cc(-c4ccn[nH]4)ccc23)cc1] | 409.1 | 0.92 | δ 8.13-8.03 (m, 1H), 7.79 (s, 2H), 7.77-7.70 (m, 1H), 7.70-7.49 (m, 1H), 7.35 (d, J = 8.4 Hz, 2H), 7.18 (d, J = 8.5 Hz, 2H), 6.81 (d, J = 1.8 Hz, 1H), 6.77-6.63 (m, 1H), 5.64 (s, 1H), 4.44 (br d, J = 5.8 Hz, 2H), 2.96 (s, 3H) |

-continued

| Compd. No. | Structure | LC/MS [M + H]+ | RT (min) | 1H NMR (500 MHz, DMSO-d6) |
|---|---|---|---|---|
| 259 | 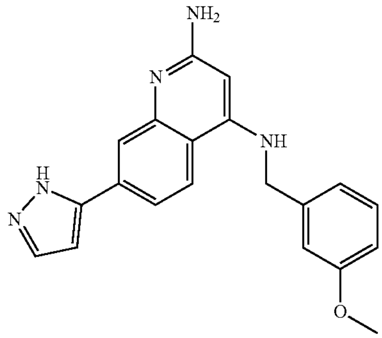 [SMILES: COc1cccc(CNc2cc(N)nc3cc(-c4ccn[nH]4)ccc23)c1] | 346.1 | 1.17 | δ 8.83-8.60 (m, 1H), 8.26 (br d, J = 8.5 Hz, 1H), 7.85 (br s, 2H), 7.50 (br s, 1H), 7.27 (t, J = 8.1 Hz, 1H), 6.95-6.90 (m, 2H), 6.89-6.80 (m, 2H), 5.69 (s, 1H), 4.52 (br d, J = 5.8 Hz, 2H), 3.72 (s, 3H) |
| 260 | 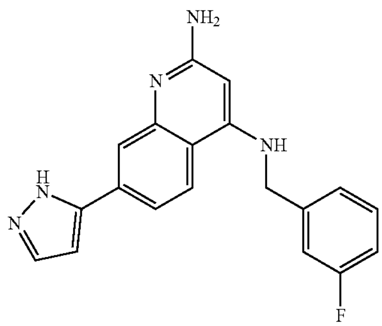 [SMILES: Nc1cc(NCc2cccc(F)c2)c2ccc(-c3ccn[nH]3)cc2n1] | 334.1 | 1.19 | δ 8.90-8.75 (m, 1H), 8.33-8.24 (m, 1H), 8.00-7.95 (m, 1H), 7.89 (br d, J = 8.9 Hz, 2H), 7.61 (br s, 2H), 7.53-7.35 (m, 2H), 7.27-7.17 (m, 2H), 7.12 (br t, J = 9.0 Hz, 1H), 6.88 (s, 1H), 5.70 (s, 1H), 4.60 (br d, J = 5.8 Hz, 2H) |
| 261 | 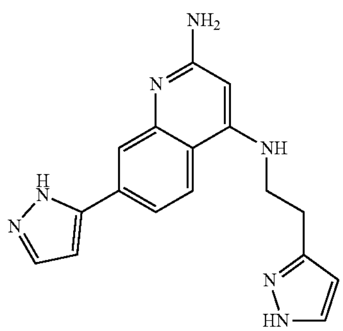 [SMILES: Nc1cc(NCCc2cc[nH]n2)c2ccc(-c3ccn[nH]3)cc2n1] | 320.1 | 1.06 | δ 8.21 (br d, J = 6.7 Hz, 2H), 7.85 (br d, J = 2.0 Hz, 2H), 7.68 (br s, 2H), 7.57 (s, 1H), 6.90-6.85 (m, 1H), 6.20 (s, 1H), 5.88 (s, 1H), 3.01 (br t, J = 7.5 Hz, 2H). One methylene is not visible, possibly due to overlap with suppressed water peak. |
| 262 | 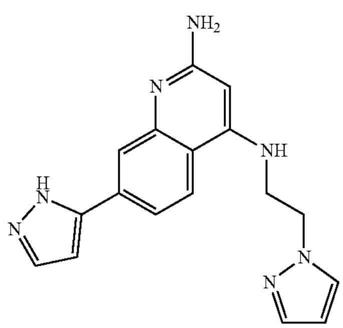 [SMILES: Nc1cc(NCCn2cccn2)c2ccc(-c3ccn[nH]3)cc2n1] | 320.3 | 1.03 | δ 8.13 (br d, J = 7.2 Hz, 1H), 8.01-7.90 (m, 1H), 7.85 (br d, J = 9.3 Hz, 1H), 7.80-7.70 (m, 1H), 7.70-7.59 (m, 1H), 7.59-7.40 (m, 1H), 6.86 (d, J = 2.1 Hz, 1H), 6.23 (t, J = 1.6 Hz, 1H), 5.76 (s, 1H), 3.59-3.49 (m, 4H) |
| 263 | 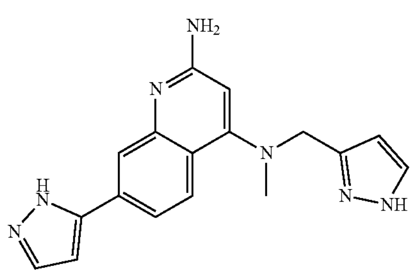 [SMILES: CN(Cc1cc[nH]n1)c1cc(N)nc2cc(-c3ccn[nH]3)ccc12] | 320.1 | 0.90 | δ 8.24 (br d, J = 8.9 Hz, 1H), 8.03 (s, 1H), 7.87 (br s, 2H), 7.83 (br d, J = 8.5 Hz, 1H), 7.77 (br s, 1H), 6.85 (br s, 1H), 6.35-6.24 (m, 1H), 6.21 (s, 1H), 4.62 (br s, 2H), 3.01 (br s, 3H) |

-continued

| Compd. No. | Structure | LC/MS [M + H]+ | RT (min) | 1H NMR (500 MHz, DMSO-d6) |
|---|---|---|---|---|
| 264 | 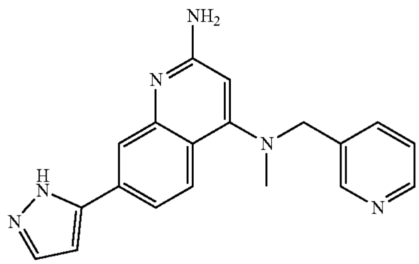 [SMILES: CN(Cc1cccnc1)c1cc(N)nc2cc(-c3ccn[nH]3)ccc12] | 331.0 | 0.96 | δ 8.52-8.48 (m, 1H), 8.48-8.46 (m, 1H), 7.85-7.79 (m, 2H), 7.79-7.66 (m, 2H), 7.66-7.50 (m, 1H), 7.40 (dd, J = 7.6, 4.6 Hz, 1H), 6.76 (d, J = 2.1 Hz, 1H), 6.77-6.71 (m, 1H), 6.26 (br s, 1H), 6.24-6.20 (m, 1H), 4.42 (s, 2H), 2.76 (s, 3H) |
| 265 | 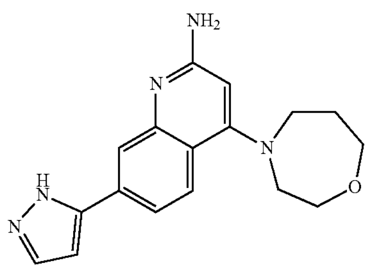 [SMILES: Nc1cc(N2CCCOCC2)c2ccc(-c3ccn[nH]3)cc2n1] | 310.2 | 1.08 | δ 7.80 (d, J = 1.2 Hz, 1H), 7.76 (s, 1H), 7.71 (br s, 1H), 7.56 (br d, J = 8.2 Hz, 1H), 6.76 (d, J = 2.1 Hz, 1H), 6.30-6.19 (m, 2H), 3.88-3.76 (m, 4H), 3.45-3.34 (m, 2H), 2.06 (quin, J = 5.6 Hz, 2H). One proton from sidechain is missing in NMR, likely due to overlap with suppressed water peak. |
| 266 | 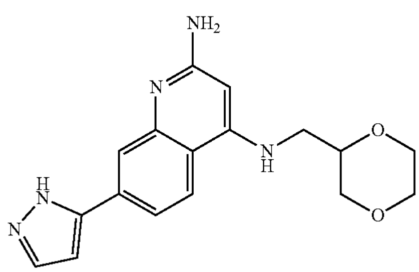 [SMILES: Nc1cc(NCC2COCCO2)c2ccc(-c3ccn[nH]3)cc2n1] | 326.2 | 0.88 | δ 8.08-7.98 (m, 1H), 7.83-7.71 (m, 2H), 7.57 (br d, J = 8.4 Hz, 1H), 7.13-7.00 (m, 1H), 6.84-6.76 (m, 1H), 6.73-6.58 (m, 1H), 5.75 (s, 1H), 3.85 (br d, J = 9.6 Hz, 2H), 3.81-3.74 (m, 1H), 3.72-3.55 (m, 2H), 3.41-3.29 (m, 1H), 3.26-3.20 (m, 1H). One proton from sidechain is missing in NMR, likely due to overlap with suppressed water peak. |
| 267 | 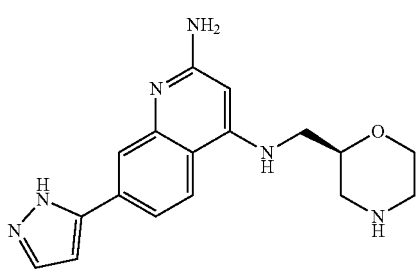 [SMILES: Nc1cc(NC[C@@H]2CNCCO2)c2ccc(-c3ccn[nH]3)cc2n1] | 325.1 | 0.58 | δ 8.32-8.20 (m, 1H), 8.17 (br t, J = 5.5 Hz, 1H), 7.97 (br s, 1H), 7.86 (br d, J = 8.2 Hz, 2H), 7.78 (br s, 2H), 6.86 (d, J = 1.2 Hz, 1H), 5.91 (s, 1H), 4.02 (br dd, J = 12.1, 3.2 Hz, 2H), 3.80-3.69 (m, 1H), 3.46-3.33 (m, 1H), 3.29-3.13 (m, 1H), 3.10-3.00 (m, 1H), 2.94-2.89 (m, 1H) One proton from sidechain is missing in NMR, likely due to overlap with suppressed water peak. |
| 268 | 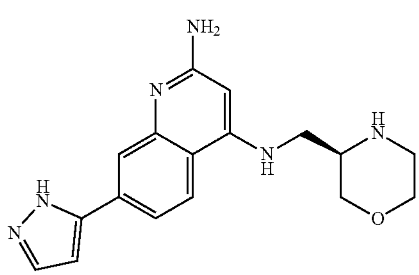 [SMILES: Nc1cc(NC[C@@H]2COCCN2)c2ccc(-c3ccn[nH]3)cc2n1] | 325.1 | 0.68 | δ 8.20 (d, J = 8.9 Hz, 1H), 7.98-7.92 (m, 1H), 7.91-7.82 (m, 2H), 7.78-7.69 (m, 1H), 6.87 (d, J = 1.8 Hz, 1H), 5.90 (s, 1H), 4.03-3.93 (m, 1H), 3.86-3.78 (m, 1H), 3.16-3.07 (m, 1H), 3.03-2.95 (m, 1H). A number of the protons from sidechain is missing in NMR, likely due to overlap with suppressed water peak. |

-continued

| Compd. No. | Structure | LC/MS [M + H]+ | RT (min) | 1H NMR (500 MHz, DMSO-d6) |
|---|---|---|---|---|
| 269 | 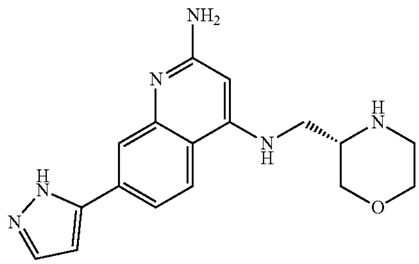 [SMILES: Nc1cc(NC[C@H]2COCCN2)c2ccc(-c3ccn[nH]3)cc2n1] | 325.1 | 0.92 | δ 8.18 (d, J = 8.8 Hz, 1H), 8.13-8.06 (m, 1H), 7.97 (s, 1H), 7.92-7.87 (m, 1H), 7.85 (br s, 1H), 7.79 (br s, 2H), 6.87 (d, J = 2.1 Hz, 1H), 5.92 (s, 1H), 4.06 (br dd, J = 11.9, 2.1 Hz, 1H), 3.97-3.89 (m, 1H), 3.78-3.53 (m, 2H), 3.52-3.41 (m, 1H), 3.34 (br d, J = 13.1 Hz, 1H), 3.16-3.07 (m, 1H), 2.97-2.86 (m, 1H) |
| 270 | 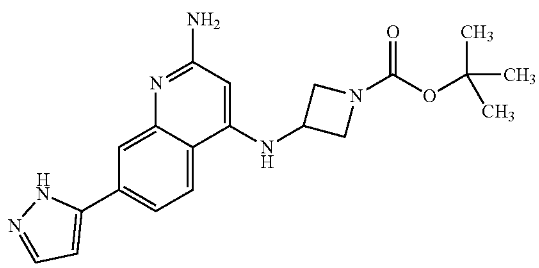 [SMILES: CC(C)(C)OC(=O)N1CC(Nc2cc(N)nc3cc(-c4ccn[nH]4)ccc23)C1] | 381.1 | 1.21 | δ 13.27-13.10 (m, 1H), 12.69-12.60 (m, 1H), 8.34 (br d, J = 5.0 Hz, 1H), 8.30 (br d, J = 8.5 Hz, 1H), 7.96 (br s, 1H), 7.89-7.83 (m, 2H), 7.76-7.75 (m, 1H), 7.81-7.73 (m, 1H), 6.86 (d, J = 1.7 Hz, 1H), 5.59 (s, 1H), 4.40-4.32 (m, 1H), 4.29-4.22 (m, 2H), 3.99 (br dd, J = 8.4, 4.8 Hz, 2H), 1.40 (s, 9H). One extra proton likely due to TFA salt. |
| 271 | 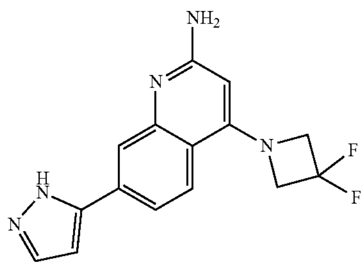 [SMILES: Nc1cc(N2CC(F)(F)C2)c2ccc(-c3ccn[nH]3)cc2n1] | 301.9 | 1.10 | δ 13.25-13.12 (m, 1H), 8.01-7.95 (m, 1H), 7.90-7.87 (m, 1H), 7.86-7.77 (m, 4H), 6.84 (d, J = 1.9 Hz, 1H), 5.65 (s, 1H), 4.96 (br t, J = 11.8 Hz, 4H) |
| 272 | 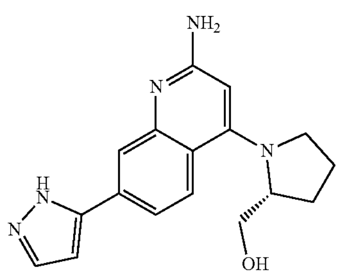 [SMILES: Nc1cc(N2CCC[C@@H]2CO)c2ccc(-c3ccn[nH]3)cc2n1] | 310.2 | 1.02$^a$ | δ 8.02-7.96 (m, 1H), 7.81 (s, 1H), 7.78-7.72 (m, 1H), 7.63-7.55 (m, 1H), 6.77 (d, J = 1.7 Hz, 1H), 6.67-6.50 (m, 2H), 6.08-6.00 (m, 1H), 4.88-4.77 (m, 1H), 4.09-4.02 (m, 1H), 3.88-3.80 (m, 2H), 2.21-2.13 (m, 1H), 2.03-1.92 (m, 2H), 1.90 (s, 2H), 1.79-1.70 (m, 1H) |
| 273 | 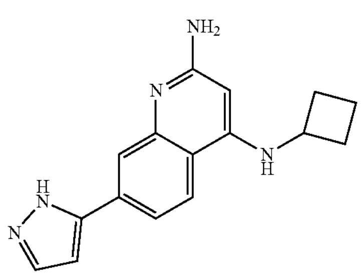 [SMILES: Nc1cc(NC2CCC2)c2ccc(-c3ccn[nH]3)cc2n1] | 280.2 | 1.17$^a$ | δ 8.16-8.11 (m, 1H), 7.82-7.79 (m, 1H), 7.78-7.73 (m, 1H), 7.68-7.62 (m, 1H), 7.46-7.37 (m, 1H), 6.99-6.83 (m, 1H), 6.80 (d, J = 1.7 Hz, 1H), 5.66-5.63 (m, 1H), 4.01-3.95 (m, 1H), 2.45-2.38 (m, 2H), 2.15-2.06 (m, 2H), 1.88 (s, 2H), 1.84-1.75 (m, 2H) |

-continued

| Compd. No. | Structure | LC/MS [M + H]+ | RT (min) | ¹H NMR (500 MHz, DMSO-d₆) |
|---|---|---|---|---|
| 274 | 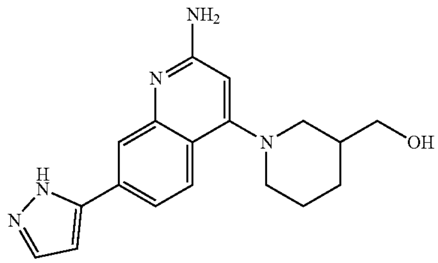 [SMILES: Nc1cc(N2CCCC(CO)C2)c2ccc(-c3ccn[nH]3)cc2n1] | 324.1 | 0.96 | δ 7.85-7.81 (m, 1H), 7.75-7.73 (m, 1H), 7.72 (s, 1H), 7.63-7.55 (m, 1H), 6.76 (d, J = 1.7 Hz, 1H), 6.43-6.33 (m, 2H), 6.23 (s, 1H), 4.65-4.52 (m, 1H), 2.69 (br t, J = 10.3 Hz, 1H), 1.98-1.91 (m, 1H), 1.90 (s, 1H), 1.84-1.74 (m, 3H), 1.21-1.12 (m, 1H). Several protons from piperidine ring are not visible, likely due to overlap with water/DMSO. |
| 275 | 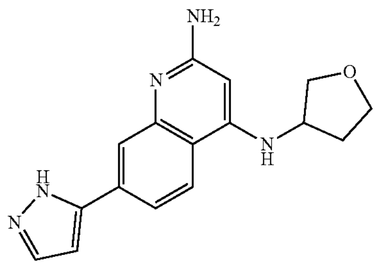 [SMILES: Nc1cc(NC2CCOC2)c2ccc(-c3ccn[nH]3)cc2n1] | 296.1 | 0.97 | δ 8.17-8.09 (m, 1H), 7.82-7.80 (m, 1H), 7.78-7.72 (m, 1H), 7.62-7.53 (m, 1H), 6.81-6.74 (m, 1H), 5.79-5.69 (m, 1H), 4.16-4.05 (m, 1H), 4.00-3.95 (m, 2H), 3.94-3.85 (m, 2H), 2.34-2.21 (m, 1H), 2.19 2.03 (m, 1H) |
| 276 | 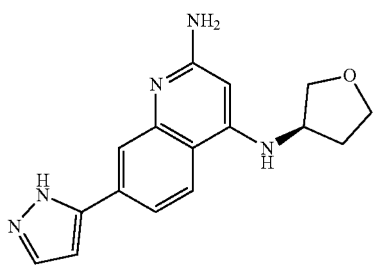 [SMILES: Nc1cc(N[C@@H]2CCOC2)c2ccc(-c3ccn[nH]3)cc2n1] | 296.4 | 0.96 | δ 8.27-8.22 (m, 1H), 7.90-7.87 (m, 1H), 7.87-7.85 (m, 1H), 7.80-7.77 (m, 1H), 6.92-6.81 (m, 1H), 5.93-5.86 (m, 1H), 4.39-4.29 (m, 1H), 4.11-4.03 (m, 2H), 3.99-3.88 (m, 2H), 2.51-2.40 (m, 1H), 2.22-2.13 (m, 1H) |
| 277 | 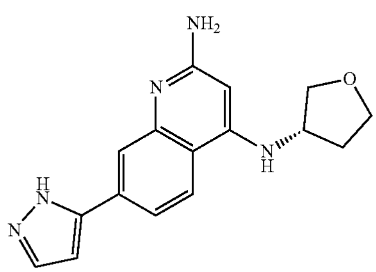 [SMILES: Nc1cc(N[C@H]2CCOC2)c2ccc(-c3ccn[nH]3)cc2n1] | 296.2 | 0.98 | δ 8.39-8.29 (m, 1H), 7.98-7.91 (m, 1H), 7.89-7.74 (m, 2H), 6.93-6.82 (m, 1H), 5.87-5.78 (m, 1H), 4.25-4.14 (m, 1H), 4.01-3.88 (m, 2H), 3.88-3.74 (m, 2H), 2.35-2.25 (m, 1H), 2.20-2.04 (m, 1H) |
| 278 | 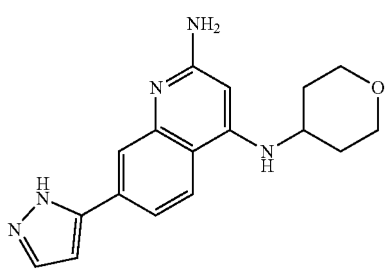 [SMILES: Nc1cc(NC2CCOCC2)c2ccc(-c3ccn[nH]3)cc2n1] | 310.2 | 0.87 | δ 8.40-8.25 (m, 2H), 8.02-7.93 (m, 1H), 7.88-7.81 (m, 1H), 6.91-6.80 (m, 1H), 6.01-5.90 (m, 1H), 3.79-3.64 (m, 1H), 3.57-3.36 (m, 2H), 2.93-2.91 (m, 2H), 2.00-1.90 (m, 2H), 1.81-1.64 (m, 2H) |

-continued
| Compd. No. | Structure | LC/MS [M + H]+ | RT (min) | 1H NMR (500 MHz, DMSO-d6) |
|---|---|---|---|---|
| 279 | 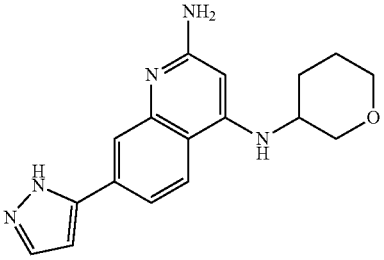 [SMILES: Nc1cc(NC2CCCOC2)c2ccc(-c3ccn[nH]3)cc2n1] | 310.4 | 0.75 | δ 8.29-8.15 (m, 1H), 7.94-7.85 (m, 2H), 7.82-7.76 (m, 1H), 7.39-7.31 (m, 1H), 6.87-6.82 (m, 1H), 4.14-4.05 (m, 1H), 3.64-3.54 (m, 2H), 3.51-3.41 (m, 2H), 1.99-1.71 (m, 4H) |
| 280 | 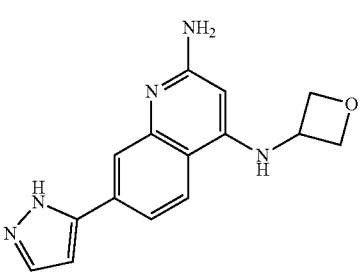 [SMILES: Nc1cc(NC2COC2)c2ccc(-c3ccn[nH]3)cc2n1] | 282.0 | 0.75 | δ 8.13-8.03 (m, 1H), 7.80-7.74 (m, 1H), 7.63-7.54 (m, 1H), 7.39-7.28 (m, 1H), 6.84-6.75 (m, 1H), 6.26-6.09 (m, 1H), 5.48-5.41 (m, 1H), 4.96-4.87 (m, 2H), 4.71-4.58 (m, 2H) |
| 281 | 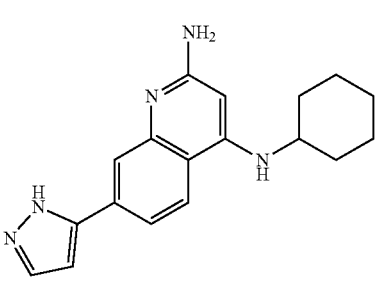 [SMILES: Nc1cc(NC2CCCCC2)c2ccc(-c3ccn[nH]3)cc2n1] | 308.0 | 1.32 | δ 8.40-8.24 (m, 1H), 7.98-7.92 (m, 1H), 7.89-7.80 (m, 1H), 7.76-7.65 (m, 1H), 6.93-6.81 (m, 1H), 5.94-5.83 (m, 1H), 3.03-2.85 (m, 3H), 2.06-1.95 (m, 2H), 1.87-1.76 (m, 2H), 1.51-1.29 (m, 4H) |
| 282 | 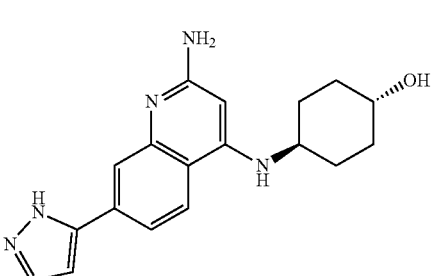 | 323.9 | 1.02 | δ 8.37-8.25 (m, 1H), 7.93-7.78 (m, 1H), 7.74-7.67 (m, 1H), 7.66-7.58 (m, 1H), 7.43-7.32 (m, 1H), 7.30-7.21 (m, 1H), 5.92-5.84 (m, 1H), 2.99-2.84 (m, 1H), 2.52-2.51 (m, 1H), 2.41-2.32 (m, 1H), 2.12-1.86 (m, 1H), 1.61-1.43 (m, 1H), 1.37-1.22 (m, 1H), 1.19-1.12 (m, 2H) |
| 283 | 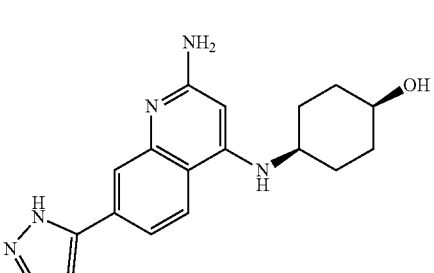 | 324.0 | 1.02 | δ 8.35-8.23 (m, 1H), 7.78-7.65 (m, 1H), 7.73-7.65 (m, 1H), 7.63-7.55 (m, 1H), 7.39-7.32 (m, 1H), 7.30-7.20 (m, 1H), 5.91-5.83 (m, 1H), 3.47-3.27 (m, 1H), 2.58-2.54 (m, 1H), 2.54-2.47 (m, 1H), 2.41-2.33 (m, 1H), 2.13-1.90 (m, 1H), 1.60-1.42 (m, 1H), 1.38-1.21 (m, 1H), 1.17-1.11 (m, 2H) |

| Compd. No. | Structure | LC/MS [M + H]+ | RT (min) | 1H NMR (500 MHz, DMSO-d6) |
|---|---|---|---|---|
| 284 | 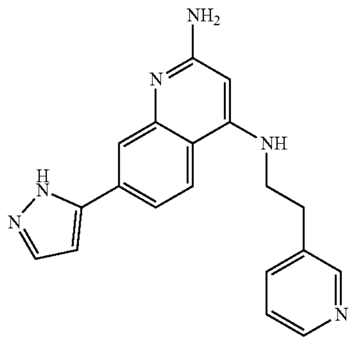 [SMILES: Nc1cc(NCCc2cccnc2)c2ccc(-c3ccn[nH]3)cc2n1] | 331.2 | 0.99 | δ 8.59 (br s, 1H), 8.50 (br d, J = 3.1 Hz, 1H), 8.24-8.12 (m, 2H), 7.94 (s, 1H), 7.88-7.80 (m, 3H), 7.71-7.60 (m, 2H), 7.45 (dd, J = 7.6, 5.2 Hz, 1H), 6.85 (d, J = 2.1 Hz, 1H), 5.89 (s, 1H), 3.62-3.38 (m, 2H), 3.04 (br t, J = 7.5 Hz, 2H) |
| 285 | 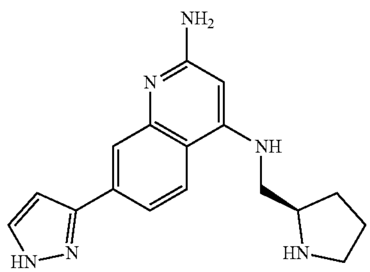 [SMILES: Nc1cc(NC[C@H]2CCCN2)c2ccc(-c3cc[nH]n3)cc2n1] | 309.2 | 0.86 | δ 13.22-13.17 (m, 1H), 8.20-8.12 (m, 1H), 8.11-8.02 (m, 1H), 8.01-7.92 (m, 1H), 7.91-7.82 (m, 2H), 7.80-7.64 (m, 2H), 6.86 (d, J = 1.9 Hz, 1H), 5.93-5.81 (m, 1H), 3.92-3.83 (m, 2H), 3.31-3.25 (m, 1H), 3.25-3.18 (m, 1H), 3.17-3.14 (m, 1H), 2.21-2.11 (m, 1H), 2.04-1.90 (m, 2H), 1.75-1.67 (m, 1H) |
| 286 | 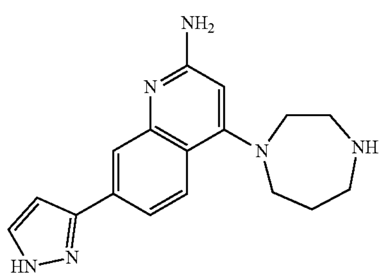 [SMILES: Nc1cc(N2CCCNCC2)c2ccc(-c3cc[nH]n3)cc2n1] | 309.2 | 0.61 | δ 7.82-7.76 (m, 2H), 7.72 (br s, 1H), 7.55 (br d, J = 7.9 Hz, 1H), 6.76 (d, J = 1.5 Hz, 1H), 6.23 (s, 1H), 6.19 (s, 1H), 3.44-3.32 (m, 2H), 3.08-2.95 (m, 4H), 1.94 (br d, J = 4.6 Hz, 2H). Two of the diazepine protons are not observed likely due to overlap with the H2O suppression. |
| 287 | 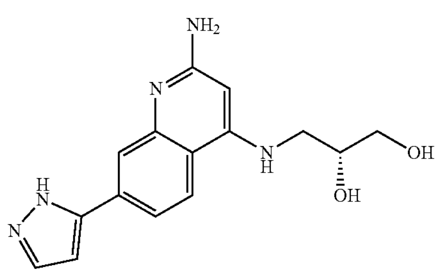 [SMILES: Nc1cc(NC[C@@H](O)CO)c2ccc(-c3ccn[nH]3)cc2n1] | 300.3 | 0.72 | δ 8.11 (br d, J = 8.5 Hz, 1H), 7.90-7.82 (m, 1H), 7.80-7.66 (m, 2H), 7.62-7.45 (m, 1H), 7.24-7.03 (m, 1H), 6.82 (s, 1H), 5.81 (s, 1H), 3.86-3.79 (m, 1H), 3.66-3.53 (m, 1H), 3.49-3.32 (m, 2H), 3.25-3.16 (m, 1H) |
| 288 | 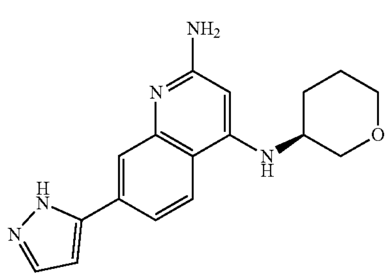 [SMILES: Nc1cc(N[C@H]2CCCOC2)c2ccc(-c3ccn[nH]3)cc2n1] | 310.1 | 1.13 | δ 8.34-8.26 (m, 1H), 7.96-7.90 (m, 1H), 7.88-7.81 (m, 2H), 7.62-7.58 (m, 1H), 6.90-6.77 (m, 1H), 6.04-5.92 (m, 1H), 4.02-3.90 (m, 1H), 3.86-3.78 (m, 1H), 3.67-3.63 (m, 1H), 3.46-3.25 (m, 2H), 2.16-2.03 (m, 1H), 1.83-1.71 (m, 2H), 1.71-1.57 (m, 1H) |

| Compd. No. | Structure | LC/MS [M + H]+ | RT (min) | 1H NMR (500 MHz, DMSO-d6) |
|---|---|---|---|---|
| 289 | 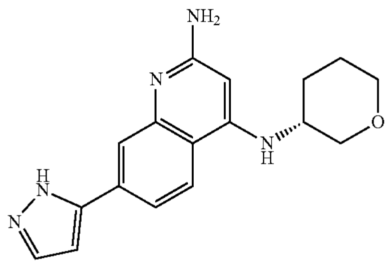 [SMILES: Nc1cc(N[C@@H]2CCCOC2)c2ccc(-c3ccn[nH]3)cc2n1] | 310.2 | 1.05 | δ 8.39-8.23 (m, 1H), 8.01-7.92 (m, 1H), 7.93-7.79 (m, 2H), 7.63-7.59 (m, 1H), 6.90-6.82 (m, 1H), 6.03-5.92 (m, 1H), 4.03-3.93 (m, 1H), 3.88-3.77 (m, 1H), 3.46-3.33 (m, 2H), 2.20-2.02 (m, 1H), 1.86-1.72 (m, 2H), 1.72-1.55 (m, 1H) |
| 290 | 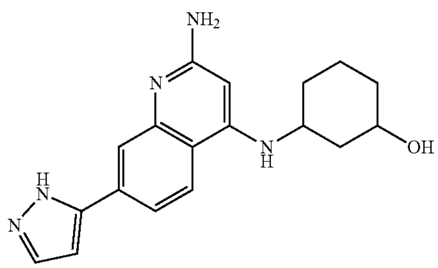 [SMILES: Nc1cc(NC2CCCC(O)C2)c2ccc(-c3ccn[nH]3)cc2n1] | 342.4 | 0.95 | δ 8.17-8.16 (m, 1H), 8.16-8.14 (m, 1H), 8.11-8.09 (m, 1H), 7.89-7.85 (m, 2H), 7.80-7.78 (m, 1H), 3.86-3.76 (m, 1H), 3.74-3.61 (m, 1H), 2.38-2.27 (m, 1H), 2.11-1.86 (m, 4H), 1.67-1.32 (m, 4H) |
| 291 | 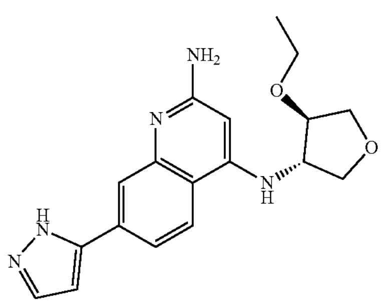 [SMILES: CCO[C@H]1COC[C@@H]1Nc1cc(N)nc2cc(-c3ccn[nH]3)ccc12] | 340.4 | 0.90 | δ 8.43-8.33 (m, 1H), 8.00-7.93 (m, 1H), 7.93-7.89 (m, 1H), 7.88-7.82 (m, 2H), 6.89-6.81 (m, 1H), 5.94-5.85 (m, 1H), 4.20-4.10 (m, 2H), 4.10-4.03 (m, 1H), 4.00-3.92 (m, 1H), 3.88-3.80 (m, 1H), 3.80-3.64 (m, 2H), 1.20-1.12 (m, 3H) |
| 351 | | 310.3 | 0.84 | δ 8.32-8.19 (m, 1H), 8.17-8.05 (m, 1H), 7.99-7.91 (m, 1H), 7.62-7.41 (m, 1H), 6.92-6.80 (m, 1H), 5.91-5.81 (m, 1H), 3.86-3.77 (m, 1H), 3.76-3.71 (m, 1H), 3.71-3.63 (m, 1H), 3.59-3.44 (m, 1H), 3.32-3.23 (m, 2H), 2.75-2.61 (m, 1H), 2.14-1.96 (m, 1H), 1.74-1.58 (m, 1H) | aLC/MS conditions: Column: Waters XBridge C18, 2.1 mm x 50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Example II-3: Synthesis of 4-(1H-imidazol-1-yl)-7-(1H-pyrazol-5-yl)quinolin-2-amine (Compound 167)

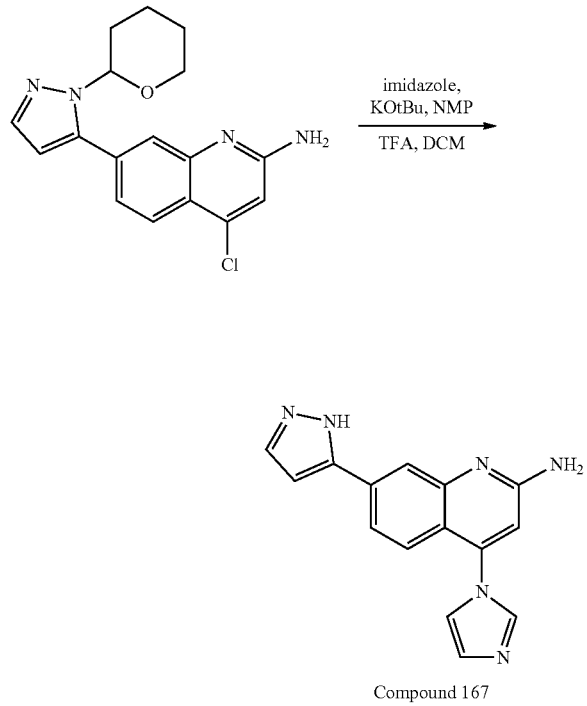 [SMILES: Nc1cc(Cl)c2ccc(-c3ccnn3C3CCCCO3)cc2n1 ; Nc1cc(-n2ccnc2)c2ccc(-c3ccn[nH]3)cc2n1]

Compound 167

To a solution of 1H-imidazole (45.6 mg, 0.669 mmol) and 4-chloro-7-(1-(tetrahydro-2H-pyran-2-yl)-1H-pyrazol-5-yl)quinolin-2-amine (22 mg, 0.067 mmol) in NMP (446 µl) was added potassium tert-butoxide (18.77 mg, 0.167 mmol). The reaction was heated to 100° C. overnight. The reaction was diluted with water and extracted twice with EtOAc. The organic layers were concentrated. The residue was dissolved in 0.4 mL DCM and 0.4 mL TFA. After 1 hour, the reaction was concentrated and azeotroped with DCM. The reaction was dissolved in DMF, filtered through a syringe filter, and The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile: water with 10-mM ammonium acetate; Gradient: a 0-minute hold at 2% B, 2-42% B over minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give (1.8 mg, 9.5%). $^1$H NMR (500 MHz, DMSO-$d_6$) δ 8.50-8.28 (m, 1H), 8.10 (br s, 1H), 7.95-7.75 (m, 3H), 7.57 (br d, J=8.2 Hz, 1H), 7.40 (br s, 1H), 7.00-6.80 (m, 2H). LC/MS Conditions: Column: Waters XBridge C18, 2.1 mm×50 mm, 1.7 µm particles; Mobile Phase A: 5:95. acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC RT: 0.89 min. M/Z=277.4.

Example II-4: Synthesis of 4-Substituted Quinolines from an Unprotected Intermediate

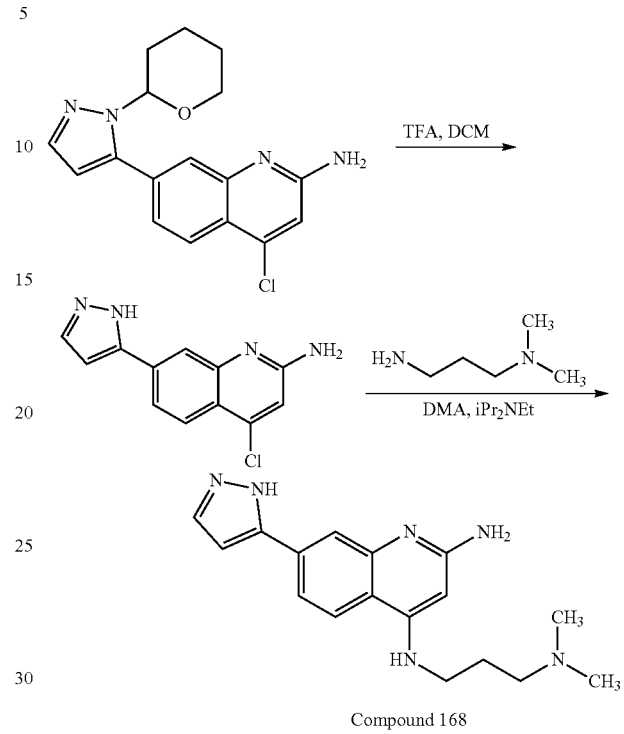

Compound 168

Step 1: Preparation of 4-chloro-7-(1H-pyrazol-5-yl)quinolin-2-amine

4-Chloro-7-(1-(tetrahydro-2H-pyran-2-yl)-1H-pyrazol-5-yl)quinolin-2-amine (100 mg, 0.304 mmol) was dissolved in DCM (1.5 mL) and TFA (1.5 mL). After 1 hour, the reaction was complete by LC/MS. The reaction was concentrated and azeotroped with DCM. The residue was dissolved in a small amount of DCM, and then saturated sodium bicarbonate solution was added. The precipitated solid was filtered, washed with water, and dried. The solid was suspended in saturated sodium bicarbonate solution, stirred for 15 minutes, then filtered and washed twice with water to give 4-chloro-7-(1H-pyrazol-5-yl)quinolin-2-amine (66 mg, 0.270 mmol, 89% yield). $^1$H NMR (400 MHz, DMSO-$d_6$) δ 7.93-7.86 (m, 2H), 7.84-7.72 (m, 2H), 6.91 (s, 1H), 6.84 (d, J=2.1 Hz, 1H), 6.64 (br s, 2H).

Step 2: Preparation of N4-(3-(dimethylamino)propyl)-7-(1H-pyrazol-5-yl)quinoline-2,4-diamine, 2 TFA (Compound 168)

N1,N1-Dimethylpropane-1,3-diamine (104 mg, 1.022 mmol) in DMA (681 µl) was added Hunig's Base (53.5 µl, 0.307 mmol). The reaction was heated to 120° C. overnight, then the reaction was heated to 150° C. for a further 24 hours. The reaction was cooled, quenched with AcOH, diluted with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 3-minute hold at 0% B, 0-40% B over minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give N4-(3-(dimethylamino)propyl)-7-(1H-pyrazol-5-yl)quinoline-2,4-diamine, 2 TFA (12.2 mg, 22.1%). $^1$H NMR (500 MHz, DMSO-$d_6$) δ 8.21 (br d, J=8.5 Hz, 1H), 8.09 (br s, 1H), 7.95 (br s, 1H), 7.85 (br d, J=7.9 Hz, 2H), 7.78 (br s, 2H), 6.85 (s, 1H), 5.85 (s, 1H), 3.44-3.33 (m, 1H), 3.23-3.13 (m, 2H), 2.80 (s, 6H), 2.11-1.98 (m, 2H). Note: one proton from methylene of sidechain is missing, likely due to overlap with suppressed water peak. Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC RT: 0.90 min. M/Z=311.1.

Compound 169 to Compound 171 were prepared according to the synthetic procedures described for Compound 168 from the appropriate starting materials.

| Compd. No. | Structure | LC/MS [M + H]$^+$ | RT (min) | $^1$H NMR (500 MHz, DMSO-$d_6$) |
|---|---|---|---|---|
| 169 | 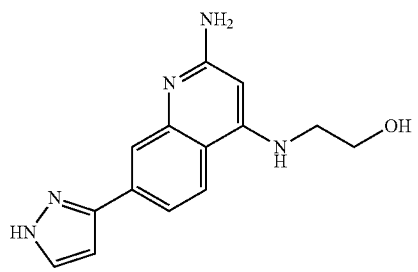 [SMILES: Nc1cc(NCCO)c2ccc(-c3cc[nH]n3)cc2n1] | 270.0 | 1.11 | δ 8.03 (br d, J = 8.5 Hz, 1H), 7.80 (s, 1H), 7.74 (br s, 1H), 7.66 (br d, J = 7.6 Hz, 1H), 7.28 (br s, 1H), 6.83 (s, 1H), 5.76 (s, 1H), 3.67 (br t, J = 5.8 Hz, 2H), 3.36-3.27 (m, 2H) |
| 170 | 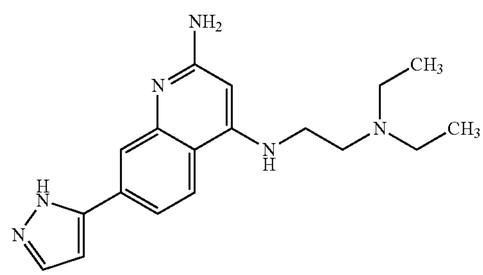 [SMILES: CCN(CC)CCNc1cc(N)nc2cc(-c3ccn[nH]3)ccc12] | 325.1 | 1.05 | δ 8.17 (br d, J = 8.5 Hz, 1H), 8.07-8.01 (m, 1H), 7.97 (br s, 1H), 7.90-7.73 (m, 3H), 6.83 (d, J = 1.9 Hz, 1H), 5.95 (s, 1H), 3.71 (br d, J = 5.2 Hz, 2H), 1.29-1.19 (m, 6H). Several protons from amino sidechain are missing, likely due to overlap with suppressed water peak. |
| 171 | 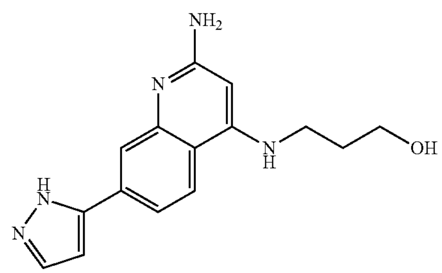 [SMILES: Nc1cc(NCCCO)c2ccc(-c3ccn[nH]3)cc2n1] | 284.0 | 0.81 | δ 7.97 (br d, J = 8.5 Hz, 1H), 7.77 (s, 1H), 7.73 (br s, 1H), 7.55 (br d, J = 7.9 Hz, 1H), 6.96 (br s, 1H), 6.77 (s, 1H), 5.71 (s, 1H), 3.55 (br t, J = 6.1 Hz, 1H), 3.25 (br d, J = 5.8 Hz, 2H), 1.85-1.78 (m, 2H). One proton from alcohol sidechain is missing, likely due to overlap with suppressed water peak. |

Example 5: Synthesis of a 4-ether Substituted Quinoline from an Unprotected Intermediate

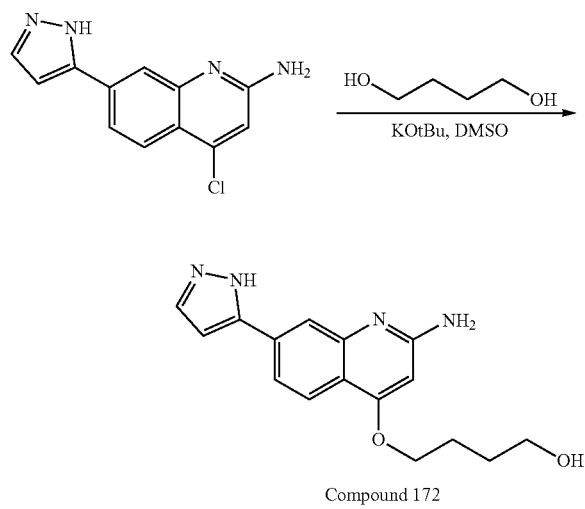 [SMILES: Nc1cc(Cl)c2ccc(-c3ccn[nH]3)cc2n1 ; OCCCCO ; Nc1cc(OCCCCO)c2ccc(-c3ccn[nH]3)cc2n1]

Compound 172

Step 1: Synthesis of 4-((2-amino-7-(1H-pyrazol-5-yl)quinolin-4-yl)oxy)butan-1-ol, TFA (Compound 172)

To a solution of 4-chloro-7-(1H-pyrazol-5-yl)quinolin-2-amine (22 mg, 0.090 mmol) and butane-1,4-diol (81 mg, 0.899 mmol) in DMSO (599 µl) was added potassium tert-butoxide (20.18 mg, 0.180 mmol). The reaction was heated to 100° C. overnight, then potassium tert-butoxide (10.09 mg, 0.90 mmol) was added and the reaction was heated to 120° C. After 8 hours, the reaction was cooled, quenched with AcOH, diluted with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-46% B over 25 minutes, then a 6-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 4-((2-amino-7-(1H-pyrazol-5-yl)quinolin-4-yl)oxy)butan-1-ol, TFA (5.2 mg, 14%). $^1$H NMR (500 MHz, DMSO-d$_6$) δ 8.32-8.13 (m, 1H), 8.07-7.96 (m, 2H), 7.93-7.81 (m, 2H), 6.84 (s, 1H), 6.36 (s, 1H), 4.29 (br t, J=6.3 Hz, 2H), 3.55-3.34 (m, 2H), 1.98-1.86 (m, 2H), 1.73-1.60 (m, 2H). LC RT: 1.04 min. M/Z=299.31.

Example II-6: Synthesis of a 4-amino Substituted Quinoline with an N-Linked Pyrazole

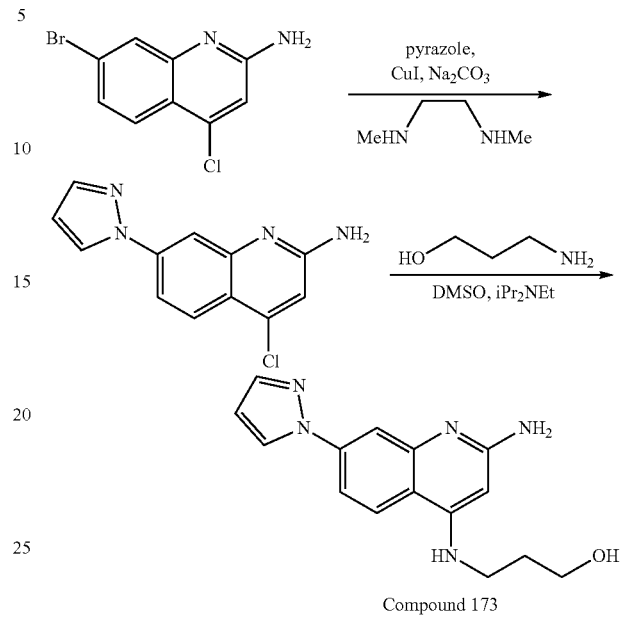

Compound 173

Step 1: Preparation of 4-chloro-7-(1H-pyrazol-1-yl)quinolin-2-amine

7-Bromo-4-chloroquinolin-2-amine (250 mg, 0.971 mmol), 1H-pyrazole (132 mg, 1.942 mmol), copper(I) iodide (370 mg, 1.942 mmol), and sodium carbonate (412 mg, 3.88 mmol) were placed in a pressure vial. The vial was placed under vacuum and backfilled with nitrogen three times. DMSO (9708 µl) was added and nitrogen was bubbled through the solution. N,N'-dimethylethane-1,2-diamine (257 mg, 2.91 mmol) was added and the reaction was heated to 120° C. After 4 hours, the reaction was cooled, diluted with water, and extracted three times with EtOAc. The organic layers were washed with half water/half saturated ammonium hydroxide solution, dried with sodium sulfate, and concentrated. The residue was dissolved in DCM/MeOH and absorbed onto silica gel. The residue was purified via ISCO (24 g column; DCM/MeOH; 0 to 10% gradient) to give 4-chloro-7-(1H-pyrazol-1-yl)quinolin-2-amine (144 mg, 0.589 mmol, 60.6% yield). $^1$H NMR (400 MHz, DMSO-d$_6$) δ 8.67 (d, J=2.5 Hz, 1H), 7.96 (d, J=8.9 Hz, 1H), 7.90 (d, J=2.0 Hz, 1H), 7.85-7.79 (m, 2H), 6.93 (s, 1H), 6.77 (s, 2H), 6.61-6.57 (m, 1H).

Step 2: Preparation of 3-((2-amino-7-(1H-pyrazol-1-yl)quinolin-4-yl)amino)propan-1-ol (Compound 173)

To a solution of 4-chloro-7-(1H-pyrazol-1-yl)quinolin-2-amine (20 mg, 0.082 mmol) and 3-aminopropan-1-ol (61.4 mg, 0.817 mmol) in DMSO (0.5 mL) was added Hunig's base (0.043 mL, 0.245 mmol). The reaction was heated to 120° C. overnight. LC/MS showed that the reaction was complete. The reaction was cooled, diluted with MeOH and a small amount of AcOH, filtered through a syringe filter, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 3-minute hold at 0% B, 0-38% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-7-(1H-pyrazol-1-yl)quinolin-4-yl)amino)propan-1-ol (14.2 mg, 61.3%). $^1$H NMR (500 MHz, DMSO-$d_6$) δ 8.55 (br s, 1H), 8.06 (br d, J=8.9 Hz, 1H), 7.75 (br d, J=14.0 Hz, 2H), 7.61 (br d, J=7.9 Hz, 1H), 7.03 (br s, 1H), 6.68 (br s, 1H), 6.56 (br s, 1H), 5.72 (s, 1H), 3.52 (br s, 2H), 3.30-3.17 (m, 2H), 1.84-1.77 (m, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 1.08 min. M/Z=283.96.

Compound 174 to Compound 176, Compound 292 to Compound 309 were prepared according to the synthetic procedures described for Compound 173 from the appropriate starting materials.

| Compd. No. | Structure | LC/MS [M + H]$^+$ | RT (min) | $^1$H NMR (500 MHz, DMSO-$d_6$) |
|---|---|---|---|---|
| 174 | 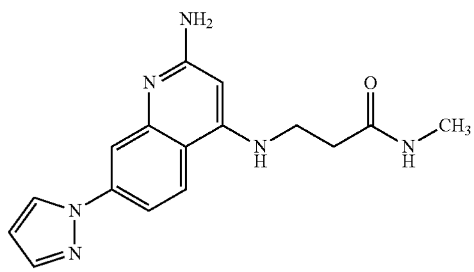 [SMILES: CNC(=O)CCNc1cc(N)nc2cc(-n3cccn3)ccc12] | 310.9 | 1.08 | δ 8.55 (br s, 1H), 8.00 (br d, J = 8.9 Hz, 1H), 7.89 (br s, 1H), 7.75 (br d, J = 17.4 Hz, 2H), 7.59 (br d, J = 7.9 Hz, 1H), 6.98 (br s, 1H), 6.55 (br s, 1H), 6.49 (br s, 1H), 5.74 (s, 1H), 3.55-3.35 (m, 2H), 2.59 (br d, J = 4.3 Hz, 3H). Two protons from sidechain are not visible, likely due to overlap with suppressed water peak or low integration. |
| 175 | 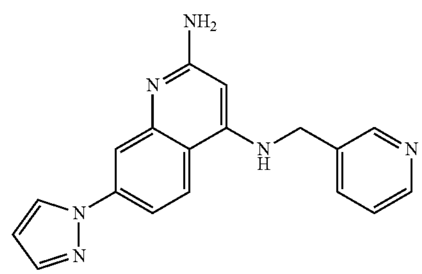 [SMILES: Nc1cc(NCc2cccnc2)c2ccc(-n3cccn3)cc2n1] | 317.0 | 1.19 | δ 8.60 (br s, 1H), 8.53 (br s, 1H), 8.45 (br d, J = 3.1 Hz, 1H), 8.09 (br d, J = 8.9 Hz, 1H), 7.76 (br s, 2H), 7.71 (s, 1H), 7.67 (br d, J = 4.6 Hz, 1H), 7.61 (br d, J = 9.2 Hz, 1H), 7.41-7.32 (m, 1H), 6.56 (br s, 1H), 6.25-6.16 (m, 1H), 5.65 (s, 1H), 4.49 (br d, J = 5.2 Hz, 2H) |
| 176 | 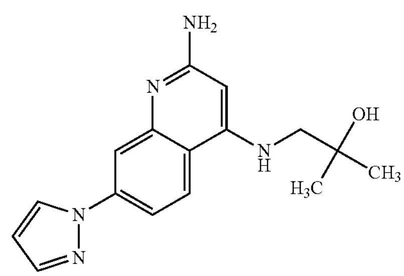 [SMILES: CC(C)(O)CNc1cc(N)nc2cc(-n3cccn3)ccc12] | 297.9 | 1.11 | δ 8.63 (br s, 1H), 8.37 (br d, J = 8.9 Hz, 1H), 7.97 (s, 1H), 7.91-7.79 (m, 3H), 7.60 (br s, 2H), 6.64 (br s, 1H), 5.98 (s, 1H), 3.26 (br d, J = 5.5 Hz, 2H), 1.24-1.16 (m, 6H) |
| 292 | 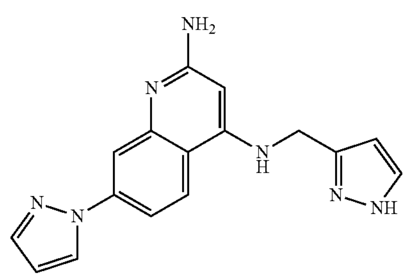 [SMILES: Nc1cc(NCc2cc[nH]n2)c2ccc(-n3cccn3)cc2n1] | 306.1 | 0.82 | δ 8.55 (s, 1H), 8.07 (d, J = 8.8 Hz, 1H), 7.76 (d, J = 1.5 Hz, 1H), 7.72 (d, J = 2.3 Hz, 1H), 7.61-7.54 (m, 2H), 7.49-7.40 (m, 1H), 6.61-6.52 (m, 1H), 6.35 (br d, J = 2.1 Hz, 1H), 6.21 (d, J = 2.1 Hz, 1H), 5.78 (s, 1H), 4.42 (br d, J = 5.6 Hz, 2H) |

| Compd. No. | Structure | LC/MS [M + H]+ | RT (min) | 1H NMR (500 MHz, DMSO-d6) |
|---|---|---|---|---|
| 293 | 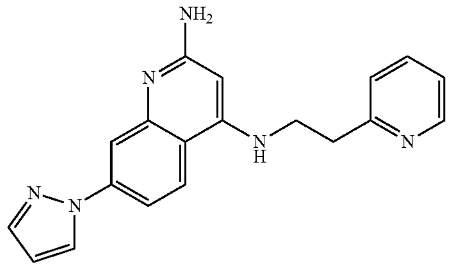 [SMILES: Nc1cc(NCCc2ccccn2)c2ccc(-n3cccn3)cc2n1] | 331.2 | 1.2 | δ 8.67-8.54 (m, 2H), 8.28-8.16 (m, 2H), 8.03-7.94 (m, 2H), 7.91-7.81 (m, 2H), 7.79-7.66 (m, 1H), 7.56 (br d, J = 7.6 Hz, 1H), 7.50-7.42 (m, 1H), 6.64 (d, J = 1.8 Hz, 1H), 5.88 (s, 1H), 3.68 (br s, 2H), 3.23 (br t, J = 7.0 Hz, 2H) |
| 294 | 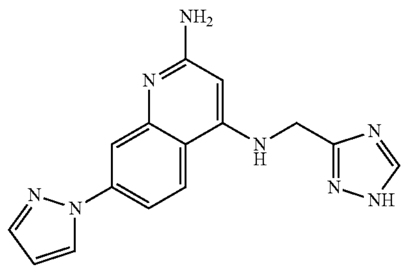 [SMILES: Nc1cc(NCc2nc[nH]n2)c2ccc(-n3cccn3)cc2n1] | 307.0 | 0.78 | δ 8.59 (d, J = 2.1 Hz, 1H), 8.30 (br s, 1H), 8.14 (d, J = 8.8 Hz, 1H), 7.79 (s, 3H), 7.68 (dd, J = 8.9, 2.1 Hz, 1H), 6.67-6.48 (m, 2H), 5.75 (s, 1H), 4.54 (br d, J = 5.8 Hz, 2H) |
| 295 | 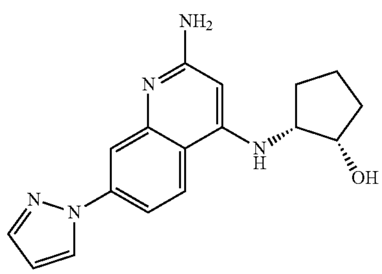 [SMILES: Nc1cc(N[C@@H]2CCC[C@@H]2O)c2ccc(-n3cccn3)cc2n1] | 310.1 | 0.91 | δ 8.57 (d, J = 2.1 Hz, 1H), 8.07 (d, J = 8.8 Hz, 1H), 7.78 (d, J = 1.2 Hz, 1H), 7.76 (d, J = 2.1 Hz, 1H), 7.63 (dd, J = 8.9, 2.1 Hz, 1H), 6.58 (br d, J = 1.8 Hz, 2H), 6.41-6.35 (m, 1H), 5.82 (s, 1H), 4.26 (br d, J = 2.4 Hz, 1H), 3.69-3.61 (m, 1H), 2.11-1.98 (m, 1H), 1.87-1.64 (m, 4H), 1.61-1.50 (m, 1H) |
| 296 | 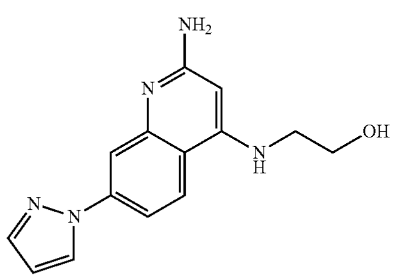 [SMILES: Nc1cc(NCCO)c2ccc(-n3cccn3)cc2n1] | 270.2 | 0.93[a] | δ 8.57 (d, J = 2.4 Hz, 1H), 8.11 (d, J = 9.2 Hz, 1H), 7.78 (dd, J = 6.7, 1.5 Hz, 2H), 7.66 (dd, J = 8.9, 2.1 Hz, 1H), 7.14 (br s, 1H), 6.88 (br s, 1H), 6.58 (s, 1H), 5.77 (s, 1H), 3.78-3.61 (m, 1H), 3.31 (q, J = 5.6 Hz, 2H). One of ethylene proton signals is minimized likely due to overlap with suppressed water. |
| 297 | 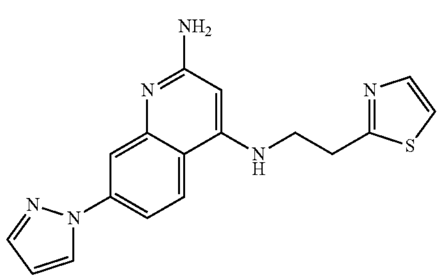 [SMILES: Nc1cc(NCCc2nccs2)c2ccc(-n3cccn3)cc2n1] | 337.1 | 1.14 | δ 8.56 (d, J = 2.4 Hz, 1H), 8.04 (d, J = 8.9 Hz, 1H), 7.84-7.72 (m, 2H), 7.64 (dd, J = 8.9, 2.1 Hz, 1H), 7.59 (d, J = 3.1 Hz, 1H), 7.33-7.17 (m, 1H), 6.70 (br s, 1H), 6.57 (d, J = 1.5 Hz, 1H), 5.82 (s, 1H), 3.71-3.54 (m, 1H), 3.40 (t, J = 7.0 Hz, 1H).). Two of ethylene proton signals are minimized likely due to overlap with suppressed water. |

| Compd. No. | Structure | LC/MS [M + H]+ | RT (min) | ¹H NMR (500 MHz, DMSO-d₆) |
|---|---|---|---|---|
| 298 | 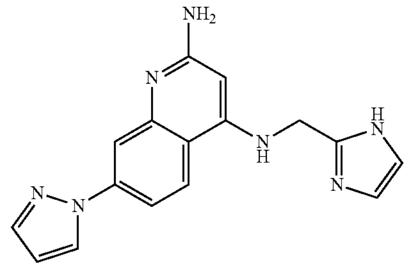 [SMILES: Nc1cc(NCc2ncc[nH]2)c2ccc(-n3cccn3)cc2n1] | 306.1 | 0.74 | δ 8.57 (d, J = 2.1 Hz, 1H), 8.13 (d, J = 8.8 Hz, 1H), 7.85-7.76 (m, 2H), 7.68 (br dd, J = 8.9, 2.1 Hz, 2H), 6.96 (s, 2H), 6.77 (br s, 1H), 6.58 (d, J = 1.5 Hz, 1H), 5.75 (s, 1H), 4.48 (br d, J = 5.5 Hz, 2H) |
| 299 | 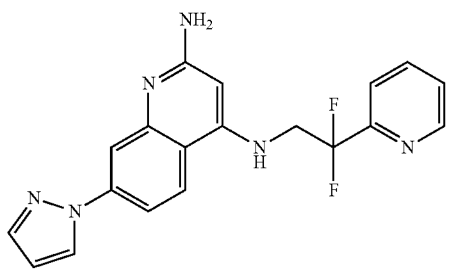 [SMILES: Nc1cc(NCC(F)(F)c2ccccn2)c2ccc(-n3cccn3)cc2n1] | 367.2 | 1.26 | ¹H NMR (500 MHz, DMSO-d₆) δ 8.76 (br d, J = 4.3 Hz, 1H), 8.58 (d, J = 2.4 Hz, 1H), 8.13 (d, J = 9.2 Hz, 1H), 8.00 (td, J = 7.7, 1.7 Hz, 1H), 7.80 (dd, J = 7.6, 1.8 Hz, 2H), 7.75 (d, J = 7.9 Hz, 1H), 7.69 (dd, J = 8.9, 1.8 Hz, 1H), 7.64-7.52 (m, 2H), 6.71 (br s, 1H), 6.60-6.52 (m, 1H), 5.97 (s, 1H), 4.18 (td, J = 14.7, 6.3 Hz, 2H) |
| 300 | 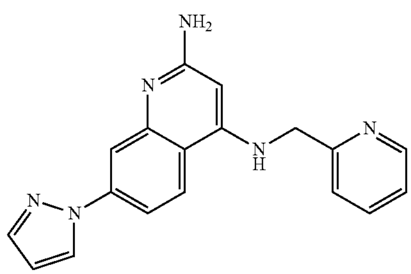 [SMILES: Nc1cc(NCc2ccccn2)c2ccc(-n3cccn3)cc2n1] | 317.2 | 0.96 | δ 8.62-8.52 (m, 2H), 8.13 (d, J = 8.8 Hz, 1H), 7.81-7.72 (m, 3H), 7.70-7.59 (m, 2H), 7.34 (d, J = 7.9 Hz, 1H), 7.32-7.26 (m, 1H), 6.57 (d, J = 1.8 Hz, 1H), 6.16 (br s, 2H), 5.60 (s, 1H), 4.55 (d, J = 5.8 Hz, 2H) |
| 301 | 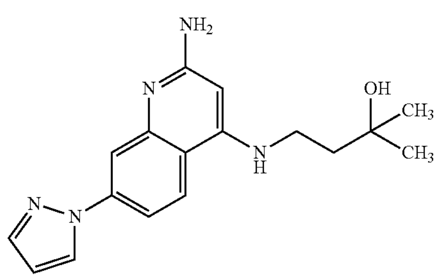 [SMILES: CC(C)(O)CCNc1cc(N)nc2cc(-n3cccn3)ccc12] | 312.1 | 1.24 | δ 8.57 (d, J = 2.1 Hz, 1H), 8.05 (d, J = 9.2 Hz, 1H), 7.79 (s, 2H), 7.65 (dd, J = 8.9, 1.5 Hz, 1H), 7.22 (br d, J = 4.6 Hz, 1H), 6.77 (br s, 1H), 6.58 (s, 1H), 5.73 (s, 1H), 3.34-3.22 (m, 2H), 1.84-1.73 (m, 2H), 1.20 (s, 6H) |
| 302 | 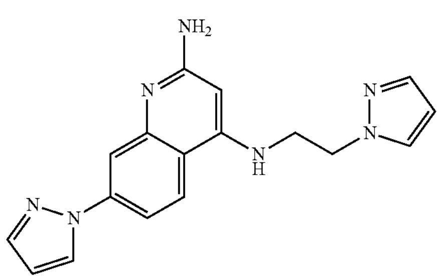 [SMILES: Nc1cc(NCCn2cccn2)c2ccc(-n3cccn3)cc2n1] | 320.2 | 1.04 | δ 8.62-8.54 (m, 1H), 8.04 (d, J = 9.2 Hz, 1H), 7.81 (d, J = 1.8 Hz, 1H), 7.79 (d, J = 1.2 Hz, 1H), 7.75 (d, J = 1.8 Hz, 1H), 7.69 (dd, J = 9.0, 2.0 Hz, 1H), 7.49 (d, J = 1.2 Hz, 1H), 7.34 (br s, 1H), 6.78-6.65 (m, 2H), 6.58 (d, J = 1.8 Hz, 1H), 6.26-6.21 (m, 1H), 5.76 (s, 1H), 4.43 (t, J = 6.4 Hz, 2H), 3.63 (q, J = 6.0 Hz, 2H) |

| Compd. No. | Structure | LC/MS [M + H]⁺ | RT (min) | ¹H NMR (500 MHz, DMSO-d₆) |
|---|---|---|---|---|
| 303 | 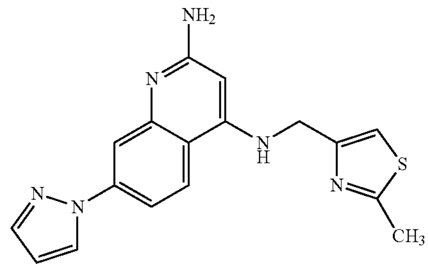 [SMILES: Cc1nc(CNc2cc(N)nc3cc(-n4cccn4)ccc23)cs1] | 337.1 | 1.01 | δ 8.54 (d, J = 2.4 Hz, 1H), 8.13-8.08 (m, 1H), 7.76 (d, J = 1.2 Hz, 1H), 7.73 (d, J = 2.1 Hz, 1H), 7.61 (br dd, J = 8.9, 2.1 Hz, 2H), 7.21 (s, 1H), 6.62-6.48 (m, 2H), 6.41-6.37 (m, 1H), 5.72 (s, 1H), 4.48 (br d, J = 5.8 Hz, 2H), 2.63 (s, 3H) |
| 304 | 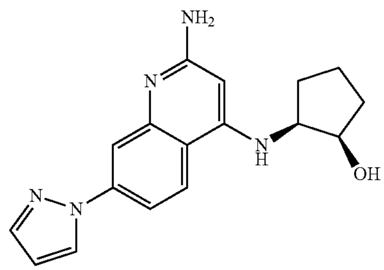 [SMILES: Nc1cc(N[C@H]2CCC[C@H]2O)c2ccc(-n3cccn3)cc2n1] | 310.1 | 0.93 | δ 8.62-8.52 (m, 1H), 8.06 (d, J = 9.2 Hz, 1H), 7.77 (s, 1H), 7.74 (d, J = 1.8 Hz, 1H), 7.62 (dd, J = 8.7, 2.0 Hz, 1H), 6.63-6.58 (m, 1H), 6.56 (d, J = 1.8 Hz, 1H), 6.44-6.35 (m, 1H), 5.81 (s, 1H), 4.24 (br d, J = 2.4 Hz, 1H), 2.07-1.98 (m, 1H), 1.85-1.80 (m, 1H), 1.79-1.71 (m, 2H), 1.70-1.62 (m, 1H), 1.60-1.50 (m, 2H). Several protons from cyclopentyl ring are not visible, likely due to overlap with water/DMSO. |
| 305 | 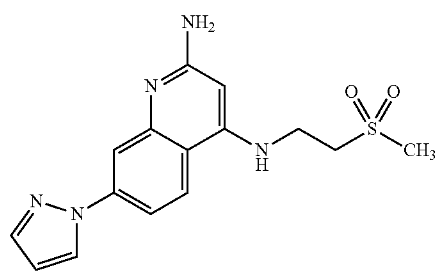 [SMILES: CS(=O)(=O)CCNc1cc(N)nc2cc(-n3cccn3)ccc12] | 332.1 | 0.99 | δ 8.62-8.56 (m, 1H), 8.04 (d, J = 8.8 Hz, 1H), 7.80 (d, J = 2.1 Hz, 1H), 7.79 (d, J = 1.2 Hz, 1H), 7.68 (dd, J = 9.0, 1.7 Hz, 1H), 7.34-7.24 (m, 1H), 6.65-6.53 (m, 3H), 5.80 (s, 1H), 3.74-3.62 (m, 2H), 3.58-3.47 (m, 1H), 3.08 (s, 3H). A proton from ethyl chain is not visible, likely due to overlap with water/DMSO. |
| 306 | 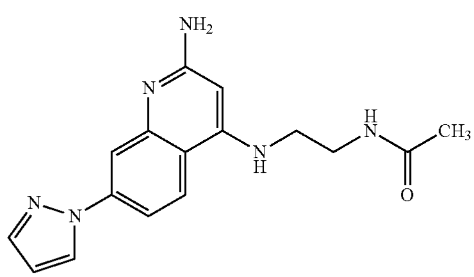 [SMILES: CC(=O)NCCNc1cc(N)nc2cc(-n3cccn3)ccc12] | 311.1 | 0.77 | δ 8.60-8.52 (m, 1H), 8.14 (br t, J = 5.2 Hz, 1H), 7.99 (d, J = 8.5 Hz, 1H), 7.77 (d, J = 1.2 Hz, 1H), 7.75 (d, J = 2.1 Hz, 1H), 7.62 (dd, J = 9.0, 2.0 Hz, 1H), 7.05 (br s, 1H), 6.60-6.51 (m, 2H), 5.73 (s, 1H), 1.85 (s, 3H). Several protons from ethyl chain is not visible, likely due to overlap with water/DMSO. |
| 307 | 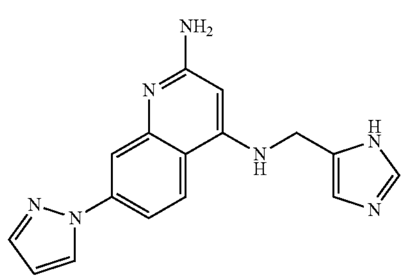 [SMILES: Nc1cc(NCc2cnc[nH]2)c2ccc(-n3cccn3)cc2n1] | 306.1 | 0.97 | δ 8.94-8.90 (m, 1H), 8.65 (d, J = 2.4 Hz, 1H), 8.62-8.57 (m, 1H), 8.30 (br d, J = 9.2 Hz, 1H), 8.01 (d, J = 1.8 Hz, 1H), 7.97-7.91 (m, 1H), 7.90-7.81 (m, 3H), 7.61-7.57 (m, 1H), 6.67-6.60 (m, 1H), 5.82 (s, 1H), 4.63 (br d, J = 5.2 Hz, 2H) |

-continued

| Compd. No. | Structure | LC/MS [M + H]+ | RT (min) | 1H NMR (500 MHz, DMSO-d6) |
|---|---|---|---|---|
| 308 | 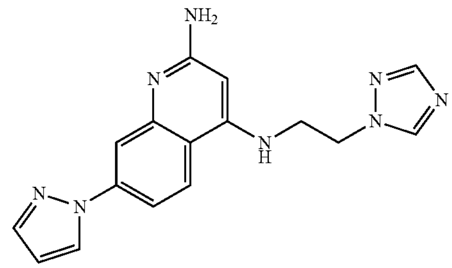 [SMILES: Nc1cc(NCCn2cncn2)c2ccc(-n3cccn3)cc2n1] | 321.1 | 0.74 | δ 8.57 (d, J = 2.1 Hz, 1H), 8.50 (s, 1H), 8.01 (d, J = 10.0 Hz, 2H), 7.79 (dd, J = 3.5, 1.7 Hz, 2H), 7.66 (dd, J = 8.9, 1.8 Hz, 1H), 7.27 (br s, 1H), 6.64-6.56 (m, 2H), 5.76 (s, 1H), 4.49 (t, J = 6.0 Hz, 2H), 3.76-3.55 (m, 2H) |
| 309 | | 318.1 | 1.11 | δ 9.17-9.10 (m, 1H), 8.54 (br d, J = 2.5 Hz, 1H), 8.12 (d, J = 9.2 Hz, 1H), 8.00-7.89 (m, 1H), 7.77 (d, J = 1.2 Hz, 1H), 7.74 (d, J = 1.9 Hz, 1H), 7.69-7.66 (m, 1H), 7.65 (d, J = 4.7 Hz, 1H), 7.64-7.61 (m, 1H), 6.59-6.54 (m, 1H), 6.48-6.34 (m, 1H), 5.64 (s, 1H), 4.77 (br d, J = 5.6 Hz, 2H) | aLC/MS conditions: Column: Waters XBridge C18, 2.1 mm × 50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Example II-7: Synthesis of a 4-Ether Substituted Quinoline with an N-Linked Pyrazole

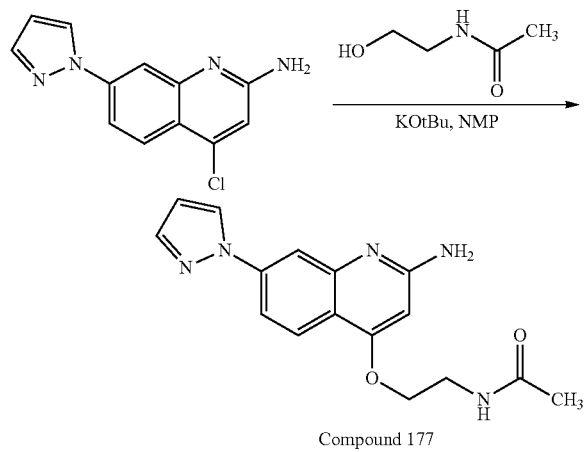

Compound 177

Step 1: Preparation of N-(2-((2-amino-7-(1H-pyrazol-1-yl)quinolin-4-yl)oxy)ethyl)acetamide, TFA (Compound 177)

To a solution of N-(2-hydroxyethyl)acetamide (63.2 mg, 0.613 mmol) and 4-chloro-7-(1H-pyrazol-1-yl)quinolin-2-amine (20 mg, 0.082 mmol) in NMP (0.5 mL) was added potassium tert-butoxide (22.93 mg, 0.204 mmol). The reaction was heated to 100° C. overnight. Then, the temperature was increased to 120° C., and the reaction was heated overnight. Potassium tert-butoxide (11.5 mg, 0.102 mmol) was added, and the reaction was heated for a further 6 hours. The reaction was cooled, diluted with MeOH and a small amount of AcOH, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 1% B, 1-41% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 4-minute hold at 0% B, 0-32% B over 25 minutes, then a 6-minute hold at 100% B; Flow Rate: 20 mL/min; Column Temperature: 25° C. Fraction collection was triggered by MS signals. Fractions containing the desired product were combined and dried via centrifugal evaporation to give N-(2-((2-amino-7-(1H-pyrazol-1-yl)quinolin-4-yl)oxy)ethyl)acetamide, TFA (2.8 mg, 8.1%). 1H NMR (500 MHz, DMSO-d6) δ 8.59 (br s, 1H), 8.23 (br s, 1H), 8.01 (br d, J=8.8 Hz, 1H), 7.79 (br d, J=8.9 Hz, 2H), 7.67 (br d, J=8.5 Hz, 1H), 6.57 (br s, 1H), 6.18 (s, 1H), 4.12 (br t, J=4.7 Hz, 2H), 3.56 (br d, J=5.5 Hz, 1H), 1.86 (s, 3H). One proton from sidechain is not visible due to low integration or overlap with suppressed water peak. LC/MS Conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm. LC RT: 1.09 min. M/Z=312.1.

Example II-8: Preparation of a 4-ether Substituted Quinoline with a C-Linked Pyrazole

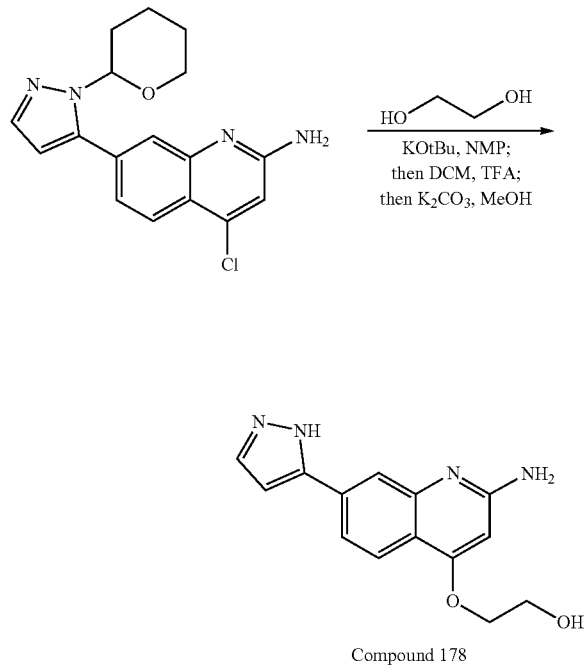

Compound 178

Step 1: Preparation of 2-((2-amino-7-(1H-pyrazol-5-yl)quinolin-4-yl)oxy)ethan-1-ol (Compound 178)

To a solution of 4-chloro-7-(1-(tetrahydro-2H-pyran-2-yl)-1H-pyrazol-5-yl)quinolin-2-amine (80 mg, 0.243 mmol) and ethane-1,2-diol (151 mg, 2.433 mmol) in NMP (1622 μl) was added potassium tert-butoxide (54.6 mg, 0.487 mmol). The reaction was heated to 100° C. overnight. LC/MS showed the reaction was complete. The reaction was cooled, diluted with water, and extracted three times with EtOAc. The organic layers were concentrated. The residue was dissolved in 1 mL DCM and 1 mL TFA. After 2 hours, LC/MS showed that the reaction was complete and that some trifluoroacetate ester had formed. The reaction was concentrated and azeotroped with DCM. The residue was dissolved in 1 mL MeOH and potassium carbonate (67.3 mg, 0.487 mmol) was added. After 1.5 hours, LC/MS showed that the trifluoroacetate ester had been completely hydrolyzed. The reaction was concentrated. The residue was purified via ISCO (24 g column; DCM/MeOH; 0 to 20% gradient) to give 2-((2-amino-7-(1H-pyrazol-5-yl)quinolin-4-yl)oxy)ethan-1-ol (28 mg, 41.3% yield). $^1$H NMR (400 MHz, METHANOL-$d_4$) δ 8.23 (d, J=8.5 Hz, 1H), 8.00-7.88 (m, 2H), 7.78 (br s, 1H), 6.85 (d, J=2.2 Hz, 1H), 6.37 (s, 1H), 4.37 (t, J=4.5 Hz, 2H), 4.09-4.01 (m, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). LC RT: 0.71 min. M/Z=271.24.

Compound 179 to Compound 201, Compound 310 to Compound 312 were prepared according to the synthetic procedures described for Compound 178 from the appropriate starting materials.

| Compd. No. | Structure | LC/MS [M + H]$^+$ | RT (min) | $^1$H NMR (500 MHz, DMSO-$d_6$) |
|---|---|---|---|---|
| 179 | 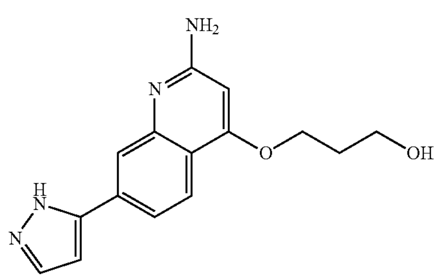 [SMILES: Nc1cc(OCCCO)c2ccc(-c3ccn[nH]3)cc2n1] | 285.4 | 0.93 | δ 8.05-7.96 (m, 2H), 7.89 (br d, J = 8.8 Hz, 1H), 7.81 (br s, 1H), 6.83 (d, J = 2.2 Hz, 1H), 6.39 (s, 1H), 4.35 (t, J = 6.2 Hz, 2H), 3.66 (br t, J = 6.1 Hz, 2H), 2.05 (quin, J = 6.2 Hz, 2H) |
| 180 | 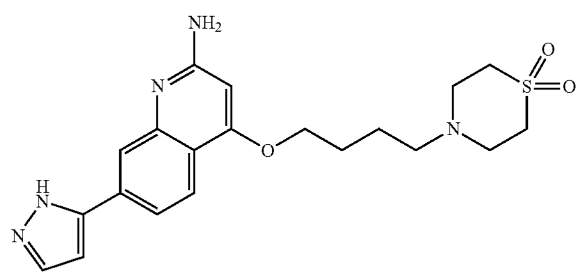 [SMILES: Nc1cc(OCCCCN2CCS(=O)(=O)CC2)c2ccc(-c3ccn[nH]3)cc2n1] | 416.2 | 1.25 | δ 7.87 (d, J = 8.4 Hz, 1H), 7.83 (s, 1H), 7.71 (br s, 1H), 7.64 (br s, 1H), 6.75 (s, 1H), 6.23 (s, 1H), 4.17 (t, J = 6.3 Hz, 2H), 3.04 (br d, J = 4.9 Hz, 4H), 2.96-2.87 (m, 4H), 2.57 (br t, J = 7.2 Hz, 2H), 1.88 (quin, J = 6.8 Hz, 2H), 1.66 (quin, J = 7.2 Hz, 2H) |

-continued

| Compd. No. | Structure | LC/MS [M + H]+ | RT (min) | 1H NMR (500 MHz, DMSO-d6) |
|---|---|---|---|---|
| 181 | 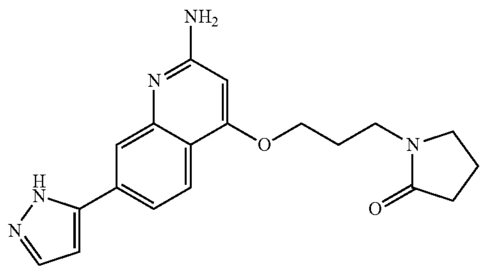 [SMILES: Nc1cc(OCCCN2CCCC2=O)c2ccc(-c3ccn[nH]3)cc2n1] | 352.1 | 1.11 | δ 7.94 (br d, J = 8.5 Hz, 1H), 7.90 (br s, 1H), 7.83-7.68 (m, 2H), 6.81 (s, 1H), 6.23 (s, 1H), 4.17 (br t, J = 5.6 Hz, 2H), 2.24-2.15 (m, 2H), 2.12-2.02 (m, 2H), 1.95-1.84 (m, 2H) Two methylenes are not visible in NMR; probably due to overlap with suppressed water peak. |
| 182 | 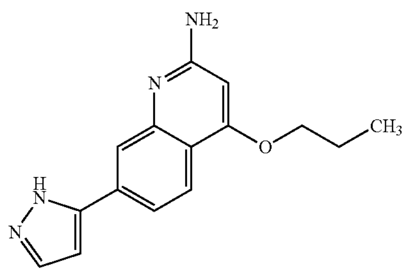 [SMILES: CCCOc1cc(N)nc2cc(-c3ccn[nH]3)ccc12] | 269.0 | 1.59 | δ 8.40-8.19 (m, 1H), 8.06-7.97 (m, 2H), 7.93-7.83 (m, 2H), 6.84 (s, 1H), 6.37 (s, 1H), 4.23 (br t, J = 6.3 Hz, 2H), 1.96-1.84 (m, 2H), 1.07 (t, J = 7.3 Hz, 3H) |
| 183 | 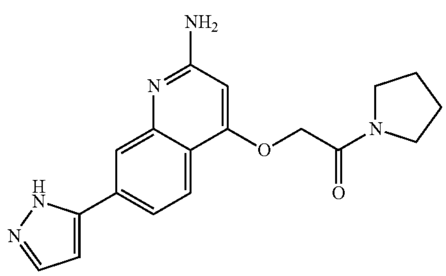 [SMILES: Nc1cc(OCC(=O)N2CCCC2)c2ccc(-c3ccn[nH]3)cc2n1] | 338.1 | 1.13 | δ 8.11-8.01 (m, 2H), 7.93 (br d, J = 8.4 Hz, 1H), 7.83 (br s, 1H), 6.83 (d, J = 2.2 Hz, 1H), 6.33 (s, 1H), 5.14 (s, 2H), 3.51 (br t, J = 6.7 Hz, 2H), 3.38 (br t, J = 6.9 Hz, 2H), 2.00-1.90 (m, 2H), 1.86-1.75 (m, 2H) |
| 184 | 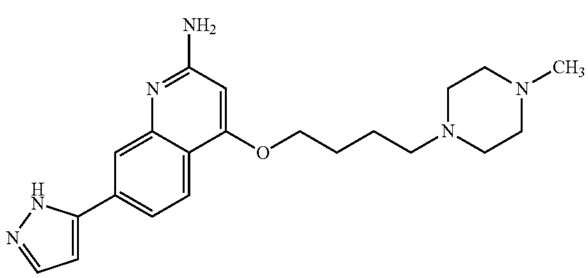 [SMILES: CN1CCN(CCCCOc2cc(N)nc3cc(-c4ccn[nH]4)ccc23)CC1] | 381.0 | 1.21 | δ 7.84 (d, J = 8.4 Hz, 1H), 7.78 (s, 1H), 7.69 (s, 1H), 7.56 (br d, J = 7.8 Hz, 1H), 6.73 (d, J = 1.9 Hz, 1H), 6.19 (s, 1H), 4.13 (t, J = 6.4 Hz, 2H), 2.42-2.26 (m, 8H), 2.13 (s, 2H), 1.87-1.81 (m, 2H), 1.69-1.59 (m 2H) One methylene from sidechain is not visible in NMR, likely due to overlap with suppressed water peak. |
| 185 | 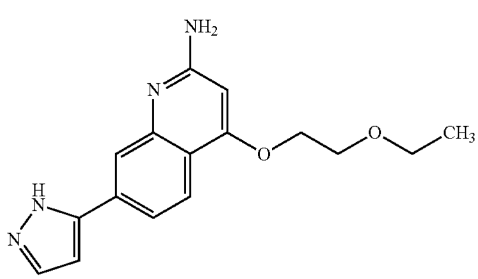 [SMILES: CCOCCOc1cc(N)nc2cc(-c3ccn[nH]3)ccc12] | 299.1 | 1.30 | δ 7.85 (d, J = 8.4 Hz, 1H), 7.80 (s, 1H), 7.70 (s, 1H), 7.58 (br d, J = 8.6 Hz, 1H), 6.74 (d, J = 1.9 Hz, 1H), 6.22 (s, 1H), 4.29-4.19 (m, 2H), 3.88-3.79 (m, 2H), 3.58 (q, J = 7.0 Hz, 2H), 1.15 (t, J = 7.0 Hz, 3H) |

| Compd. No. | Structure | LC/MS [M + H]+ | RT (min) | ¹H NMR (500 MHz, DMSO-d₆) |
|---|---|---|---|---|
| 186 | 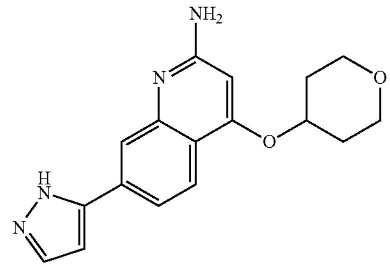 [SMILES: Nc1cc(OC2CCOCC2)c2ccc(-c3ccn[nH]3)cc2n1] | 311.3 | 1.05 | δ 8.10-7.98 (m, 2H), 7.92 (br d, J = 8.2 Hz, 1H), 7.86 (br s, 1H), 6.85 (s, 1H), 6.47 (s, 1H), 4.98-4.86 (m, 1H), 3.97-3.88 (m, 2H), 3.59 (br t, J = 8.5 Hz, 1H), 3.42-3.31 (m, 1H), 2.11 (br d, J = 9.8 Hz, 2H), 1.82 (br d, J = 8.5 Hz, 2H) |
| 187 | 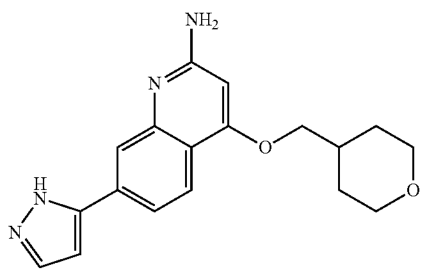 [SMILES: Nc1cc(OCC2CCOCC2)c2ccc(-c3ccn[nH]3)cc2n1] | 325.2 | 1.30 | δ 8.02 (br d, J = 8.4 Hz, 2H), 7.92-7.77 (m, 2H), 6.82 (d, J = 1.9 Hz, 1H), 6.40 (s, 1H), 4.15 (d, J = 6.2 Hz, 2H), 3.93 (br dd, J = 11.2, 3.0 Hz, 2H), 3.41 (br t, J = 10.9 Hz, 1H), 2.21 (br s, 1H), 1.77 (br d, J = 11.1 Hz, 2H), 1.47 (qd, J = 12.2, 4.4 Hz, 2H). One proton is missing from THP sidechain, likely due to overlap with suppressed water peak. |
| 188 | 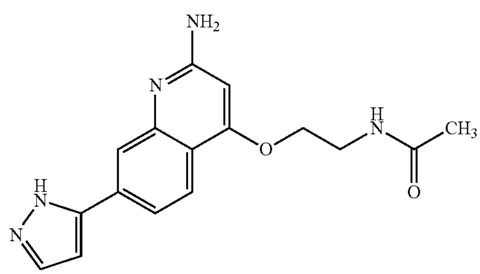 [SMILES: CC(=O)NCCOc1cc(N)nc2cc(-c3ccn[nH]3)ccc12] | 312.3 | 0.97 | δ 8.10 (br s, 1H), 8.04 (d, J = 8.5 Hz, 1H), 7.93 (br s, 1H), 7.78 (br s, 2H), 6.83-6.77 (m, 1H), 6.30 (s, 1H), 4.22 (br t, J = 5.0 Hz, 2H), 3.59 (q, J = 5.3 Hz, 2H), 1.86 (s, 3H) |
| 189 | 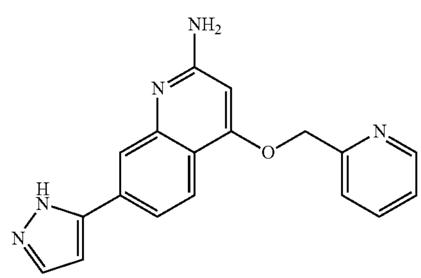 [SMILES: Nc1cc(OCc2ccccn2)c2ccc(-c3ccn[nH]3)cc2n1] | 318.0 | 1.12 | δ 8.62 (br d, J = 4.3 Hz, 1H), 7.95 (br d, J = 8.2 Hz, 1H), 7.92-7.86 (m, 1H), 7.81 (s, 1H), 7.73 (br s, 1H), 7.65-7.56 (m, 2H), 7.42-7.36 (m, 1H), 6.78 (s, 1H), 6.31 (br s, 2H), 6.26 (s, 1H), 5.33 (s, 2H) |
| 190 | 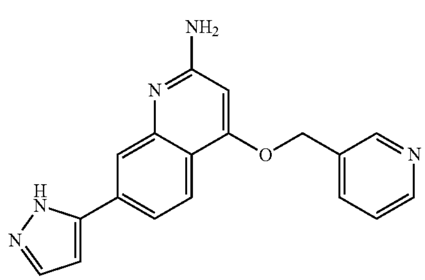 [SMILES: Nc1cc(OCc2cccnc2)c2ccc(-c3ccn[nH]3)cc2n1] | 318.1 | 1.06 | δ 8.77 (s, 1H), 8.60 (br d, J = 4.3 Hz, 1H), 7.98 (br d, J = 7.6 Hz, 1H), 7.85 (br d, J = 8.5 Hz, 1H), 7.80 (s, 1H), 7.72 (br s, 1H), 7.57 (br d, J = 8.2 Hz, 1H), 7.51-7.45 (m, 1H), 6.77 (s, 1H), 6.32 (br d, J = 7.9 Hz, 3H), 5.31 (s, 2H) |

-continued

| Compd. No. | Structure | LC/MS [M + H]+ | RT (min) | ¹H NMR (500 MHz, DMSO-d₆) |
|---|---|---|---|---|
| 191 | 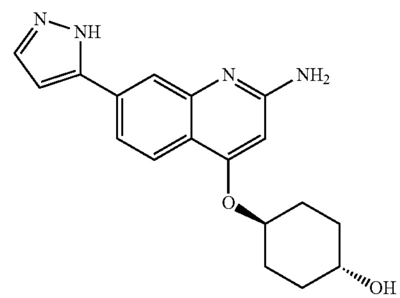 [SMILES: Nc1cc(O[C@H]2CC[C@H](O)CC2)c2ccc(-c3ccn[nH]3)cc2n1] | 325.3 | 0.99 | δ 7.84-7.75 (m, 2H), 7.71 (br s, 1H), 7.55 (br d, J = 8.2 Hz, 1H), 6.75 (s, 1H), 6.22 (br d, J = 9.2 Hz, 2H), 4.45 (br d, J = 3.7 Hz, 1H), 3.62 (br s, 1H), 2.17-2.05 (m, 2H), 1.89 (br s, 2H), 1.65-1.53 (m, 2H), 1.45-1.30 (m, 2H) |
| 192 | 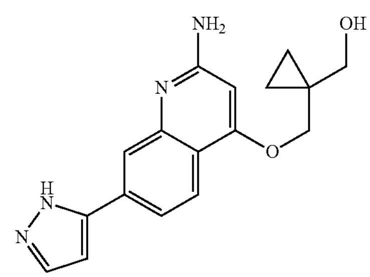 [SMILES: Nc1cc(OCC2(CO)CC2)c2ccc(-c3ccn[nH]3)cc2n1] | 311.0 | 1.02 | δ 8.33-8.12 (m, 1H), 8.03 (br d, J = 7.9 Hz, 2H), 7.96-7.80 (m, 2H), 6.85 (s, 1H), 6.34 (s, 1H), 4.18 (s, 2H), 0.63 (br d, J = 11.0 Hz, 4H). One Methylene from sidechain is missing, likely due to overlap with suppressed water peak. |
| 193 | 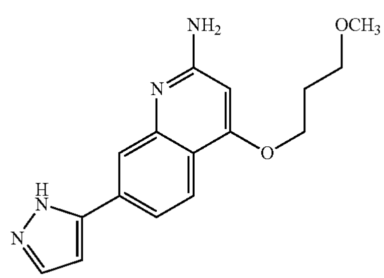 [SMILES: COCCCOc1cc(N)nc2cc(-c3ccn[nH]3)ccc12] | 299.4 | 1.10 | δ 8.02 (br d, J = 8.2 Hz, 2H), 7.98-7.80 (m, 2H), 6.85 (s, 1H), 6.37 (s, 1H), 4.32 (br t, J = 6.0 Hz, 2H), 3.61-3.40 (m, 2H) (overlaps suppressed water peak), 3.27 (s, 2H), 2.19-2.06 (m, 2H) |
| 194 | 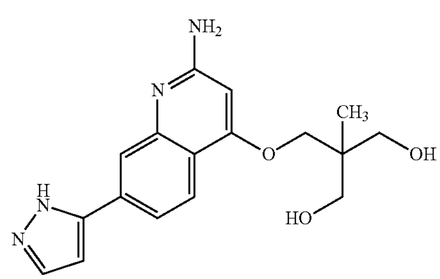 [SMILES: CC(CO)(CO)COc1cc(N)nc2cc(-c3ccn[nH]3)ccc12] | 329.3 | 0.82 | δ 8.00 (br d, J = 8.2 Hz, 2H), 7.88 (br d, J = 9.8 Hz, 2H), 6.84 (br s, 1H), 6.38 (s, 1H), 4.06 (br s, 2H), 3.24 (br s, 2H), 1.00 (s, 3H). One methylene from sidechain is missing in NMR, likely due to overlap with suppressed water peak. |
| 195 | 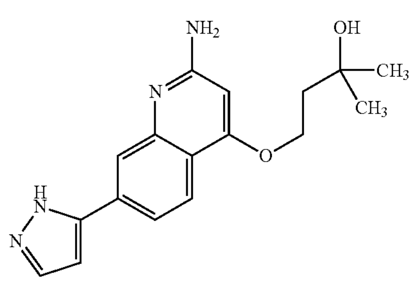 [SMILES: CC(C)(O)CCOc1cc(N)nc2cc(-c3ccn[nH]3)ccc12] | 313.2 | 1.22 | δ 7.86-7.77 (m, 2H), 7.72 (br s, 1H), 7.57 (br d, J = 7.6 Hz, 1H), 6.77 (s, 1H), 6.30 (br s, 2H), 6.21 (s, 1H), 4.23 (br t, J = 6.7 Hz, 2H), 1.99 (br t, J = 6.7 Hz, 2H), 1.22 (s, 6H) |

| Compd. No. | Structure | LC/MS [M + H]⁺ | RT (min) | ¹H NMR (500 MHz, DMSO-d₆) |
|---|---|---|---|---|
| 196 | 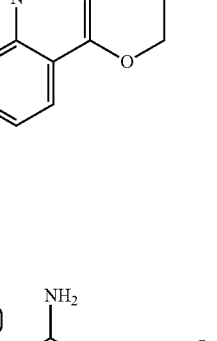 | 335.3 | 1.07 | δ 7.87 (br d, J = 8.5 Hz, 1H), 7.81-7.68 (m, 3H), 7.58 (br d, J = 7.0 Hz, 1H), 7.46 (s, 1H), 6.77 (s, 1H), 6.25 (br d, J = 11.0 Hz, 3H), 6.11 (s, 1H), 4.38 (br t, J = 6.6 Hz, 2H), 4.05 (br t, J = 5.6 Hz, 2H), 2.36 (br t, J = 6.1 Hz, 2H) |
| 197 | 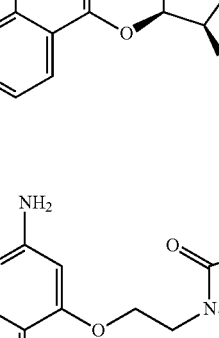 | 313.2 | 0.79 | δ 8.09 (br d, J = 8.5 Hz, 1H), 7.99-7.69 (m, 3H), 6.82 (br s, 1H), 6.34 (br s, 1H), 4.97 (br s, 1H), 4.58-4.44 (m, 1H), 4.16 (br dd, J = 9.5, 5.5 Hz, 1H), 4.03-3.86 (m, 2H), 3.79-3.64 (m, 2H) |
| 198 | 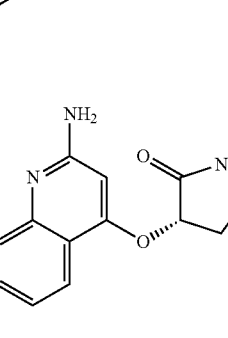 | 339.2 | 0.82 | δ 7.84 (br d, J = 8.2 Hz, 1H), 7.78 (s, 1H), 7.75-7.50 (m, 2H), 6.76 (s, 1H), 6.35 (s, 1H), 6.24 (br s, 2H), 6.18 (s, 1H), 4.18 (br s, 2H), 3.60-3.38 (m, 4H) (overlaps suppressed water peak), 3.24 (br t, J = 7.8 Hz, 2H) |
| 199 | 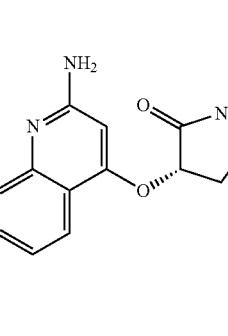 | 310.0 | 1.06 | δ 8.19 (br s, 1H), 7.84-7.77 (m, 2H), 7.72 (br d, J = 4.9 Hz, 1H), 7.57 (br d, J = 7.6 Hz, 1H), 6.77 (s, 1H), 6.34 (s, 1H), 6.28 (br s, 2H), 5.02 (br t, J = 7.5 Hz, 1H), 2.74-2.62 (m, 1H), 2.19-2.06 (m, 1H). Two protons are not visible, possibly due to overlap with suppressed water peak or low integration. |
| 200 | 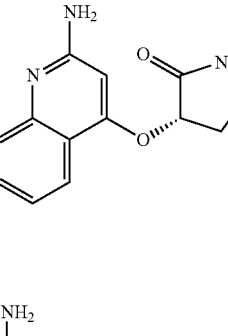 | 326.0 | 0.79 | δ 8.02-7.65 (m, 5H), 6.80 (br s, 1H), 6.24 (s, 1H), 4.18 (br s, 2H), 2.00 (br t, J = 6.3 Hz, 2H), 1.81 (s, 3H). Two protons from sidechain are not visible, likely due to overlap with suppressed water peak. |

-continued

| Compd. No. | Structure | LC/MS [M + H]+ | RT (min) | ¹H NMR (500 MHz, DMSO-d₆) |
|---|---|---|---|---|
| 201 | 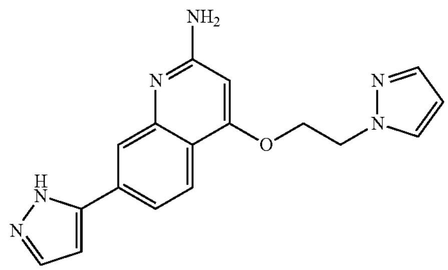 [SMILES: Nc1cc(OCCn2cccn2)c2ccc(-c3ccn[nH]3)cc2n1] | 321.3 | 1.13 | δ 8.08 (s, 1H), 8.01-7.90 (m, 2H), 7.84-7.62 (m, 3H), 6.81 (br d, J = 15.9 Hz, 2H), 6.67 (br s, 1H), 3.71-3.55 (m, 2H), 2.69 (br t, J = 6.7 Hz, 2H) |
| 310 | 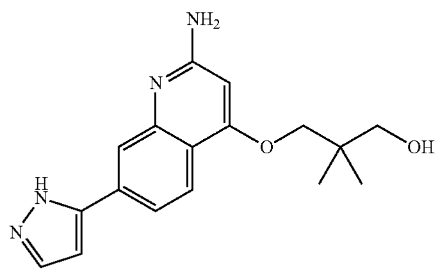 [SMILES: CC(C)(CO)COc1cc(N)nc2cc(-c3ccn[nH]3)ccc12] | 313.3 | 1.05 | δ 7.89 (d, J = 8.5 Hz, 1H), 7.83 (s, 1H), 7.75 (br s, 1H), 7.70-7.54 (m, 1H), 6.79 (d, J = 1.8 Hz, 2H), 6.53 (br s, 2H), 6.22 (s, 1H), 3.87 (s, 2H), 3.39 (br s, 1H), 1.03 (s, 6H). One methylene is not visible, possibly due to overlap with suppressed water peak. |
| 311 | 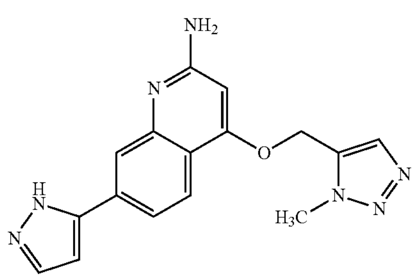 [SMILES: Cn1nncc1COc1cc(N)nc2cc(-c3ccn[nH]3)ccc12] | 322.0 | 1.01 | δ 8.02-7.91 (m, 3H), 7.87-7.72 (m, 2H), 6.82 (s, 1H), 6.46 (s, 1H), 5.57 (br s, 2H), 4.11 (s, 3H) |
| 312 | 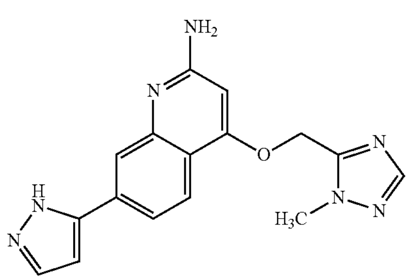 [SMILES: Cn1ncnc1COc1cc(N)nc2cc(-c3ccn[nH]3)ccc12] | 322.2 | 1.00 | δ 8.05-7.98 (m, 3H), 7.92-7.83 (m, 2H), 6.85 (d, J = 2.1 Hz, 1H), 6.54 (s, 1H), 5.65 (s, 2H), 3.97 (s, 3H) |

Example II-9: Synthesis of 2-((2-amino-7-(1H-pyrazol-5-yl)quinolin-4-yl)oxy)propane-1,3-diol

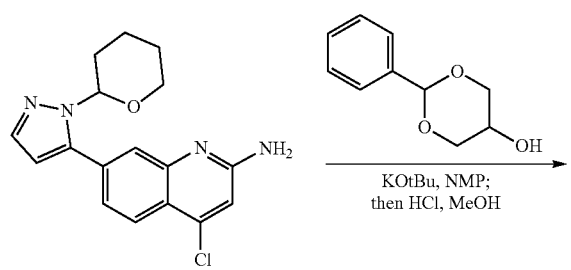

Step 1: Preparation of 2-((2-amino-7-(1H-pyrazol-5-yl)quinolin-4-yl)oxy)propane-1,3-diol (Compound 202)

To a solution of 2-phenyl-1,3-dioxan-5-ol (110 mg, 0.608 mmol) and 4-chloro-7-(1-(tetrahydro-2H-pyran-2-yl)-1H-pyrazol-5-yl)quinolin-2-amine (20 mg, 0.061 mmol) in NMP (406 μl) was added potassium tert-butoxide (17.06 mg, 0.152 mmol). The reaction was heated to 100° C. After 5 hours, the reaction was cooled, diluted with water, and extracted three times with EtOAC. The organic layers were concentrated. The residue was dissolved in 0.8 mL MeOH, and 0.2 mL concentrated HCl was added. After 4 hours, 0.2 mL HCl was added. After a further 4 hours, the reaction was heated to 50° C. overnight. The reaction was concentrated and azeotroped with MeOH. The residue was dissolved in MeOH, neutralized with solid $K_2CO_3$, filtered through a syringe filter, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over minutes, then a 4-minute hold at 100% B; Flow Rate: 20 mL/min; Column Temperature: 25° C. Fraction collection was triggered by UV signals. Fractions containing the desired product were combined and dried via centrifugal evaporation to give 2-((2-amino-7-(1H-pyrazol-5-yl)quinolin-4-yl)oxy)propane-1,3-diol (4.1 mg, 28.1%). $^1$H NMR (500 MHz, DMSO-$d_6$) δ 7.94 (br d, J=8.2 Hz, 1H), 7.81 (s, 1H), 7.74 (br s, 1H), 7.60 (br d, J=7.6 Hz, 1H), 6.78 (s, 1H), 6.52 (br s, 1H), 6.30 (s, 1H), 4.49-4.40 (m, 1H), 3.81-3.61 (m, 4H). LC/MS Conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.56 min.

M/Z=301.0.

Example II-10: Synthesis of 4-diaminoethane Substituted Quinolines

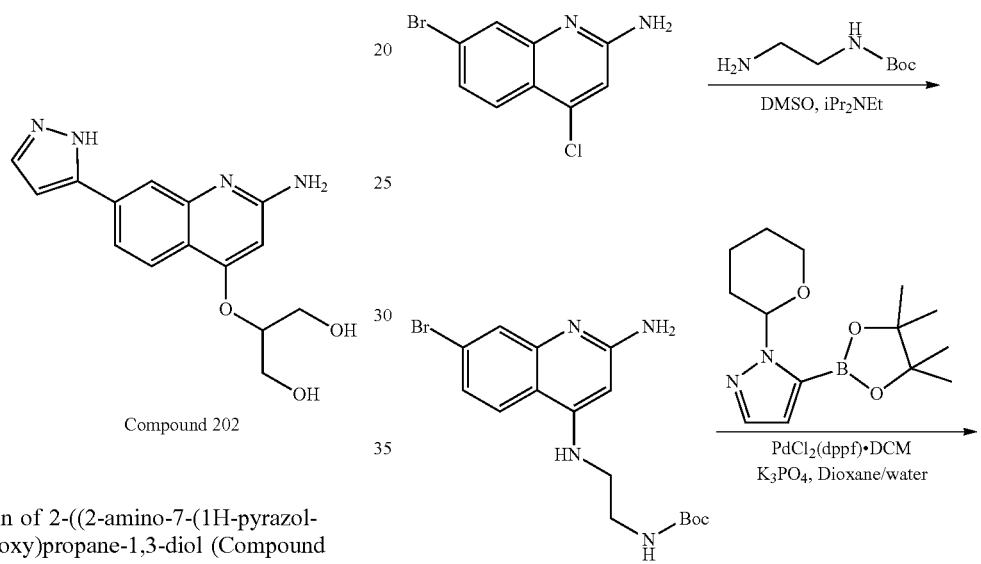

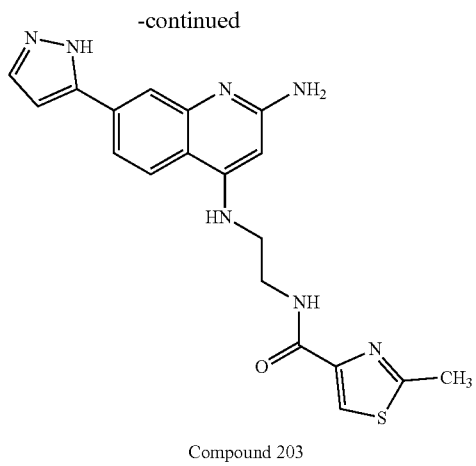

Compound 203

Step 1: Preparation of tert-butyl (2-((2-amino-7-bromoquinolin-4-yl)amino)ethyl)carbamate To a solution of 7-bromo-4-chloroquinolin-2-amine (200 mg, 0.777 mmol) and tert-butyl (2-aminoethyl)carbamate (622 mg, 3.88 mmol) in DMSO (3883 µl) was added Hunig's Base (407 µl, 2.330 mmol). The reaction was heated to 120° C. overnight. The reaction was diluted with water and extracted three times with EtOAc. The organic layers were dried with sodium sulfate and concentrated. The residue was purified via ISCO (24 g column; DCM/MeOH; 0 to 20% gradient). The material was triturated with DCM/hexanes to give tert-butyl (2-((2-amino-7-bromoquinolin-4-yl)amino)ethyl)carbamate (170 mg, 57.4% yield) containing a small amount of residual tert-butyl (2-aminoethyl)carbamate. This material was used in the next step without further purification. $^1$H NMR (400 MHz, CHLOROFORM-d) δ 7.79 (d, J=2.0 Hz, 1H), 7.54 (d, J=8.7 Hz, 1H), 7.32-7.28 (m, 1H), 6.71 (br d, J=1.2 Hz, 1H), 6.12-5.87 (m, 2H), 5.53 (s, 1H), 5.14-5.04 (m, 1H), 3.63-3.53 (m, 2H), 3.36-3.26 (m, 2H), 1.48 (s, 9H).

Step 2: Preparation of tert-butyl (2-((2-amino-7-(1-(tetrahydro-2H-pyran-2-yl)-1H-pyrazol-5-yl)quinolin-4-yl)amino)ethyl)carbamate 1-(Tetrahydro-2H-pyran-2-yl)-5-(4,4,5,5-tetramethyl-1,3,2-dioxaborolan-2-yl)-1H-pyrazole (171 mg, 0.613 mmol), tert-butyl (2-((2-amino-7-bromoquinolin-4-yl)amino)ethyl)carbamate (187 mg, 0.490 mmol), and PdCl$_2$(dppf)-DCM adduct (40.1 mg, 0.049 mmol) were placed in a pressure vial. The vial was placed under vacuum and backfilled with nitrogen three times. Dioxane (3270 µl) and tripotassium phosphate (2M aqueous) (736 µl, 1.471 mmol) were added and nitrogen was bubbled through the solution. The vial was capped and heated to 100° C. overnight. The reaction was cooled, diluted with water, and extracted three times with EtOAc. The organic layers were washed with brine, dried with sodium sulfate and concentrated. The residue was purified via ISCO (12 g column; DCM/MeOH; 0 to 20% gradient) to give tert-butyl (2-((2-amino-7-(1-(tetrahydro-2H-pyran-2-yl)-1H-pyrazol-5-yl)quinolin-4-yl)amino)ethyl)carbamate (160 mg, 0.354 mmol, 72.1% yield). $^1$H NMR (400 MHz, CHLOROFORM-d) δ 7.77 (d, J=8.5 Hz, 1H), 7.72 (s, 1H), 7.60 (d, J=1.5 Hz, 1H), 7.34 (br d, J=8.4 Hz, 1H), 6.85 (br s, 1H), 6.68-6.43 (m, 1H), 6.40 (d, J=1.7 Hz, 1H), 5.63 (s, 1H), 5.57 (br t, J=5.8 Hz, 1H), 5.25 (dd, J=10.2, 1.9 Hz, 1H), 4.13 (br dd, J=9.4, 1.6 Hz, 1H), 3.66-3.57 (m, 1H), 3.52 (br d, J=4.4 Hz, 2H), 3.28 (br d, J=3.3 Hz, 2H), 2.63-2.47 (m, 1H), 2.01 (br s, 1H), 1.86 (br d, J=12.7 Hz, 1H), 1.80-1.66 (m, 1H), 1.62-1.49 (m, 2H), 1.48-1.44 (m, 9H).

Step 3: Preparation of N4-(2-aminoethyl)-7-(1H-pyrazol-5-yl)quinoline-2,4-diamine 4M HCl in dioxane (3535 µl) was added to tert-butyl (2-((2-amino-7-(1-(tetrahydro-2H-pyran-2-yl)-1H-pyrazol-5-yl)quinolin-4-yl)amino)ethyl)carbamate (160 mg, 0.354 mmol). After 2 hours, the reaction was concentrated and azeotroped twice with DCM. 217 mg material was obtained and taken on to next reaction, assuming 50% purity. $^1$H NMR (500 MHz, DMSO-d$_6$) δ 8.20 (br d, J=8.5 Hz, 1H), 8.06-7.95 (m, 2H), 7.87 (br d, J=8.5 Hz, 4H), 6.86 (br s, 1H), 5.87 (s, 1H), 3.55 (br d, J=4.6 Hz, 2H), 3.21 (br d, J=5.2 Hz, 1H). One proton from sidechain is not visible, likely due to overlap with suppressed water peak.

Step 4: Preparation of N-(2-((2-amino-7-(1H-pyrazol-5-yl)quinolin-4-yl)amino)ethyl)-2-methylthiazole-4-carboxamide, TFA (Compound 203)

N4-(2-Aminoethyl)-7-(1H-pyrazol-5-yl)quinoline-2,4-diamine (30 mg, 0.056 mmol) (assumed to be 50% by weight HCl) and 2-methylthiazole-4-carboxylic acid (16.01 mg, 0.112 mmol) were dissolved in DMF (0.4 mL). Triethylamine (0.078 mL, 0.559 mmol) and T3P (50% in DMF) (49.8 mg, 0.078 mmol) were added. After 2 hours, the reaction was quenched with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give N-(2-((2-amino-7-(1H-pyrazol-5-yl)quinolin-4-yl)amino)ethyl)-2-methylthiazole-4-carboxamide, TFA (15.1 mg, 52.5%). $^1$H NMR (500 MHz, DMSO-d$_6$) δ 8.69 (br s, 1H), 8.16 (br d, J=8.5 Hz, 1H), 8.11-8.04 (m, 2H), 7.92 (br s, 1H), 7.87-7.77 (m, 2H), 7.59 (br s, 2H), 6.85 (s, 1H), 5.85 (s, 1H), 3.67-3.35 (m, 4H), 2.68 (s, 3H). LC RT: 1.07 min. M/Z=394.34.

Compound 204 was prepared according to the synthetic procedures described for Compound 203 from the appropriate starting material

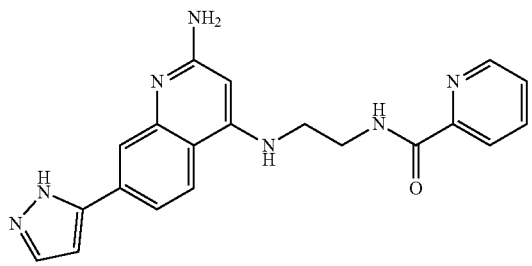

Compound 204

$^1$H NMR (500 MHz, DMSO-d$_6$) δ 9.22-9.06 (m, 1H), 8.65 (br d, J=4.3 Hz, 1H), 8.11-8.04 (m, 1H), 8.03-7.93 (m, 2H), 7.77 (s, 1H), 7.72 (br s, 1H), 7.63-7.51 (m, 2H), 7.03 (br s, 1H), 6.77 (s, 1H), 6.51 (br s, 1H), 5.78 (s, 1H), 3.67 (br d, J=6.1 Hz, 1H), 3.51-3.33 (m, 1H). Two protons from sidechain are not visible, likely due to low integration or overlap with suppressed water peak. LC RT: 1.06 min. M/Z=374.3.

Example II-11: Preparation of methyl (2-((2-amino-7-(1H-pyrazol-5-yl)quinolin-4-yl)amino)ethyl)carbamate (Compound 205)

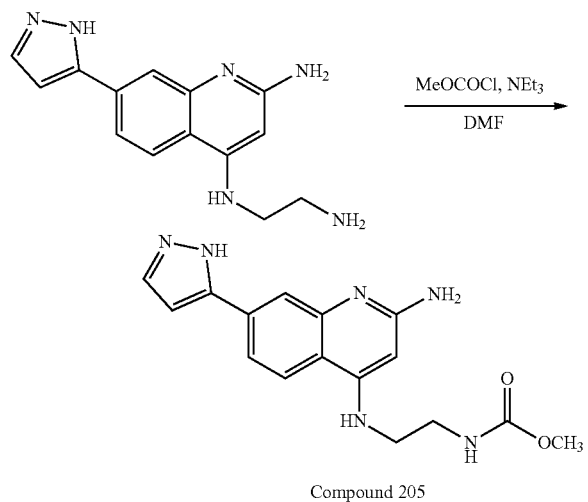

Compound 205

To a suspension of N4-(2-aminoethyl)-7-(1H-pyrazol-5-yl)quinoline-2,4-diamine (30 mg, 0.056 mmol) (assumed to be 50% HCl by weight) in DMF (0.4 mL) was added methyl chloroformate (6.49 µL, 0.084 mmol). After 1.5 hours, 4 µL methyl chloroformate was added. After 40 minutes, the reaction was quenched with MeOH. K$_2$CO$_3$ was added, and the reaction was stirred overnight. The reaction was quenched with AcOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-60% B over 40 minutes, then a 4-minute hold at 100% B; Flow Rate: 20 mL/min; Column Temperature: 25° C. Fraction collection was triggered by UV signals. Fractions containing the desired product were combined and dried via centrifugal evaporation to give methyl (2-((2-amino-7-(1H-pyrazol-5-yl)quinolin-4-yl)amino)ethyl)carbamate (3.6 mg, 19.3%). $^1$H NMR (500 MHz, DMSO-d$_6$) δ 7.96 (br d, J=7.9 Hz, 1H), 7.86-7.71 (m, 2H), 7.64 (br d, J=6.7 Hz, 1H), 7.33-7.17 (m, 1H), 6.83 (br s, 1H), 5.83-5.69 (m, 1H), 3.55-3.46 (m, 2H), 3.37-3.22 (m, 3H). Two protons from sidechain are not visible, likely due to overlap with suppressed water peak. LC/MS Conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.89 min. M/Z=327.12.

Example II-12: Preparation of N-(2-((2-amino-7-(1H-pyrazol-5-yl)quinolin-4-yl)amino)ethyl)methanesulfonamide, TFA (Compound 206)

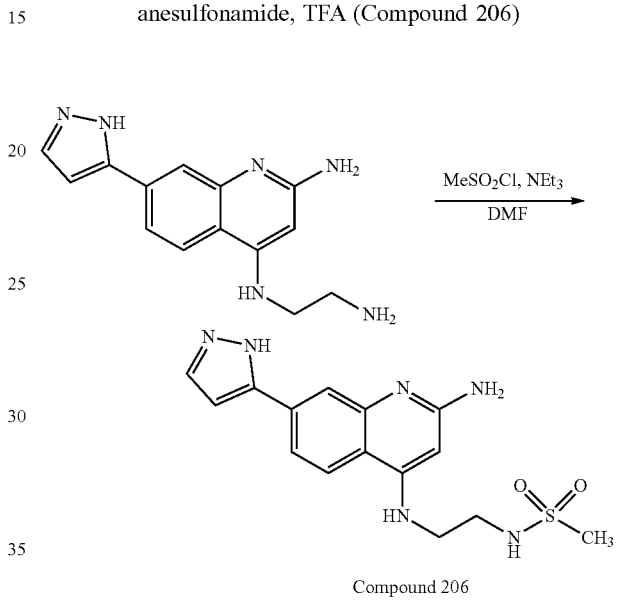

Compound 206

To a suspension of N4-(2-aminoethyl)-7-(1H-pyrazol-5-yl)quinoline-2,4-diamine (30 mg, 0.056 mmol) (assumed to be 50% HCl by weight) in DMF (0.4 mL) was added MsCl (6.53 µl, 0.084 mmol). After 1.5 hours, 3.5 µL MsCl was added. After 40 minutes, the reaction was quenched with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give N-(2-((2-amino-7-(1H-pyrazol-5-yl)quinolin-4-yl)amino)ethyl)methanesulfonamide, TFA (5.7 mg, 21.5%). $^1$H NMR (500 MHz, DMSO-d$_6$) δ 8.17 (br d, J=8.5 Hz, 1H), 8.04 (br s, 1H), 7.93 (br s, 1H), 7.85 (br d, J=9.2 Hz, 2H), 7.62 (br s, 2H), 7.29 (br t, J=5.8 Hz, 1H), 6.86 (s, 1H), 3.43 (br d, J=5.5 Hz, 2H), 3.28 (br d, J=5.8 Hz, 2H), 2.93 (s, 3H). Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.85 min. M/Z=347.27.

Example II-13: Preparation of 1-(2-((2-amino-7-(1H-pyrazol-5-yl)quinolin-4-yl)amino)ethyl)-3-ethylurea, TFA (Compound 207)

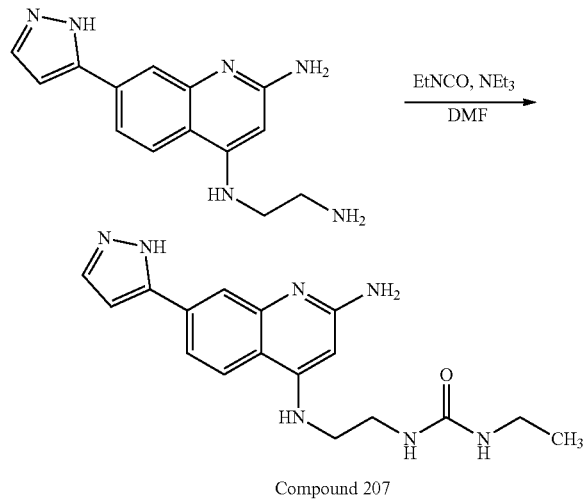

Compound 207

To a suspension of N4-(2-aminoethyl)-7-(1H-pyrazol-5-yl)quinoline-2,4-diamine (30 mg, 0.056 mmol) (assumed to be 50% HCl by weight) in DMF (0.4 mL) was added ethyl isocyanate (6.64 µl, 0.084 mmol). After 40 minutes, the reaction was quenched with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 1-(2-((2-amino-7-(1H-pyrazol-5-yl)quinolin-4-yl)amino)ethyl)-3-ethylurea (7.3, 38.5%). $^1$H NMR (500 MHz, DMSO-$d_6$) δ 12.36 (br s, 1H), 8.43-8.31 (m, 1H), 8.12 (br d, J=8.5 Hz, 1H), 7.94 (s, 1H), 7.88-7.78 (m, 2H), 7.63 (br s, 2H), 6.86 (s, 1H), 5.79 (s, 1H), 3.44-3.25 (m, 2H), 3.04 (br d, J=6.7 Hz, 2H), 0.99 (t, J=7.2 Hz, 3H). One methylene from sidechain is missing, likely due to overlap with suppressed water peak. LC RT: 1.07 min. M/Z=339.94.

Example II-14: Preparation of 3-(2-((2-amino-7-(1H-pyrazol-5-yl)quinolin-4-yl)amino)ethyl)-1,1-dimethylurea (Compound 208)

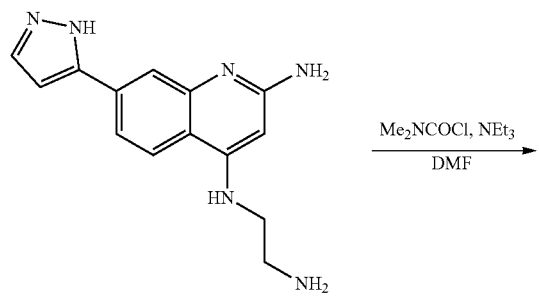

Compound 208

To a suspension of N4-(2-aminoethyl)-7-(1H-pyrazol-5-yl)quinoline-2,4-diamine (30 mg, 0.056 mmol) (assumed to be 50% HCl by weight) in DMF (0.4 mL) was added dimethylcarbamoyl chloride (7.71 µl, 0.084 mmol). After 1.5 hours, dimethylcarbamoyl chloride (7.71 µl, 0.084 mmol) was added. After a further 1.5 hours, dimethylcarbamoyl chloride (7.71 µl, 0.084 mmol) was added, and the reaction was stirred overnight. Triethylamine (0.078 mL, 0.559 mmol) was added. After 2 hours, the reaction was quenched with MeOH, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by UV signals. Fractions containing the desired product were combined and dried via centrifugal evaporation. The material was further purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 3-(2-((2-amino-7-(1H-pyrazol-5-yl)quinolin-4-yl)amino)ethyl)-1,1-dimethylurea (8.7 mg, 45.9%). $^1$H NMR (500 MHz, DMSO-$d_6$) δ 7.91 (br d, J=8.5 Hz, 1H), 7.82-7.66 (m, 2H), 7.60 (br d, J=7.6 Hz, 1H), 7.34 (br s, 1H), 6.80 (s, 2H), 6.69-6.57 (m, 1H), 5.73 (s, 1H), 3.36 (br d, J=5.5 Hz, 2H), 3.26-3.16 (m, 2H), 2.80 (s, 6H). LC RT: 0.96 min. M/Z=340.22.

Example II-15: Synthesis of 4-diaminopropane Substituted Quinolines

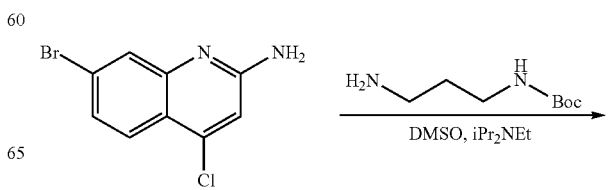

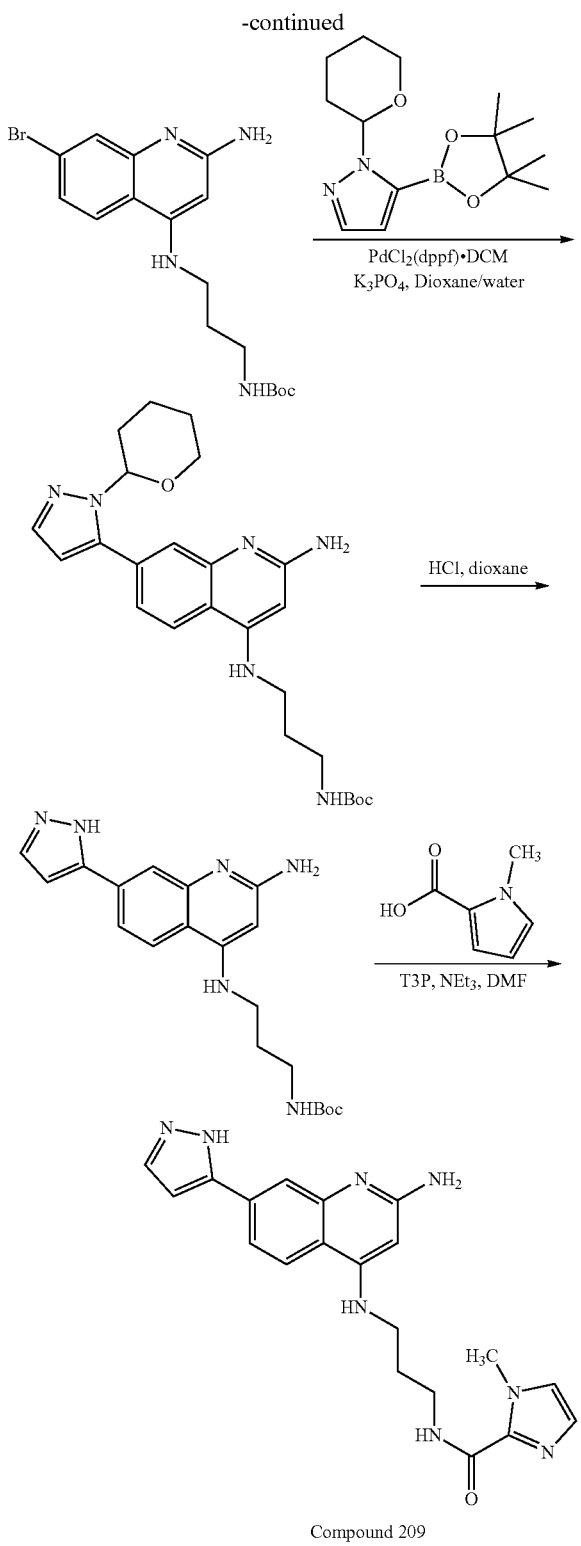

Compound 209

Step 1: Preparation of tert-butyl (3-((2-amino-7-bromoquinolin-4-yl)amino)propyl)carbamate To a solution of 7-bromo-4-chloroquinolin-2-amine (520 mg, 2.019 mmol) and tert-butyl (3-aminopropyl)carbamate (1759 mg, 10.10 mmol) in DMSO (5 mL) was added Hunig's Base (1.058 mL, 6.06 mmol). The reaction was heated to 120° C. overnight. The reaction was partitioned between DCM and water. The organic layer was dried sodium sulfate and evaporated. The residue was purified via ISCO (40 g column; DCM/EtOAc; 0 to 100% gradient) to give tert-butyl (3-((2-amino-7-bromoquinolin-4-yl)amino)propyl)carbamate (478 mg, 1.20 mmol, 60% yield). $^1$H NMR (400 MHz, DMSO-$d_6$) δ 7.86 (d, J=8.8 Hz, 1H), 7.43 (d, J=2.0 Hz, 1H), 7.15 (dd, J=8.7, 2.0 Hz, 1H), 6.89 (br t, J=5.3 Hz, 1H), 6.72 (br t, J=5.0 Hz, 1H), 6.12 (s, 2H), 5.71 (s, 1H), 3.21-3.11 (m, 2H), 3.10-2.97 (m, 2H), 1.85-1.70 (m, 2H), 1.38 (s, 9H).

Step 2: Preparation of tert-butyl (3-((2-amino-7-(1-(tetrahydro-2H-pyran-2-yl)-1H-pyrazol-5-yl)quinolin-4-yl)amino)propyl)carbamate A two phase solution of 1-(tetrahydro-2H-pyran-2-yl)-5-(4,4,5,5-tetramethyl-1,3,2-dioxaborolan-2-yl)-1H-pyrazole (420 mg, 1.512 mmol), tert-butyl (3-((2-amino-7-bromoquinolin-4-yl)amino)propyl)carbamate (478 mg, 1.209 mmol), PdCl$_2$(dppf)-DCM adduct (99 mg, 0.121 mmol), and tripotassium phosphate (2M aqueous) (1.814 mL, 3.63 mmol) in dioxane (10 mL) was heated to 110° C. overnight. The reaction mixture was diluted with 100 ml DCM, dried with sodium sulfate and evaporated under reduced pressure. The residue was purified via ISCO (40 g column; DCM/MeOH; 0 to 25% gradient) to give tert-butyl (3-((2-amino-7-(1-(tetrahydro-2H-pyran-2-yl)-1H-pyrazol-5-yl)quinolin-4-yl)amino)propyl)carbamate (400 mg, 0.85 mmol, 71% yield). LC/MS conditions: Column: Aquity UPLC BEH C18, 2.1 mm×50 mm, 1.7 µm particles; Mobile Phase A: 100% water with 0.05% TFA; Mobile Phase B: 100% acetonitrile with 0.05% TFA; Gradient: 2% B to 98% B over 1 min, then a 0.50 min hold at 100% B; Flow: 0.8 mL/min. LC RT: 0.77 min. M/Z=467.

Step 3: Preparation of N4-(3-aminopropyl)-7-(1H-pyrazol-5-yl)quinoline-2,4-diamine, 3 HCl To a solution of tert-butyl (3-((2-amino-7-(1-(tetrahydro-2H-pyran-2-yl)-1H-pyrazol-5-yl)quinolin-4-yl)amino)propyl)carbamate (400 mg, 0.857 mmol) in dioxane (10 mL) was added HCl (4M in dioxane) (4 mL, 16.00 mmol). After 2 hours, the reaction was evaporated under high vacuum to give N4-(3-aminopropyl)-7-(1H-pyrazol-5-yl)quinoline-2,4-diamine, 3 HCl (336 mg, 0.85 mmol, 100% yield). LC/MS conditions: Column: Aquity UPLC BEH C18, 2.1 mm×50 mm, 1.7 µm particles; Mobile Phase A: 100% water with 0.05% TFA; Mobile Phase B: 100% acetonitrile with 0.05% TFA; Gradient: 2% B to 98% B over 1 min, then a 0.50 min hold at 100% B; Flow: 0.8 mL/min. LC RT: 0.45 min. M/Z=283.

Step 4: Preparation of N-(3-((2-amino-7-(1H-pyrazol-5-yl)quinolin-4-yl)amino)propyl)-1-methyl-1H-imidazole-2-carboxamide, 2TFA (Compound 209)

To a solution of N4-(3-aminopropyl)-7-(1H-pyrazol-5-yl)quinoline-2,4-diamine, 3 HCl (30 mg, 0.077 mmol) and 1-methyl-1H-imidazole-2-carboxylic acid (19.32 mg, 0.153 mmol) and triethylamine (0.213 mL, 1.532 mmol) in DMF (1 mL) was added T3P (50% in DMF) (97 mg, 0.153 mmol). After stirring the reaction at room temperature overnight the reaction was concentrated under high vacuum. The reaction was diluted with 1 ml of a mixture of 1:1 DMF:acetic acid and filtered through a syringe filter and purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 5-minute hold at 0% B, 0-33% B over 25 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give N-(3-((2-amino-7-(1H-pyrazol-5-yl)quinolin-4-yl)amino)propyl)-1-methyl-1H-imidazole-2-carboxamide as the bis-trifluoroacetate salt (7.1 mg, 15%). $^1$H NMR (500 MHz, DMSO-$d_6$) δ 8.44 (br s, 1H), 8.22 (br d, J=8.7 Hz, 1H), 8.02 (br s, 1H), 7.93 (br s, 1H), 7.90-7.76 (m, 3H), 7.55 (br s, 1H), 7.30 (s, 1H), 6.99 (s, 1H), 6.87-6.80 (m, 1H), 5.85 (s, 1H), 3.94 (s, 3H), 2.01-1.93 (m, 2H). Four protons from sidechain missing, likely due to overlap with suppressed water peak. LC RT: 1.01 min. M/Z=391.1.

Compound 210 to Compound 212 were prepared according to the synthetic procedures described for Compound 209 from the appropriate starting materials.

| Compd. No. | Structure | LC/MS [M + H]$^+$ | RT (min) | $^1$H NMR (500 MHz, DMSO-$d_6$) |
|---|---|---|---|---|
| 210 | 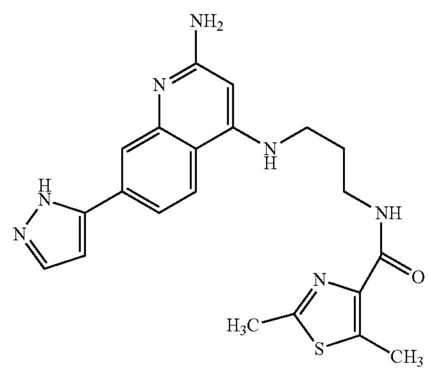 [SMILES: Cc1nc(C(=O)NCCCNc2cc(N)nc3cc(-c4ccn[nH]4)ccc23)c(C)s1] | 422.1 | 1.21 | δ 8.40-8.29 (m, 1H), 8.00 (br d, J = 8.9 Hz, 1H), 7.81 (br s, 1H), 7.74 (br s, 1H), 7.58 (br d, J = 7.9 Hz, 1H), 7.15-7.03 (m, 1H), 6.92-6.79 (m, 1H), 6.76 (s, 1H), 5.72 (s, 1H), 3.25 (br d, J = 5.8 Hz, 1H), 2.68 (s, 3H), 2.59 (s, 3H), 1.96-1.83 (m, 2H). Three protons from sidechain are not visible, possibly due to overlap with suppressed water peak. |
| 211 | 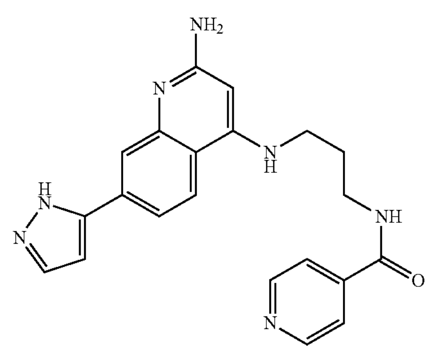 [SMILES: Nc1cc(NCCCNC(=O)c2ccncc2)c2ccc(-c3ccn[nH]3)cc2n1] | 388.1 | 1.02 | δ 8.77 (br s, 1H), 8.74-8.69 (m, 2H), 8.24 (br d, J = 8.6 Hz, 1H), 8.02 (br s, 1H), 7.99-7.91 (m, 2H), 7.87-7.79 (m, 2H), 7.79-7.72 (m, 2H), 7.72-7.52 (m, 1H), 6.83 (d, J = 1.9 Hz, 1H), 5.86 (s, 1H), 2.02 (br t, J = 6.7 Hz, 2H). Four protons from sidechain are not visible, likely due to overlap with suppressed water peak. |
| 212 | 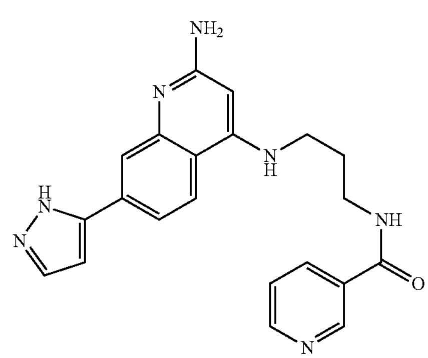 [SMILES: Nc1cc(NCCCNC(=O)c2cccnc2)c2ccc(-c3ccn[nH]3)cc2n1] | 388.1 | 0.95 | δ 8.99 (s, 1H, 8.75-8.63 (m, 2H), 8.26-8.14 (m, 2H), 8.01 (br s, 1H), 7.93 (br d, J = 11.6 Hz, 1H), 7.84-7.74 (m, 2H), 7.50 (br dd, J = 7.8, 4.9 Hz, 2H), 6.82 (d, J = 1.9 Hz, 1H), 5.85 (s, 1H), 2.00 (quin, J = 6.7 Hz, 2H). Four protons from sidechain are not visible, likely due to overlap with suppressed water peak. |

Example II-16: Synthesis of N-(3-((2-amino-7-(1H-pyrazol-5-yl)quinolin-4-yl)amino)propyl)acetamide, 2TFA (Compound 213)

Example II-17: Synthesis of 3-(3-((2-amino-7-(1H-pyrazol-5-yl)quinolin-4-yl)amino)propyl)-1,1-dimethylurea, 2TFA (Compound 214)

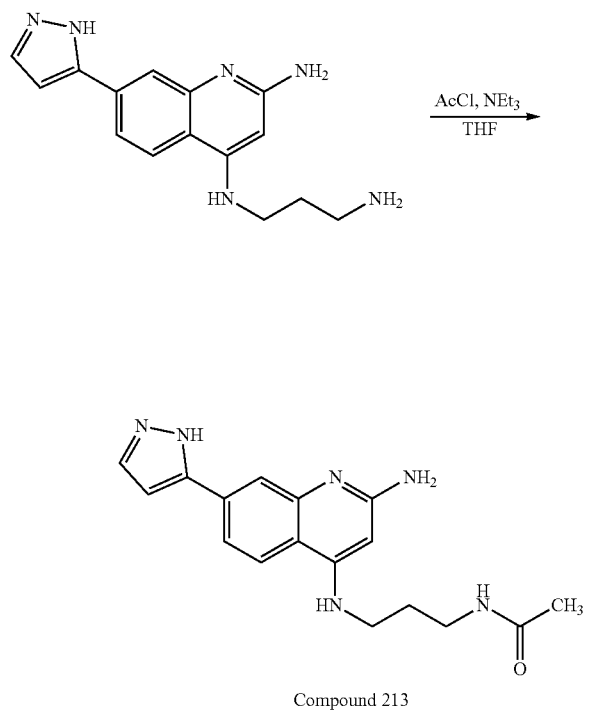

Compound 213

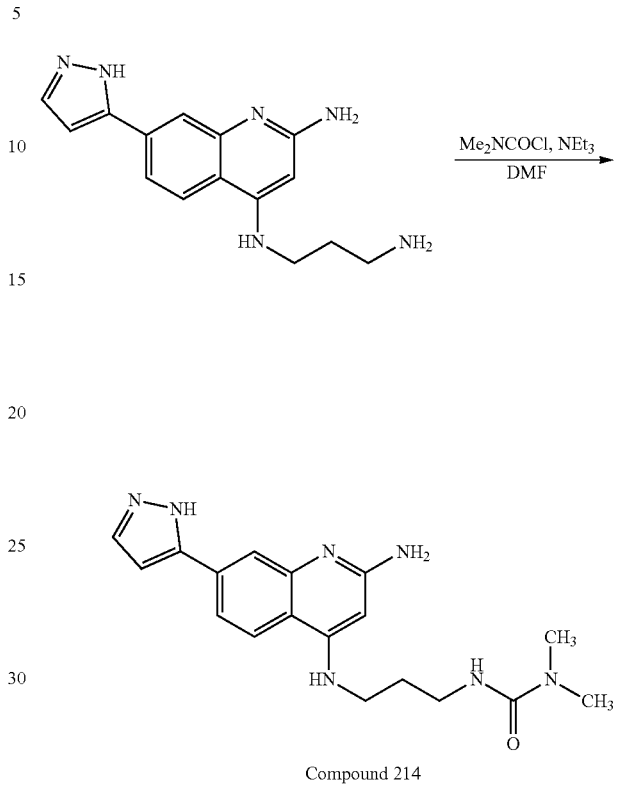

Compound 214

To a solution of N4-(3-aminopropyl)-7-(1H-pyrazol-5-yl)quinoline-2,4-diamine, 3 HCl (30 mg, 0.077 mmol) and triethylamine (0.213 mL, 1.532 mmol) in THF (1 mL) was added acetyl chloride (0.016 mL, 0.230 mmol). After stirring the reaction at room temperature overnight, the reaction was concentrated under high vacuum. The reaction was diluted with a mixture of 1:1 DMF:acetic acid, filtered through a syringe filter, and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 3-minute hold at 0% B, 0-33% B over 23 minutes, then a 5-minute hold at 100% B; Flow Rate: 20 mL/min; Column Temperature: 25° C. Fraction collection was triggered by MS signals. Fractions containing the desired product were combined and dried via centrifugal evaporation to give N-(3-((2-amino-7-(1H-pyrazol-5-yl)quinolin-4-yl)amino)propyl)acetamide as the bis-trifluoroacetate salt (17.5 mg, 52%). $^1$H NMR (500 MHz, DMSO-$d_6$) δ 8.01-7.89 (m, 2H), 7.74 (br s, 2H), 7.55-7.44 (m, 1H), 6.80 (br s, 1H), 6.75 (br s, 1H), 6.30 (br s, 1H), 5.70 (s, 1H), 3.23-3.11 (m, 2H), 1.84-1.73 (m, 5H). Two protons from sidechain are not visible, likely due to overlap with suppressed water peak. LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min. RT: 0.91 min. M/Z=325.1.

To a solution of N4-(3-aminopropyl)-7-(1H-pyrazol-5-yl)quinoline-2,4-diamine, 3 HCl (30 mg, 0.077 mmol) and triethylamine (0.213 mL, 1.532 mmol) in DMF (1 mL) was added dimethylcarbamoyl chloride (0.021 mL, 0.230 mmol). After stirring the reaction at room temperature overnight, the reaction was concentrated under high vacuum. The reaction was diluted with a mixture of 1:1 DMF:acetic acid, filtered through a syringe filter, and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 25 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 3-(3-((2-amino-7-(1H-pyrazol-5-yl)quinolin-4-yl)amino)propyl)-1,1-dimethylurea as the bis-trifluoroacetate salt (7.8 mg, 18%). $^1$H NMR (500 MHz, DMSO-$d_6$) δ 8.00 (br d, J=8.2 Hz, 1H), 7.78 (br s, 1H), 7.76-7.67 (m, 1H), 7.58 (br s, 1H), 7.06 (br s, 1H), 6.77 (br s, 2H), 6.35 (br s, 1H), 5.70 (br s, 1H), 3.20 (br s, 2H), 3.18-3.06 (m, 2H), 2.54 (br d, J=1.5 Hz, 6H), 1.80 (br s, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min. LC RT: 0.96 min. M/Z=354.1.

Example II-18: Preparation of N-(3-((2-amino-7-(1H-pyrazol-5-yl)quinolin-4-yl)amino)propyl)methanesulfonamide (Compound 215)

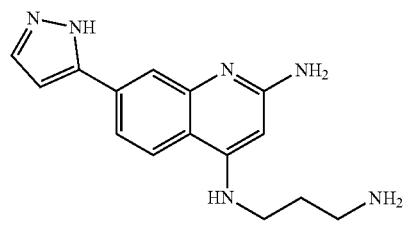

To a solution of N4-(3-aminopropyl)-7-(1H-pyrazol-5-yl)quinoline-2,4-diamine, 3 HCl (30 mg, 0.077 mmol) and triethylamine (0.213 mL, 1.532 mmol) in DMF (1 mL) was added Ms-Cl (0.018 mL, 0.230 mmol). After stirring the reaction at room temperature overnight, the reaction was concentrated under high vacuum. The reaction was diluted with a mixture of 1:1 DMF:acetic acid, filtered through a syringe filter, and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 24 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give N-(3-((2-amino-7-(1H-pyrazol-5-yl)quinolin-4-yl)amino)propyl)methanesulfonamide as the bis-trifluoroacetate salt (7.2 mg, 15%). $^1$H NMR (500 MHz, DMSO-$d_6$) δ 8.04-7.91 (m, 1H), 7.75 (br s, 2H), 7.54 (br s, 1H), 7.12-7.02 (m, 1H), 6.93-6.66 (m, 2H), 6.55-6.19 (m, 1H), 5.72 (s, 1H), 3.32-3.19 (m, 1H), 3.19-3.04 (m, 2H), 2.95-2.86 (m, 3H), 1.89 (s, 2H). One proton from sidechain is not visible, likely due to overlap with suppressed water peak. LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min. LC RT: 0.89 min. M/Z=361.1.

Example II-19: Synthesis of 3-(2-amino-7-(1H-pyrazol-1-yl)quinolin-4-yl)propan-1-ol (Compound 216)

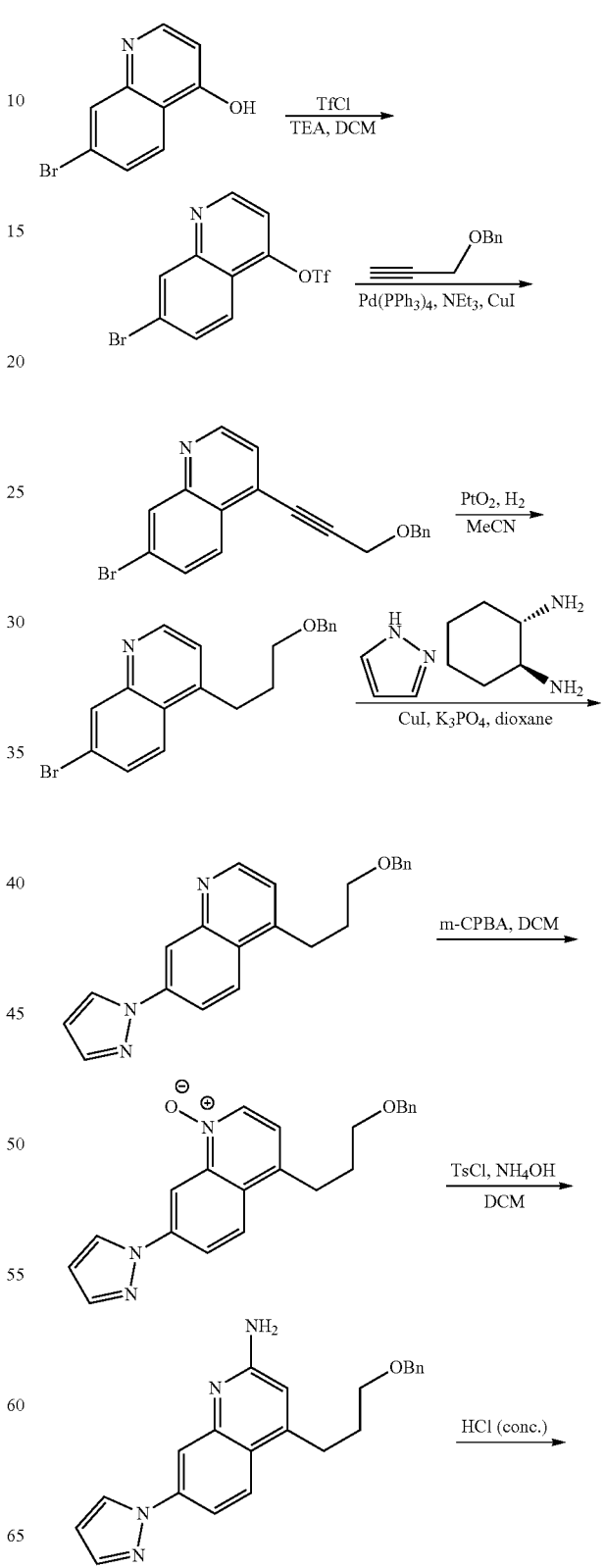

-continued

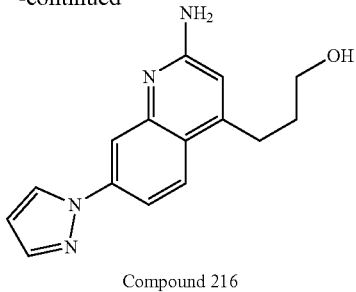

Compound 216

Step 1. 7-bromoquinolin-4-yl trifluoromethanesulfonate

Into a 1000-mL round-bottom flask, was placed 7-bromoquinolin-4-ol (22.4 g, 99.98 mmol, 1 equiv), Hunig's base (3.8 g, 299.93 mmol, 3 equiv), and DMAP (1.2 g, 10.00 mmol, 0.100 equiv) in DMF (1000 mL, 6.84 mmol, 0.068 equiv), then trifluoromethanesulfonyl chloride (25.3 g, 150 mmol, 1.502 equiv) was added. The resulting solution was stirred for 16 hours at room temperature in a water/ice bath. The resulting solution was diluted with 1.5 L of ethyl acetate. The resulting mixture was washed with 2×500 ml of water and 2×500 ml of brine. The mixture was dried over anhydrous sodium sulfate and concentrated. The resulting mixture was concentrated. The residue was applied onto a silica gel column with ethyl acetate/petroleum ether (1:5). This resulted in 20 g (56.18%) of 7-bromoquinolin-4-yl trifluoromethanesulfonate as a yellow solid. LC-MS: (ES, m/z): [M+H]$^+$=355.9.

Step 2. 4-[3-(benzyloxy)prop-1-yn-1-yl]-7-bromoquinoline

In a 1000-mL round-bottom flask purged and maintained with an inert atmosphere of nitrogen was placed 7-bromoquinolin-4-yl trifluoromethanesulfonate (10 g, 28.08 mmol, 1 equiv) in THF (280 ml), then Hunig's base (10.9 g, 84.24 mmol, 3 equiv), CuI (1.1 g, 5.62 mmol, 0.2 equiv), [(prop-2-yn-1-yloxy)methyl]benzene(6.2 g, 42.12 mmol, 1.5 equiv), Pd(PPh$_3$)$_4$ (3.2 g, 0.1 equiv) were added. The resulting solution was stirred for 16 hours at 70° C. in an oil bath. The resulting mixture was concentrated. The residue was applied onto a silica gel column with ethyl acetate/petroleum ether (1:5). This resulted in 6 g (60.66%) of 4-[3-(benzyloxy)prop-1-yn-1-yl]-7-bromoquinoline as a yellow solid. LC-MS: (ES, m/z): [M+H]$^+$=352.0.

Step 3. 4-[3-(benzyloxy)propyl]-7-bromoquinoline

In a 500-mL round-bottom flask was placed 4-[3-(benzyloxy)prop-1-yn-1-yl]-7-bromoquinoline (6 g, 17.03 mmol, 1 equiv), and PtO$_2$ (0.56 g, 2.64 mmol, 0.155 equiv) in acetonitrile (170 mL). The resulting solution was stirred for 16 hours at room temperature under H$_2$. The solids were filtered off. The filtrate was concentrated. The residue was applied onto a silica gel column with ethyl acetate/petroleum ether (1:5). This resulted in 4.8 g (79.09%) of 4-[3-(benzyloxy)propyl]-7-bromoquinoline as a yellow solid. LC-MS: (ES, m/z): [M+H]$^+$=356.1.

Step 4. 4-[3-(benzyloxy)propyl]-7-(1H-pyrazol-1-yl)quinoline

In a 100-mL round-bottom flask purged and maintained with an inert atmosphere of nitrogen was placed 4-[3-(benzyloxy)propyl]-7-bromoquinoline (1 g, 2.81 mmol, 1 equiv), 1H-pyrazole (955.5 mg, 14.03 mmol, 5 equiv), K$_3$PO$_4$ (1.2 g, 5.61 mmol, 2 equiv), CuI (106.9 mg, 0.56 mmol, 0.2 equiv), and (1S,2S)-cyclohexane-1,2-diamine (32.1 mg, 0.28 mmol, 0.1 equiv) in dioxane (28 mL, 0.32 mmol, 0.113 equiv). The resulting solution was stirred for 5 days at 100° C. in an oil bath. The solids were filtered off. The resulting mixture was concentrated. The residue was applied onto a silica gel column with ethyl acetate/petroleum ether (1:1). This resulted in 370 mg (38.38%) of 4-[3-(benzyloxy)propyl]-7-(1H-pyrazol-1-yl)quinoline as a yellow solid. LC-MS: (ES, m/z): [M+H]$^+$=344.2.

Step 5. 4-[3-(benzyloxy)propyl]-7-(1H-pyrazol-1-yl)quinolin-1-ium-1-olate

In a 50-mL round-bottom flask purged and maintained with an inert atmosphere of nitrogen, was placed 4-[3-(benzyloxy)propyl]-7-(1H-pyrazol-1-yl)quinoline (300 mg, 0.87 mmol, 1 equiv) in DCM (10 mL), then m-CPBA (226.1 mg, 1.31 mmol, 1.5 equiv) was added. The resulting solution was stirred for 12 hours at room temperature. The reaction was then quenched by the addition of 10 mL of Na$_2$S$_2$O$_4$. The pH value of the solution was adjusted to 10 with NaHCO$_3$. The resulting solution was extracted with 3×10 ml of dichloromethane. The resulting mixture was washed with 1×10 ml of brine. The resulting mixture was concentrated. The residue was applied onto a silica gel column with dichloromethane/methanol (10:1). This resulted in 200 mg (63.70%) of 4-[3-(benzyloxy)propyl]-7-(1H-pyrazol-1-yl)quinolin-1-ium-1-olate as a yellow solid. LC-MS: (ES, m/z): [M+H]$^+$=360.2.

Step 6. 4-[3-(benzyloxy)propyl]-7-(1H-pyrazol-1-yl)quinolin-2-amine

Into a 50-mL round-bottom flask purged and maintained with an inert atmosphere of nitrogen, was placed 4-[3-(benzyloxy)propyl]-7-(1H-pyrazol-1-yl)quinolin-1-ium-1-olate (150 mg, 0.42 mmol, 1 equiv) in DCM (2 mL, 0.02 mmol) and NH$_4$OH (1 mL), then TsCl (159.1 mg, 0.83 mmol, 2 equiv) was added. The resulting solution was stirred for 20 minutes at room temperature. The resulting mixture was concentrated. The residue was applied onto a silica gel column with dichloromethane/methanol (10:1). This resulted in 100 mg (66.85%) of 4-[3-(benzyloxy)propyl]-7-(1H-pyrazol-1-yl)quinolin-2-amine as a yellow solid. LC-MS: (ES, m/z): [M+H]$^+$=359.2.

Step 7. 3-[2-amino-7-(1H-pyrazol-1-yl)quinolin-4-yl]propan-1-ol (Compound 216)

In a 50-mL round-bottom flask purged and maintained with an inert atmosphere of nitrogen, was placed 4-[3-(benzyloxy)propyl]-7-(1H-pyrazol-1-yl)quinolin-2-amine (100 mg, 0.28 mmol, 1 equiv) in concentrated HCl (6 mL, 0.16 mmol, 0.590 equiv). The resulting solution was stirred for 2 hours at 40° C. The pH value of the solution was adjusted to 10 with ammonium hydroxide. The resulting mixture was concentrated. The crude product was purified by Flash-Prep-HPLC with the following conditions: Flash Column, C18 spherical, 20-35 um, 100A, 20 g; mobile phase, Water (10 mmol/L NH$_4$HCO$_3$) and MeCN (15% Phase B up to 75% in 9 min); Detector, 254/210 nm UV. This resulted in 46 mg (61.45%) of 3-[2-amino-7-(1H-pyrazol-1-yl)quinolin-4-yl]propan-1-ol as a white solid. $^1$H NMR (400 MHz, DMSO-d$_6$) δ 8.62 (d, J=2.5 Hz, 1H), 7.92 (d, J=8.9 Hz, 1H), 7.84 (d, J=2.2 Hz, 1H), 7.78 (d, J=1.7 Hz, 1H), 7.70 (dd, J=8.9, 2.3 Hz, 1H), 6.64-6.51 (m, 2H), 6.48 (s, 2H), 4.60 (t, J=5.2 Hz, 1H), 3.53 (q, J=6.0 Hz, 2H), 2.97-2.89 (m, 2H), 1.86-1.75 (m, 2H). LC Methods: Column: Kinetex EVO, 3.0 mm×50 mm, 2.6 μm particles; Mobile Phase A: water with 0.03% NH₄OH; Mobile Phase B: acetonitrile; Temperature: 40° C.; Gradient: 10% B to 95% B over 1.9 min, then a 0.6 min hold at 95% B; Flow: 1.2 mL/min. LC retention time: 0.981 min. LC-MS: (ES, nm/z): [M+H]⁺=269.1.

Example II-20: Synthesis of N-(2-(2-amino-7-(1H-pyrazol-5-yl)quinolin-4-yl)ethyl)acetamide (Compound 217)

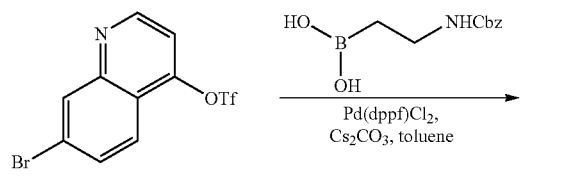

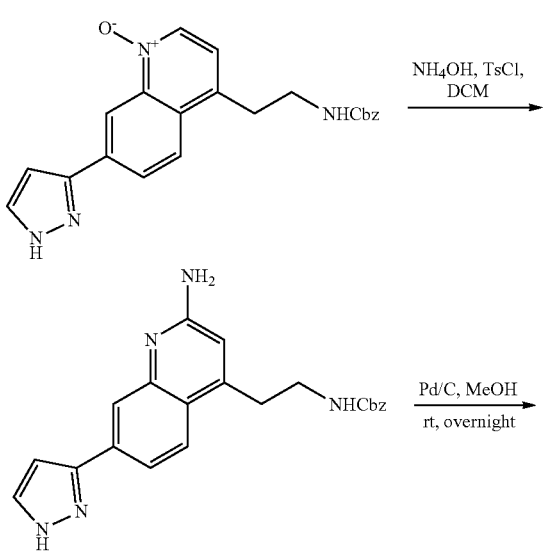

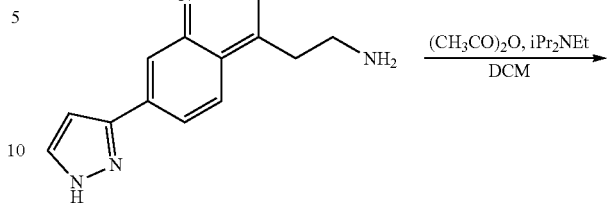

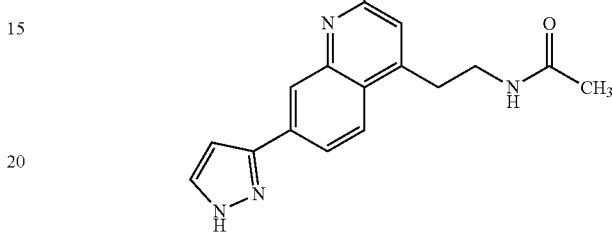

Compound 217

Step 1. benzyl N-[2-(7-bromoquinolin-4-yl)ethyl] carbamate

In a 500-ml, 3-necked round-bottom flask purged and maintained with an inert atmosphere of nitrogen was placed 7-bromoquinolin-4-yl trifluoromethanesulfonate (7.5 g, 21.06 mmol, 1 equiv), Cs₂CO₃ (20585.8 mg, 63.18 mmol, 3.0 equiv), (2-[[(benzyloxy)carbonyl]amino]ethyl)boronic acid (9394.4 mg, 42.12 mmol, 2 equiv), and Pd(dppf)Cl₂ (1541.0 mg, 2.11 mmol, 0.1 equiv) in toluene (200 mL) and 1H₂O (50 mL). The resulting solution was stirred for 16 hours at 70° C. The resulting mixture was cooled to room temperature and concentrated. The residue was applied onto a silica gel column with ethyl acetate/petroleum ether (1:1). This resulted in 3.5 g (43.14%) of benzyl N-[2-(7-bromoquinolin-4-yl)ethyl]carbamate as a white solid. LC-MS: [M+H]⁺=385.0.

Step 2. benzyl N-[2-[7-(1H-pyrazol-3-yl)quinolin-4-yl]ethyl]carbamate

In a 500-mL round-bottom flask purged and maintained with an inert atmosphere of nitrogen, was placed benzyl N-[2-(7-bromoquinolin-4-yl)ethyl]carbamate (2 g, 5.19 mmol, 1 equiv), 3-(tetramethyl-1,3,2-dioxaborolan-2-yl)-1H-pyrazole (1007.3 mg, 5.19 mmol, 1.0 equiv), Pd(PPh₃)₄ (599.9 mg, 0.52 mmol, 0.1 equiv), and Na₂CO₃ (1100.5 mg, 10.38 mmol, 2.0 equiv) in dioxane (80 mL, 944.33 mmol, 181.903 equiv) and H₂O (20 mL, 1110.17 mmol, 213.848 equiv). The resulting solution was stirred for 16 hours at room temperature in an oil bath. The resulting mixture was cooled to room temperature and concentrated. The residue was applied onto a silica gel column with dichloromethane/methanol (10:1). This resulted in 1.8 g (93.10%) of benzyl N-[2-[7-(1H-pyrazol-3-yl)quinolin-4-yl]ethyl]carbamate as an off-white solid. LC-MS: [M+H]⁺=373.2.

Step 3. 4-(2-[[(benzyloxy)carbonyl]amino]ethyl)-7-(1H-pyrazol-3-yl)quinolin-1-ium-1-olate In a 100-mL round-bottom flask, was placed benzyl N-[2-[7-(1H-pyrazol-3-yl)quinolin-4-yl]ethyl]carbamate (1.7 g, 4.56 mmol, 1 equiv) in DCM (50 mL, 0.59 mmol, 0.129 equiv), then m-CPBA (1575.4 mg, 9.13 mmol, 2.0 equiv) was added. The resulting solution was stirred for 16 hours at room temperature. The reaction was then quenched by the addition of 50 mL of saturated aqueous $Na_2S_2O_3$ solution. The resulting solution was extracted with 3×50 ml of dichloromethane and the combined organic layers were concentrated. The residue was applied onto a silica gel column with dichloromethane/methanol (10:1). This resulted in 1.4 g (78.96%) of 4-(2-[[(benzyloxy)carbonyl]amino]ethyl)-7-(1H-pyrazol-3-yl)quinolin-1-ium-1-olate as a solid. LC-MS: $[M+H]^+$=389.2.

Step 4. benzyl N-[2-[2-amino-7-(1H-pyrazol-3-yl)quinolin-4-yl]ethyl]carbamate

In a 25-mL round-bottom flask, was placed 4-(2-[[(benzyloxy)carbonyl]amino]ethyl)-7-(1H-pyrazol-3-yl)quinolin-1-ium-1-olate (100 mg, 0.26 mmol, 1 equiv) in DCM (4 mL) and $NH_4OH$ (2 mL). TsCl (97.8 mg, 0.51 mmol, 2.0 equiv) was added. The resulting solution was stirred for 2 hours at room temperature. The reaction was then quenched by the addition of 10 mL of MeOH. The resulting mixture was concentrated. The crude product was purified by Prep-HPLC with the following conditions: Column, XBridge Shield RP18 OBD Column, 19*250 mm, 10 um; mobile phase, Water (10 mmol/L $NH_4HCO_3$) and MeCN (30% Phase B up to 47% in 10 min); Detector, 254/210 nm UV. This resulted in 39.4 mg (39.50%) of benzyl N-[2-[2-amino-7-(1H-pyrazol-3-yl)quinolin-4-yl]ethyl]carbamate as a white solid. $^1$H-NMR: (300 MHz, DMSO-$d_6$) δ 7.87-7.63 (m, 5H), 7.46-7.27 (m, 5H), 6.77 (s, 1H), 6.57 (s, 1H), 6.31 (s, 2H), 5.02 (s, 2H), 3.29 (m, 2H), 3.03-2.98 (m, 2H). LC Methods: Column: Kinetex EVO, 3.0 mm×50 mm, 2.6 μm particles; Mobile Phase A: water with 0.03% $NH_4OH$; Mobile Phase B: acetonitrile; Temperature: 40° C.; Gradient: 10% B to 95% B over 1.9 min, then a 0.60 min hold at 95% B; Flow: 1.2 mL/min. LC retention time: 1.291 min. LC-MS: $[M+H]^+$=388.2.

Step 5. 4-(2-aminoethyl)-7-(1H-pyrazol-3-yl)quinolin-2-amine

In a 25-mL round-bottom flask was placed benzyl N-[2-[2-amino-7-(1H-pyrazol-3-yl)quinolin-4-yl]ethyl]carbamate (50 mg, 0.13 mmol, 1 equiv) in MeOH (3 mL, 0.09 mmol, 0.725 equiv), then Pd/C (15 mg, 0.14 mmol, 1.092 equiv) was added. The resulting solution was stirred for 16 hours at room temperature under $N_2$. The solids were filtered off. The resulting mixture was concentrated. The crude product was purified by Prep-HPLC with the following conditions: Column, XBridge Shield RP18 OBD Column, 19*250 mm, 10 um; mobile phase, Water (10 mmol/L $NH_4HCO_3$) and MeCN (10% Phase B up to 20% in 6 min); Detector, 254/210 nm UV. This resulted in 14 mg (42.83%) of 4-(2-aminoethyl)-7-(1H-pyrazol-3-yl)quinolin-2-amine as a white solid. LC Methods: Column: Kinetex EVO, 3.0 mm×50 mm, 2.6 μm particles; Mobile Phase A: water with 0.03% $NH_3H_2O$; Mobile Phase B: acetonitrile; Temperature: 40° C.; Gradient: 10% B to 40% B over 2.49 min, 40% B to 95% B over 0.9 min, then a 0.75 min hold at 95% B; Flow: 1.2 mL/min. LC retention time: 1.338 min. LC-MS: $[M+H]^+$=254.1. H-NMR: (400 MHz, DMSO-$d_4$) S 7.89-7.84 (m, 2H), 7.72 (s, 1H), 7.62 (d, J=8 Hz, 1H), 6.84-6.78 (m, 1H), 6.58 (s, 1H), 6.33 (d, J=4 Hz, 1H), 3.99-3.37 (m, 1H), 3.02-2.87 (m, 3H), 1.72-1.64 (m, 2H), 1.58-1.52 (m, 2H).

Step 6. N-[2-[2-amino-7-(1H-pyrazol-3-yl)quinolin-4-yl]ethyl]acetamide (Compound 217)

In a 25-mL round-bottom flask, was placed 4-(2-aminoethyl)-7-(1H-pyrazol-3-yl)quinolin-2-amine (50 mg, 0.20 mmol, 1 equiv) in DCM (3 mL, 0.04 mmol, 0.179 equiv), then $(CH_3CO)_2O$ (20.2 mg, 0.20 mmol, 1.0 equiv) and Hunig's base (76.5 mg, 0.59 mmol, 3.0 equiv) were added. The resulting solution was stirred for 2 hours at room temperature. The reaction was then quenched by the addition of 5 mL of MeOH. The resulting mixture was concentrated. The crude product was purified by Prep-HPLC with the following conditions: Column, XBridge Shield RP18 OBD Column, 19*250 mm, 10 um; mobile phase, Water (10 mmol/L $NH_4HCO_3$) and MeCN (12% PhaseB up to 35% in 6 min); Detector, 254/210 nm UV. This resulted in 12.7 mg (21.78%) of N-[2-[2-amino-7-(1H-pyrazol-3-yl)quinolin-4-yl]ethyl]acetamide as a solid. H-NMR: (300 MHz, DMSO-$d_6$) δ 8.06-8.02 (m, 1H), 7.90-7.86 (m, 2H), 7.74-7.65 (m, 2H), 6.80 (s, 1H), 6.58 (s, 1H), 6.34 (s, 2H), 3.38-3.32 (m, 2H), 3.03-2.98 (m, 2H), 1.82 (s, 3H). LC Methods: Column: Kinetex EVO, 3.0 mm×50 mm, 2.6 μm particles; Mobile Phase A: water with 0.03% $NH_4OH$; Mobile Phase B: acetonitrile; Temperature: 40° C.; Gradient: 10% B to 95% B over 1.9 min, then a 0.15 min hold at 95% B; Flow: 1.2 mL/min. LC retention time: 0.851 min. LC-MS: $[M+H]^+$=296.1.

Example II-21: Preparation of 4-(2-amino-7-(1H-pyrazol-5-yl)quinolin-4-yl)butan-1-ol (Compound 218)

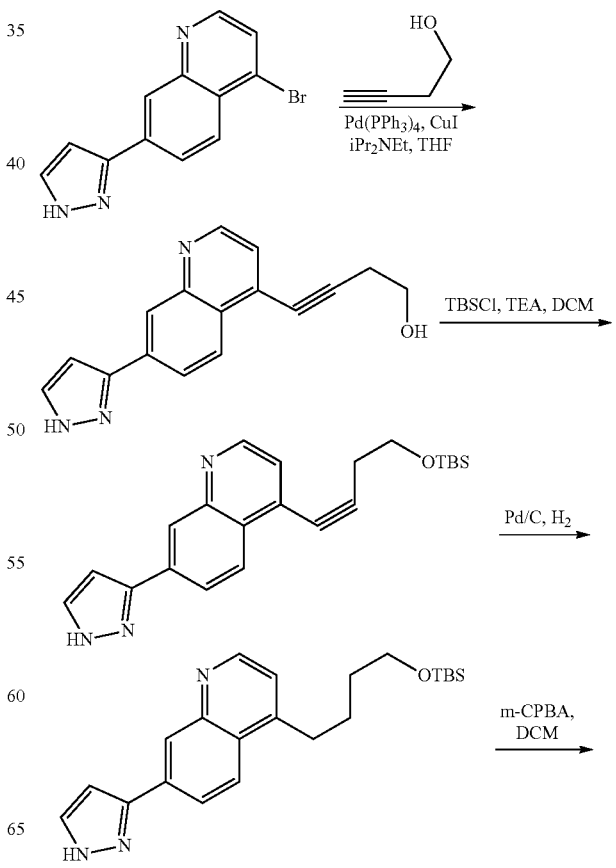

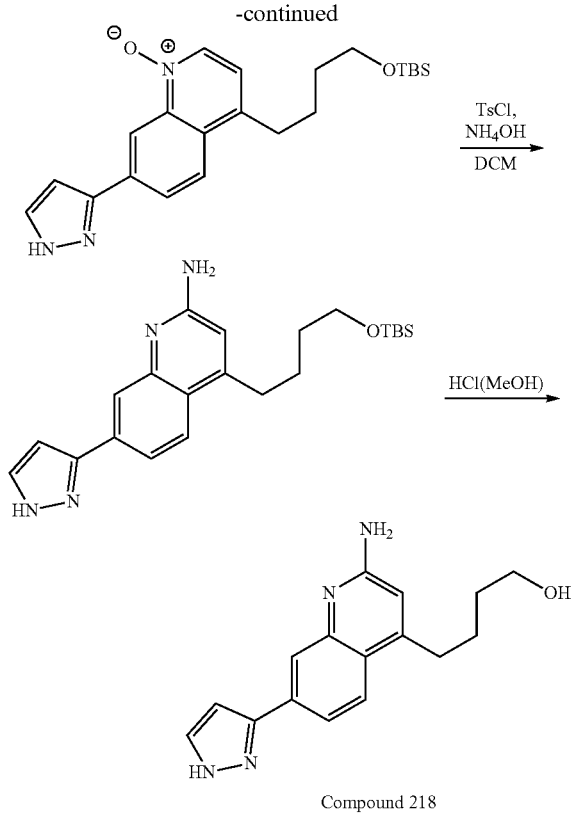

Step 1. 4-[7-(1H-pyrazol-3-yl)quinolin-4-yl]but-3-yn-1-ol

In a 40-mL sealed tube was placed a solution of 4-bromo-7-(1H-pyrazol-3-yl)quinoline (1.2 g, 4.38 mmol, 1.00 equiv) in tetrahydrofuran (20 mL). Pd(PPh$_3$)$_4$ (500 mg, 0.43 mmol, 0.10 equiv), CuI (166 mg, 0.87 mmol, 0.20 equiv), DIPEA (1.7 g, 13.15 mmol, 3.00 equiv) and but-3-yn-1-ol (620 mg, 8.85 mmol, 2.00 equiv) were added. The resulting solution was stirred for 16 h at 70° C. in an oil bath. The resulting mixture was cooled to room temperature and concentrated under vacuum. The residue was applied onto a silica gel column with dichloromethane/methanol (0-10%). This resulted in 500 mg (43%) of 4-[7-(1H-pyrazol-3-yl)quinolin-4-yl]but-3-yn-1-ol as a brown crude solid. LC-MS: (ES, m/z): [M+H]$^+$=264.1.

Step 2. 4-[4-[(tert-butyldimethylsilyl)oxy]but-1-yn-1-yl]-7-(1H-pyrazol-3-yl)quinoline In a 250-mL round-bottom flask was placed a solution of 4-[7-(1H-pyrazol-3-yl)quinolin-4-yl]but-3-yn-1-ol (500 mg, 1.90 mmol, 1.00 equiv) in dichloromethane (100 mL), TBSCl (1.45 g, 4.00 equiv), triethylamine (780 mg, 7.71 mmol, 4.00 equiv). The resulting solution was stirred for 2 days at 40° C. in an oil bath. The resulting mixture was concentrated under vacuum. The residue was applied onto a silica gel column with ethyl acetate: petroleum ether (1:0). This resulted in 650 mg (91%) of 4-[4-[(tert-butyldimethylsilyl)oxy]but-1-yn-1-yl]-7-(1H-pyrazol-3-yl)quinoline as a light-brown solid. LC-MS: (ES, m/z): [M+H]$^+$=378.2.

Step 3. 4-[4-[(tert-butyldimethylsilyl)oxy]butyl]-7-(1H-pyrazol-3-yl)quinoline

In a 100-mL round-bottom flask, was placed a solution of 4-[4-[(tert-butyldimethylsilyl)oxy]but-1-yn-1-yl]-7-(1H-pyrazol-3-yl)quinoline (550 mg, 1.46 mmol, 1.00 equiv) in CH$_3$OH (30 mL). Palladium on carbon (200 mg) was added. The resulting solution was stirred for 16 hours at room temperature under H2. The solids were filtered off. The organic mixture was concentrated and the residue was applied onto a silica gel column with dichloromethane/methanol (10:1). This resulted in 350 mg (63%) of 4-[4-[(tert-butyldimethylsilyl)oxy]butyl]-7-(1H-pyrazol-3-yl)quinoline as a light yellow solid. LC-MS: (ES, m/z): [M+H]$^+$=382.2.

Step 4. 4-[4-[(tert-butyldimethylsilyl)oxy]butyl]-7-(1H-pyrazol-3-yl)quinolin-1-ium-1-olate In a 50-mL round-bottom flask was placed a solution of 4-[4-[(tert-butyldimethylsilyl)oxy]butyl]-7-(1H-pyrazol-3-yl)quinoline (300 mg, 0.79 mmol, 1.00 equiv) in dichloromethane (20 mL), m-CPBA (270 mg, 1.56 mmol, 2.00 equiv) was added. The resulting solution was stirred for 5 hours at room temperature. The reaction was then quenched by the addition of Na$_2$S$_2$O$_3$. The resulting mixture was washed with 50 mL of sodium bicarbonate. The resulting aqueous solution was extracted with 3×50 mL of dichloromethane. The organic layers were combined and concentrated. The residue was applied onto a silica gel column with dichloromethane/methanol (10:1). This resulted in 320 mg (102%) of 4-[4-[(tert-butyldimethylsilyl)oxy]butyl]-7-(1H-pyrazol-3-yl)quinolin-1-ium-1-olate as a white solid. LC-MS: (ES, m/z): [M+H]$^+$=398.2.

Step 5. 4-[4-[(tert-butyldimethylsilyl)oxy]butyl]-7-(1H-pyrazol-3-yl)quinolin-2-amine Into a 50-mL round-bottom flask, was placed a solution of 4-[4-[(tert-butyldimethylsilyl)oxy]butyl]-7-(1H-pyrazol-3-yl)quinolin-1-ium-1-olate (270 mg, 0.68 mmol, 1.00 equiv) in dichloromethane (15 mL) and NH$_4$OH (5 mL). TsCl (260 mg, 2.00 equiv) was added. The resulting solution was stirred for 2 hours at room temperature. The resulting mixture was concentrated under vacuum. This resulted in 240 mg (89%) of 4-[4-[(tert-butyldimethylsilyl)oxy]butyl]-7-(1H-pyrazol-3-yl)quinolin-2-amine as a light yellow solid. LC-MS: (ES, m/z): [M+H]$^+$=397.2.

Step 6. 4-[2-amino-7-(1H-pyrazol-3-yl)quinolin-4-yl]butan-1-ol (Compound 218)

In a 50-mL round-bottom flask was placed a solution of 4-[4-[(tert-butyldimethylsilyl)oxy]butyl]-7-(1H-pyrazol-3-yl)quinolin-2-amine (200 mg, 0.50 mmol, 1.00 equiv) in hydrogen chloride in methanol (10 mL). The resulting solution was stirred for 4 hours at room temperature. The pH value of the solution was adjusted to 10 with NH$_4$OH. The resulting mixture was concentrated under vacuum. The crude product was purified by Prep-HPLC with the following conditions: Column, XBridge Shield RP18 OBD Column, 19*250 mm, 10 um; mobile phase, Water (10 mmol/L NH$_4$HCO$_3$) and MeCN (10.0% MeCN up to 70.0% in 7 min); Detector, UV 254/210 nm. This resulted in 101 mg (71%) of 4-[2-amino-7-(1H-pyrazol-3-yl)quinolin-4-yl]butan-1-ol as a white solid. $^1$H-NMR: (300 MHz, DMSO-d$_6$) δ 13.38-12.90 (d, J=8.4 Hz, 1H), 7.85-7.55 (m, 4H), 6.78 (s, 1H), 6.59 (d, J=7.2 Hz, 1H), 6.35-6.27 (d, J=24 Hz, 2H), 4.42-4.39 (m, 1H), 3.48-3.42 (m, 2H), 2.90-2.85 (m, 2H), 1.72-1.64 (m, 2H), 1.58-1.52 (m, 2H).

LC Methods: Column: Waters Xbridge shield RP18, 4.6 mm×50 mm, 3.5 μm particles; Mobile Phase A: water with 0.03% NH₄OH; Mobile Phase B: acetonitrile; Temperature: 40° C.; Gradient: 10% B to 70% B over 2.4 min, 70% B to 95% B over 0.7 min, then a 0.98 min hold at 95% B; Flow: 1.5 mL/min. LC retention time: 1.837 min. LC-MS: (ES, m/z): [M+H]⁺=283.

Example II-22: Preparation of 3-(2-amino-7-(isothiazol-3-yl)quinolin-4-yl)propan-1-ol (Compound 219)

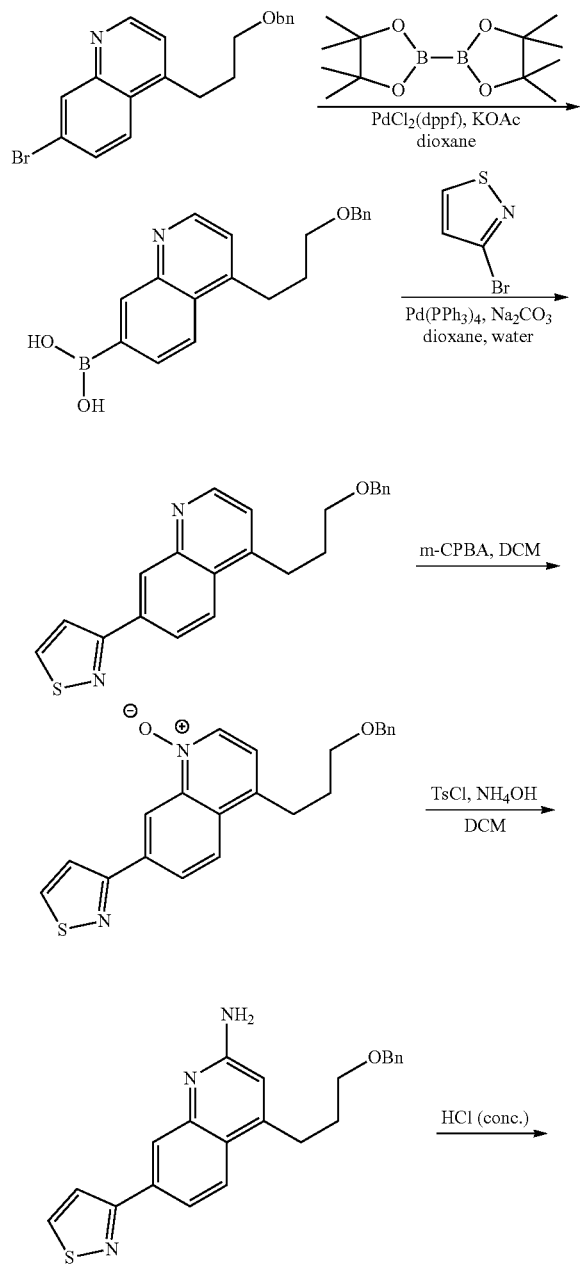

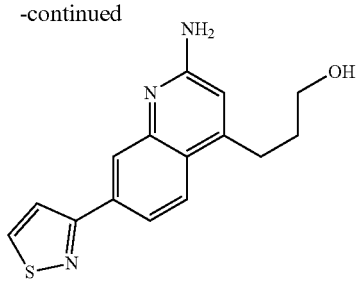

Compound 219

Step 1. [4-[3-(benzyloxy)propyl]quinolin-7-yl]boronic acid

In a 100-mL round-bottom flask purged and maintained with an inert atmosphere of nitrogen was placed 4-[3-(benzyloxy)propyl]-7-bromoquinoline (1 g, 2.81 mmol, 1 equiv), KOAc (551.0 mg, 5.61 mmol, 2 equiv), 4,4,5,5-tetramethyl-2-(tetramethyl-1,3,2-dioxaborolan-2-yl)-1,3,2-dioxaborolane (1425.6 mg, 5.61 mmol, 2 equiv), and Pd(dppf)Cl₂ (205.4 mg, 0.28 mmol, 0.1 equiv) in dioxane (20 mL). The resulting solution was stirred for 16 hours at 90° C. in an oil bath. The solids were filtered off. The resulting mixture was concentrated. This resulted in 904 mg of [4-[3-(benzyloxy)propyl]quinolin-7-yl]boronic acid as a light yellow solid. LC-MS: (ES, m/z): [M+H]⁺=322.2.

Step 2. 4-[3-(benzyloxy)propyl]-7-(1,2-thiazol-3-yl) quinolone

In a 50-mL round-bottom flask purged and maintained with an inert atmosphere of nitrogen, was placed [4-[3-(benzyloxy)propyl]quinolin-7-yl]boronic acid (904 mg, 2.81 mmol, 1 equiv), Na₂CO₃ (596.6 mg, 5.63 mmol, 2 equiv), 3-bromo-1,2-thiazole (923.3 mg, 5.63 mmol, 2 equiv), and Pd(PPh₃)₄ (325.2 mg, 0.28 mmol, 0.1 equiv) in dioxane (20 mL) and H₂O (5 mL). The resulting solution was stirred for 4 hours at 80° C. in an oil bath. The resulting mixture was cooled to room temperature and concentrated. The residue was applied onto a silica gel column with ethyl acetate/petroleum ether (1:1). This resulted in 500 mg (49.28%) of 4-[3-(benzyloxy)propyl]-7-(1,2-thiazol-3-yl)quinoline as a light brow solid. LC-MS: (ES, m/z): [M+H]⁺=361.1.

Step 3. 4-[3-(benzyloxy)propyl]-7-(1,2-thiazol-3-yl) quinolin-1-ium-1-olate

In a 25-mL 3-necked round-bottom flask purged and maintained with an inert atmosphere of nitrogen, was placed 4-[3-(benzyloxy)propyl]-7-(1,2-thiazol-3-yl)quinoline (450 mg, 1.25 mmol, 1 equiv) in DCM (12 mL), m-CPBA (430.9 mg, 2.50 mmol, 2 equiv) was added. The resulting solution was stirred for 5 hours at room temperature. The reaction was then quenched by the addition of Na₂S₂O₄. The pH value of the solution was adjusted to 10 with NaHCO₃. The resulting solution was extracted with 3×20 mL of ethyl acetate and concentrated. The residue was applied onto a silica gel column with dichloromethane/methanol (20:1). This resulted in 130 mg (27.66%) of 4-[3-(benzyloxy) propyl]-7-(1,2-thiazol-3-yl)quinolin-1-ium-1-olate as a light yellow solid. LC-MS: (ES, m/z): [M+H]⁺=377.1.

Step 4. 4-[3-(benzyloxy)propyl]-7-(1,2-thiazol-3-yl)quinolin-2-amine

In a 25-mL round-bottom flask purged and maintained with an inert atmosphere of nitrogen was placed 4-[3-(benzyloxy)propyl]-7-(1,2-thiazol-3-yl)quinolin-1-ium-1-olate (130 mg, 0.35 mmol, 1 equiv) in DCM (3 mL) and NH$_4$OH (1.5 mL, 38.52 mmol). TsCl (131.7 mg, 0.69 mmol, 2 equiv) was added. The resulting solution was stirred for 2 hours at room temperature. The resulting mixture was concentrated. The residue was applied onto a silica gel column with dichloromethane/methanol (10:1). This resulted in 120 mg (92.55%) of 4-[3-(benzyloxy)propyl]-7-(1,2-thiazol-3-yl)quinolin-2-amine as a light yellow solid. LC-MS: (ES, m/z): [M+H]$^+$=376.1.

Step 5. 3-(2-amino-7-(isothiazol-3-yl)quinolin-4-yl)propan-1-ol (Compound 219)

In a 25-mL round-bottom flask was placed 4-[3-(benzyloxy)propyl]-7-(1,2-thiazol-3-yl)quinolin-2-amine in hydrogen chloride in MeOH (4M). The resulting solution was stirred for 16 hours at room temperature. The pH value of the solution was adjusted to 10 with NH$_4$OH. The resulting mixture was concentrated. The crude product was purified by Prep-HPLC with the following conditions (Prep-HPLC-018): Column, XBridge Prep OBD C18 Column, 19*250 mm, 5 um; mobile phase, Water (10 mmol/L NH$_4$HCO$_3$) and MeCN (10% Phase B up to 50% in 7 min); Detector, UV. This resulted in 26 mg (41.91%) of 3-[2-amino-7-(1,2-thiazol-3-yl)quinolin-4-yl]propan-1-ol as a white solid. $^1$H-NMR: (400 MHz, DMSO-d$_6$, ppm): δ 9.19 (d, J=4.4 Hz, 1H) 8.08-8.05 (m, 2H), 7.92-7.84 (m, 2H), 6.65 (s, 1H), 6.41 (s, 2H), 4.63-4.60 (m, 1H), 3.55-3.50 (m, 2H), 2.95-2.92 (m, 2H), 1.83-1.79 (m, 2H). LC Methods: Column: Kinetex EVO 3.0 mm×50 mm, 2.6 μm particles; Mobile Phase A: water with 0.03% NH$_4$OH; Mobile Phase B: acetonitrile; Temperature: 40° C.; Gradient: 10% B to 95% B over 2 min, then a 0.60 min hold at 95% B; Flow: 1.2 mL/min. LC retention time: 1.073 min. LC-MS: (ES, m/z): [M+H]$^+$=286.

Procedure for Compound 109:

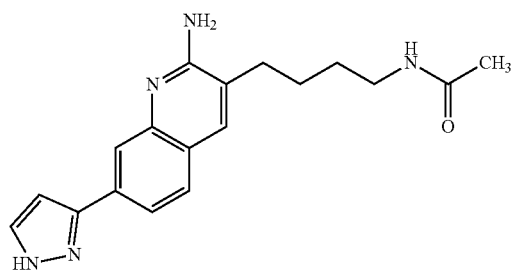 [SMILES: CC(=O)NCCCCc1cc2ccc(-c3cc[nH]n3)cc2nc1N]

Compound 109 was prepared following the same procedure given for Compound 110. M/Z=295.6.

Procedure for Compound 111:

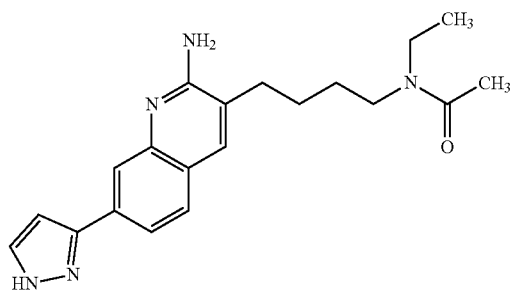 [SMILES: CCN(CCCCc1cc2ccc(-c3cc[nH]n3)cc2nc1N)C(C)=O]

Compound 111 was prepared following the same procedure given for Compound 112. $^1$H NMR (400 MHz, Methanol-d$_4$) δ 7.95-7.84 (m, 1H), 7.80 (d, J=6.1 Hz, 1H), 7.73-7.58 (m, 3H), 6.75 (br s, 1H), 3.47-3.34 (m, 4H), 2.71 (br d, J=6.4 Hz, 2H), 2.10 (d, J=9.1 Hz, 3H), 1.83-1.62 (m, 4H), 1.26-1.01 (m, 3H). LC/MS conditions: Column: BEH C18 2.1×50 mm, 1.7 μm particles; Mobile Phase A: water with 0.05% trifluoroacetic acid; Mobile Phase B: acetonitrile with 0.05% trifluoroacetic acid; Temperature: 25° C.; Gradient: 2% B to 98% B over 1.6 min, then a 0.4 min hold at 98% B; Flow: 0.8 mL/min; Detection: MS and UV (220 nm). LC RT: 0.62 min. M/Z=352.1.

Example III-1: Synthesis of (S)-3-((2-amino-7-(1H-pyrazol-5-yl)quinolin-4-yl)oxy)propane-1,2-diol

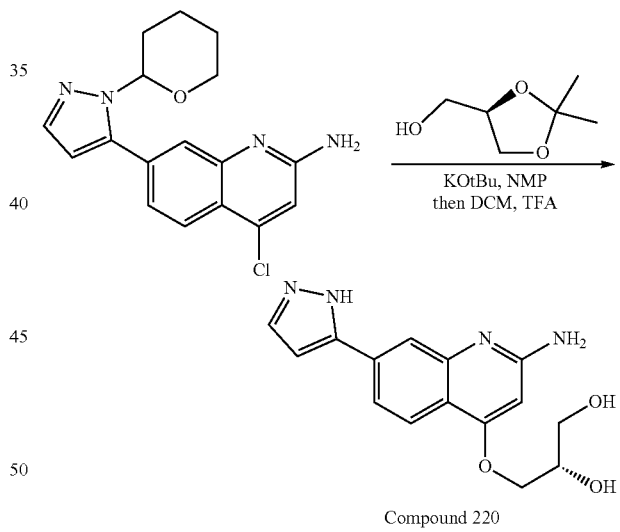

Compound 220

Step 1. Preparation of (S)-3-((2-amino-7-(1H-pyrazol-5-yl)quinolin-4-yl)oxy)propane-1,2-diol (Compound 220)

To a solution of (R)-(2,2-dimethyl-1,3-dioxolan-4-yl)methanol (60.3 mg, 0.456 mmol) and 4-chloro-7-(1-(tetrahydro-2H-pyran-2-yl)-1H-pyrazol-5-yl)quinolin-2-amine (20 mg, 0.061 mmol) in NMP (406 μl) was added potassium tert-butoxide (17.06 mg, 0.152 mmol). The reaction was heated to 100° C. overnight. The reaction was diluted with water and extracted three times with EtOAc. The organic layers were concentrated. The residue was dissolved in 0.4 mL DCM and 0.4 mL TFA. After 1 hour, the reaction was concentrated and azeotroped with DCM. The residue was dissolved in DMF, filtered through a syringe filter, and submitted to SCP purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 24 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give (7(S)-3-((2-amino-7-(1H-pyrazol-5-yl)quinolin-4-yl)oxy)propane-1,2-diol (7.6 mg, 41%). $^1$H NMR (500 MHz, DMSO-d$_6$) δ 8.10 (br d, J=8.2 Hz, 1H), 8.04 (br s, 1H), 7.94-7.80 (m, 2H), 6.86 (s, 1H), 6.39 (s, 1H), 4.30 (br dd, J=9.5, 3.4 Hz, 1H), 4.17 (br dd, J=9.6, 6.3 Hz, 1H), 3.98 (br s, 1H), 3.56 (br s, 1H), 3.34 (br s, 1H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.57 min. M/Z=301.0.

Compound 221 was prepared according to the synthetic procedures described for Compound 220 from the appropriate starting materials.

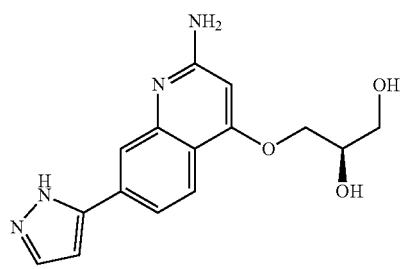 [SMILES: Nc1cc(OC[C@H](O)CO)c2ccc(-c3ccn[nH]3)cc2n1]

$^1$H NMR (400 MHz, MeOH-d$_4$) δ 8.18 (d, J=8.5 Hz, 1H), 7.93 (s, 1H), 7.86 (br d, J=8.3 Hz, 1H), 7.75 (d, J=1.7 Hz, 1H), 6.83 (d, J=2.0 Hz, 1H), 6.36 (s, 1H), 4.42-4.33 (m, 1H), 4.32-4.24 (m, 1H), 4.20-4.10 (m, 1H), 3.76 (d, J=5.6 Hz, 2H). LC RT: 0.84 min. M/Z=301.0.

Example III-2: Preparation of 4-((1H-pyrazol-5-yl)methoxy)-7-(1H-pyrazol-5-yl)quinolin-2-amine (Compound 313)

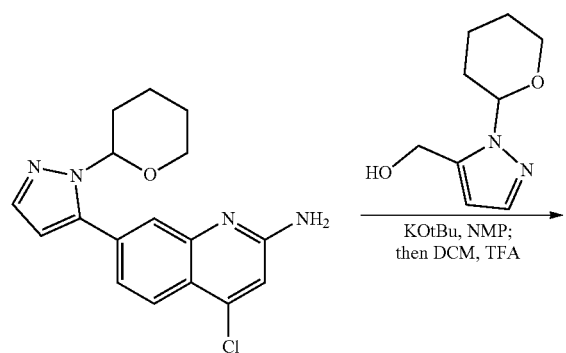

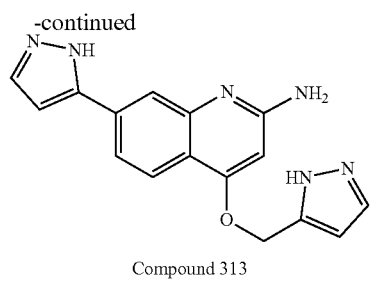

Compound 313

4-((1H-pyrazol-5-yl)methoxy)-7-(1H-pyrazol-5-yl)quinolin-2-amine was prepared from (1-(tetrahydro-2H-pyran-2-yl)-1H-pyrazol-5-yl)methanol (55.4 mg, 0.304 mmol) and 4-chloro-7-(1-(tetrahydro-2H-pyran-2-yl)-1H-pyrazol-5-yl)quinolin-2-amine (20 mg, 0.061 mmol) in the same manner as described in Example II-8. $^1$H NMR (500 MHz, DMSO-d6) δ 7.97-7.61 (m, 5H), 6.80 (s, 1H), 6.54-6.39 (m, 2H), 5.29 (br s, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min. Detection: MS and UV (220 nm). LC RT: 1.16 min. M/Z=307.3.

Example III-3: Synthesis of 7-(1H-pyrazol-5-yl)quinolin-2-amine (Compound 314)

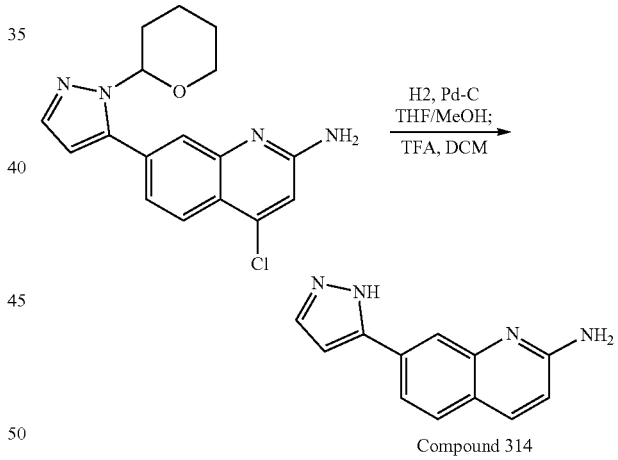

Compound 314

4-Chloro-7-(1-(tetrahydro-2H-pyran-2-yl)-1H-pyrazol-5-yl)quinolin-2-amine (20 mg, 0.061 mmol) was dissolved in MeOH (0.75 mL) and THF (0.25 mL). The flask was briefly placed under vacuum and backfilled with nitrogen twice. Pd—C (10% on carbon, 50% wet, 3 mg, 0.028 mmol) was added, then the flask was fitted with a hydrogen balloon, briefly placed under vacuum, backfilled with hydrogen, and stirred overnight. The reaction was diluted with MeOH and filtered through a syringe filter. The filtrate was concentrated. The residue was dissolved in 0.5 mL DCM and 0.5 mL TFA. After 1 hour, the reaction was concentrated and azeotroped with DCM. The residue was dissolved in DMF, filtered through a syringe filter, and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 2% B, 2-42% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 7-(1H-pyrazol-5-yl)quinolin-2-amine (5.3 mg, 41%). $^1$H NMR (500 MHz, DMSO-d6) δ 7.87 (d, J=8.9 Hz, 1H), 7.83 (s, 1H), 7.71 (br s, 1H), 7.67-7.58 (m, 2H), 6.78 (d, J=2.1 Hz, 1H), 6.73 (d, J=8.5 Hz, 1H), 6.38 (s, 1H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.91 min. M/Z=211.2.

Example III-4: Synthesis 2-((2-amino-7-(1H-pyrazol-5-yl)quinolin-4-yl)amino)propane-1,3-diol (Compound 315)

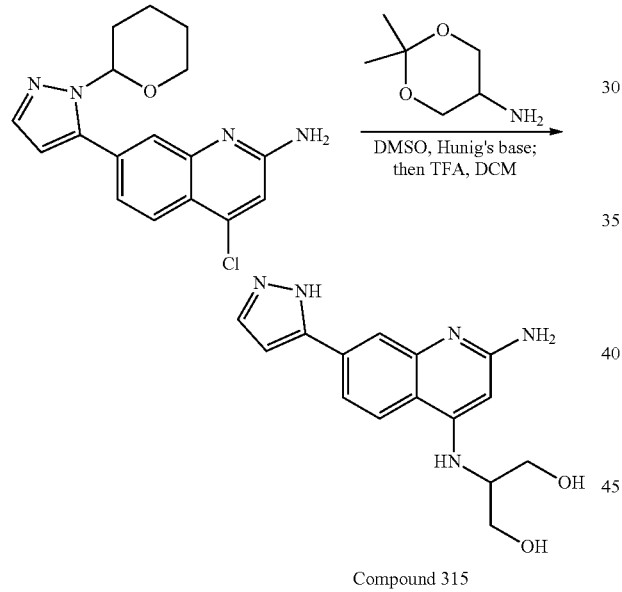

Compound 315

To a solution of 2,2-dimethyl-1,3-dioxan-5-amine (39.9 mg, 0.304 mmol) and 4-chloro-7-(1-(tetrahydro-2H-pyran-2-yl)-1H-pyrazol-5-yl)quinolin-2-amine (20 mg, 0.061 mmol) in DMSO (406 μl) was added 2,2-dimethyl-1,3-dioxan-5-amine (39.9 mg, 0.304 mmol). The reaction was heated to 120° C. After 16 hours, additional 2,2-dimethyl-1,3-dioxan-5-amine (39.9 mg, 0.304 mmol) and hunig's base (31.9 μl, 0.182 mmol) were added. After a further 24 hours, the reaction was cooled, diluted with water, and extracted three times with EtOAC. The organic layers were concentrated. The residue was dissolved in 0.5 mL MeOH 0.3 mL concentrated HCl was added. After 4 hours, the reaction was concentrated and azeotroped with MeOH. The residue was dissolved in MeOH, neutralized with solid K$_2$CO$_3$, filtered through a syringe filter, and The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 2-minute hold at 0% B, 0-45% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give 2-((2-amino-7-(1H-pyrazol-5-yl)quinolin-4-yl)amino)propane-1,3-diol (5.9 mg, 31%). $^1$H NMR (500 MHz, DMSO-d$_6$) δ 7.99 (br d, J=8.5 Hz, 1H), 7.93 (s, 1H), 7.78 (br s, 1H), 7.76-7.70 (m, 1H), 7.62-7.55 (m, 1H), 6.79 (s, 1H), 5.76 (s, 1H), 3.86-3.78 (m, 1H), 3.57-3.49 (m, 1H), 3.45 (br t, J=5.3 Hz, 1H), 3.37-3.28 (m, 1H), 3.15-3.08 (m, 1H). Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.61 min. M/Z=300.1.

Example III-5: Synthesis of 7-(1H-pyrazol-5-yl)-N4-(pyrimidin-2-ylmethyl)quinoline-2,4-diamine (Compound 316)

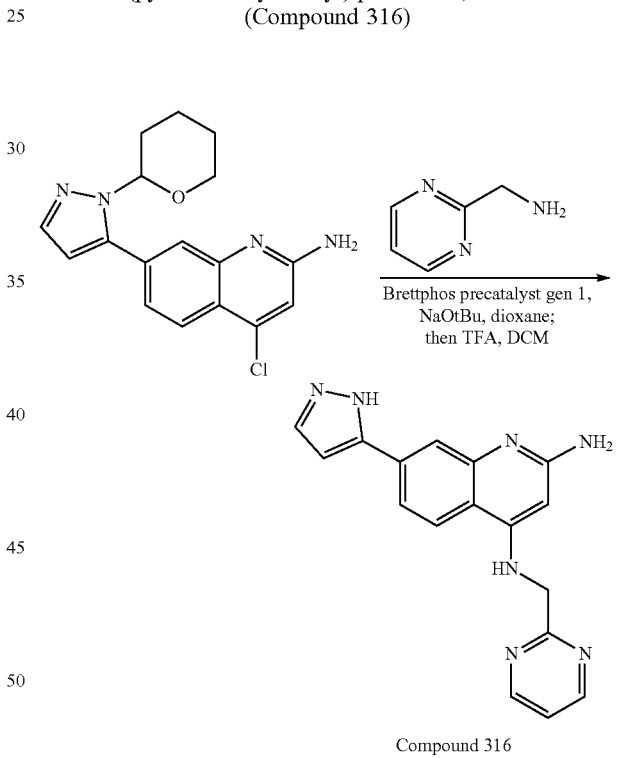

Compound 316

Brettphos precatalyst generation 1 (4.86 mg, 6.08 μmol), 4-chloro-7-(1-(tetrahydro-2H-pyran-2-yl)-1H-pyrazol-5-yl)quinolin-2-amine (20 mg, 0.061 mmol), and sodium tert-butoxide (14.61 mg, 0.152 mmol) were placed in a vial. The vial was placed under vacuum an backfilled with nitrogen twice. Dioxane (0.5 mL) and pyrimidin-2-ylmethanamine (13.28 mg, 0.122 mmol) were added, nitrogen was bubbled through the solution, and the reaction was heated to 100° C. overnight. The reaction was cooled, diluted with water, and extracted three times with EtOAc. The organic layers were concentrated. The residue was dissolved in 0.5 mL DCM and 0.5 mL TFA. After 1 hour, the reaction was concentrated and azeotroped with DCM. The residue was dissolved in DMF, filtered through a syringe filter, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-30% B over 25 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 7-(1H-pyrazol-5-yl)-N4-(pyrimidin-2-ylmethyl)quinoline-2,4-diamine (4.9 mg, 25%). $^1$H NMR (500 MHz, DMSO-$d_6$) δ 8.79 (d, J=4.9 Hz, 2H), 8.10 (d, J=8.5 Hz, 1H), 8.05-7.92 (m, 1H), 7.81 (br s, 1H), 7.78-7.72 (m, 1H), 7.70-7.64 (m, 1H), 7.42 (t, J=4.9 Hz, 1H), 6.81 (d, J=1.8 Hz, 1H), 5.61 (s, 1H), 4.68 (br d, J=5.8 Hz, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 1.01 min. M/Z=318.3, Compound 317 was prepared according to the synthetic procedures described for Compound 316 from the appropriate starting materials.

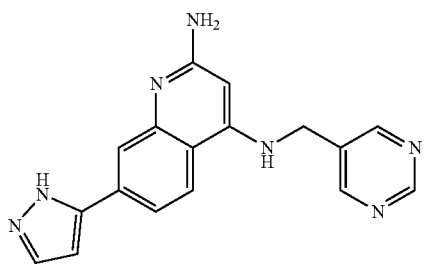 [SMILES: Nc1cc(NCc2cncnc2)c2ccc(-c3ccn[nH]3)cc2n1]

$^1$H NMR (500 MHz, DMSO-$d_6$) δ 9.09 (s, 1H), 8.81 (s, 2H), 8.04 (br d, J=8.7 Hz, 1H), 7.79 (s, 1H), 7.77-7.71 (m, 1H), 7.68-7.60 (m, 1H), 6.82-6.77 (m, 1H), 5.68 (s, 1H), 4.53 (br d, J=3.4 Hz, 2H). LC RT: 0.90 min W/Z=318.2.

Example III-6: Synthesis of 6 substituted 4-aminoquinolines

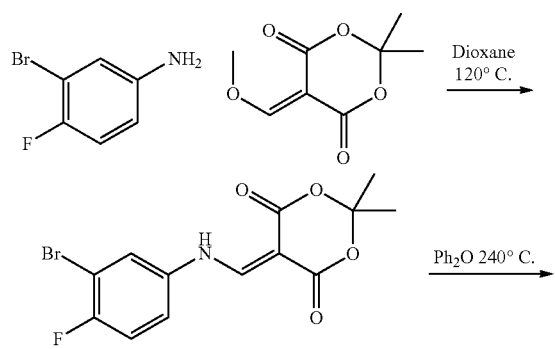

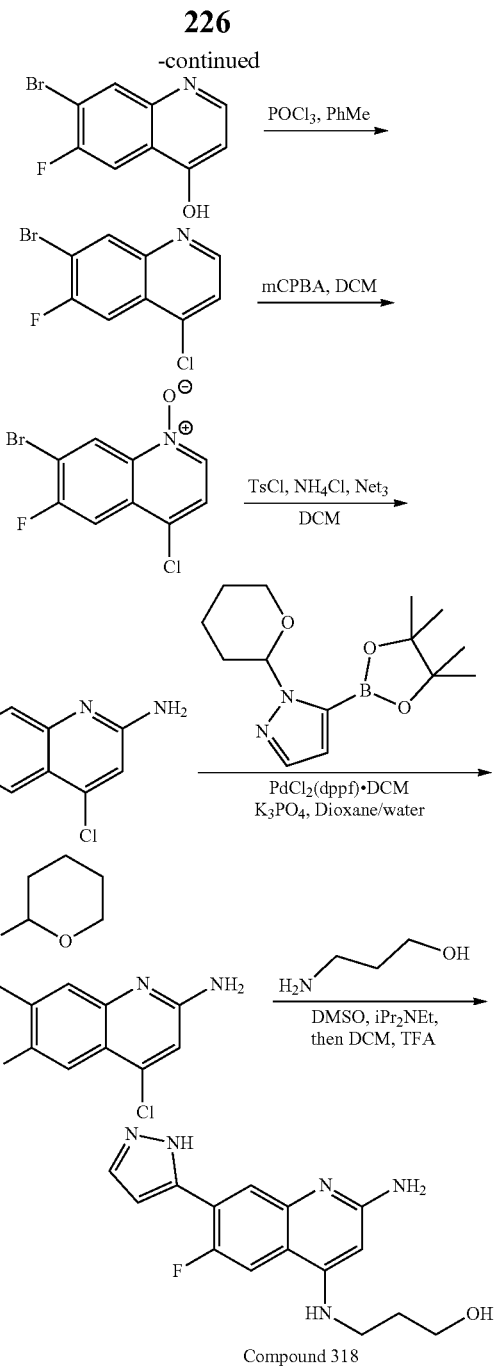

Compound 318

Step 1. Preparation of 5-(((3-bromo-4-fluorophenyl)amino)methylene)-2,2-dimethyl-1,3-dioxane-4,6-done A solution of 3-bromo-4-fluoroaniline (1.9 g, 10.00 mmol) and 5-(methoxymethylene)-2,2-dimethyl-1,3-dioxane-4,6-dione (2.234 g, 12.00 mmol) in dioxane (5 mL) was heated to 120° C. for 20 minutes. The reaction mixture is then cooled to room temperature and diluted with 50 ml of dietheyl ether. The solid was filtered and dried to give 5-(((3-bromo-4-fluorophenyl)amino)methylene)-2,2-dimethyl-1,3-dioxane-4,6-dione (2.77 g, 8.0 mmol, 80%). $^1$H NMR (400 MHz, DMSO-$d_6$) δ 11.23 (br d, J=14.4 Hz, 1H), 8.53 (d, J=14.5 Hz, 1H), 8.06 (dd, J=6.0, 2.8 Hz, 1H), 7.69-7.61 (m, 1H), 7.44 (t, J=8.7 Hz, 1H), 1.73-1.63 (m, 6H).

Step 2. Preparation of 7-bromo-6-fluoroquinolin-4-ol

A solution of 5-(((3-bromo-4-fluorophenyl)amino)methylene)-2,2-dimethyl-1,3-dioxane-4,6-dione (2.77 g, 8.05 mmol) in phenyl ether (7 mL) is heated to 240° C. for 10 minutes. The reaction mixture is then cooled to room temperature and diluted with 50 ml of dietheyl ether. The solid was filtered and dried to give a 1:1 mixture of 7-bromo-6-fluoroquinolin-4-ol and 5-bromo-6-fluoroquinolin-4-ol (0.982 g, 4.0 mmol, 50%).

Step 3. Preparation of 7-bromo-4-chloro-6-fluoroquinoline

To a suspension of a 1:1 mixture of 7-bromo-6-fluoroquinolin-4-ol and 5-bromo-6-fluoroquinolin-4-ol (982 mg, 4.06 mmol) in toluene (7 mL) was added $POCl_3$ (0.756 mL, 8.11 mmol). The reaction mixture was then heated to 100° C. for 1 hour. The cooled reaction mixture was poured over ice and then partitioned between DCM and saturated sodium carbonate solution. The organic layer was dried with sodium sulfate and concentrated. The residue was purified via ISCO (80 g column; Hexanes/Ethyl acetate; 0 to 100% gradient) to give 7-bromo-4-chloro-6-fluoroquinoline (203 mg, 0.8 mmol, 19%). $^1$H NMR (400 MHz, DMSO-$d_6$) δ 8.88 (d, J=4.7 Hz, 1H), 8.54 (d, J=6.8 Hz, 1H), 8.09 (d, J=9.5 Hz, 1H), 7.88 (d, J=4.8 Hz, 1H)

Step 4. Preparation of 7-bromo-4-chloro-6-fluoroquinoline 1-oxide

To a solution of 7-bromo-4-chloro-6-fluoroquinoline (0.203 g, 0.779 mmol) in DCM (10.0 ml) was added mCPBA (0.576 g, 2.34 mmol). The reaction was stirred overnight, then quenched with saturated sodium thiosulfate solution. The reaction was stirred for 0.5 hours, then saturated aqueous sodium bicarbonate was added. The reaction was extracted twice with DCM. The organic layers were washed with brine, dried with sodium sulfate, and concentrated to give 7-bromo-4-chloro-6-fluoroquinoline 1-oxide (0.215 g, 0.779 mmol, quantitative yield). $^1$H NMR (400 MHz, DMSO-$d_6$) δ 8.87 (d, J=6.7 Hz, 1H), 8.60 (d, J=6.6 Hz, 1H), 8.13 (d, J=9.2 Hz, 1H), 7.80 (d, J=6.6 Hz, 1H).

Step 5: Preparation of 7-bromo-4-chloro-6-fluoroquinolin-2-amine

In one round-bottomed flask, 7-bromo-4-chloro-6-fluoroquinoline 1-oxide (240 mg, 0.868 mmol) was suspended in DCM (8 mL). TsCl (182 mg, 0.955 mmol) was added. This mixture was stirred for one hour. In a second round-bottomed flask, ammonium chloride (232 mg, 4.34 mmol) (dried in an oven at 110° C. overnight) was suspended in DCM (4 mL). Triethylamine (0.605 mL, 4.34 mmol) was added and the mixture was stirred for 0.5 hours, then the contents of the first roundbottom flask were added to the second. The reaction was stirred overnight, then filtered and concentrated. The residue was purified via ISCO (24 g column; Hexanes/Ethyl acetate; 0 to 100% gradient) to give 7-bromo-4-chloro-6-fluoroquinolin-2-amine (128 mg, 0.47 mmol, 54%).

Step 6: Preparation of 4-chloro-6-fluoro-7-(1-(tetrahydro-2H-pyran-2-yl)-1H-pyrazol-5-yl)quinolin-2-amine In a pressure vial was placed 1-(tetrahydro-2H-pyran-2-yl)-5-(4,4,5,5-tetramethyl-1,3,2-dioxaborolan-2-yl)-1H-pyrazole (0.174 g, 0.626 mmol), 7-bromo-4-chloroquinolin-2-amine (0.115 g, 0.417 mmol), and $PdCl_2$(dppf)-DCM adduct (0.034 g, 0.042 mmol). The vial was placed under vacuum and backfilled with nitrogen three times. Dioxane (10 ml) and tripotassium phosphate (2M aqueous) (0.63 ml, 1.25 mmol) were added, nitrogen was bubbled through the solution, then the reaction was heated to 100° C. overnight. The reaction was cooled to room temperature, diluted with 50 ml of ethyl acetate, dried with sodium sulfate, and concentrated. The residue was purified via ISCO (12 g column; Hexanes/Etheyl acetate; 0 to 100% gradient) to give of 4-chloro-6-fluoro-7-(1-(tetrahydro-2H-pyran-2-yl)-1H-pyrazol-5-yl)quinolin-2-amine (0.113 g, 0.22 mmol, 52% yield).

Step 7: Preparation of 3-((2-amino-6-fluoro-7-(1H-pyrazol-5-yl)quinolin-4-yl)amino)propan-1-ol (Compound 318)

To a solution of 4-chloro-6-fluoro-7-(1-(tetrahydro-2H-pyran-2-yl)-1H-pyrazol-5-yl)quinolin-2-amine (60 mg, 0.173 mmol) and 3-aminopropan-1-ol (39 mg, 0.52 mmol) in DMSO (0.5 mL) was added Hunig's Base (0.3 mL, 1.7 mmol). The reaction was heated to 120° C. overnight. The reaction was cooled, diluted with water, and extracted three times with DCM. The organic layers were concentrated, dissolved in 5 mL DCM, and 4N HCl in dioxane (1.038 mL, 4.15 mmol) was added. After 20 minutes, the reaction was complete by LCMS. The reaction was concentrated. The residue was dissolved in DMF, filtered through a syringe filter, and the crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give 3-((2-amino-6-fluoro-7-(1H-pyrazol-5-yl)quinolin-4-yl)amino)propan-1-ol (3.7 mg, 7.1%). $^1$H NMR (500 MHz, DMSO-$d_6$) δ 8.19-8.13 (m, 1H), 8.11 (br s, 1H), 7.98-7.92 (m, 1H), 7.88 (br s, 1H), 7.58 (br s, 1H), 6.77 (br s, 1H), 5.83 (s, 1H), 3.55 (br d, J=4.0 Hz, 2H), 3.45-3.25 (m, 2H), 1.84 (quin, J=6.6 Hz, 2H) One methylene from sidechain is not visible, likely due to overlap with suppressed water peak. LC RT: 0.80 min. M/Z=302.1

Compound 319 and Compound 320 were prepared according to the synthetic procedures described for Compound 318 from the appropriate starting materials.

| Compd. No. | Structure | LC/MS [M + H]+ | RT (min) | 1H NMR (500 MHz, DMSO-d6) |
|---|---|---|---|---|
| 319 | 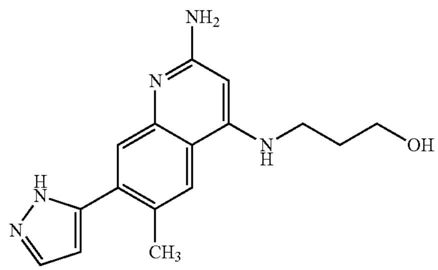 [SMILES: Cc1cc2c(NCCCO)cc(N)nc2cc1-c1ccn[nH]1] | 298.1 | 0.81 | δ 7.95-7.90 (m, 1H), 7.76 (br s, 1H), 7.57 (s, 1H), 7.24-7.05 (m, 2H), 6.56 (s, 1H), 5.72 (s, 1H), 3.29 (br d, J = 6.1 Hz, 2H), 2.49 (s, 3H), 1.87-1.79 (m, 2H).). One methylene is not visible, possibly due to overlap with suppressed water peak. |
| 320 | 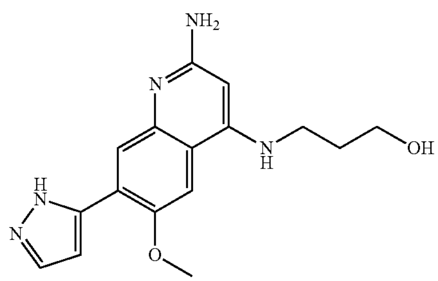 [SMILES: COc1cc2c(NCCCO)cc(N)nc2cc1-c1ccn[nH]1] | 314.1 | 0.83 | δ 8.31-8.00 (m, 2H), 7.92-7.68 (m, 2H), 7.63-7.38 (m, 2H), 6.87 (br s, 1H), 5.84 (s, 1H), 3.98 (s, 3H), 3.57 (t, J = 6.1 Hz, 1H), 1.91-1.82 (m, 2H). Three protons are not visible, possibly due to overlap with suppressed water peak. |

Example III-7. Preparation of (S)-7-(1H-pyrazol-3-yl)-N4-(pyrrolidin-3-yl)quinoline-2,4-diamine (Compound 321)

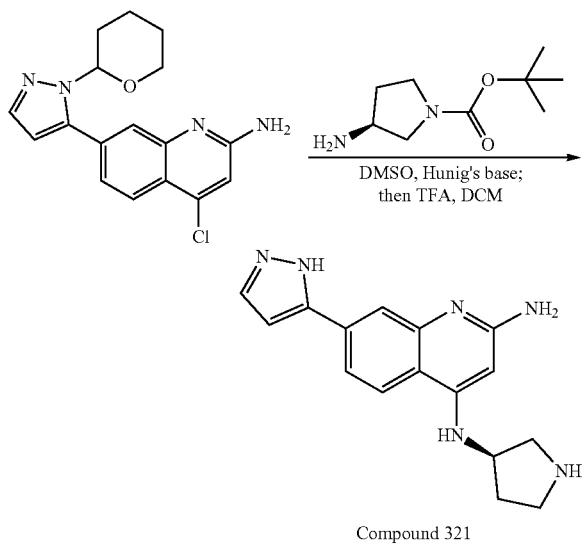

Compound 321

To a solution of 4-chloro-7-(1-(tetrahydro-2H-pyran-2-yl)-1H-pyrazol-5-yl)quinolin-2-amine (100 mg, 0.304 mmol) in NMP (1 mL) was added tert-butyl (3S)-3-((2-amino-7-(1-(tetrahydro-2H-pyran-2-yl)-1H-pyrazol-5-yl) quinolin-4-yl)amino)pyrrolidine-1-carboxylate and Hunig's base (0.531 mL, 3.04 mmol). The resulted mixture was heated to 150° C. overnight. The reaction was cooled, diluted with water, and extracted three times with EtOAc. The organic layers were concentrated. The residue was dissolved in 0.4 mL DCM and 0.4 mL TFA. After 1 hour, the THP deprotection was complete by LCMS. The reaction was concentrated and azeotroped with DCM. The residue was dissolved in DMF, filtered through a syringe filter, and the crude material was purified by preparative reverse-phase HPLC with the following conditions: Column: Luna 30×100 mm 5 μM particle size; Mobile Phase A: 10:9 methanol: water with 0.1% trifluoroacetic acid; Mobile Phase B: 90:10 methanol: water with 0.1% trifluoroacetic acid; Gradient: a 0-minute hold at 0% B, 0-100% B over 10 minutes, then a 2-minute hold at 100% B; Flow Rate: 40 mL/min; Column Temperature: 25° C. to give (S)-7-(1H-pyrazol-3-yl)-N4-(pyrrolidin-3-yl)quinoline-2,4-diamine (55 mg, 0.187 mmol, 61.4% yield). 1H NMR (400 MHz, METHANOL-d4) δ 8.34-8.27 (m, 1H), 7.98-7.91 (m, 1H), 7.90-7.84 (m, 1H), 7.80-7.77 (m, 1H), 6.94-6.83 (m, 1H), 6.02-5.89 (m, 1H), 3.75-3.64 (m, 2H), 3.35-3.30 (m, 1H), 2.44-2.28 (m, 2H), 2.13-1.98 (m, 2H). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.58 min. M/Z=295.0.

Example III-8: Preparation of 7-(1H-pyrazol-3-yl)-N4-(2-(thiophen-2-yl)ethyl)quinoline-2,4-diamine (Compound 322)

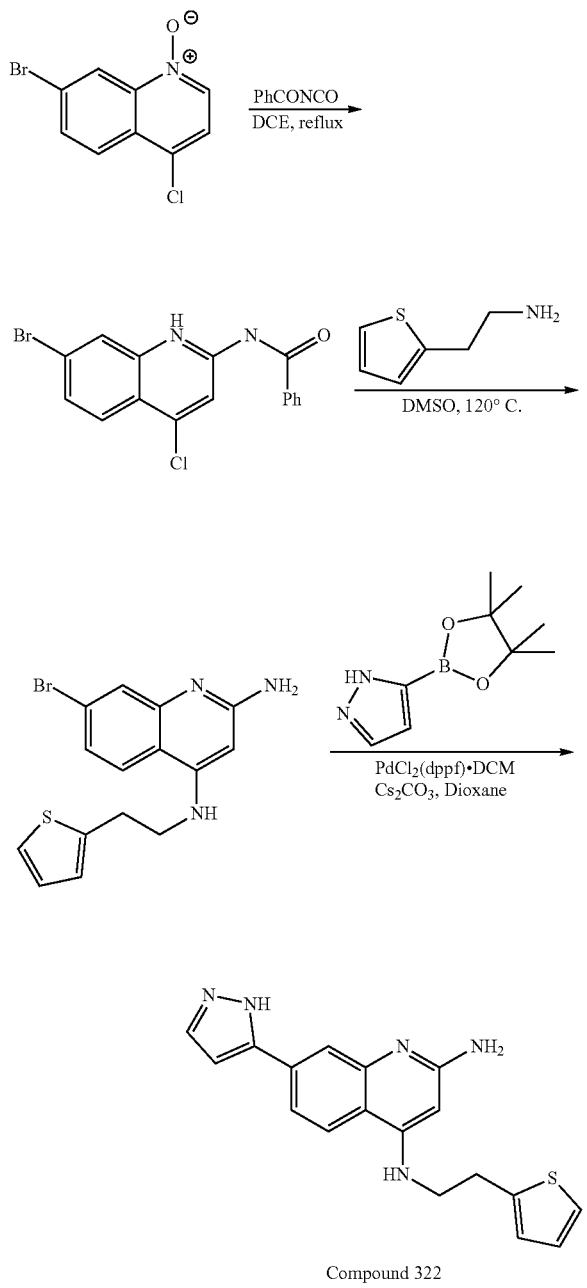

Compound 322

Step 1. Preparation of N-(7-bromo-4-chloroquinolin-2-yl)benzamide

A solution of 7-bromo-4-chloroquinoline 1-oxide (2.326 g, 9 mmol) in dichloroethane (22.50 ml) was treated with benzoyl isocyanate (2.94 g, 18.00 mmol), and the resulting mixture was heated to reflux for 16h. The reaction was cooled to RT, applied to a silica gel column and eluted with 5-25% EtOAc-hexane. (The column and mobile phase were kept warm with a heat gun to keep product from precipitating extensively.) Concentration of the appropriate fractions afforded N-(7-bromo-4-chloroquinolin-2-yl)benzamide (2.8 g, 7.74 mmol, 86% yield) as an off-white solid, mp. 142-143° C. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. LC RT: 1.10 min. M/Z=363.0.

Step 2. Preparation of 7-bromo-4-(2-(thiophen-3-yl)ethoxy)quinoline

A solution of 2-(thiophen-2-yl)ethan-1-amine (132 mg, 1.037 mmol) and N-(7-bromo-4-chloroquinolin-2-yl)benzamide (75 mg, 0.207 mmol) in DMSO (518 µl) was heated at 120° C. for four hours then cooled to RT. The reaction was then purified by reverse-phase prep. HPLC (MeOH-water gradient, 0.1% TFA in both mobile phases). Concentration of the appropriate fractions afforded 7-bromo-N4-(2-(thiophen-2-yl)ethyl)quinoline-2,4-diamine-TFA (39 mg, 41% yield) as a colorless glass. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. LC RT: 0.75 min. M/Z=350.2.

Step 3. Preparation of 7-(1H-pyrazol-3-yl)-N4-(2-(thiophen-2-yl)ethyl)quinoline-2,4-diamine (Compound 351)

A mixture of 5-(4,4,5,5-tetramethyl-1,3,2-dioxaborolan-2-yl)-1H-pyrazole (29.4 mg, 0.151 mmol), 7-bromo-N4-(2-(thiophen-2-yl)ethyl)quinoline-2,4-diamine, TFA (35 mg, 0.076 mmol), $PdCl_2$(dppf)-$CH_2Cl_2$ adduct (6.18 mg, 7.57 µmol), and cesium carbonate (99 mg, 0.303 mmol) in nitrogen-saturated dioxane (757 µL) was placed under nitrogen and heated at 95° C. for 2h. The reaction was cooled and stirred at RT. The reaction was quenched with 50% aq. HOAc, diluted to 2 mL with DMF, and purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile: ammonium acetate; Gradient: a 0-minute hold at 12% B, 12-52% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford 7-(1H-pyrazol-3-yl)-N4-(2-(thiophen-2-yl)ethyl)quinoline-2,4-diamine (13.6 mg, 54% yield). $^1$H NMR (500 MHz, DMSO-$d_6$) δ 8.03 (d, J=8.9 Hz, 1H), 7.83 (br. s, 1H), 7.73-7.78 (m, 1H), 7.63-7.68 (m, 1H), 7.41-7.48 (m, 1H), 7.34 (d, J=4.6 Hz, 1H), 6.96-7.00 (m, 3H), 6.84 (d, J=1.8 Hz, 1H), 5.80 (s, 1H), 3.47-3.53 (m, 2H), 3.20 (t, J=7.0 Hz, integral distorted by water suppression). LC RT: 1.36 min. M/Z=336.1.

Compound 323 through Compound 327 were prepared according to the synthetic procedures described for Compound 321 from the appropriate starting materials.

| Compd. No. | Structure | LC/MS [M + H]+ | RT (min) | 1H NMR (500 MHz, DMSO-d6) |
|---|---|---|---|---|
| 323 | 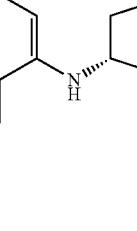 | 295.3 | 0.45 | δ 8.29-8.18 (m, 1H), 7.94-7.93 (m, 1H), 7.92-7.90 (m, 1H), 7.83-7.77 (m, 1H), 6.91-6.84 (m, 1H), 5.98-5.90 (m, 1H), 4.62-4.51 (m, 1H), 3.81-3.70 (m, 2H), 3.66-3.53 (m, 2H), 2.60-2.48 (m, 2H) |
| 324 | 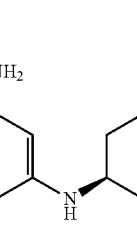 | 309.2 | 0.82 | δ 8.25-8.17 (m, 1H), 8.08-8.00 (m, 1H), 7.93-7.88 (m, 2H), 6.89-6.79 (m, 1H), 6.41-6.29 (m, 1H), 3.77-3.66 (m, 1H), 3.61-3.49 (m, 1H), 3.00-2.87 (m, 1H), 2.17-1.94 (m, 3H), 1.86-1.73 (m, 1H), 1.74-1.58 (m, 2H) |
| 325 | 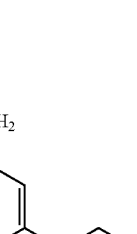 | 295.4 | 0.55 | δ 8.17-8.12 (m, 1H), 7.91-7.88 (m, 1H), 7.88-7.85 (m, 1H), 7.80-7.78 (m, 1H), 6.90-6.81 (m, 1H), 5.95-5.86 (m, 1H), 4.18-4.08 (m, 2H), 3.83-3.70 (m, 2H), 3.67-3.62 (m, 1H), 3.39-3.35 (m, 2H) |
| 326 | 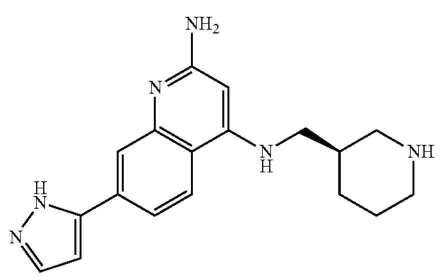 [SMILES: Nc1cc(NC[C@@H]2CCCNC2)c2ccc(-c3ccn[nH]3)cc2n1] | 323.2 | 0.65 | δ 8.02-7.94 (m, 2H), 7.91-7.87 (m, 1H), 7.81-7.77 (m, 1H), 7.65-7.59 (m, 1H), 7.52-7.46 (m, 1H), 4.12-3.81 (m, 1H), 3.09-2.66 (m, 2H), 2.18-1.85 (m, 2H), 1.82-1.60 (m, 2H), 1.44-1.20 (m, 4H) |
| 327 | 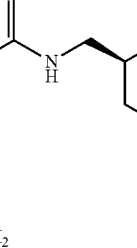 | 309.2 | 0.45 | δ 8.20-8.10 (m, 1H), 7.95-7.86 (m, 2H), 7.82-7.77 (m, 1H), 6.88-6.83 (m, 1H), 5.94-5.87 (m, 1H), 3.64-3.54 (m, 2H), 3.50-3.42 (m, 2H), 3.24-3.08 (m, 2H), 2.99-2.65 (m, 2H), 1.89-1.76 (m, 1H) |

Example III-9: Synthesis of 4-alkoxy Substituted Quinolines by Mitsunobu Route

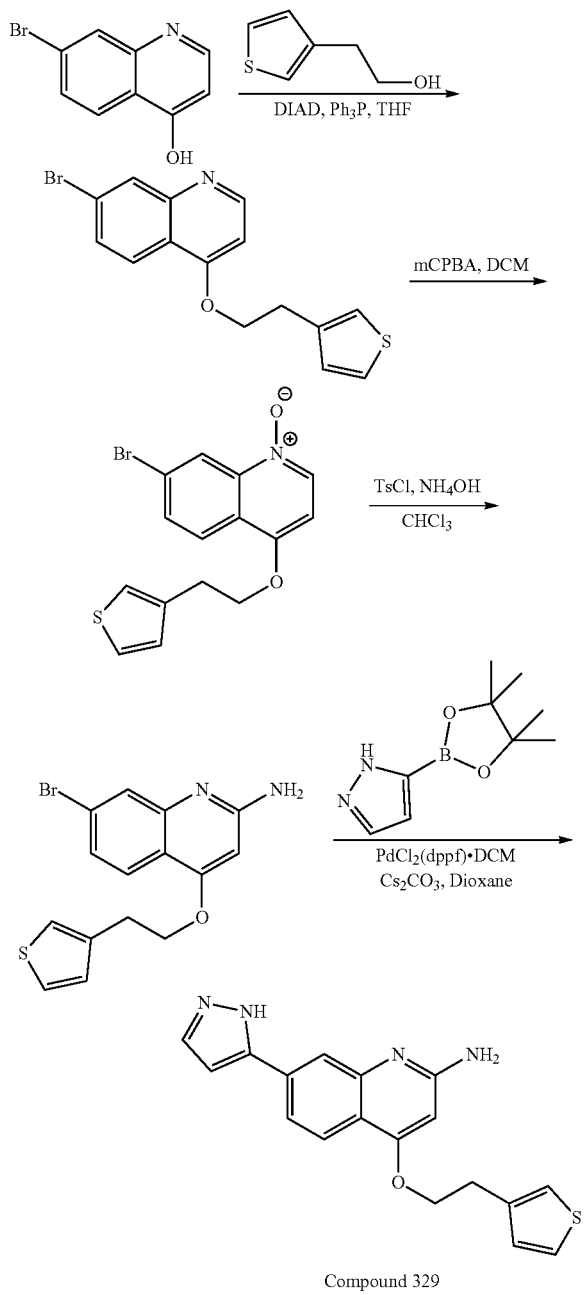

Compound 329

Step 1. Preparation of 7-bromo-4-(2-(thiophen-3-yl)ethoxy)quinoline

A stirred suspension of 2-(thiophen-3-yl)ethan-1-ol (256 mg, 2.000 mmol), triphenylphosphine (367 mg, 1.400 mmol), and 7-bromoquinolin-4-ol (224 mg, 1 mmol) in THF (5000 µl) was heated to reflux then cooled to RT. This suspension was treated with DIAD (272 µl, 1.400 mmol) over 1-2 min. The resulting mixture was stirred 1 h at RT then purified by flash chromatography (25-50% EtOAc-hexane). Concentration of the appropriate fractions afforded a pale amber oil. This was treated with ~5 mL of hexanes and swirled. A little EtOAc was added, and the mixture was swirled. A bit of dichloromethane was added, and the mixture was swirled and heated. This gives a solution which was swirled while cooling. Product precipitated onto the glass, and the mixture was then evaporated to dryness, affording 7-bromo-4-(2-(thiophen-3-yl)ethoxy)quinoline (270 mg, 0.81 mmol, 81% yield) as an off-white solid, mp 92-95° C. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. LC RT: 0.76 min. M/Z=336.1.

Step 2. Preparation of 7-bromo-4-(2-(thiophen-3-yl)ethoxy)quinoline 1-oxide

A solution of 7-bromo-4-(2-(thiophen-3-yl)ethoxy)quinoline (250 mg, 0.748 mmol) in chloroform (3740 µl) was treated with m-CPBA (516 mg, 2.99 mmol). The reaction was stirred 1h at RT then poured into EtOAc-hexane (to give an organic phase with density <1). A precipitate formed which was re-dissolved by adding more EtOAc and EtOH and heating. This mixture was shaken with 5% aq. sodium thiosulfate.

Saturated aq. sodium bicarbonate was added, and when bubbling ceased the mixture was carefully shaken. The org. phase was washed (brine), dried, stripped and chromatographed on silica gel (5-10% MeOH—CH$_2$Cl$_2$). Concentration of the appropriate fractions afforded 7-bromo-4-(2-(thiophen-3-yl)ethoxy)quinoline 1-oxide (140 mg, 0.40 mmol, 53% yield) as an amber glass. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. LC RT: 0.79 min. M/Z=352.1.

Step 3. Preparation of 7-bromo-4-(2-(thiophen-3-yl)ethoxy)quinolin-2-amine

A solution of 7-bromo-4-(2-(thiophen-3-yl)ethoxy)quinoline 1-oxide (137 mg, 0.391 mmol) in chloroform (3 mL) was treated with 1 mL of conc. aq. ammonia and stirred rapidly for 3-4 min. Stirring was slowed, and the resulting mixture was treated with Ts-Cl (78 mg, 0.411 mmol) in 1 mL of chloroform by syringe (sub-surface) over ~40 seconds. The reaction was stirred 20 min. at RT then applied to a silica gel column and eluted with 5-10% MeOH—CH$_2$Cl$_2$. Concentration of the appropriate fractions afforded 7-bromo-4-(2-(thiophen-3-yl)ethoxy)quinolin-2-amine (113 mg, 0.324 mmol, 83% yield) as an oil which crystallized upon standing to a waxy tan solid, mp 150-156° C. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 mi/min; Mobile phase A: 100% Water, 0.05% TFA; Mobile phase B: 100% Acetonitrile, 0.05% TFA. LC RT: 0.78 min. M/Z=351.1.

Step 4. Preparation of 7-(1H-pyrazol-3-yl)-4-(2-(thiophen-3-yl)ethoxy)quinolin-2-amine (Compound 329)

A suspension of 5-(4,4,5,5-tetramethyl-1,3,2-dioxaborolan-2-yl)-1H-pyrazole (16.67 mg, 0.086 mmol), 7-bromo-4-(2-(thiophen-3-yl)ethoxy)quinolin-2-amine (15 mg, 0.043 mmol), $PdCl_2(dppf)$-$CH_2Cl_2$ adduct (7.01 mg, 8.59 μmol), and cesium carbonate (42.0 mg, 0.129 mmol) in nitrogen-saturated dioxane (429 μl) was placed under nitrogen and heated at 95° C. for 2h. The reaction was cooled to RT, quenched with a few drops of 50% aq. HOAc, filtered, and purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-59% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to afford 7-(1H-pyrazol-3-yl)-4-(2-(thiophen-3-yl)ethoxy)quinolin-2-amine (7.1 mg, 48% yield). $^1$H NMR (500 MHz, DMSO-$d_6$) δ 7.82-7.88 (m, 2H), 7.76 (br. s, 1H), 7.65 (br. s, 1H), 7.50 (dd, J=4.8, 2.9 Hz, 1H), 7.39 (d, J=2.1 Hz, 1H), 7.18 (d, J=4.6 Hz, 1H), 6.80 (d, J=1.8 Hz, 1H), 6.64-6.81 (m, 2H), 6.25 (s, 1H), 4.35 (t, J=6.4 Hz, 2H), 3.21 (t, J=6.6 Hz, integral distorted by water suppression). LC RT: 1.49 min. M/Z=337.1.

Compound 330 and Compound 331 were prepared according to the synthetic procedures described for Compound 329 from the appropriate starting materials.

| Compd. No. | Structure | LC/MS [M + H]$^+$ | RT (min) | $^1$H NMR (500 MHz, DMSO-$d_6$) |
|---|---|---|---|---|
| 331 | 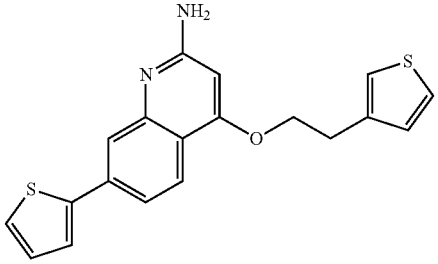 [SMILES: Nc1cc(OCCc2ccsc2)c2ccc(-c3cccs3)cc2n1] | 353.1 | 2.16 | δ 7.85 (d, J = 8.3 Hz, 1H), 7.58-7.63 (m, 2H), 7.47-7.53 (m, 2H), 7.38 (d, J = 1.8 Hz, 1H), 7.15-7.20 (m, 2H), 6.74 (s, 2H), 6.25 (s, 1H), 4.34 (t, J = 6.4 Hz, 2H), 3.20 (t, J = 6.4 Hz, 2H). |
| 331 | 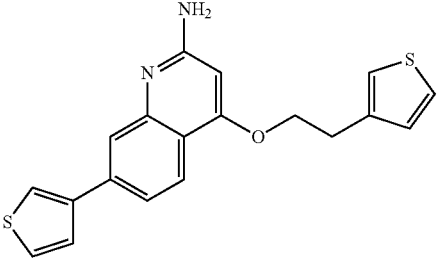 [SMILES: Nc1cc(OCCc2ccsc2)c2ccc(-c3ccsc3)cc2n1] | 353.1 | 2.12 | δ 8.38 (br. s, 3H), 8.07-8.11 (m, 1H), 8.07-8.11 (m, 1H), 7.97 (d, J = 8.9 Hz, 1H), 7.81-7.86 (m, 1H), 7.73-7.77 (m, 1H), 7.59-7.63 (m, 1H), 7.50-7.53 (m, 1H), 7.40-7.43 (m, 1H), 7.17-7.20 (m, 1H), 8.44 (t, J = 6.4 Hz, 2H), 3.25 (t, J = 6.4 Hz, integral distorted by water suppression). Primary amine integrates to three because this sample is a TFA salt. |

Example III-10: Synthesis of 4-alkoxy substituted quinolines by $Sn_{Ar}$ on 7-bromo-4-chloroquinolin-2-amine

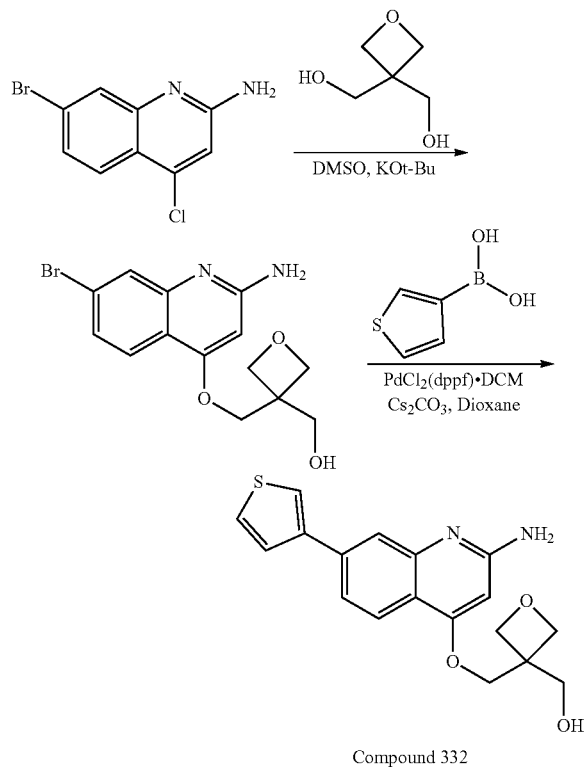

Compound 332

Step 1. Preparation of (3-(((2-amino-7-bromoquinolin-4-yl)oxy)methyl)oxetan-3-yl)methanol A stirred solution of oxetane-3,3-diyldimethanol (229 mg, 1.942 mmol) in DMSO (388 μl) was treated with KOtBu (582 μl, 0.582 mmol) in THF over 1-2 min. This solution was stirred 5 min. then treated with 7-bromo-4-chloroquinolin-2-amine (50 mg, 0.194 mmol). The resulting solution was heated at 90° C. for 20 min., then the temperature was raised to 95° C., and stirring was continued for 3h longer. The reaction was cooled to RT and transferred by pipette into water (with stirring). This gave a suspension with some material adhering to the glass. Stirring was continued for 40 min., after which time the suspension was filtered, washed with water, and air-dried to afford (3-(((2-amino-7-bromoquinolin-4-yl)oxy)methyl)oxetan-3-yl)methanol (52 mg, 0.153 mmol, 79% yield) as an amorphous tan solid. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50 20° C.); Flow rate: 0.8 ml/min; Mobile phase A: 100% Water, 0.05% TFA; Mobile phase B: 100% Acetonitrile, 0.05% TFA. LC RT: 0.57 min. M/Z=341.1.

Step 2. Preparation of (3-(((2-amino-7-(thiophen-3-yl)quinolin-4-yl)oxy)methyl)oxetan-3-yl)methanol (Compound 332)

A suspension of (3-(((2-amino-7-bromoquinolin-4-yl)oxy)methyl)oxetan-3-yl)methanol (20 mg, 0.059 mmol), thiophen-3-ylboronic acid (15.09 mg, 0.118 mmol), PdCl₂(dppf)-CH₂Cl₂ adduct (4.82 mg, 5.90 μmol), and cesium carbonate (57.6 mg, 0.177 mmol) in nitrogen-saturated dioxane (590 μl) was placed under nitrogen and heated to 95° C. After 2h, LCMS shows a complete reaction. It was cooled and quenched with a few drops of 50% aq. HOAc. When all the solids had dissolved, the reaction was diluted to 2 mL with DMF and filtered. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 14% B, 14-54% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to afford (3-(((2-amino-7-(thiophen-3-yl)quinolin-4-yl)oxy)methyl)oxetan-3-yl)methanol (11.6 mg, 55% yield). ¹H NMR (500 MHz, DMSO-d₆) δ 7.95-7.97 (m, 1H), 7.84 (d, J=8.6 Hz, 1H), 7.70 (d, J=1.8 Hz, 1H), 7.65-7.68 (m, 1H), 7.61-7.64 (m, 1H), 7.50 (dd, J=8.6, 1.5 Hz, 1H), 6.34 (s, 2H), 6.25 (s, 1H), 4.55 (d, J=6.1 Hz, 2H), 4.48 (d, J=6.1 Hz, 2H), 4.28 (s, 2H), 3.82 (s, 2H). LC RT: 1.33 min. M/Z=343.3.

Compound 333 was prepared according to the synthetic procedures described for Compound 332 from the appropriate starting materials.

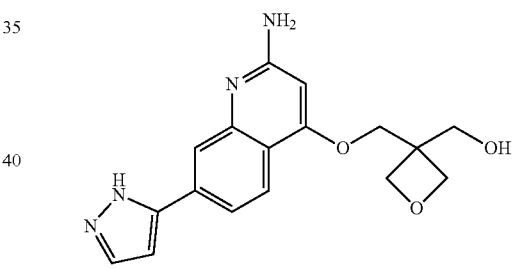

¹H NMR (500 MHz, DMSO-d₆) δ 7.84 (d, J=8.3 Hz, 1H), 7.81 (s, 1H), 7.74 (d, J=1.3 Hz, 1H), 7.59 (dd, J=8.3, 1.0 Hz, 1H), 6.78 (s, 1H), 6.33 (s, 2H), 6.26 (s, 1H), 4.55 (d, J=5.6 Hz, 1H), 4.49 (d, J=5.1 Hz, 1H), 4.28 (s, 2H), 3.82 (s, 2H). LC RT: 0.93 min. M/Z=326.9.

Example III-11: Synthesis of 4-alkoxy Substituted Quinolines by $Sn_{Ar}$ on 7-bromo-4-chloroquinolin-2-amine

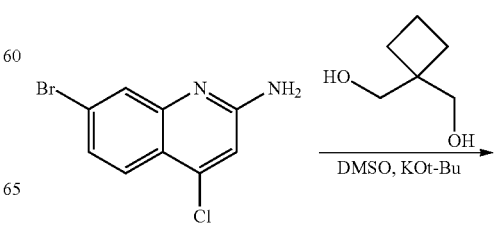

241

-continued

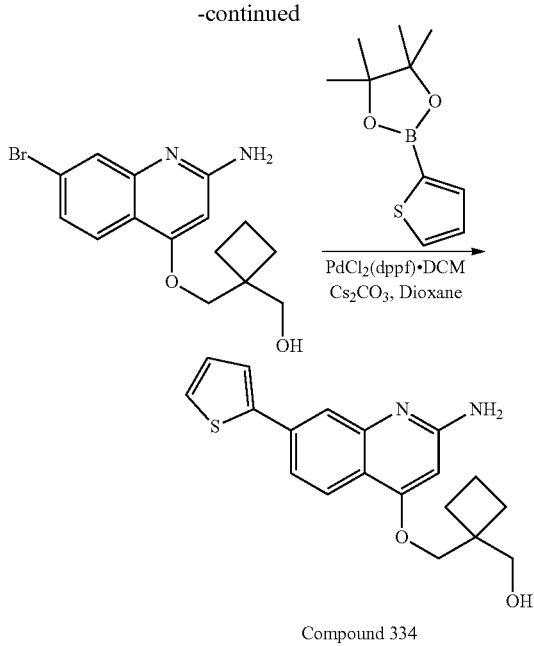

Compound 334

Step 1. Preparation of (1-(((2-amino-7-bromoquinolin-4-yl)oxy)methyl)cyclobutyl)methanol (1-(((2-amino-7-bromoquinolin-4-yl)oxy)methyl)cyclobutyl)methanol was prepared from cyclobutane-1,1-diyldimethanol and 7-bromo-4-chloroquinolin-2-amine in 89% yield using the procedure for the preparation of (3-(((2-amino-7-bromoquinolin-4-yl)oxy)methyl)oxetan-3-yl)methanol. LCMS method: Waters Acquity SDS using the following method: Linear Gradient of 2% to 98% solvent B over 1.00 min; UV visualization at 220 or 254 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. LC RT: 0.82 min. M/Z=339.2.

Step 2. Preparation of (1-(((2-amino-7-(thiophen-2-yl)quinolin-4-yl)oxy)methyl)cyclobutyl)methanol (Compound 334)

A suspension of 4,4,5,5-tetramethyl-2-(thiophen-2-yl)-1,3,2-dioxaborolane (24.92 mg, 0.119 mmol), (1-(((2-amino-7-bromoquinolin-4-yl)oxy)methyl)cyclobutyl)methanol (20 mg, 0.059 mmol), cesium carbonate (58.0 mg, 0.178 mmol), and PdCl$_2$(dppf)-CH$_2$Cl$_2$ adduct (4.84 mg, 5.93 μmol) in nitrogen-saturated dioxane (593 μl) was placed under nitrogen and heated at 95° C. for 1.5 h. The reaction was then cooled to room temperature, quenched with 50% aq. HOAc, filtered, and filtered. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to afford (1-(((2-amino-7-(thiophen-2-yl)quinolin-4-yl)oxy)methyl)cyclobutyl)methanol (11.2 mg, 56% yield). $^1$H NMR (500 MHz, DMSO-d$_6$) δ 7.84 (d, J=8.4 Hz, 1H), 7.61 (d, J=1.6 Hz, 1H), 7.56-7.60 (m, 2H), 7.47 (dd, J=8.4, 1.8 Hz, 1H), 7.17 (dd, J=4.7, 3.9 Hz, 1H), 6.40 (s, 2H), 6.24 (s, 1H), 4.06 (s, 2H), 1.87-2.00 (n, 6H). One methylene is not visible, likely due to overlap with the suppressed water peak. LC RT: 1.79 min. M/Z=341.2.

Compound 335 through Compound 337 were prepared according to the synthetic procedures described for Compound 334 from the appropriate starting materials.

| Compd. No. | Structure | LC/MS [M + H]$^+$ | RT (min) | $^1$H NMR (500 MHz, DMSO-d$_6$) |
|---|---|---|---|---|
| 335 | 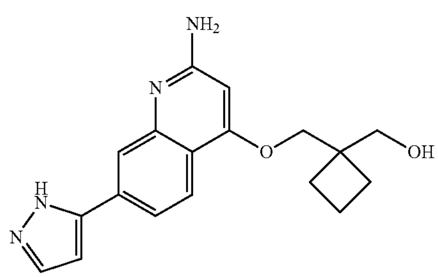 [SMILES: Nc1cc(OCC2(CO)CCC2)c2ccc(-c3ccn[nH]3)cc2n1] | 325.2 | 1.21 | δ 7.84 (d, J = 8.4 Hz, 1H), 7.81 (s, 1H), 7.74 (d, J = 0.7 Hz, 1H), 7.59 (dd, J = 8.5, 0.6 Hz, 1H), 6.78 (d, J = 2.0 Hz, 1H), 6.35 (s, 2H), 6.23 (s, 1H), 4.06 (s, 2H), 1.89-2.00 (m, 6H). One methylene group is not visible, likely due to water suppression. |
| 336 | 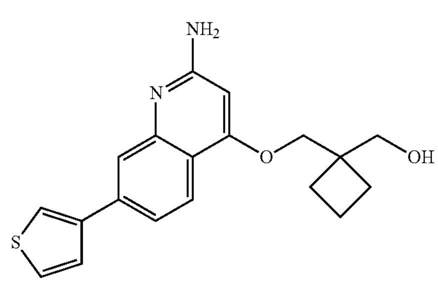 [SMILES: Nc1cc(OCC2(CO)CCC2)c2ccc(-c3ccsc3)cc2n1] | 341.2 | 1.79 | δ 7.94-7.97 (m, 1H), 7.84 (d, J = 8.4 Hz, 1H), 7.70 (br. s, 1H), 7.65-7.68 (m, 1H), 7.61-7.64 (m, 1H), 7.53 (dd, J = 8.5, 1.5 Hz, 1H), 6.42 (br. s, 2H), 6.24 (s, 1H), 4.06 (s, 2H), 1.90-1.98 (m, 6H). One methylene group is not visible, likely due to water suppression. |

| Compd. No. | Structure | LC/MS [M + H]+ | RT (min) | 1H NMR (500 MHz, DMSO-d6) |
|---|---|---|---|---|
| 337 | 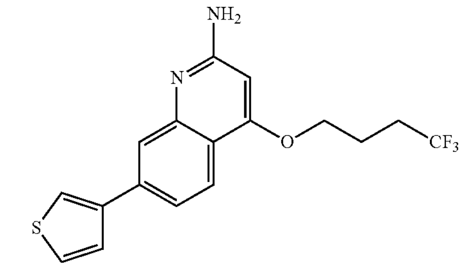 [SMILES: Nc1cc(OCCCC(F)(F)F)c2ccc(-c3ccsc3)cc2n1] | 352.9 | 1.95 | δ 8.04 (br s, 1H), 8.00 (d, J = 8.2 Hz, 1H), 7.78 (br. s, 1H), 7.67-7.73 (m, 2H), 7.61-7.64 (m, 1H), 7.46 (br. s, 2H), 6.29 (s, 1H), 4.28 (t, J = 4.6 Hz, 2H), 2.08-2.16 (m, 2H). Two protons from sidechain are not visible, likely due to overlap with DMSO-d6 peak. |

Example III-12: Synthesis of 4-amino Substituted Quinolines Using N-(7-bromo-4-chloroquinolin-2-yl)benzamide

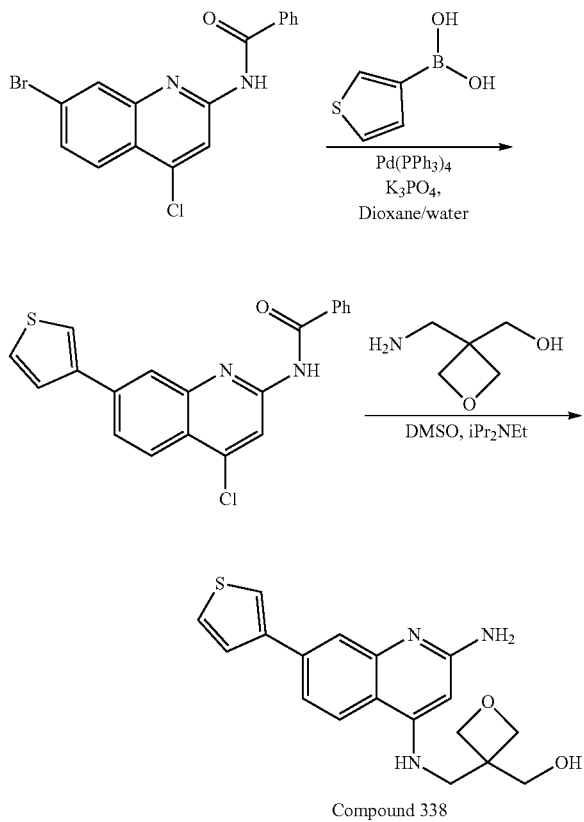 [SMILES: O=C(Nc1cc(Cl)c2ccc(Br)cc2n1)c1ccccc1 ; OB(O)c1ccsc1 ; O=C(Nc1cc(Cl)c2ccc(-c3ccsc3)cc2n1)c1ccccc1 ; NCC1(CO)COC1 ; Nc1cc(NCC2(CO)COC2)c2ccc(-c3ccsc3)cc2n1]

Compound 338

Step 1. Preparation of N-(4-chloro-7-(thiophen-3-yl)quinolin-2-yl)benzamide

A reaction vial was charged with N-(7-bromo-4-chloroquinolin-2-yl)benzamide (164 mg, 0.454 mmol), thiophen-3-ylboronic acid (75 mg, 0.590 mmol), and potassium phosphate (337 mg, 1.587 mmol). Dioxane (6.25 mL) and water (0.25 mL) were then added. The reaction was degassed for 10 minutes with a stream of nitrogen. Tetrakis(triphenylphosphine)palladium(0) (52.4 mg, 0.045 mmol) was then added and the vial was sealed and warmed to 90° C. After three hours, the cooled reaction was partitioned between water and ethyl acetate. The water layer was extracted with an additional portion of ethyl acetate. The combined organic layers were then washed with brine. Drying over magnesium sulfate, filtration and evaporation provided the crude product. The product was purified on a 24 g silica gel column, eluting with 20-100% ethyl acetate in hexanes. Evaporation of the product containing fractions provided N-(4-chloro-7-(thiophen-3-yl)quinolin-2-yl)benzamide (158 mg, 0.433 mmol, 95% yield). 1H NMR (400 MHz, DMSO-d6) δ 11.35 (br s, 1H), 8.53 (s, 1H), 8.20 (m, 1H), 8.17 (s, 2H), 8.12-8.05 (m, 3H), 7.79-7.71 (m, 2H), 7.64 (t, J=7.2 Hz, 1H), 7.55 (t, J=7.8 Hz, 2H).

Step 2. Preparation of (3-(((2-amino-7-(thiophen-3-yl)quinolin-4-yl)amino)methyl)oxetan-3-yl)methanol (Compound 338)

A reaction vial was charged with N-(4-chloro-7-(thiophen-3-yl)quinolin-2-yl)benzamide (21.2 mg, 0.058 mmol) in dimethylsulfoxide (0.75 mL). (3-(Aminomethyl)oxetan-3-yl)methanol hydrochloride (44.6 mg, 0.291 mmol) and diisopropylethylamine (60.9 μl, 0.349 mmol) were added and the vial was flushed with nitrogen. The reaction was then warmed to 120° C. and stirred overnight. The cooled reaction was diluted with DMSO (1 mL) and purified by preparative LC using the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give (3-(((2-amino-7-(thiophen-3-yl)quinolin-4-yl)amino)methyl)oxetan-3-yl)methanol (7.0 mg, 0.021 mmol, 35%). 1H NMR (500 MHz, DMSO-d6) δ 8.01 (br s, 1H), 7.87 (d, J=8.9 Hz, 1H), 7.71 (s, H), 7.71-7.68 (m, 1H), 7.60 (d, J=4.9 Hz, 1H), 7.57 (br d, J=8.9 Hz, 1H), 6.91 (br s, 2H), 5.49 (s, 1H), 4.11 (br s, 4H), 3.59 (s, 4H). LC/MS conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). LC RT: 1.13 min. M/Z=341.92.

Example III-13: Synthesis of 4-heteroaryl Substituted Quinolines

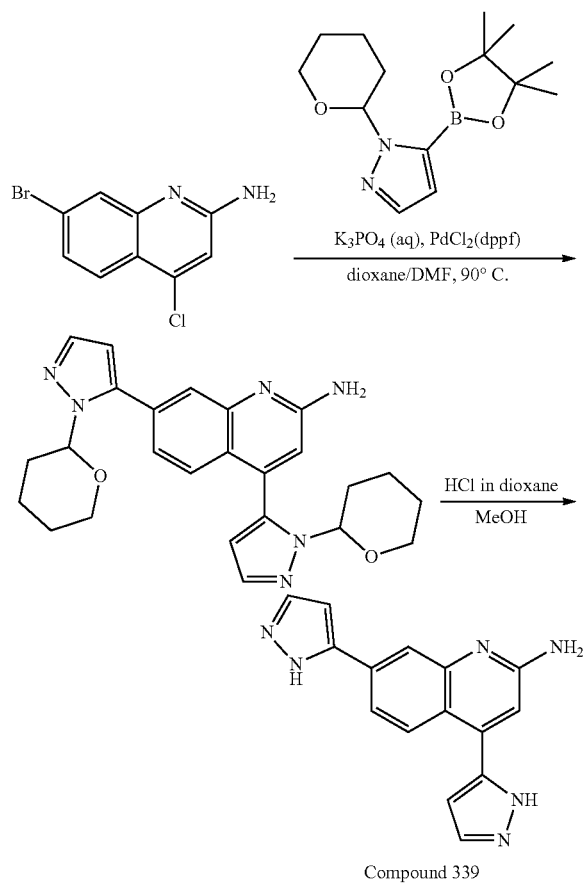

Compound 339

Step 1. Preparation of 4,7-bis(1-(tetrahydro-2H-pyran-2-yl)-1H-pyrazol-5-yl)quinolin-2-amine To a solution of 7-bromo-4-chloroquinolin-2-amine (431.2 mg, 1.67 mmol) in anhydrous dioxane (5 ml) and anhydrous DMF (5 ml), at room temperature under nitrogen atmosphere, was added $K_3PO_4$ (2M aq. solution, 2.51 ml, 5.02 mmol) followed by 1-(tetrahydro-2h-pyran-2-yl)-5-(4,4,5,5-tetramethyl-1,3,2-dioxaborolan-2-yl)-1h-pyrazole (605 mg, 2.18 mmol). The mixture was sparged with argon for approximately thirty minutes before $PdCl_2(dppf) \cdot CH_2Cl_2$ (68.4 mg, 0.084 mmol) was added and the mixture was heated, with stirring, at 90° C. After 12 hours, the reaction was allowed to cool to room temperature before being partitioned between DCM and water. The layers were separated and the aqueous layer was extracted twice more with DCM. These organic extracts were combined with the original organic layer and were washed with brine, dried over anhydrous sodium sulfate, filtered through a pad of Celite then concentrated in vacuo to afford a dark brown oil. The crude product was purified by silica gel chromatography (Isco CombiFlash; RediSep normal phase silica flash column (40 g); EtOAc in hexane; 0-100% gradient) to afford the title compound as an oil (87.5 mg; 11.8% yield). $^1$H NMR (400 MHz, DMSO-d$_6$) δ 7.75-7.72 (m, 1H), 7.69 (d, J=1.4 Hz, 1H), 7.60 (d, J=1.6 Hz, 1H), 7.47 (dd, J=8.4, 1.7 Hz, 1H), 7.28 (dd, J=8.5, 1.3 Hz, 1H), 6.88-6.83 (m, 1H), 6.77 (s, 2H), 6.57-6.51 (m, 2H), 5.34-5.27 (m, 1H), 5.07 (br dd, J=7.0, 2.2 Hz, 1H), 3.92-3.83 (m, 1H), 3.63-3.53 (m, 1H), 2.49-2.27 (m, 4H), 1.92 (br d, J=12.4 Hz, 2H), 1.79 (br d, J=12.7 Hz, 2H), 1.62-1.42 (m, 6H). LC/MS Conditions: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. MS (ES): m/z=445 [M+H]$^+$. T$_r$=0.71 min.

Step 2. Preparation of 4,7-di(1H-pyrazol-5-yl)quinolin-2-amine, HCl (Compound 339)

To a solution of 4,7-bis(1-(tetrahydro-2H-pyran-2-yl)-1H-pyrazol-5-yl)quinolin-2-amine (87.5 mg, 0.197 mmol) in MeOH (1 ml), at room temperature in a sealable reaction vial, was added HCl (4N in dioxane; 0.3 ml, 1.20 mmol). The vial was capped and the resulting solution was stirred for twenty minutes before being concentrated in vacuo to afford a tan solid. The crude material was dissolved in MeOH, filtered through an Acrodisc 13 mm 0.45 μm syringe filter then purified by RP Prep HPLC with the following conditions: Column: Phen Axia C18 30×100, 5 μm particle size; Mobile Phase A:=90:10 H2O:MeOH with 0.1% trifluoroacetic acid; Mobile Phase B:=10:90 H$_2$O:MeOH with 0.1% trifluoroacetic acid; Run time=20 minutes using 10 minute gradient from 20 to 100% Mobile Phase B; Flow rate=40 mL/minute. Fractions containing desired product, as determined by LCMS, were combined and concentrated in vacuo to remove volatiles. The resultant residue was treated with HCl (4N in dioxane; 0.3 ml, 1.20 mmol) and stirred at ambient temperature for ten minutes before being concentrated in vacuo to afford the title compound as a pale yellow solid (38.4 mg; 61.8% yield) as the HCl salt. $^1$H NMR (DMSO-d$_6$): δ 8.84-8.62 (m, 2H), 8.16 (d, J=1.4 Hz, 1H), 8.04 (d, J=2.3 Hz, 1H), 7.97 (dd, J=8.7, 1.6 Hz, 1H), 7.88 (d, J=2.2 Hz, 1H), 7.30 (s, 1H), 6.91-6.85 (m, 2H), 6.00-5.11 (m, 3H). Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. T$_r$=0.55 min. MS (ES): m/z=277 [M+H]$^+$.

Example III-14: Synthesis of 4-aminoethyl Substituted Quinolines

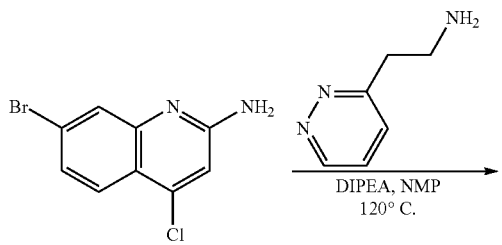

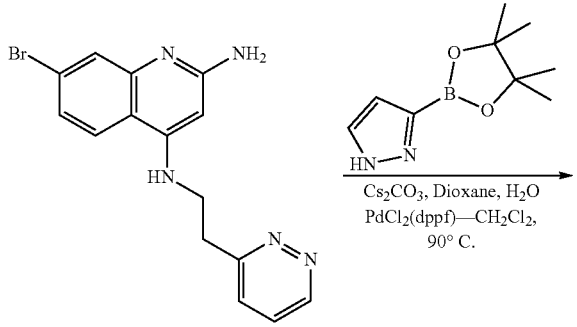

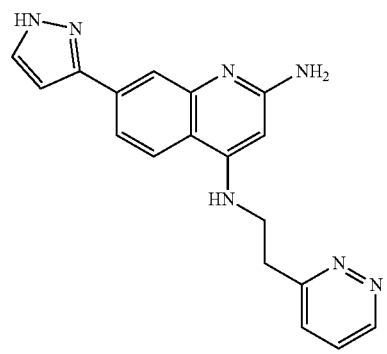

Compound 340

Step 1. Preparation of 7-bromo-N4-(2-(pyridazin-3-yl)ethyl)quinolin-2,4-diamine To a homogeneous mixture of 7-bromo-4-chloroquinolin-2-amine (150 mg, 0.58 mmol) in NMP (2 mL), in a sealable reaction vial, was added 2-pyridazin-3-ylethanamine (100 mg, 0.81 mmol) followed by DIPEA (0.42 mL, 2.40 mmol). The vial was capped and the mixture was stirred and heated at 120° C. for 15 hours. After cooling to room temperature, the reaction mixture was purified directly by silica gel chromatography (Isco CombiFlash; RediSep normal phase silica flash column (24 g); MeOH in DCM; 0-20% gradient) to afford the title compound as a yellow residue (101.4 mg; 45.5% yield).

LC/MS conditions: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 mi/min; Mobile phase A: 100% Water, 0.05% TFA; Mobile phase B: 100% Acetonitrile, 0.05% TFA. $T_r$=0.62 min. MS (ES): m/z=344 [M+H]$^+$.

Step 2. Preparation of 7-(1H-pyrazol-3-yl)-N4-(2-(pyridazin-3-yl)ethyl)quinolin-2,4-diamine (Compound 340)

A mixture of 7-bromo-N4-(2-(pyridazin-3-yl)ethyl)quinoline-2,4-diamine (20 mg, 0.06 mmol), 3-(4,4,5,5-tetramethyl-1,3,2-dioxaborolane)-pyrazole (24.80 mg, 0.13 mmol) and Cs$_2$CO$_3$ (56.8 mg, 0.17 mmol) in dioxane (1.5 mL) and water (0.2 mL), in a sealable reaction vial, was sparged with argon for approximately ten minutes before PdCl$_2$(dppf)-CH$_2$Cl$_2$ adduct (9.49 mg, 0.012 mmol) was added. The vial was sealed and the reaction was heated at 90° C. for 18 hours. After cooling to room temperature, the reaction was concentrated in vacuo to remove volatiles, dissolved in DMF then purified by preparative HPLC/MS via the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to afford the title compound (9.7 mg; 47.5% yield). $^1$H NMR (500 MHz, DMSO-d$_6$) δ 9.11 (br d, J=3.1 Hz, 1H), 8.24-8.17 (m, 1H), 8.14 (br d, J=8.5 Hz, 1H), 7.97-7.88 (m, 1H), 7.87-7.79 (m, 2H), 7.70-7.57 (m, 3H), 6.85 (d, J=1.2 Hz, 1H), 5.90 (s, 1H), 3.81-3.72 (m, integral distorted by water suppression), 3.33 (br t, J=7.2 Hz, integral distorted by water suppression). LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.76 min. M/Z=332.12.

Compound 341: N4-(2-(pyridazin-3-yl)ethyl)-7-(thiophen-3-yl)quinolin-2,4-diamine

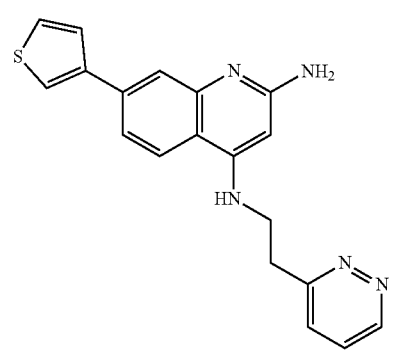 [SMILES: Nc1cc(NCCc2cccnn2)c2ccc(-c3ccsc3)cc2n1]

Compound 341 (8.8 mg; 41.7% yield) was prepared following a procedure analogous to that for the synthesis of Compound 340, except that 4,4,5,5-tetramethyl-2-(thiophen-3-yl)-1,3,2-dioxaborolane (26.9 mg; 0.13 mmol) was used instead of 3-(4,4,5,5-tetramethyl-1,3,2-dioxaborolane)-pyrazole. $^1$H NMR (500 MHz, DMSO-d$_6$) δ 9.17-9.04 (m, 1H), 8.25-8.18 (m, 1H), 8.17-8.11 (m, 1H), 8.09-8.03 (m, 1H), 7.79-7.70 (m, 3H), 7.68-7.59 (m, 4H), 5.90 (s, 1H), 3.77 (q, J=6.5 Hz, integral distorted by water suppression), 3.33 (t, J=7.2 Hz, integral distorted by water suppression). LC RT: 1.27 min. M/Z=348.08.

Compound 342: N4-(2-(pyridazin-3-yl)ethyl)-7-(thiophen-2-yl)quinolin-2,4-diamine

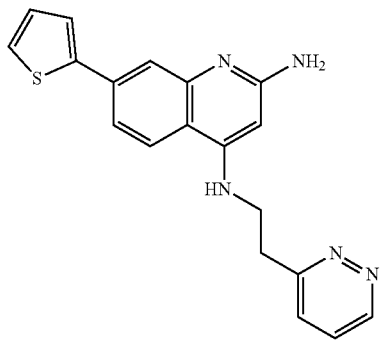 [SMILES: Nc1cc(NCCc2cccnn2)c2ccc(-c3cccs3)cc2n1]

Compound 342 (8.6 mg; 40.8% yield) was prepared following a procedure analogous to that for the synthesis of Compound 340), except that 4,4,5,5-tetramethyl-2-(thiophen-2-yl)-1,3,2-dioxaborolane (26.9 mg; 0.13 mmol) was used instead of 3-(4,4,5,5-tetramethyl-1,3,2-dioxaborolane)-pyrazole. $^1$H NMR (500 MHz, DMSO-$d_6$) δ 9.19-8.98 (m, 1H), 8.19 (br t, J=5.2 Hz, 1H), 8.10 (d, J=8.5 Hz, 1H), 7.73-7.57 (m, 6H), 7.24-7.17 (m, 1H), 5.87 (s, 1H), 3.76-3.72 (m, integral distorted by water suppression), 3.31 (t, J=7.2 Hz, integral distorted by water suppression). LC RT: 1.23 min. M/Z=348.10.

Example III-15: Preparation of 7-(1H-pyrazol-1-yl)-N4-(2-(pyridazin-3-yl)ethyl)quinoline-2,4-diamine (Compound 343)

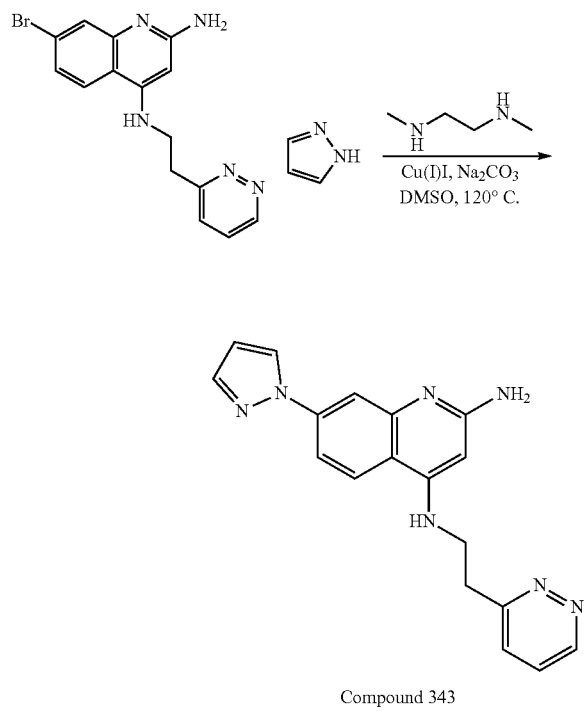

Compound 343

To a mixture of 7-bromo-N4-(2-(pyridazin-3-yl)ethyl)quinoline-2,4-diamine (20 mg, 0.06 mmol) in anhydrous DMSO (2.9 mL), in a sealable reaction vial, was added 1H-pyrazole (7.91 mg, 0.12 mmol) and copper(I) iodide (22.13 mg, 0.12 mmol) followed by Na$_2$CO$_3$ (24.63 mg, 0.23 mmol). The homogeneous mixture was sparged with argon for approximately 5 minutes before N,N'-dimethylethylenediamine (0.02 mL, 0.19 mmol) was added. The vial was capped and the reaction heated at 120° C. with stirring. After 18 hours, the reaction was cooled to room temperature, diluted with DMSO, then purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 5% B, 5-45% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to afford the title compound (7.5 mg; 37.2% yield). $^1$H NMR (500 MHz, DMSO-$d_6$) δ 9.08 (br d, J=3.1 Hz, 1H), 8.51 (d, J=2.1 Hz, 1H), 8.01 (d, J=9.2 Hz, 1H), 7.80-7.71 (m, 2H), 7.68-7.60 (m, 2H), 7.41-7.23 (m, 1H), 6.74-6.50 (m, 2H), 5.84 (s, 1H), 3.77-3.59 (m, integral distorted by water suppression), 3.30 (br t, J=7.0 Hz, 2H). LC/MS Conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.83 min. M/Z=332.12.

Example III-16: 7-(1H-pyrazol-3-yl)-N4-(2-(tetrahydro-2H-pyran-4-yl)ethyl)quinoline-2,4-diamine (Compound 344)

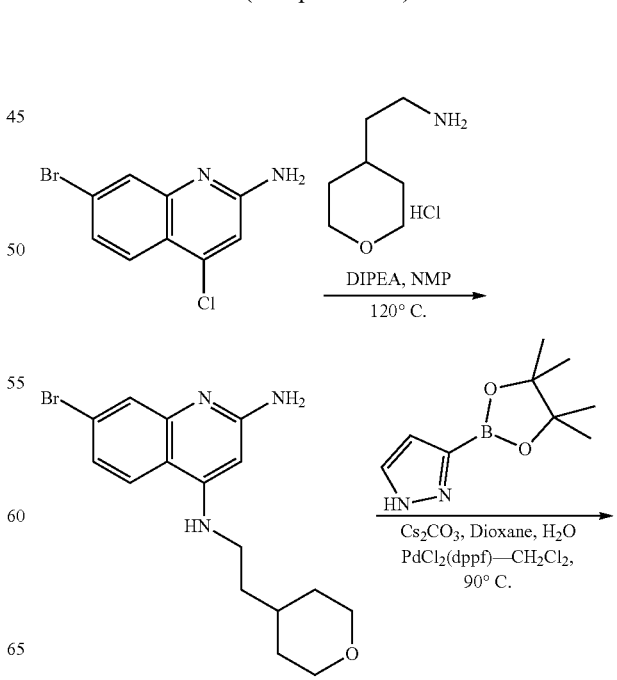

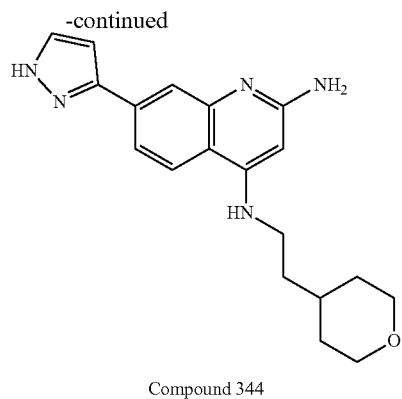

Compound 344

Step 1. Preparation of 7-bromo-N4-(2-(tetrahydro-2H-pyran-4-yl)ethyl)quinoline-2,4-diamine To a homogeneous mixture of 7-bromo-4-chloroquinolin-2-amine (100 mg, 0.39 mmol) in NMP (0.5 mL), in a sealable reaction vial, was added 4-(2-aminoethyl)tetrahydropyran hydrochloride (90 mg, 0.54 mmol) followed by DIPEA (0.35 mL, 2.00 mmol). The vial was capped and the mixture was stirred and heated at 120° C. for 20 hours. After cooling to room temperature, the reaction was partitioned between EtOAc and brine. The layers were separated and the aqueous layer was extracted once more with EtOAc. The organic layers were combined, dried ($Na_2SO_4$), filtered and concentrated in vacuo to afford a gold oil which was purified directly by silica gel chromatography (Isco CombiFlash; RediSep normal phase silica flash column (12 g); MeOH in DCM; 0-20% gradient) to afford the title compound as an off-white solid (93.0 mg; 68.4% yield). $^1$H NMR (400 MHz, DMSO-$d_6$) δ 8.20-8.09 (m, 1H), 7.93 (br s, 1H), 7.69 (d, J=2.0 Hz, 1H), 7.55-7.24 (m, 3H), 5.80 (s, 1H), 3.85 (dd, J=11.1, 3.5 Hz, 2H), 3.30-3.25 (m, 4H), 1.62 (br t, J=11.8 Hz, 5H), 1.33-1.13 (m, 2H). LC/MS Conditions: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. $T_r$=0.70 min. MS (ES): m/z=350 [M+H]$^+$.

Step 2. Preparation of 7-(1H-pyrazol-3-yl)-N4-(2-(tetrahydro-2H-pyran-4-yl)ethyl)quinoline-2,4-diamine diamine (Compound 344)

A mixture of 7-bromo-N4-(2-(tetrahydro-2H-pyran-4-yl)ethyl)quinoline-2,4-diamine (18 mg, 0.05 mmol), 3-(4,4,5,5-tetramethyl-1,3,2-dioxaborolane)-pyrazole (21.9 mg, 0.11 mmol) and $Cs_2CO_3$ (50.2 mg, 0.15 mmol) in dioxane (1.5 mL) and water (0.2 mL), in a sealable reaction vial, was sparged with argon for approximately ten minutes before $PdCl_2$(dppf)-$CH_2Cl_2$ adduct (8.39 mg, 0.010 mmol) was added. The vial was sealed and the reaction was heated at 90° C. for 17 hours. After cooling to room temperature, the reaction was concentrated in vacuo to remove volatiles, dissolved in DMF then purified by preparative HPLC/MS via the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to afford the title compound (17.2 mg; 97% yield). $^1$H NMR (500 MHz, DMSO-$d_6$) δ 8.22 (br d, J=8.5 Hz, 1H), 8.12-8.03 (m, 1H), 7.97-7.90 (m, 1H), 7.90-7.80 (m, 2H), 7.59 (br s, 2H), 6.85 (s, 1H), 5.79 (s, 1H), 3.85 (br dd, J=11.3, 3.1 Hz, 2H), 3.44-3.24 (m, integral distorted by water suppression), 1.70-1.43 (m, 6H), 1.31-1.18 (m, 2H). Some protons are unobserved either due to overlap with suppressed water peak or low integration. LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 1.12 min. M/Z=338.26.

Compound 345: N4-(2-(tetrahydro-2H-pyran-4-yl)ethyl)-7-(thiophen-3-yl)quinoline-2,4-diamine

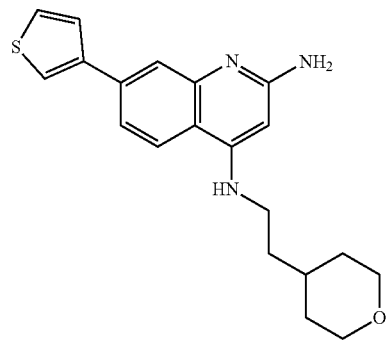 [SMILES: Nc1cc(NCCC2CCOCC2)c2ccc(-c3ccsc3)cc2n1]

Compound 345 (15.3 mg; 84% yield) was prepared following a procedure analogous to that for the synthesis of Compound 344, except that 4,4,5,5-tetramethyl-2-(thiophen-3-yl)-1,3,2-dioxaborolane (23.8 mg; 0.11 mmol) was used instead of 3-(4,4,5,5-tetramethyl-1,3,2-dioxaborolane)-pyrazole. $^1$H NMR (500 MHz, DMSO-$d_6$) δ 8.26-8.19 (m, 1H), 8.14-8.05 (m, 2H), 7.81-7.77 (m, 1H), 7.76-7.71 (m, 2H), 7.65-7.52 (m, 3H), 5.80 (s, 1H), 3.85 (br dd, J=11.3, 3.4 Hz, 2H), 3.45-3.25 (m, integral distorted by water suppression), 1.68-1.58 (m, 5H), 1.30-1.18 (m, 2H). Protons may be unobserved either due to overlap with suppressed water peak or low integration. LC RT: 1.62 min. M/Z=354.06.

Example III-17: 7-(1H-pyrazol-1-yl)-N4-(2-(tetrahydro-2H-pyran-4-yl)ethyl)quinoline-2,4-diamine (Compound 346)

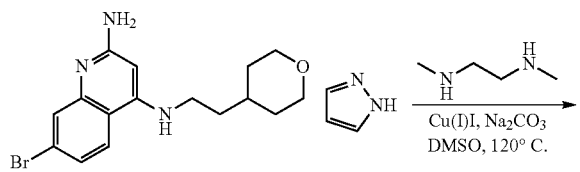

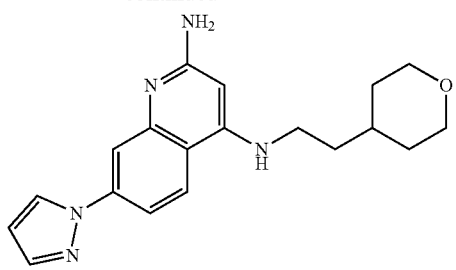

Compound 346

To a mixture of 7-bromo-N4-(2-(tetrahydro-2H-pyran-4-yl)ethyl)quinoline-2,4-diamine (17.5 mg, 0.05 mmol) in anhydrous DMSO (2.5 mL), in a sealable reaction vial, was added 1H-pyrazole (6.80 mg, 0.10 mmol) and copper(I) iodide (19.03 mg, 0.10 mmol) followed by $Na_2CO_3$ (21.18 mg, 0.20 mmol). The homogeneous mixture was sparged with Argon for approximately 5 minutes before N,N'-dimethylethylenediamine (0.02 mL, 0.19 mmol) was added. The vial was capped and the reaction heated at 120° C. with stirring. After 18 hours, the reaction was cooled to room temperature, diluted with DMSO, then purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 6% B, 6-46% B over 28 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford the title compound (13.3 mg; 76% yield). $^1$H NMR (500 MHz, DMSO-$d_6$) δ 8.56 (br s, 1H), 8.18-8.03 (m, 1H), 7.83-7.70 (m, 2H), 7.60 (br dd, J=8.6, 2.0 Hz, 1H), 7.16-6.94 (m, 1H), 6.76-6.51 (m, 3H), 5.87-5.63 (m, 1H), 3.87-3.78 (m, 1H), 3.69-3.58 (m, 3H), 3.37-3.17 (m, 2H), 1.69-1.56 (m, 5H), 1.28-1.14 (m, 2H). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 1.24 min. M/Z=337.91.

Example III-18: 4-(1H-pyrazol-4-yl)-7-(1H-pyrazol-5-yl)quinolin-2-amine (Compound 347)

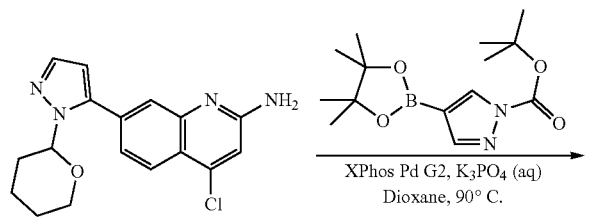

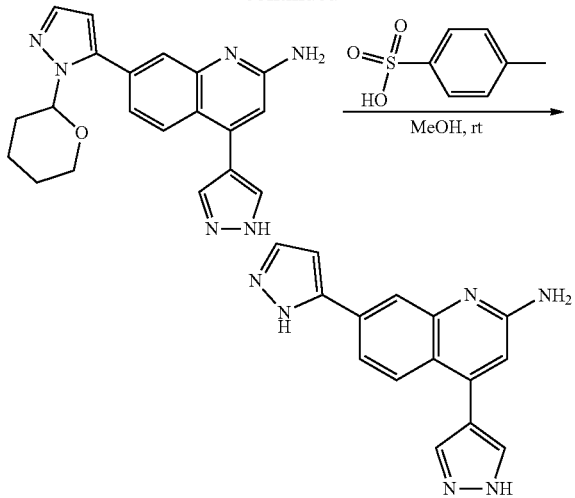

Compound 347

Step 1. Preparation of 4-(1H-pyrazol-4-yl)-7-(1-(tetrahydro-2H-pyran-2-yl)-1H-pyrazol-5-yl)quinolin-2-amine To a mixture of 4-chloro-7-(1-(tetrahydro-2H-pyran-2-yl)-1H-pyrazol-5-yl)quinolin-2-amine (48.3 mg, 0.15 mmol) and 1-Boc-pyrazole-4-boronic acid pinacol ester (43.2 mg, 0.15 mmol) in anhydrous dioxane (3 mL), in a sealable reaction vial, was added potassium phosphate (2M aqueous; 0.22 mL; 0.44 mmol). The resulting mixture was sparged with argon for approximately 10 min before Xphos Pd G2 (CAS: 1310584-14-5; 5.78 mg, 7.34 μmol) was added. The mixture was sparged with argon for approximately 2 minutes before the vial was sealed and the mixture stirred at 65° C. After 14 hours, the reaction was cooled to room temperature then purified by silica gel chromatography (Isco CombiFlash; RediSep normal phase silica flash column (12 g); MeOH in DCM; 0-20% gradient) to afford the title compound as a yellow residue (31.0 mg; 58.6% yield). Waters Acquity SDS using the following method: Linear Gradient of 2% to 98% solvent B over 1.7 min; UV visualization at 220 nm; Column: BEH C18 2.1 mm×50 mm; 1.7 um particle (Heated to Temp. 50° C.); Flow rate: 0.8 ml/min; Mobile phase A: 100% Water, 0.05% TFA; Mobile phase B: 100% Acetonitrile, 0.05% TFA. $T_r$=0.66 min. MS (ES): m/z=361 [M+H]$^+$.

Step 2. Preparation of 4-(1H-pyrazol-4-yl)-7-(1H-pyrazol-5-yl)quinolin-2-amine (Compound 347)

To a solution of 4-(1H-pyrazol-4-yl)-7-(1-(tetrahydro-2H-pyran-2-yl)-1H-pyrazol-5-yl)quinolin-2-amine (31.0 mg, 0.09 mmol) in anyhydrous MeOH (1 mL), at room temperature under nitrogen, was added p-toluenesulfonic acid (4.2 mg, 0.024 mmol). The resulting mixture was stirred at ambient temperature for one hour then concentrated in vacuo to remove volatiles. The crude material was dissolved in DMF, filtered through an Acrodisc 13 mm 0.45 μm syringe filter then purified by RP Prep HPLC with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 2% B, 2-42% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford the title compound (1.7 mg; 6.8%). $^1$H NMR (500 MHz, DMSO-d$_6$) δ 8.11-7.94 (m, 2H), 7.92-7.84 (m, 2H), 7.78-7.70 (m, 1H), 7.68-7.58 (m, 1H), 6.79 (d, J=1.4 Hz, 1H), 6.72 (s, 1H), 6.38 (br s, 2H). Protons may be unobserved either due to overlap with suppressed water peak or low integration. LC/MS conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.71 min. M/Z=277.04.

Compound 348: 2-(4-(2-amino-7-(1H-pyrazol-5-yl)quinolin-4-yl)-1H-pyrazol-1-yl)ethan-1-ol

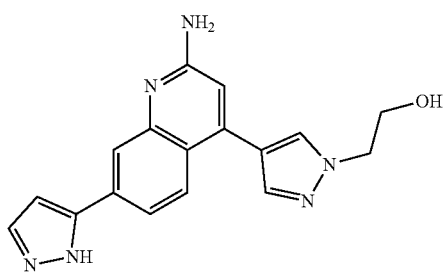 [SMILES: Nc1cc(-c2cnn(CCO)c2)c2ccc(-c3ccn[nH]3)cc2n1]

Compound 348) (1.3 mg; 3.3% yield) was prepared following a procedure analogous to that for the synthesis of Compound 347, except that 2-(4-(4,4,5,5-tetramethyl-1,3,2-dioxaborolan-2-yl)-1h-pyrazol-1-yl)ethanol (35.0 mg, 0.15 mmol) was used instead of 1-Boc-pyrazole-4-boronic acid pinacol ester. $^1$H NMR (500 MHz, DMSO-d$_6$) δ 8.29-8.16 (m, 1H), 8.04-7.92 (m, 2H), 7.90-7.83 (m, 1H), 7.82-7.55 (m, 2H), 6.88-6.68 (m, 2H), 4.27 (t, J=5.3 Hz, 2H), 3.88-3.74 (m, 2H). Protons may be unobserved either due to overlap with suppressed water peak or low integration. LC RT: 0.80 min. M/Z=321.07.

Example III-19: Preparation of (R)-1-((2-amino-7-(1H-pyrazol-5-yl)quinolin-4-yl)oxy)-3-morpholinopropan-2-ol (Compound 349)

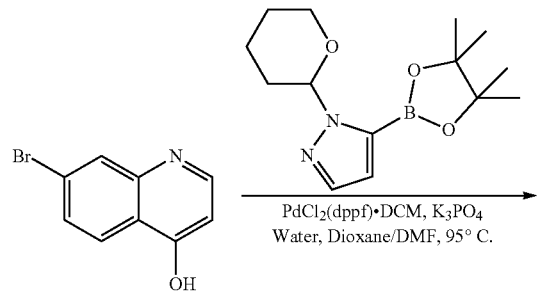

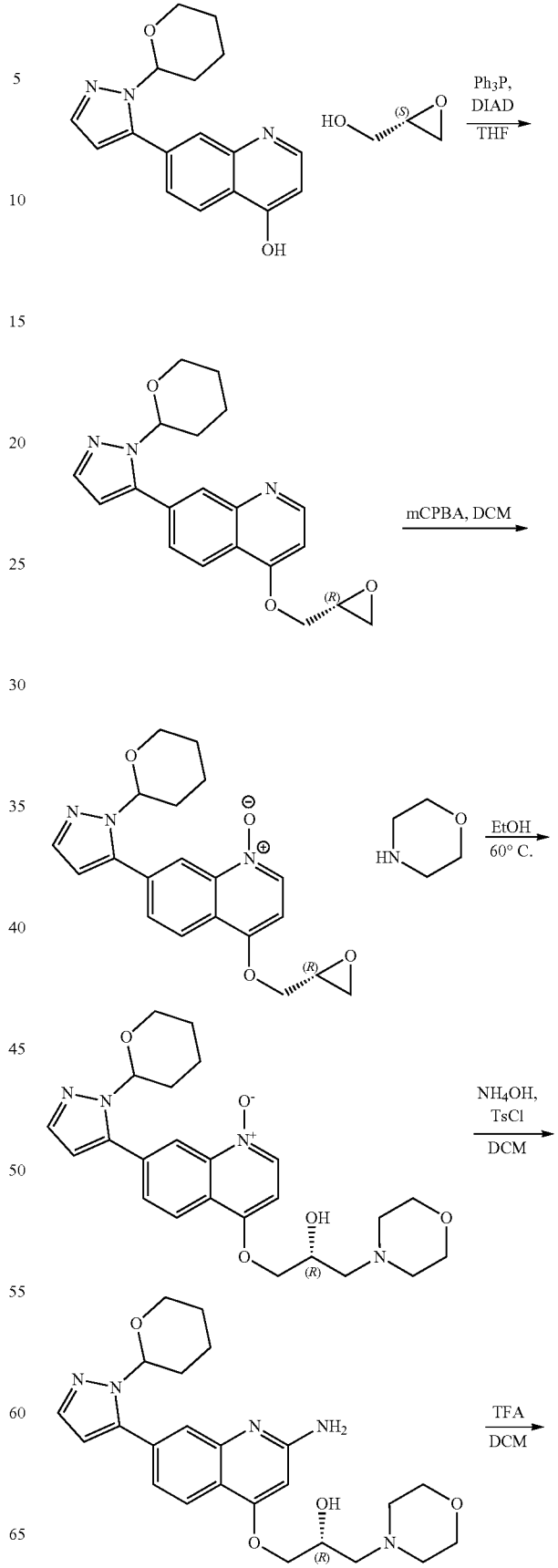

-continued

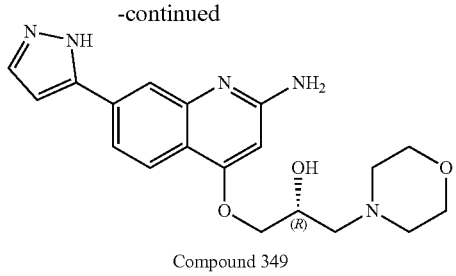

Compound 349

Step 1: Preparation of 7-(1-(tetrahydro-2H-pyran-2-yl)-1H-pyrazol-5-yl)quinolin-4-ol 7-Bromoquinolin-4-ol (1.5 g, 6.69 mmol) and 1-(tetrahydro-2H-pyran-2-yl)-5-(4,4,5,5-tetramethyl-1,3,2-dioxaborolan-2-yl)-1H-pyrazole (2.421 g, 8.70 mmol) were suspended in a 1:1 mixture of Dioxane:DMF (33 mL). Nitrogen gas was bubbled through the reaction mixture for 5 min, then $PdCl_2$(dppf)-$CH_2Cl_2$ adduct (0.273 g, 0.335 mmol) was added followed by aqueous tripotassium phosphate (2M, 10.04 mL, 20.08 mmol). Nitrogen gas was bubbled through the reaction mixture for another 5 minutes. The reaction was then heated under $N_2$ for 16 h. After cooling to rt, the reaction mixture was partitioned between EtOAc and $H_2O$. The organic layer was separated and the aqueous phase was extracted with 2 additional portions of EtOAc. The combined organic phases were dried over $Na_2SO_4$, filtered through celite and concentrated. The residue was triturated with $Et_2O$ to afford 7-(1-(tetrahydro-2H-pyran-2-yl)-1H-pyrazol-5-yl)quinolin-4-ol as a light brown solid (1.20 g). $^1$H NMR (400 MHz, DMSO-$d_6$) δ 11.90 (br d, J=5.0 Hz, 1H), 8.18 (d, J=8.4 Hz, 1H), 7.96 (dd, J=7.2, 6.0 Hz, 1H), 7.69 (d, J=1.2 Hz, 1H), 7.63 (d, J=1.6 Hz, 1H), 7.45 (dd, J=8.4, 1.5 Hz, 1H), 6.58 (d, J=1.8 Hz, 1H), 6.08 (d, J=7.3 Hz, 1H), 5.28 (dd, J=9.9, 2.0 Hz, 1H), 4.02 (br d, J=12.5 Hz, 1H), 3.62 (td, J=10.9, 3.3 Hz, 1H), 2.46-2.33 (m, 1H), 1.95 (br d, J=8.6 Hz, 1H), 1.80 (br d, J=13.0 Hz, 1H), 1.66-1.46 (m, 3H).

Step 2. Preparation of 4-(((R)-oxiran-2-yl)methoxy)-7-(1-(tetrahydro-2H-pyran-2-yl)-1H-pyrazol-5-yl)quinoline To a solution of 7-(1-(tetrahydro-2H-pyran-2-yl)-1H-pyrazol-5-yl)quinolin-4-ol (542 mg, 1.84 mmol) in THF (9 mL) was added (S)-oxiran-2-ylmethanol (0.244 mL, 3.67 mmol), triphenylphosphine (1267 mg, 3.67 mmol) and DIAD (0.714 mL, 3.67 mmol). The reaction was stirred for 16 h at room temperature. Additional DIAD (0.200 mL, 1.03 mmol) was added. After 4 h, the reaction was complete by LC/MS. The reaction mixture was concentrated and the residue purified by column chromatography (40 g $SiO_2$, 0 to 30% $CH_2Cl_2$-acetone, gradient elution) to give 4-(((R)-oxiran-2-yl)methoxy)-7-(1-(tetrahydro-2H-pyran-2-yl)-1H-pyrazol-5-yl)quinoline (392.7 mg, 61%). $^1$H NMR (400 MHz, CHLOROFORM-d) δ 8.85-8.78 (m, 1H), 8.35 (d, J=8.6 Hz, 1H), 8.24-8.17 (m, 1H), 7.73-7.68 (m, 1H), 7.68-7.67 (m, 1H), 6.81 (d, J=5.3 Hz, 1H), 6.49 (d, J=1.8 Hz, 1H), 5.36-5.28 (m, 1H), 4.56 (ddd, J=11.1, 2.7, 0.9 Hz, 1H), 4.24-4.12 (m, 2H), 3.65 (td, J=11.7, 2.2 Hz, 1H), 3.54 (dq, J=6.0, 2.9 Hz, 1H), 3.06-3.00 (m, 1H), 2.89 (dt, J=4.8, 2.4 Hz, 1H), 2.72-2.56 (m, 1H), 2.13-2.02 (m, 1H), 1.91 (br d, J=13.1 Hz, 1H), 1.84-1.72 (m, 1H), 1.40-1.24 (m, 2H).

Step 3. Preparation of 4-(((R)-oxiran-2-yl)methoxy)-7-(1-(tetrahydro-2H-pyran-2-yl)-1H-pyrazol-5-yl)quinoline 1-oxide mCPBA (511 mg, 2.22 mmol) was added to a solution of 4-(((R)-oxiran-2-yl)methoxy)-7-(1-(tetrahydro-2H-pyran-2-yl)-1H-pyrazol-5-yl)quinoline (390 mg, 1.11 mmol) in $CH_2Cl_2$ (12.3 mL). The reaction was stirred for 2 h, then quenched with saturated sodium thiosulfate solution. The biphasic mixture was stirred for 0.5 h, then saturated aqueous sodium bicarbonate was added. The reaction was extracted twice with $CH_2Cl_2$. The combined organic layers were washed with brine, dried over sodium sulfate, and concentrated to give 4-(((R)-oxiran-2-yl)methoxy)-7-(1-(tetrahydro-2H-pyran-2-yl)-1H-pyrazol-5-yl)quinoline 1-oxide (408 mg, 1.11 mmol, quantitative yield). $^1$H NMR (400 MHz, CHLOROFORM-d) δ 9.04-8.95 (m, 1H), 8.50 (d, J=6.9 Hz, 1H), 8.35 (dd, J=8.7, 0.7 Hz, 1H), 7.87 (dt, J=8.6, 1.5 Hz, 1H), 7.67 (d, J=1.6 Hz, 1H), 6.74 (d, J=6.9 Hz, 1H), 6.58 (d, J=1.8 Hz, 1H), 5.35-5.30 (m, 1H), 4.68-4.54 (m, 1H), 4.26-4.19 (m, 1H), 4.15 (ddd, J=11.1, 6.2, 3.4 Hz, 1H), 3.84-3.73 (m, 1H), 3.56-3.49 (m, 1H), 3.04 (t, J=4.5 Hz, 1H), 2.90-2.85 (m, 1H), 2.70-2.57 (m, 1H), 2.12-2.04 (m, 1H), 1.92 (br d, J=12.4 Hz, 1H), 1.85-1.73 (m, 1H), 1.38-1.25 (m, 2H)

Step 4. Preparation of 4-((R)-2-hydroxy-3-morpholinopropoxy)-7-(1-(tetrahydro-2H-pyran-2-yl)-1H-pyrazol-5-yl)quinoline 1-oxide 4-(((R)-oxiran-2-yl)methoxy)-7-(1-(tetrahydro-2H-pyran-2-yl)-1H-pyrazol-5-yl)quinoline 1-oxide (59 mg, 0.16 mmol), ethanol (1.6 mL) and morpholine (16.8 mg, 0.193 mmol) was added to a 2 dram pressure vial and the reaction mixture was heated at 60° C. After 3 hours, the reaction was complete by LC/MS. The reaction mixture was concentrated and the residue was dissolved in small amount of $CH_2Cl_2$ followed by the addition of $Et_2O$ which resulted in the formation of a solid. The supernatant was decanted and the solid washed with $Et_2O$. The solid was dried to give 4-((R)-2-hydroxy-3-morpholinopropoxy)-7-(1-(tetrahydro-2H-pyran-2-yl)-1H-pyrazol-5-yl)quinoline 1-oxide (42.7 mg, 59%). $^1$H NMR (400 MHz, CHLOROFORM-d) δ 9.05-8.95 (m, 1H), 8.51 (d, J=6.8 Hz, 1H), 8.31 (d, J=8.6 Hz, 1H), 7.85 (dd, J=8.6, 1.1 Hz, 1H), 7.67 (d, J=1.7 Hz, 1H), 6.74 (d, J=6.9 Hz, 1H), 6.62-6.51 (m, 1H), 5.34-5.31 (m, 1H), 4.35-4.28 (m, 1H), 4.27 (s, 1H), 4.21 (dt, J=11.4, 2.0 Hz, 1H), 3.81-3.75 (m, 4H), 2.80-2.72 (m, 2H), 2.69-2.64 (m, 2H), 2.63-2.57 (m, 1H), 2.57-2.49 (m, 2H), 2.12-2.05 (m, 2H), 1.92 (br d, J=12.9 Hz, 2H), 1.78 (dt, J=7.9, 4.0 Hz, 2H), 1.59 (br dd, J=9.6, 3.3 Hz, 2H).

Step 5. Preparation of (2R)-1-((2-amino-7-(1-(tetrahydro-2H-pyran-2-yl)-1H-pyrazol-5-yl)quinolin-4-yl)oxy)-3-morpholinopropan-2-ol To a solution of 4-((R)-2-hydroxy-3-morpholinopropoxy)-7-(1-(tetrahydro-2H-pyran-2-yl)-1H-pyrazol-5-yl)quinoline 1-oxide (42 mg, 0.092 mmol) in $CH_2Cl_2$ was added ammonia hydroxide (30%) solution (0.9 mL, 14.3 mmol) followed by tosyl chloride (35.2 mg, 0.185 mmol). After 20 min, the reaction was complete by LC/MS. The reaction mixture was diluted with $CH_2Cl_2$ and water, and extracted two times with $CH_2Cl_2$. The combined organic layers were dried over sodium sulfate, and concentrated to give the crude (2R)-1-((2-amino-7-(1-(tetrahydro-2H- pyran-2-yl)-1H-pyrazol-5-yl)quinolin-4-yl)oxy)-3-morpholinopropan-2-ol (25 mg, 60%). LC RT: 0.56 min. M/Z=454.5

Step 6: Preparation of (R)-1-((2-amino-7-(1H-pyrazol-5-yl)quinolin-4-yl)oxy)-3-morpholinopropan-2-ol (Compound 349)

To a solution of the crude (2R)-1-((2-amino-7-(1-(tetrahydro-2H-pyran-2-yl)-1H-pyrazol-5-yl)quinolin-4-yl)oxy)-3-morpholinopropan-2-ol (25 mg, 0.055 mmol) in CH$_2$Cl$_2$ (0.7 mL) was added TFA (350 μL, 4.54 mmol) and the reaction mixture was stirred at rt. After 1 hour, the reaction was complete by LCMS. The reaction was concentrated and azeotroped with CH$_2$Cl$_2$(1×). The residue was dissolved in DMF, filtered through a syringe filter, and the crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-40% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to give (R)-1-((2-amino-7-(1H-pyrazol-5-yl)quinolin-4-yl)oxy)-3-morpholinopropan-2-ol (12.7 mg, 62%). $^1$H NMR (500 MHz, DMSO-d$_6$) δ 8.16 (d, J=8.2 Hz, 1H), 7.99 (s, 1H), 7.90 (br d, J=7.9 Hz, 1H), 7.83 (br s, 1H), 6.87 (d, J=2.1 Hz, 1H), 6.36 (s, 1H), 4.50-4.42 (m, 1H), 4.29-4.20 (m, 2H), 3.32-3.20 (m, 2H), 2.94-2.87 (m, 1H). Some aliphatic protons are not visible in the $^1$H-NMR due to to overlap with the water peak. LC RT: 0.96 min. M/Z=370.22.

Example III-20: Preparation of 3-((2-amino-7-(1H-pyrazol-5-yl)quinolin-4-yl)amino)-1-morpholinopropan-1-one (Compound 350)

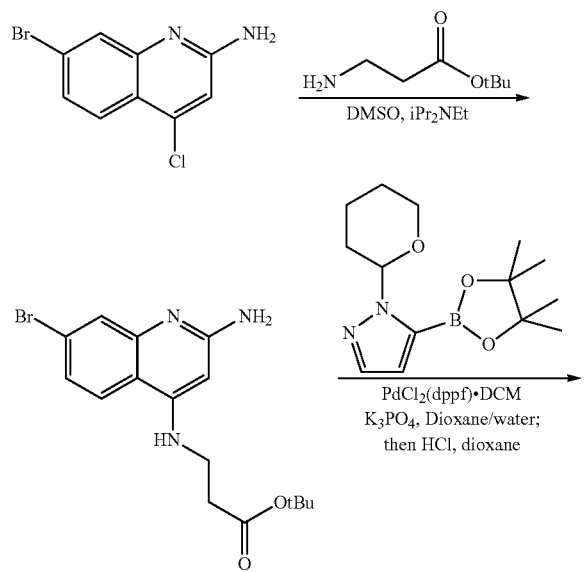

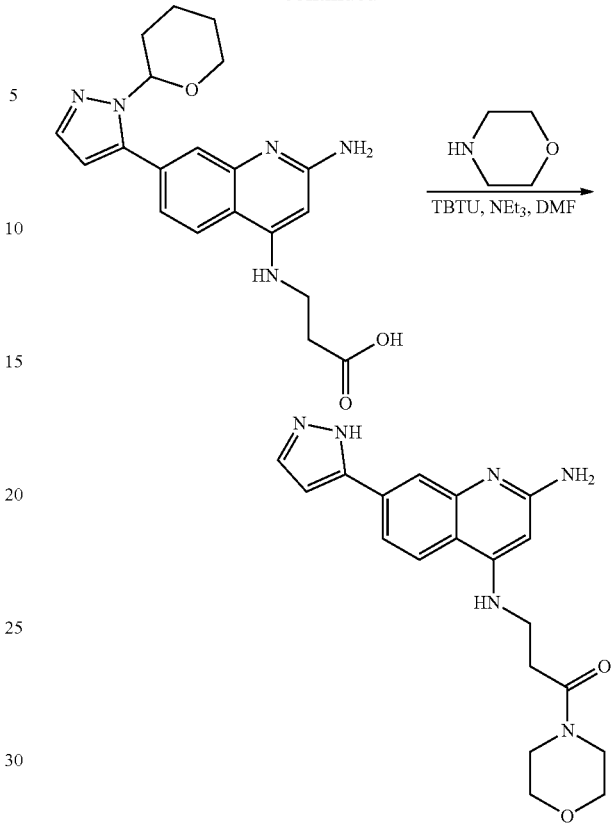

Compound 350

Step 1: Preparation of tert-butyl 3-((2-amino-7-bromoquinolin-4-yl)amino)propanoate To a solution of 7-bromo-4-chloroquinolin-2-amine (100 mg, 0.388 mmol) and tert-butyl-3-aminopropanoate hydrochloride (353 mg, 1.942 mmol) in DMSO (1 mL) was added hunig's base (0.678 mL, 3.88 mmol). The reaction was heated to 120° C. overnight. The reaction was cooled, evaporated and dried under high vaccum. The residue was purified via ISCO (24 g column; Hexanes/Ethyl acetate; 0 to 100% gradient then 0 to 20% DCM/MeOH) to give tert-butyl 3-((2-amino-7-bromoquinolin-4-yl)amino)propanoate (140 mg, 0.38 mmol, 98%).

Step 2: Preparation of 3-((2-amino-7-(1H-pyrazol-5-yl)quinolin-4-yl)amino)propanoic acid In a pressure vials was placed 1-(tetrahydro-2H-pyran-2-yl)-5-(4,4,5,5-tetramethyl-1,3,2-dioxaborolan-2-yl)-1H-pyrazole (133 mg, 0.478 mmol), tert-butyl 3-((2-amino-7-bromoquinolin-4-yl)amino)propanoate (140 mg, 0.382 mmol), and PdCl$_2$(dppf)-CH$_2$Cl$_2$ adduct (31.2 mg, 0.038 mmol). The vial was placed under vacuum and backfilled with nitrogen three times. Dioxane (5 ml) and tripotassium phosphate (2M aq) (0.573 mL, 1.147 mmol) were added, nitrogen was bubbled through the solution, then the reaction was heated to 100° C. overnight. The reaction was cooled to room temperature, diluted with 50 ml of DCM, dried with sodium sulfate, and concentrated. The residue was purified via ISCO (24 g column; DCM/MeOH; 0 to 40% gradient). After evaporation, the residue was dissolved in dioxane (5 ml). To this solution was added HCl (4N dioxane) (3 mL, 12.00 mmol). After 16 hours, the reaction mixture was concentrated under reduced pressure and dried under high vaccum.

Step 3: Preparation of 3-((2-amino-7-(1H-pyrazol-5-yl)quinolin-4-yl)amino)-1-morpholinopropan-1-one (Compound 350)

A solution of 3-((2-amino-7-(1H-pyrazol-5-yl)quinolin-4-yl)amino)propanoic acid (35 mg, 0.118 mmol), morpholine (0.021 mL, 0.235 mmol), TBTU (113 mg, 0.353 mmol), and TEA (0.164 mL, 1.177 mmol) in DMF (1 mL) was stirred at room temperature for 4 hours. The reaction mixture was diluted with 0.5 ml of DMF and 0.5 ml of acetic acid, filtered through a syringe filter, and the crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 0% B, 0-25% B over 35 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to give 3-((2-amino-7-(1H-pyrazol-5-yl)quinolin-4-yl)amino)-1-morpholinopropan-1-one bis-trifluoroacetate (11.3 mg, 26%) $^1$H NMR (500 MHz, DMSO-d$_6$) δ 8.25-8.18 (m, 1H), 8.04 (br s, 1H), 7.96 (br s, 1H), 7.93-7.81 (m, 2H), 7.70-7.61 (m, 1H), 6.86 (s, 1H), 5.85 (s, 1H), 3.62-3.51 (m, 4H), 3.48 (br d, J=7.3 Hz, 2H), 2.80 (t, J=7.0 Hz, 2H) Three methylenes are not visible, likely due to overlap with suppressed water peak. LC/MS conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). LC RT: 0.97 min. M/Z=367.11.

Evaluation of Biological Activity

Measurement of IL-1β Production in PMA-Differentiated THP-1 Cells THP-1 cells were purchased from the American Type Culture Collection and sub-cultured according to instructions from the supplier. Prior to experiments, cells were cultured in RPMI 1640 containing 10% heat inactivated FBS, penicillin (100 units/ml) and streptomycin (100 µg/ml), and maintained in log phase prior to experimental setup. Prior to the experiment THP-1 were treated with PMA (Phorbol 12-myristate 13-acetate) (10 µg/ml) for 24 hours. The day of the experiment the media was removed and attaching cells were treated with trypsin for 2 minutes, cells were then collected, washed with PBS (phosphate buffer saline), spin down, resuspended in 2% heat inactivated FBS with RPMI at a concentration of 1×10$^6$ cells/ml, and 100 µl was plated in a 96 well plate. Compounds were dissolved in dimethyl sulfoxide (DMSO) and added to the culture medium to achieve desired concentration (e.g. 100, 30, 10, 3, 1, 0.3 or 0.1 µM). Cells were incubated with compounds for 4 hours. Cell free supernatant was collected and the production of IL-1β was evaluated by ELISA. A vehicle only control was run concurrently with each experiment. Final DMSO concentration was 1%. Compounds exhibit a dose-related increase of IL-1β production in PMA-differentiated THP-1 cells.

Measurement of IL-1β Production in PMA-Differentiated THP-1 Cells (Alternative Procedure)

THP-1 cells were purchased from the American Type Culture Collection and sub-cultured according to instructions from the supplier. Prior to experiments, cells were cultured in RPMI 1640 containing 10% heat inactivated FBS, penicillin (100 units/ml), streptomycin (100 µg/ml), HEPES (10 mM) and sodium pyruvate (1 mM) and maintained in log phase prior to experimental setup. Prior to the experiment, THP-1 cells were treated with PMA (Phorbol 12-myristate 13-acetate) (20 µg/ml) overnight. The day of the experiment, the media was removed and attached cells were treated with trypsin for 2 minutes, cells were then collected, washed with PBS (phosphate buffer saline), pelleted by centrifugation and resuspended in 2% heat inactivated FBS with RPMI at a concentration of 50,000 cells/well in a 384 well plate. Cell free supernatant was collected and the production of IL-1β was evaluated by ELISA. Compounds were dissolved in dimethyl sulfoxide (DMSO) and added to the culture medium to achieve desired concentration (e.g. 100, 30, 10, 3, 1, 0.3 or 0.1 µM). Cells were incubated with compounds for 2 hours. A vehicle only control was run concurrently with each experiment. Final DMSO concentration was 1%. Compounds exhibit a dose-related increase of IL-1β production in PMA-differentiated THP-1 cells.

Measurement of IL-1β Production—hTRF Protocol (Second Alternative Procedure)

Serial dilutions of compounds in DMSO were added to low volume 384 well plates at 100 nl/well using an ECHO 550 acoustic dispenser (Labcyte) to achieve final starting concentration of 10 µM in assay.

THP-1 cells in RPMI (Gibco, 11875) media with 10% FBS at a density of 1×10$^6$ cell/ml in a T175 flask were treated with a final concentration of phorbol 12-myristate 13-acetate (PMA) (Sigma, P1585) of 50 ng/ml overnight at 37° C. at 5% CO$_2$ for differentiation. Cells were harvested the next day after rinsing well with dPBS using 0.5% trypsin. A cell solution was prepared of 1×10$^6$ cells/ml for 50,000 cells in 50 µl/well in RPMI media with 2% FBS. Cells were plated using a multichannel pipette onto the compound dilutions in Greiner, 384 well, black clear bottom tissue culture treated plates (781090). The plates were incubated in 37° C. incubator at 5% CO$_2$ for 2 hours.

After 2 hour incubation, the cell plates were spun in the centrifuge for 5 minutes at 1200 rpm. Using the Felix (CyBio), 8 µl of the supernatant was transferred to 384 well, low volume, white proxy plates. (Perkin Elmer, 6008230). A human ILI beta hTRF kit was used to analyze the supernatant (CISBIO, 62HIL1BPEG). The kit instructions were followed for preparing the ILI Beta standard curve and then the antibodies from the kit were diluted 1:40 rather than 1:20 as kit instructed. Once combined, the antibodies were added across the plates, 5 µl/well. The plates were sealed and incubated at 4° C. overnight. The plates were then read on the Perkin Elmer EnVision at 665/615 nm using the hTRF laser. Compounds exhibited a dose-related increase of IL-1β production.

Measurement of IL-1β Production—Human Whole Blood Assay

Serial dilutions of compounds in DMSO were added to low volume 384 well plates at 100nl/well using an ECHO 550 acoustic dispenser (Labcyte) to achieve final starting concentration of 10 uM in assay.

Human venous whole blood obtained from healthy donors was pre-treated with LPS (Invivogen, Cat #tlrl-eblps) at 1 ng/ml for four hours at 37° C. in a humidified 95% air/5% CO$_2$ incubator. Primed blood was added to the compound plate and incubated for additional 4 hours at 37° C. IL-1beta in the supernatants was measured using AlphLISA kit (Cat #AL220) according to manufacturer's instructions. Compounds exhibited a dose-related increase of IL-1β production. EC50 was determined using primed but untreated blood as baseline.

Measurement of IL-1β Production—Mouse hTRF Protocol

Immortalized mouse macrophages derived from C57BL/6 mice were obtained from Ericke Latz, University of Bonn/University of Massachusetts Worchester, MA The cells were harvested using 0.05% Trypsin and washed with PBS. Cell were plated at 30,000 cells per well in 25ul in DMEM (Gibco, 11965) supplemented with 2% FBS and incubated for 10 minutes at 37° C. at 5% $CO_2$. LPS-EB (Invivogen, tlr-eblps) was added to a final concentration of 200 ng/ml at 5 ul/well and cells were incubated for 2 hours at 37° C. at 5% $CO_2$.

Serial dilutions of compounds in DMSO were added to cells in low volume 384 well plates at 60nl/well using an ECHO 550 acoustic dispenser (Labcyte) to achieve final starting concentration of 50 uM in assay and incubated with compounds for additional 2 hours at 37° C. at 5% $CO_2$.

After 2 hour incubation, the cell plates were spun in the centrifuge for 5 minutes at 1200 rpm. Using the Felix (CyBio), 8ul of the supernatant was transferred to 384 well, low volume, white proxy plates. (Perkin Elmer, 6008230). A human ILI beta hTRF kit was used to analyze the supernatant (CISBIO, 62MIL1BPEH). The kit instructions were followed for preparing the ILI Beta standard curve (the antibodies from the kit were diluted 1:40 rather than 1:20 as kit instructed). Once combined, the antibodies were added across the plates at 5 ul/well. The plates were sealed and incubated at 4° C. overnight. The plates were read on the Perkin Elmer EnVision at 665/615 nm using the hTRF laser. Data was then converted to pg/ml of Il1Beta. Compounds exhibited a dose-related increase of IL-1β production.

In Vitro Human TLR7 and TLR8 Binding Reporter Assays

Logarithmically-growing human HEK-Blue cells co-expressing a TLR7 or TLR8 gene and a NF-kB/AP1-inducible SEAP (secreted embryonic alkaline phosphatase; Invivogen, San Diego, CA) reporter gene are added to individual wells of a 384-well plate (15,000 cells per 20 μL per well) and maintained for 24 h at 37° C., 5% $CO_2$. Test compounds or DMSO are distributed to separate wells the next day using acoustic liquid handling technology (100 nL per well) and cells are subsequently incubated for 18 h at 37° C., 5% $CO_2$. Cellular SEAP production is measured using an Envision plate reader instrument thirty minutes after adding freshly-made Quanti-Blue reagent (prepared by following manufacturer instructions; Invivogen, San Diego, CA) to the HEK-Blue TLR Nf-kB-SEAP cell reactions. All $EC_{50}$ values (half-maximal effective concentration) are determined using proprietary data analysis software. Normalized $EC_{50}$ value=absolute value determined by setting 100% Ymax using a reference standard RLU (relative light unit) values from cells treated with 50 μM of the reference standard.

Table 1 includes biological data of compounds that were assayed using one or more of the above procedures. Key to activity ranges: A=≤1 μM; B=>1 μM, ≤20 μM; C=>20 μM, ≤100 μM; D=>100 μM; E: <50% activity at 50 μM.

TABLE 1

| COMPD_NO | NLRP3 hIL1B $IC_{50}$ (μM) | TLR7 Agonist $EC_{50}$ (μM) | TLR8 Agonist $EC_{50}$ (μM) |
| --- | --- | --- | --- |
| 101 | 0.79 | D | D |
| 102 | 1.38 | D | D |
| 103 | 1.60 | D | D |
| 104 | 0.69 | D | D |
| 105 | 2.98 | D | D |
| 106 | 3.82 | D | D |
| 107 | 0.34 | D | D |
| 108 | 1.15 | | |
| 109 | 4.33 | D | D |
| 110 | 1.64 | D | D |
| 111 | 2.46 | D | D |
| 112 | 2.56 | D | D |
| 113 | 11.90 | D | D |
| 114 | 4.25 | D | D |
| 115 | 3.04 | D | D |
| 116 | 4.07 | D | D |
| 117 | 5.80 | E | E |
| 118 | 1.73 | D | D |
| 119 | 3.07 | D | C |
| 120 | 4.24 | E | E |
| 121 | 3.03 | E | D |
| 122 | 1.87 | E | E |
| 123 | 3.01 | E | E |
| 124 | 14.51 | D | D |
| 125 | 1.98 | E | E |
| 126 | 3.53 | E | E |
| 127 | 1.15 | D | D |
| 128 | 0.10 | D | D |
| 129 | 2.29 | D | D |
| 130 | 2.76 | E | D |
| 131 | 0.85 | D | D |
| 132 | 0.53 | D | D |
| 133 | 0.30 | D | D |
| 134 | 0.29 | D | D |
| 135 | 0.12 | D | D |
| 136 | 3.02 | D | D |
| 137 | 0.55 | D | D |
| 138 | 5.95 | B | D |
| 139 | 2.01 | D | D |
| 140 | 1.41 | D | D |
| 141 | 0.63 | D | D |
| 142 | 1.43 | D | D |
| 143 | 5.81 | D | D |
| 144 | 0.48 | D | D |
| 145 | 2.55 | D | D |
| 146 | 4.07 | D | D |
| 147 | 0.99 | D | D |
| 148 | 1.64 | D | D |
| 149 | 0.14 | D | D |
| 150 | 0.22 | D | D |
| 151 | 0.31 | D | D |
| 152 | 1.03 | D | D |
| 153 | 1.11 | D | D |
| 154 | 0.44 | D | D |
| 155 | 0.42 | D | D |
| 156 | 0.20 | D | D |
| 157 | 0.73 | D | D |
| 158 | 35.84 | D | D |
| 159 | 0.52 | D | D |
| 160 | 2.76 | D | D |
| 161 | 0.15 | D | D |
| 162 | 2.49 | D | D |
| 163 | 0.16 | D | D |
| 164 | 1.91 | D | D |
| 165 | 0.47 | D | D |
| 166 | 0.56 | D | D |
| 167 | 8.33 | D | D |
| 168 | 2.40 | E | D |
| 169 | 1.37 | D | D |
| 170 | 5.82 | D | D |
| 171 | 0.38 | E | D |
| 172 | 0.41 | D | D |
| 173 | 0.28 | D | D |
| 174 | 0.82 | D | D |
| 175 | 0.97 | D | D |
| 176 | 0.70 | D | D |
| 177 | 3.07 | D | D |

TABLE 1-continued

| COMPD_NO | NLRP3 hIL1B IC$_{50}$ ($\mu$M) | TLR7 Agonist EC$_{50}$ ($\mu$M) | TLR8 Agonist EC$_{50}$ ($\mu$M) |
|---|---|---|---|
| 178 | 0.70 | D | D |
| 179 | 0.78 | D | D |
| 180 | 9.72 | D | D |
| 181 | 9.92 | E | D |
| 182 | 1.14 | D | D |
| 183 | 8.40 | D | D |
| 184 | 7.27 | E | D |
| 185 | 0.56 | D | D |
| 186 | 1.08 | D | D |
| 187 | 0.85 | D | D |
| 188 | 6.31 | D | D |
| 189 | 0.39 | D | D |
| 190 | 0.66 | D | D |
| 191 | 0.63 | D | D |
| 192 | 0.63 | D | D |
| 193 | 1.69 | D | D |
| 194 | 2.23 | D | D |
| 195 | 0.93 | D | D |
| 196 | 1.11 | D | D |
| 197 | 2.86 | D | D |
| 198 | 11.37 | D | D |
| 199 | 13.30 | D | D |
| 200 | 1.89 | D | D |
| 201 | 5.05 | D | D |
| 202 | 1.89 | D | D |
| 203 | 0.19 | D | D |
| 204 | 0.64 | D | D |
| 205 | 1.29 | D | D |
| 206 | 0.84 | D | D |
| 207 | 1.07 | D | D |
| 208 | 1.55 | D | D |
| 209 | 1.96 | D | D |
| 210 | 20.75 | D | D |
| 211 | 13.50 | D | D |
| 212 | 9.27 | D | D |
| 213 | 1.55 | D | D |
| 214 | 4.61 | D | D |
| 215 | 1.94 | D | D |
| 216 | 2.23 | D | D |
| 217 | 14.35 | D | D |
| 218 | 1.19 | D | D |
| 219 | 2.75 | D | D |
| 220 | 0.57 | D | D |
| 221 | 0.52 | D | D |
| 222 | 0.06 | D | D |
| 223 | 1.35 | D | D |
| 224 | 0.22 | D | D |
| 225 | 0.13 | D | D |
| 226 | 0.73 | D | D |
| 227 | 0.33 | D | D |
| 228 | 0.16 | D | D |
| 229 | 0.09 | D | D |
| 230 | 0.54 | D | D |
| 231 | 1.27 | D | D |
| 232 | 0.23 | D | D |
| 233 | 0.09 | D | D |
| 234 | 0.23 | D | D |
| 235 | 0.86 | D | D |
| 236 | 2.65 | D | D |
| 237 | 2.57 | D | D |
| 238 | 1.49 | D | D |
| 239 | 4.83 | D | D |
| 240 | 0.24 | D | D |
| 241 | 2.25 | D | D |
| 242 | 2.35 | D | D |
| 243 | 1.02 | D | D |
| 244 | 0.35 | D | D |
| 245 | 1.34 | D | D |
| 246 | 0.17 | D | D |
| 247 | 0.48 | D | D |
| 248 | 0.33 | D | D |
| 249 | 0.05 | D | D |
| 250 | 1.72 | D | D |
| 251 | 0.37 | D | D |
| 252 | 1.69 | D | D |
| 253 | 0.27 | D | D |
| 254 | 0.21 | D | D |
| 255 | 0.27 | D | D |
| 256 | 0.22 | D | D |
| 257 | 0.68 | D | D |
| 258 | 1.84 | D | D |
| 259 | 0.64 | D | D |
| 260 | 0.32 | D | D |
| 261 | 0.14 | D | D |
| 262 | 0.12 | D | D |
| 263 | 2.87 | D | D |
| 264 | 2.89 | D | D |
| 265 | 0.35 | D | D |
| 266 | 0.39 | D | D |
| 267 | 1.59 | D | D |
| 268 | 0.97 | D | D |
| 269 | 1.15 | D | D |
| 270 | 7.37 | D | D |
| 271 | 0.36 | D | D |
| 272 | 6.22 | D | D |
| 273 | 0.17 | D | D |
| 274 | 1.98 | D | D |
| 275 | 0.20 | D | D |
| 276 | 0.52 | D | D |
| 277 | 0.22 | D | D |
| 278 | 1.31 | D | D |
| 279 | 0.33 | D | D |
| 280 | 1.57 | D | D |
| 281 | 0.58 | D | D |
| 282 | 5.66 | D | D |
| 283 | 1.70 | D | D |
| 284 | 0.38 | D | D |
| 285 | 1.56 | D | D |
| 286 | 13.11 | D | D |
| 287 | 0.70 | D | D |
| 288 | 0.39 | D | D |
| 289 | 0.85 | D | D |
| 290 | 1.00 | D | D |
| 291 | 1.67 | D | D |
| 292 | 0.34 | D | D |
| 293 | 0.87 | D | D |
| 294 | 0.21 | D | D |
| 295 | 0.31 | D | D |
| 296 | 0.56 | D | D |
| 297 | 0.57 | D | D |
| 298 | 0.15 | D | D |
| 299 | 0.65 | D | D |
| 300 | 0.54 | D | D |
| 301 | 1.01 | D | D |
| 302 | 0.05 | D | D |
| 303 | 0.14 | D | D |
| 304 | 0.37 | D | D |
| 305 | 0.64 | D | D |
| 306 | 1.10 | D | D |
| 307 | 0.11 | D | D |
| 308 | 0.52 | D | D |
| 309 | 0.42 | D | D |
| 310 | 0.11 | D | D |
| 311 | 3.13 | D | D |
| 312 | 1.59 | D | D |
| 313 | 0.11 | D | D |
| 314 | 1.80 | D | D |
| 315 | 1.52 | D | D |
| 316 | 0.56 | D | D |
| 317 | 0.69 | D | D |
| 318 | 0.07 | D | D |
| 319 | 25.7 | D | D |
| 320 | 27.68 | D | D |
| 321 | 11.59 | D | D |
| 322 | 0.61 | D | D |
| 323 | 5.72 | D | D |
| 324 | 1.76 | D | D |
| 325 | 23.16 | D | D |
| 326 | 24.73 | D | D |
| 327 | 4.66 | D | D |
| 329 | 0.67 | D | D |
| 330 | 24.59 | D | D |

TABLE 1-continued

| COMPD_NO | NLRP3 hIL1B IC$_{50}$ (μM) | TLR7 Agonist EC$_{50}$ (μM) | TLR8 Agonist EC$_{50}$ (μM) |
|---|---|---|---|
| 331 | 14.62 | D | D |
| 332 | 0.65 | D | D |
| 333 | 1.31 | D | D |
| 334 | 2.62 | D | D |
| 335 | 0.63 | D | D |
| 336 | 2.03 | D | D |
| 337 | 9.17 | D | D |
| 338 | 3.41 | D | D |
| 339 | 0.48 | D | D |
| 340 | 0.73 | D | D |
| 341 | 0.62 | D | D |
| 342 | 1.10 | D | D |
| 343 | 0.61 | D | D |
| 344 | 1.11 | D | D |
| 345 | 1.77 | D | D |
| 346 | 0.76 | D | E |
| 347 | 1.18 | D | D |
| 348 | 7.26 | D | D |
| 349 | 5.80 | D | D |
| 350 | 4.19 | D | D |
| 351 | 0.17 | D | D |

What is claimed is:

1. A compound having formula (I), or a pharmaceutically acceptable salt thereof:

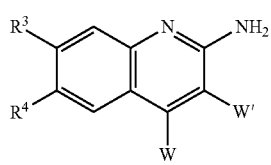
(I)

wherein:

W' is H;

W is independently selected from:

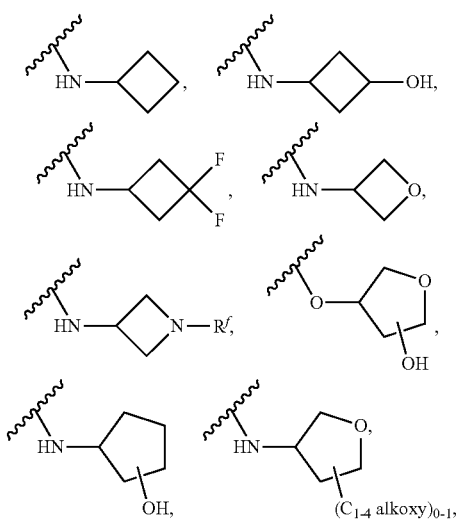

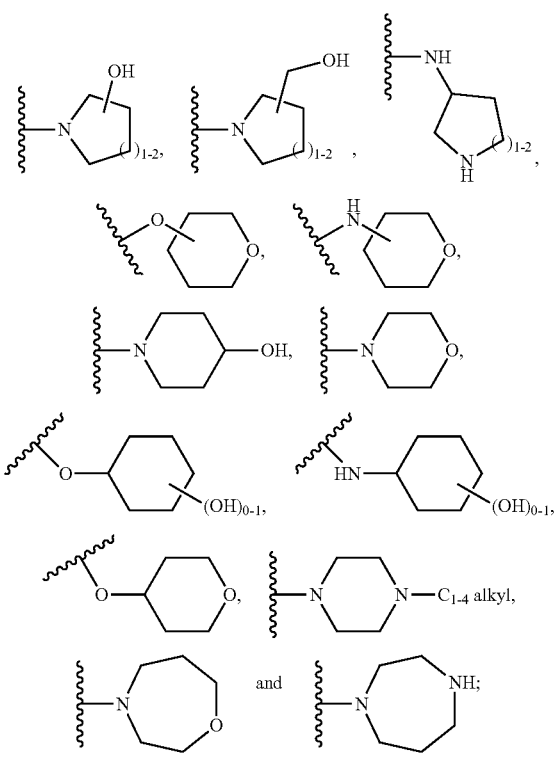

$R^3$ is independently pyrazolyl, thienyl or isothiazolyl;

$R^4$ is independently H or F; and $R^f$ is independently H, CH$_2$CH$_2$OH, or —C(O)O(C$_{1-4}$ alkyl).

2. The compound of claim 1, or a pharmaceutically acceptable salt thereof, wherein:

W' is H;

W is independently selected from:

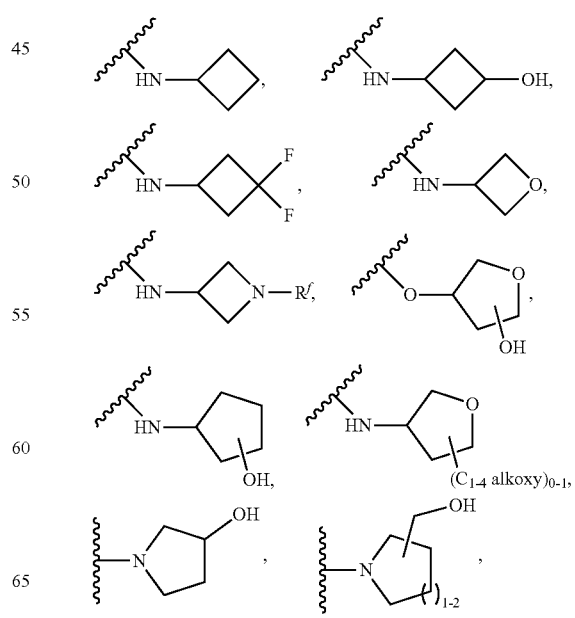

-continued

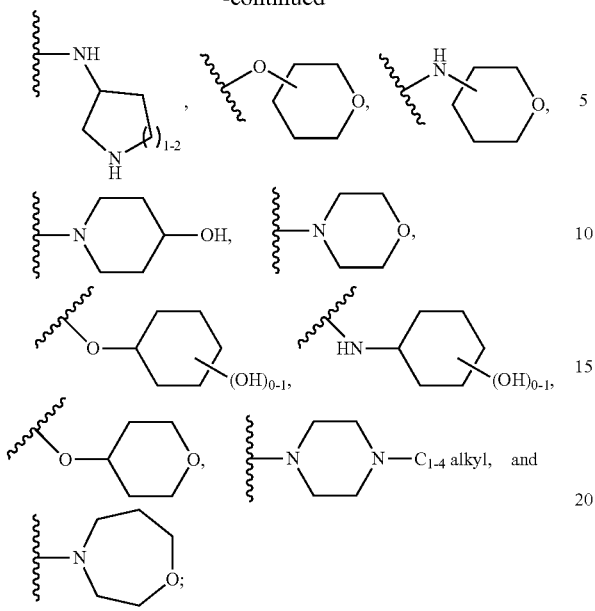

$R^3$ is independently pyrazolyl or thienyl;
$R^4$ is independently H or F; and
$R^f$ is independently H, CH$_2$CH$_2$OH, or —C(O)O(C$_{1-4}$ alkyl).

3. The compound of claim 2, or a pharmaceutically acceptable salt thereof, wherein:
W' is H;
W is independently selected from:

-continued

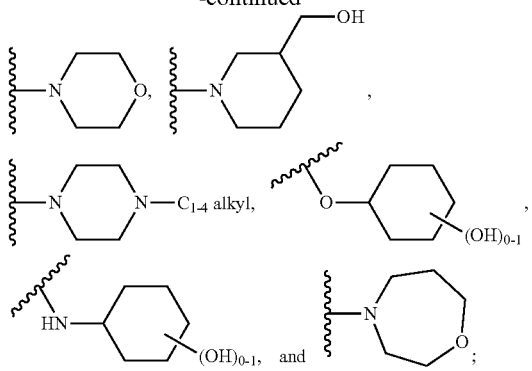

$R^3$ is independently

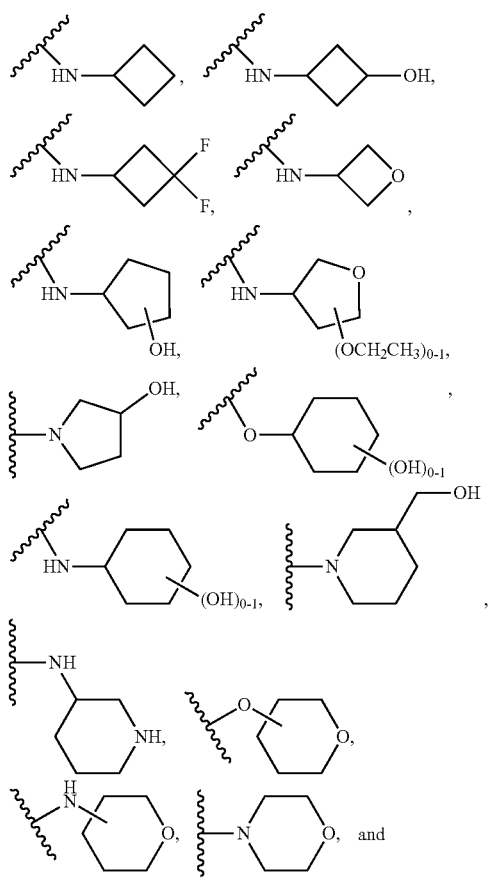

$R^4$ is independently H or F.

4. The compound of claim 3, or a pharmaceutically acceptable salt thereof, wherein:
W' is H;
W is independently selected from:

-continued

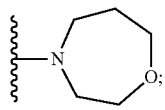

R³ is independently

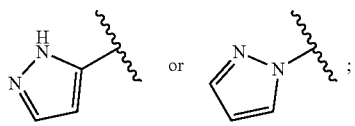

and
R⁴ is independently H or F.

5. The compound according to claim 4, or a pharmaceutically acceptable salt thereof, wherein:
W' is H;
W is independently selected from:

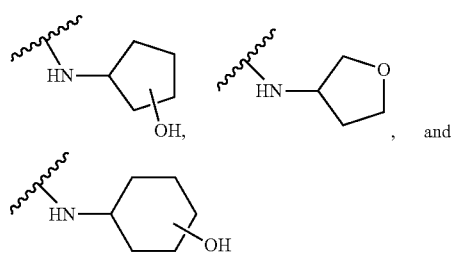

R³ is independently

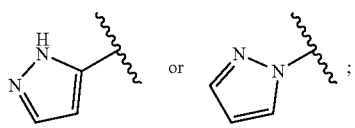 [SMILES: *c1ccn[nH]1 ; *n1cccn1]

and
R⁴ is independently H or F.

6. The compound according to claim 5, or a pharmaceutically acceptable salt thereof, wherein:
W' is H;
W is

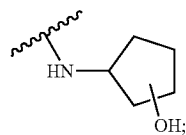

R³ is

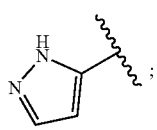 [SMILES: *c1ccn[nH]1]

and
R⁴ is H.

7. A compound selected from:

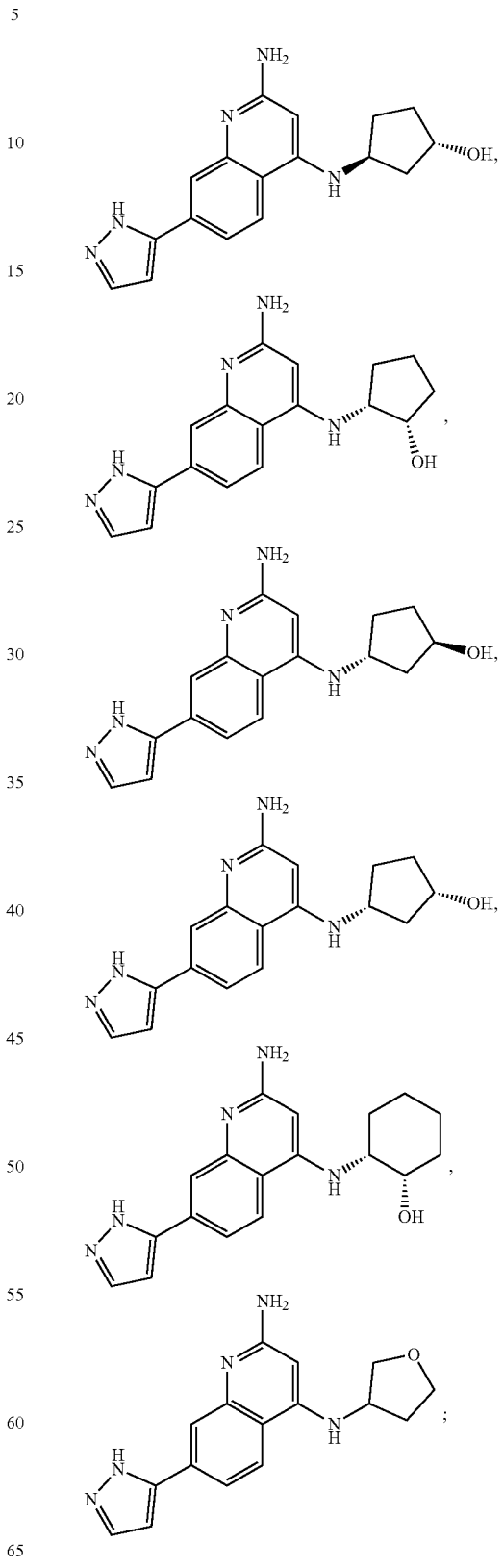

or a pharmaceutically acceptable salt thereof.

8. The compound according to claim 7, wherein the compound is selected from:

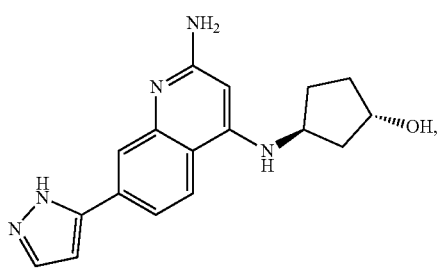 [SMILES: Nc1cc(N[C@H]2CC[C@H](O)C2)c2ccc(-c3ccn[nH]3)cc2n1]

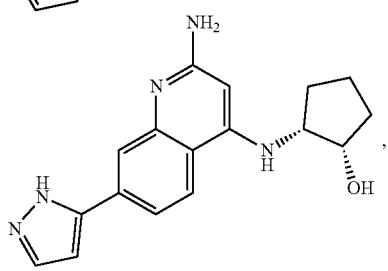

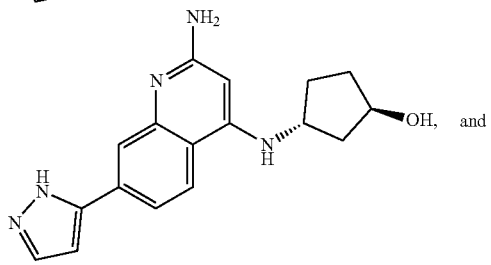 and

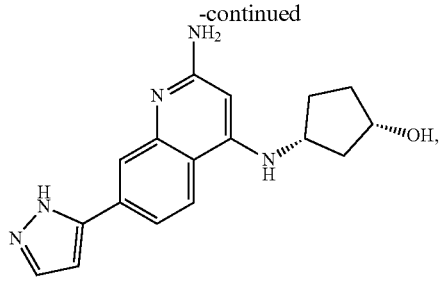

or a pharmaceutically acceptable salt thereof.

9. A compound of the formula:

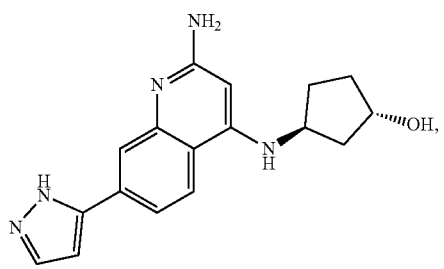

or a pharmaceutically acceptable salt thereof.

10. A pharmaceutical composition comprising a compound or a pharmaceutically acceptable salt thereof as claimed in claim 1 and one or more pharmaceutically acceptable excipients.

* * * * *